(12) United States Patent
Gilboa-Geffen et al.

(10) Patent No.: US 10,908,139 B2
(45) Date of Patent: Feb. 2, 2021

(54) SYSTEMS AND METHODS FOR ALLERGEN DETECTION

(71) Applicant: DOTS Technology Corp., Natick, MA (US)

(72) Inventors: Adi Gilboa-Geffen, Wayland, MA (US); Renuka Babu Brown, Weston, MA (US); Sarah Stidham, Brookline, MA (US); Valerie Villareal, Boston, MA (US); Adam J. Young, Dedham, MA (US); Joshua Glenn Anthony, Reading, MA (US); Patrick Murphy, Cambridge, MA (US); John H. Kepler, Lexington, MA (US); Adam Jacobs, Hollis, NH (US)

(73) Assignee: DOTS TECHNOLOGY CORP., Natick, MA (US)

( * ) Notice: Subject to any disclaimer, the term of this patent is extended or adjusted under 35 U.S.C. 154(b) by 0 days.

(21) Appl. No.: 16/084,996

(22) PCT Filed: Mar. 10, 2017

(86) PCT No.: PCT/US2017/021737
§ 371 (c)(1),
(2) Date: Sep. 14, 2018

(87) PCT Pub. No.: WO2017/160616
PCT Pub. Date: Sep. 21, 2017

(65) Prior Publication Data
US 2019/0079063 A1 Mar. 14, 2019

Related U.S. Application Data

(60) Provisional application No. 62/308,376, filed on Mar. 15, 2016, provisional application No. 62/308,377, filed on Mar. 15, 2016.

(51) Int. Cl.
*B01L 3/00* (2006.01)
*B01L 1/00* (2006.01)
(Continued)

(52) U.S. Cl.
CPC ........... *G01N 33/02* (2013.01); *C12M 1/3476* (2013.01); *C12N 15/115* (2013.01); *G01N 1/08* (2013.01);
(Continued)

(58) Field of Classification Search
CPC .................................. B01L 3/50; B01L 3/502
See application file for complete search history.

(56) References Cited

U.S. PATENT DOCUMENTS

| 5,166,052 A | 11/1992 | Cercek et al. |
| 6,032,368 A * | 3/2000 | Huang ............... A47J 25/00 30/113.1 |

(Continued)

FOREIGN PATENT DOCUMENTS

| WO | 1998005962 A1 | 2/1998 |
| WO | WO2007081387 A1 | 7/2007 |

(Continued)

OTHER PUBLICATIONS

Extended European Search Report for corresponding European Application No. 17767200.3 dated Oct. 30, 2019.
(Continued)

*Primary Examiner* — Nathan A Bowers
(74) *Attorney, Agent, or Firm* — DT Ward, PC; Donna T. Ward; Lingyun Jia

(57) ABSTRACT

The present invention provides systems, devices, signaling polynucleotides (SPNs), detection agents and methods for detecting the presence and/or absence of one or more allergens in a sample particularly a food sample. The detection system includes a separate sampler, at least one dispos-
(Continued)

able detection vessel for receiving and processing a test sample and a detection device for measuring a fluorescent signal. SPNs derived from aptamer that bind allergens are provided as detection agents. SPNs have a single open structure, and are labeled with a fluorophore. Changes in fluorescence polarization of SPNs upon the binding of allergens are measured to calculate the allergen content in a sample.

22 Claims, 21 Drawing Sheets

Specification includes a Sequence Listing.

(51) Int. Cl.
*G01N 33/02* (2006.01)
*C12M 1/34* (2006.01)
*G01N 1/08* (2006.01)
*C12N 15/115* (2010.01)
*G01N 1/14* (2006.01)
*G01N 1/28* (2006.01)
*G01N 33/53* (2006.01)
*G01N 33/58* (2006.01)

(52) U.S. Cl.
CPC .............. *G01N 1/14* (2013.01); *G01N 1/286* (2013.01); *G01N 33/5304* (2013.01); *G01N 33/5308* (2013.01); *G01N 33/58* (2013.01); *C12N 2310/16* (2013.01); *C12N 2320/11* (2013.01); *G01N 2001/1427* (2013.01); *G01N 2001/2866* (2013.01)

(56) References Cited

U.S. PATENT DOCUMENTS

| | | | |
|---|---|---|---|
| 6,398,402 B1 | 6/2002 | Thomas et al. | |
| 7,504,641 B2* | 3/2009 | Tuunanen | G01N 21/6445 250/225 |
| 8,211,715 B1 | 7/2012 | Royds | |
| 8,488,118 B2* | 7/2013 | Krishnamachari | G01J 3/02 356/301 |
| 2001/0033374 A1* | 10/2001 | Hoyt | G01N 21/6428 356/317 |
| 2004/0007387 A1* | 1/2004 | Bar-Cohen | E21B 7/24 175/50 |
| 2007/0275427 A1 | 11/2007 | Akimoto et al. | |
| 2008/0241933 A1* | 10/2008 | Barker | G01N 29/022 436/8 |
| 2008/0285378 A1 | 11/2008 | Roggero | |
| 2010/0137163 A1* | 6/2010 | Link | B01F 13/0071 506/16 |
| 2010/0210033 A1 | 8/2010 | Scott | |
| 2010/0285490 A1 | 11/2010 | Dees et al. | |
| 2012/0264232 A1 | 10/2012 | Kramer et al. | |
| 2012/0264646 A1* | 10/2012 | Link | B01F 5/0646 506/11 |
| 2015/0011020 A1 | 1/2015 | Sundvor et al. | |

FOREIGN PATENT DOCUMENTS

| | | |
|---|---|---|
| WO | 2012078455 A1 | 6/2012 |
| WO | WO2012078455 A1 | 6/2012 |
| WO | 2015/066027 A2 | 5/2015 |
| WO | 2015066027 A2 | 5/2015 |
| WO | WO2015066027 A2 | 5/2015 |
| WO | WO2015095142 A2 | 6/2015 |
| WO | 2015/151349 A1 | 10/2015 |
| WO | 2016/149253 A1 | 9/2016 |
| WO | 2016149253 A1 | 9/2016 |

OTHER PUBLICATIONS

International Search Report and Written Opinion dated Jul. 21, 2017 in Application No. PCTUS2017021737, entitled: Systems and Methods for Allergen Detection.
Nadal, P., et al. (2012) DNA Aptamers against the Lup an 1 Food Allergen, PLoS ONE 7(4): e35253. doi:10.1371/journal.pone.0035253.
Nadal, P. et al. (2013) Probing high-affinity 11-mer DNA aptamer against Lup an 1 (b-conglutin), Springer-Verlag Berlin Heidelberg 405:9343-9349.
Mairal, T. et al. (2014) FRET-based dimeric aptamer probe for selective and sensitive L an 1 allergen detection, Biosensors and Bioelectronics 54 (2014) 207-210.
Amaya-González, S. et al. (2013) Aptamer-Based Analysis: A Promising Alternative for Food Safety Control, Sensors 2013, 13, 16292-16311; doi:10.3390/s131216292.
Singapore Search Report and Written Opinion for corresponding Singapore Application No. 11201806647V dated Jan. 28, 2020.
Thailand Office Action for corresponding Thailand Application No. 11801005468 dated Jun. 1, 2020.
Australian Examination Report for corresponding Australian Application No. 2017234548 dated Aug. 26, 2020.

* cited by examiner

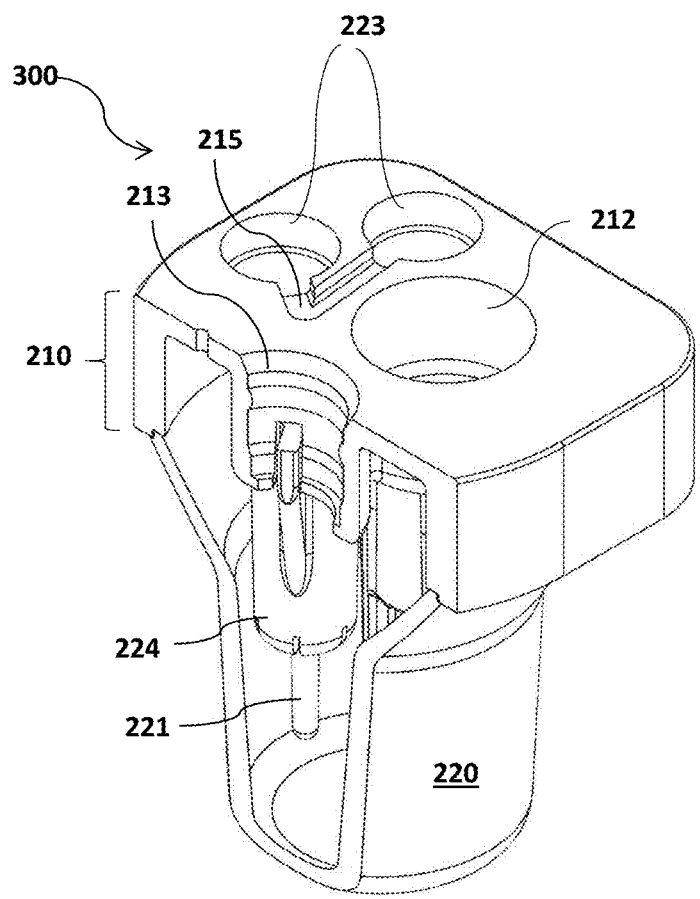
Fig. 3a
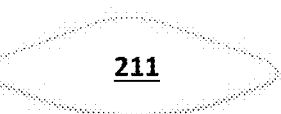
Fig. 3b
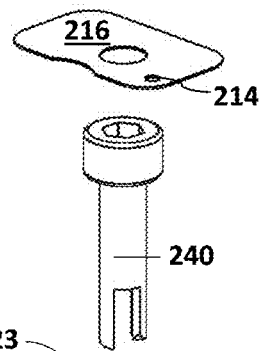
Fig. 3c
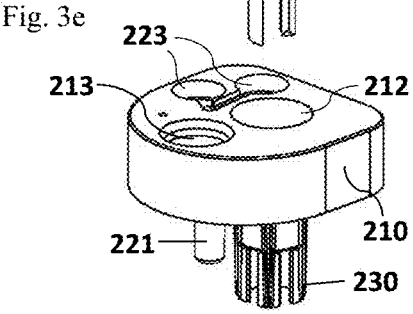
Fig. 3d
Fig. 3e
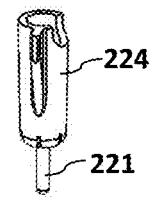
Fig. 3f
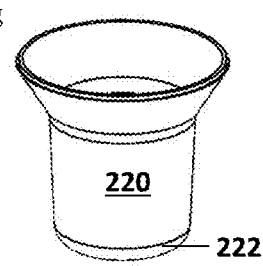
Fig. 3g

SYSTEMS AND METHODS FOR ALLERGEN DETECTION

CROSS REFERENCE TO RELATED APPLICATIONS

This application is a 35 U.S.C. § 371 U.S. National Stage Entry of International Application No. PCT/US2017/021737, entitled Systems and Methods for Allergen Detection, filed Mar. 10, 2017, which claims priority to U.S. Provisional Application No. 62/308,376, entitled Portable Allergen Detection System, filed Mar. 15, 2016, and U.S. Provisional Application No. 62/308,377, entitled Allergen Detection Agents and Methods, filed Mar. 15, 2016; the contents of each of which are incorporated herein by reference in their entireties.

REFERENCE TO SEQUENCE LISTING

The present application is being filed along with a Sequence Listing in electronic format. The Sequence Listing is provided as a file entitled 20661004US371SEQLST.txt, created on Sep. 12, 2018, which is 77,217 bytes in size. The information in the electronic format of the sequence listing is incorporated herein by reference in its entirety.

FIELD OF THE INVENTION

The present invention relates to systems, devices, aptamers, signaling polynucleotides (SPNs), detection agents and methods for detecting the presence and/or absence of a target allergen in a test sample such as a food allergen in a food sample.

BACKGROUND OF THE INVENTION

Allergy (e.g., food allergy) is a common medical condition affecting millions of people worldwide. It has been estimated that in the United States, up to 2 percent of adults and up to 8 percent of children, particularly those under three years of age, suffer from food allergies (about 15 million people), and this prevalence is believed to be increasing. During an allergic reaction, the immune system mistakenly targets an allergen as a threat and attacks it. The allergic reaction may affect the skin, the digestive system, the gastrointestinal tract, the respiratory system, the circulatory system and the cardiovascular system; in some allergic reactions, multiple organ systems are affected. Allergic reactions range from mild to severe or life-threatening. Severe symptoms may include difficulty in breathing, low blood pressure, chest pain, loss of consciousness, and anaphylaxis. People having allergies currently manage their allergies by avoiding any food that might contain that specific allergen. These restrictions have a major impact on the patients' quality of life and there remains no effective method for assessing the true allergen content of food. In the United States, food allergy symptoms send someone to the emergency room every three minutes. A rapid, sensitive and accurate method for determining the presence of an allergen would be of great benefit. A portable device that enables the patients to test their food and determine accurately and immediately the allergen content will be beneficial to provide for an informed decision on whether to consume or not.

Researchers have tried to develop suitable devices and methods to meet this need. There are many devices and systems disclosed in the field that detect the allergen content in a food sample, including U.S. Pat. No. 5,824,554 to McKay which teaches a dining mat formed of an absorbent material and small spots of chemical reagents applied to isolated zones on the mat, for detection of food allergens; US Patent Application Pub. No.: 2008/0182339 and U.S. Pat. No. 8,617,903 to Jung et al. which teach a method of detecting an allergen by processing samples with microfluidic chips configured for analysis of one or more allergen indicators, detecting the allergen indicators with one or more detection units, and displaying results with one or more display units; US Patent Application Pub. No.: 2010/0210033 to Scott et al. which teaches a portable device for detecting food allergens comprising a housing, a sample inlet port, a means for indicating the presence of the potential allergen in the sample, and an allergen detection chip using a tagged antibody to detect the potential allergen; U.S. Pat. No. 7,527,765 to Royds which teaches a food testing device for identifying the presence of harmful contaminants (including allergens) in a food sample, comprising a disposable sample container, a mechanical liquefier including a blade assembly, a test supply compartment with a reagent having an affinity for the harmful contaminant and capable of detecting the harmful contaminant in the liquefied food sample, and producing a visual cue upon recognition of the harmful contaminant; and U.S. Pat. No. 9,201,068 to Suni et al., which teaches bioelectronics tongues incorporated with antibodies for food allergy detection.

To implement sensitive and accurate allergen detection in a food sample, a specific detector that can rapidly recognize allergens is crucial to the testing result. Currently immunoassays are commonly used for food allergen detection in food industry and for customers who have food allergy. A specific allergen protein can be measured by an immunoassay such as ELISA, RIA (radioimmunoassay), latex agglutination assay, or western blotting. In these assays, antibodies with specificity to a target allergen are needed. Many immunoassays for detection of a specific food allergen have been disclosed in the prior art, for example, U.S. Pat. No. 8,377,696 which discloses immunoassays to detect crustacean tropomyosin; U.S. Pat. No. 8,361,460 which teaches ELISA using antibodies against soybean allergens to provide safety to patients with food allergy; U.S. Pat. No. 8,349,620 which relates to immunoassay system for detecting multiple allergens; and U.S. Pat. No. 6,441,142 which discloses an immunoassay for peanut allergen. However, most immunoassays are time consuming, require trained personnel to read the test results, are difficult to miniaturize, and are not fully standardized. Moreover, immunoassays suffer interferences, which are often attributed to matrix effects and cross-reactivities. As such immunoassay methods often cause false positive results.

In addition to antibodies specifically binding to an allergen, nucleic acid molecules such as aptamers, as well as devices and methods of using them in the detection of proteins in samples (e.g. food samples), are disclosed in several patents and patent applications, including U.S. Pat. No. 8,614,466 to Rasooly, et al., which teaches a method and system employing a physical principle called "electrical percolation," (flow of electricity through a random resistive network) for electrically detecting biomolecular binding in a semiconductor using aptamer as capture molecules; U.S. Pat. No. 8,563,298 to Lowery, Jr., et al. which teaches NMR systems and methods for the collection and detection of analytes; U.S. Pat. No. 8,232,584 to Lieber, et al. which teaches a fluorescence based nanoscale wire biosensor devices and methods for detecting analytes, wherein an aptamer may be indirectly immobilized relative to the nanoscale wire; U.S. Pat. No. 7,977,462 to Hornbeck et al.

which teaches lateral flow devices for detecting and quantitating novel tyrosine phosphorylation sites identified in carcinoma and/or leukemia using aptamers; U.S. Pat. No. 7,855,057 to Gordon, et al., which teaches methods, reagents and apparatus for detecting small quantities of protein isoforms (e.g., due to alternative splicing, or different disease protein isoforms or degradation products) in a sample, including using combinations of capture agents, wherein the capture agent may be an aptamer; U.S. Pat. No. 8,618,046 to Brunner, et al., teaches a method for treating atherosclerosis using aptamer-based anti-CETP-antibody-inducing antigens; U.S. Pat. No. 8,507,458 to Yokota, et al. teaches a system for delivering nucleic acids for suppressing target gene expression by utilizing endogenous chylomicron, wherein the nucleic acid may be an aptamer; and U.S. Pat. No. 7,850,964 to Vukicevic, et al., which teaches nucleic acid biosensors of bone morphogenetic proteins (BMPs) for diagnosis and treatment of bone and soft tissue defects and disorders (the contents of each of which are incorporated herein by reference). Other disclosures of use of aptamers in protein detection are also included in PCT Patent Publication NOs.: WO 2009/019007, WO 2009/040113, WO 2010/108657 and WO 2013/104540; which are incorporated by reference herein.

Aptamer derived molecular beacons (MBs) are mostly developed detection agents among nucleic acid agents, which are hairpin-shaped oligonucleotides that contain both fluorophore and quencher moieties and act like switches. When in a closed state, the fluorophore and quencher are brought together and the fluorescence is quenched ("turned off") by resonance energy transfer. When a conformational change opens the hairpin structure and the fluorophore and quencher are separated, the quencher can no longer quench and fluorescence is restored ("turned on"). MBs are particularly useful in detection devices and diagnostic assays requiring a probe to have high sensitivity and excellent molecular recognition specificity; they are extraordinarily target-specific, ignoring nucleic acid target sequences that differ by as little as a single nucleotide. MBs as detectors could allow for real-time monitoring, and for "detection without separation", where it is impossible or undesirable to isolate the probe-target hybrids from an excess of the unhybridized probes. The specificity provided by the MB loop-stem structure has been demonstrated to be applicable in a variety of biological environments.

Exemplary molecular beacons are reviewed in Leung, et al., 2011 (*Nucleic Acids Research*, 2012, 40(3): 941-955) and described in U.S. Pat. No. 8,188,255 to Litman et al., which teaches microRNA (miRNA) sequences associated with cancer, and their detection using aptamers and molecular beacons; U.S. Pat. No. 7,282,360 to Meyers et al., which generally discloses detection of novel protein kinase, serine/threonine phosphatase, prolyl oligopeptidase, trypsin, serine protease, and ubiquitin carboxy-terminal hydrolase family members, using aptamers or molecular beacons; and U.S. Pat. No. 6,730,491 to Kapeller-Libermann et al., which also generally discloses detection of three allegedly novel protein kinase family members, using aptamers or molecular beacons; which are incorporated by reference herein.

The inventors of the present invention have developed aptamer based signaling polynucleotides (SPNs) with high specificity to different allergen proteins. Such signaling polynucleotides (SPNs) are designed to have closed stem-loop structures similar to molecule beacons. SPNs are labeled with a fluorophore at one end of the polynucleotide and a fluorescent quencher at the other end. The closed loop structure brings the fluorophore and the quencher together and upon the binding of an allergen to the SPN, the closed loop structure is open and frees the fluorophore from the quencher. The fluorescent intensity changes before and after the allergen binding are measured and used to detect the allergen content in a sample. The commonly owned U.S. Patent Application Ser. Nos. 62/026,361, filed on Jul. 18, 2014, 62/009,958, filed on Jun. 10, 2014, 61/991,068, filed on May 9, 2014, 61/938,528, filed on Feb. 11, 2014, 61/896,399, filed on Oct. 28, 2013 and PCT Patent Application Serial NO.: PCT/US2014/062656, filed on Oct. 28, 2014, which are all entitled "allergen detection"; and U.S. Patent Application Ser. No. 62/154,200, filed Apr. 29, 2015, PCT Patent Application Serial No.: PCT/US 2016/029356 filed on Apr. 21, 2016, which are entitled "compositions and methods for allergen detection" (the contents of each of which are incorporated herein by reference in their entirety), discussed the sequences, structures and detection methods of these signaling polynucleotides.

The present inventors have designed detection systems, devices using such SPNs as detection agents to detect an allergen in a test sample. The detection systems are discussed in commonly owned U.S. Provisional Application Ser. No. 62/133,632, filed on Mar. 16, 2015 and U.S. Provisional Application Ser. No. 62/182,900, file on Jun. 22, 2015; the contents of each of which are incorporated herein by reference in their entirety.

In the present invention, the inventors further modify the nucleic acid sequences of aptamers that specifically bind a target allergen(s) to develop new SPNs and allergen detection agents. The identified aptamers that can specifically bind an allergen are modified at the 5' and 3' termini of the nucleic acid sequences and labeled with a fluorophore at one terminus of the polynucleotide. In some embodiments, fluorescence polarization (FP) changes may be measured upon the binding of a target allergen to the present signaling polynucleotide (SPN) and such FP signal will be used to indicate the presence and/or absence of an allergen in a food sample.

The inventors of the present invention further developed detection systems and devices which include a separate sampler, disposable vessels and a detector, for fast and accurate detection of an allergen(s) in a sample using aptamer-based signal polynucleotides (SPNs). Changes in fluorescence polarization of the SPNs can be measured by the present detection devices and used to indicate the allergen content in a sample. The detection device/apparatus may be miniaturized, portable and hand-held device for detecting food allergen in a sample.

SUMMARY OF THE INVENTION

The present invention provides systems, devices, detection vessels and methods for use in allergen detection in various types of samples, in particular, food samples. Detection agents such as nucleic acid aptamers, and signaling polynucleotides (SPNs) derived from aptamers, specific to allergen proteins, are provided as well.

One aspect of the present invention is an allergen detection system for detecting the presence and/or absence of one or more allergens in a sample, the system comprising: (a) at least one sampler for collecting a test sample; (b) at least one detection vessel for receiving and processing the test sample, and analyzing the interaction between an allergen(s) in the test sample and the detection agents; and (c) a detection device for detecting the allergen (s) in the test sample.

In some embodiments, the sampler may be provided with a means for weighing which ensures a certain amount of the test sample being picked up. In some aspects, the sampler is a food pickup corer which is configured for measuring a sized portion of a food sample and/or pre-processing the collected food sample. The food corer may have a distal portion provided with a corer top cap at the distal end and a proximal portion provided with a collecting tube, a grip for handling the corer which is connected to the collecting tube, and a plunger inside the collecting tube which has a distal end connected to the top cap and a proximal plunger tip which may protrude from the collecting tube for picking up a food sample. As a non-limiting example, the food pickup corer may further include a spring to indicate the amount of the food sample being picked up.

In some embodiments, the detection vessel is disposable, suitable for one particular allergen. The detection vessel comprises at least one reaction chamber where the detection reaction occurs. In some embodiments, the detection vessel is a disposable test cup or cup-like container. The disposable test cup or cup-like container may be designed as an analytical module in which a test sample is processed and an allergen of interest in the test sample is detected through the interaction with detection agents. In some aspects, the test cup or cup-like container comprises a cup body and a cup lid. The cup lid has several ports for holding a sampler (e.g., the food pickup corer), a homogenizer assembly and a means for the flow of the processed test sample solution. The cup body may comprise one container, or may be divided into two separate but connected parts.

Reaction chambers may be configured at various places within the test cup, including but not limited to the cup lid assembly, or the bottom and/or the side of the cup body, or one part of the divided cup body. In some embodiments, the cup lid assembly may comprise one or more reaction chambers. In some aspects, the reaction chambers may be configured to contain a volume of about 10 µL to about 200 µL.

The detection device of the present invention comprises (a) an external housing that provides support for the components of the detection device; (b) a first part that can be opened for inserting a detection vessel (e.g., a disposable test cup or cup-like container) when implementing an allergen detection testing; (c) means integrated for operating an allergen detection testing, and (d) an optional tether for carrying the detection device and an optional plug for power supply.

In accordance with the present invention, the first part of the detection device may be a drawer assembly which can be pulled out from and slide back into the housing. The drawer assembly may be configured to have a well/port for holding a disposable detection vessel (e.g., a test cup or cup-like container) when implementing an allergen detection testing. In other aspects, the first part may be a door that can be lifted and open the well/port for insertion of a detection vessel (e.g., a test cup or cup-like container).

In accordance with the present invention, the components of the detection device that are integrated for operating an allergen detection testing include (i) means for processing a test sample comprising a homogenizer; (ii) means for driving and controlling the homogenization; (iii) means for driving and controlling the flow of the processed sample during the process of an allergen detection testing; (iv) an optical subsystem for detecting a reaction signal; and (v) means for visualizing a detection result including means of converting and digitizing the detection signal and a display window; and (vi) a power supply.

In some embodiments, the homogenizer is optimized for low power and high speed homogenization of the test sample. In one aspect, the homogenizer comprises a rotor having blades at the proximal end thereof, inside a stator which has one or more slots on the axis of the proximal end thereof. The homogenizer rotor and stator are connected to a motor which can drive and control the movement of the rotor and stator for homogenizing the test sample.

In some embodiments, means for driving the liquid flow and controlling the flow rate may be a pump or an external pressure. The pump may be a gas or air pump, or an equivalent thereof. The processed sample solution is flowed into the reaction chambers configured in the detection vessel (e.g., the test cup or cup-like container).

In some embodiments, the optical subsystem may be an optical assemble that can detect a fluorescent signal generated during an allergen detection testing. In some embodiments, the fluorescent signal is fluorescence polarization (FP) changes. The optical subsystem may comprise a light source, filters and polarizers that control the plane polarization of light; and a photo detector.

In some embodiments, a printed circuit board (PCB) is connected directly or indirectly to the reaction chambers and the optical subsystem for displaying the testing readout. The result may be displayed as numbers, icons, colors and/or letters, or other equivalents.

In some embodiments, the power supply of the present detection device may be a rechargeable or replaceable battery. In other embodiments, the detection device may include a docking station and/or USB charger. In further embodiments, the detection device may be configured to be directly connected to a power supply such as AC/DC converter.

In some embodiments, the detection system may comprise a user interface that may be accessed and controlled by a software application. The software may be run by a software application on a personal device such as a smartphone, a tablet computer, a personal computer, a laptop computer, a smartwatch and/or other devices. In some cases, the software may be run by an internet browser. In some embodiments, the software may be connected to a remote and localized server referred to as the cloud.

Another aspect of the present invention provides aptamers, SPNs which can be used as detection agents to determine the presence and/or absence of an allergen in a sample. In some embodiments, the detection agents may be SPNs derived from aptamers. The SPNs of the present invention may include aptamers that have nucleic acid sequences specifically binding a target allergen, a modified nucleic acid sequence at either 5' terminus or 3' terminus of the polynucleotide, which is designed to maintain a single open structure, and a fluorophore label probed at one terminus of the polynucleotide.

In some embodiments, SPNs of the present invention may comprise nucleic acid sequences as shown in Table 1 and Table 2.

In some embodiments, the SPN of the present invention comprises a core nucleic acid sequence selected from polynucleotide sequences of SEQ ID NOs.: 2, 6, 13, 27, 35, 44, 57, 61, 65, 71, 78, 84, 98, 110, 119, 126, 132, 137, 150, 158, 168, 178, 190, 194, 204, 215, 220, 228, 237, 247, 251, 255, 259, 263, 267, 271, 279, 296, 308, 316, 332, 334, 336, 338, 340, and 341-353.

In other embodiments, the SPN of the present invention comprises a nucleic acid sequence selected from polynucleotide sequences of SEQ ID NOs.: 3, 4, 7-11, 14-25, 28-33, 36-42, 45-55, 58, 59, 62, 63, 66-69, 72-76, 79-82, 85-96, 99-108, 111-117, 120-124, 127-130, 133-135, 138-148, 151-156, 159-166, 169-176, 179-188, 191-192, 195-202, 205-213, 216-218, 221-226, 229-235, 238-245, 248, 249, 252, 253, 256, 257, 260, 261, 264, 265, 268, 269, 272-277, 280-294, 297-306, 309-314, and 317-330.

In some embodiments, SPNs of the present invention are labeled with a fluorescent molecule at either the 5' terminus or the 3' terminus, in which changes in fluorescence polarization (FP) upon a target allergen binding may be detected. In one aspect, the fluorescent molecule is Texas red.

Another aspect of the present invention relates to an allergen detection testing assay for detection of the allergen content in a sample comprising the steps of (a) obtaining a sample suspected of containing an allergen of interest, (b) processing the sample of (a) with an extraction buffer, (c) contacting the processed sample with a detection agent, (d) treating the contacted sample with an excitation means and measuring the fluorescence polarization, and (e) visualizing the interaction of the detection agent and the allergen.

In some embodiments, the present detection method may comprise the steps of (a) obtaining a test sample suspected of containing an allergen(s) of interest using a sampler, (b) processing and digesting the obtained sample in an extraction buffer, using a homogenization assembly, (c) mixing the processed sample with detection agents specific to the allergen(s) of interest, (d) treating the mixture from step (c) with a fluorescent excitation means and detecting a fluorescent signal emitted from the detection agents, and (e) digitizing the detected signals and visualizing the interaction between the detection agents and the allergen(s). The detection agents may be aptamer based SPNs that can specifically bind to specific allergens. The SPNs are probed with a fluorescent molecule. The extraction buffer may be optimized for extracting allergen proteins efficiently. The fluorescent signal, in some aspects, may be fluorescence polarization changes.

Other features and embodiments of the present invention will be apparent from the description that follows.

BRIEF DESCRIPTION OF THE DRAWINGS

The foregoing and other objects, features and advantages will be apparent from the following description of particular embodiments of the invention, as illustrated with the reference to the accompanying drawings. The accompany figures are merely for purpose of illustrating exemplary embodiments of the present invention and are not intended to limit the scope of the invention to the exemplary embodiments. Similar reference numerals among the drawings are employed to denote the identical or similar elements presented in different drawings.

FIG. 3a is an assembled disposable test cup 300 having a cup lid assembly 210 and a cup body 220; the disposable test cup 300 is an example of the detection vessel. FIG. 3b through FIG. 3g show an exploded view of the disposable test cup 300. FIG. 3b illustrates the label/final fluid seal 211. FIG. 3c illustrates the optical window/fluid seal 216. FIG. 3d illustrates the homogenizer rotor 240. FIG. 3e illustrates the cup lid assembly 210. FIG. 3f illustrates the flow tube 221, and the flow tube cap and filter assembly 224. FIG. 3g illustrates the cup body 220.

FIG. 7a is a top view of the cup body 220 and FIGS. 7b-7d show the side view of the cup body 220.

FIG. 8a illustrates that an alternative filter membrane 226 may be provided at the bottom of the cup body 220 with certain distance from the cup base 222. FIG. 8b illustrates another alternative in which the filter membrane 226 is aligned in parallel with the cup wall and a small chamber 227 may be connected to the cup body 220 for receiving the filtered sample solution.

FIG. 9a illustrates a single filter membrane 226 provided; FIG. 9b illustrates double filter membranes 226 provided.

FIG. 10a illustrates the housing 10. FIG. 10b illustrates the drawer assembly 20.

FIG. 12a illustrates the individual components of the detection device 100. FIG. 12b illustrates the components of the detection device 100 configured inside the external housing 10 (not shown).

FIG. 15a is a bottom view of the gear train/drive platen 530 and FIG. 15b is a top view of the gear train/drive platen 530.

DETAILED DESCRIPTION OF THE INVENTION

Figure 1A:
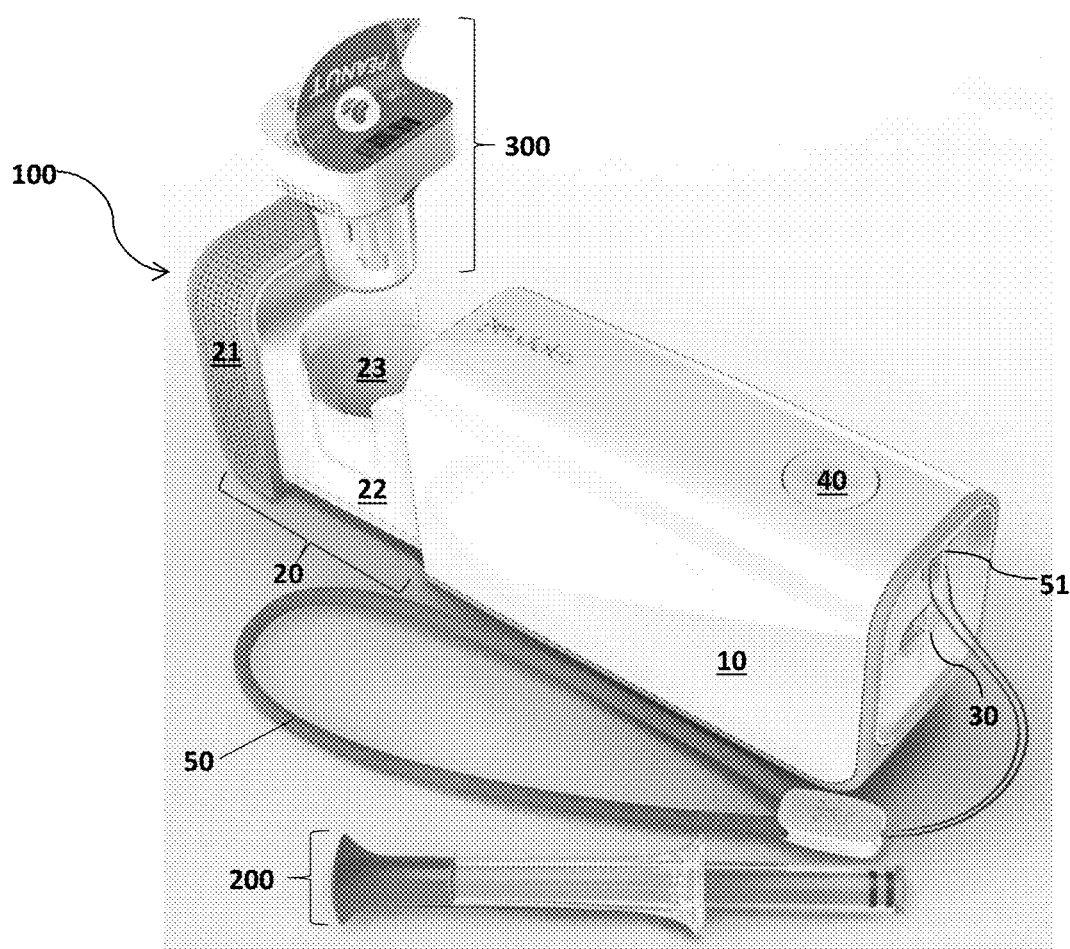
FIG. 1a illustrates an embodiment of a detection system of the present invention comprising a detection device 100, a separate food corer 200 as an example of the sampler, a disposable test cup 300 as an example of the detection vessel, and an optional tether 50.

The details of one or more embodiments of the invention are set forth in the accompanying description below. Although any materials and methods similar or equivalent to those described herein can be used in the practice or testing of the present invention, the preferred materials and methods are now described. Other features, objects and advantages of the invention will be apparent from the description. In the description, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present description will control.

The use of analytical devices to ensure food safety has not yet advanced to the point of fulfilling its promise. In particular, portable devices based on simple, yet accurate, sensitive and rapid detection schemes have not yet been developed for detection of the wide variety of known allergens. One of the more recent reviews of aptamer-based analysis in context of food safety control indicated that while a great variety of commercial analytical tools have been developed for allergen detection, most of them rely on immunoassays. It was further indicated that the selection of aptamers for this group of ingredients is emerging (Amaya-Gonzalez et al., *Sensors* 2013, 13, 16292-16311, the contents of which are incorporated herein by reference in its entirety).

The present invention provides detection systems, devices and agents that can specifically detect low concentrations of allergens in a variety of food samples. The present detection systems, devices and methods use aptamer based signal polynucleotides (SPNs) as detection agents. As used herein, the term "allergen" means a compound, substance or composition that causes, elicits or triggers an immune reaction in a subject. Allergens may also be referred to as antigens. A fluorescent signal such as fluorescence polarization (FP) is measured to indicate the allergen content in the sample.

In one embodiment, the detection system and/or device of the present invention is a miniaturized, portable and hand-held product, which is intended to have a compact size which enhances its portability and discreet operation. A user can carry the detection system and device of the present invention and implement a rapid and real-time testing of the presence and/or absence of one or more allergens in a food sample, prior to consuming the food. The detection system and device, in accordance with the present invention, can be used by a user at any location, such as at home or in a restaurant.

In one embodiment of the present invention, the detection system and/or device displays the testing result as a standard readout and the detection can be implemented by any user following the simple instructions on how to operate the detection system and device.

In some embodiments, the detection system and device is designed for simple, fast, and sensitive one-step execution. An allergen detection testing may be completed in less than 5 minutes.

In accordance with the present invention, the detection system and device may involve a mechatronic design process integrating electrical engineering, mechanical engineering and computing engineering to implement and control the process of an allergen detection testing, including rechargeable or replaceable batteries, motor drivers for processing the test sample, pumps or actuators for controlling the flow of the processed sample solution to different components of the detection device, and connectors that couple and integrate different components for a fast allergen testing. The detection system and device of the present invention also includes an optical system which is configured for detection of the presence and concentration of an allergen of interest in a test sample and convert detection signals into readable signals; and a mechanical part which provides support for other parts of the detection device and integrates different parts together as a functional product.

In some embodiments, the detection system and/or device is designed such that the disposable vessels (e.g., a disposable test cup or cup-like container), unique to one or more specific allergens, are designed for receiving and processing a test sample, and assaying the detection test, in which all the solutions are packed. Therefore, all the solutions may be confined in the disposable cup or cup-like container. As a non-limiting example, a disposable gluten test cup may be used to detect gluten in any food sample by a user and discarded after the testing. Accordingly, the detection device may be a dry device and the solutions are packed as disposables. Such a design will avoid cross-contaminations from different allergen tests.

In some embodiments, a separate sampler that can measure and size a test sample is provided. In one aspect, the sampler can further pre-process the test sample, such as cutting the sample into small pieces, blending, abrading and/or grinding, to make the sample suitable for allergen protein extraction.

In some embodiments, detection agents of the present invention comprise SPNs that specifically recognize a target allergen and generate changes in fluorescence polarization as detection signals. The SPNs may comprise aptamer sequences that are identified through a selection process with high specificity and affinity to a target allergen.

Detection Systems

In general, an allergen detection system of the present invention comprises at least one sampler for collecting a test sample, at least one disposable detection vessel for implementing an allergen detection testing, and a detection device for detecting and visualizing the result of the detection testing.

Figure 1B:
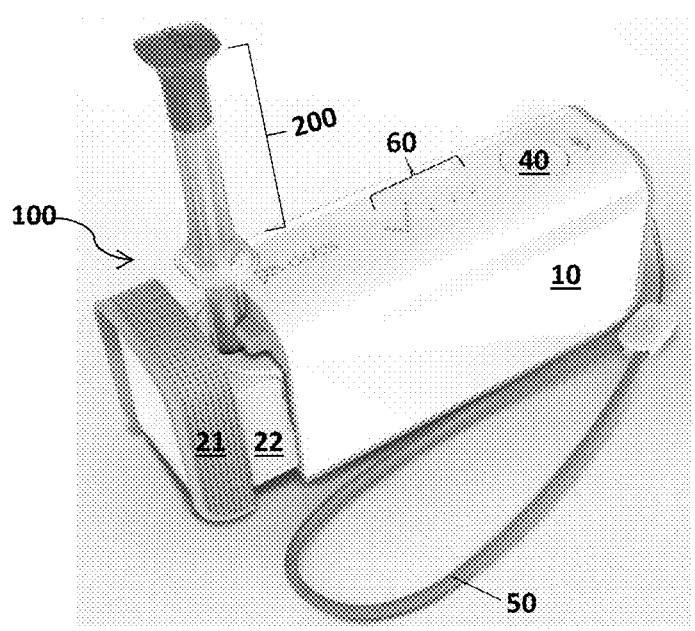
FIG. 1b illustrates an assembly of the detection system shown in FIG. 1a during the process of implementing an allergen detection testing.

As shown in FIG. 1*a* and FIG. 1*b*, an embodiment of the detection system of the present invention comprises a detection device 100 configured for processing a test sample, implementing an allergen detection testing, and detecting the result of the detection testing, a separate food corer 200 as an example of the sampler, and a disposable test cup 300 as an example of the detection vessel. Optionally, a tether 50 may be included for carrying the detection device 100. As used herein, the disposable test cup 300 may be a cup or a cup-like container. The detection device 100 includes an external housing 10 that provides support to the components (as shown in FIGS. 12*a*-12*b*, 13*a*, 14, 15*a*-15*b*, and 16-18) of the detection device 100, and a drawer assembly 20 which includes a drawer frame 22 and a drawer well/port 23 for holding a disposable test cup 300. On the front of the drawer frame 22, a drawer grip 21 may be added for a user to operate the drawer assembly in and out of the housing 10. The external housing 10 also provides surface space for buttons that a user can operate the device. An execution/action button 40 that allows a user to execute an allergen detection testing and an on/off slider 30 that allows a user to turn on and/or off the detection device 100 may be included. A display window 60 (shown in FIG. 1*b*) and an optional plug (not shown) for external power charge may also be included. Optionally, a lanyard 51 for the attachment of the optional tether 50 may be included on the outer surface of the external housing 10.

During the process of implementing an allergen detection testing, the food corer 200 with a sample being picked up is inserted into the disposable test cup 300 and the disposable test cup 300 is inserted into the drawer well/port 23 of the detection device 100 for detection, as shown in FIG. 1*b*.

The assembly of the detection system shown in FIG. 1*a* and FIG. 1*b* is not intended to be limiting. Other ways to assemble the disposable test cup 300, the food corer 200 and the detection device 100 are within the scope of the present invention. One example includes that the detection device 100 may be configured to grab the disposable test cup 300 from the side or the top of the test cup 300, such as an alternative assembly shown in FIG. 11. In another aspect, the detection device 100 may be configured to have a door that can be lifted for connecting the detection device 100 with the disposable test cup 300 and the food corer 200.

Detection System—Sampler

Collecting a right-sized sample is an important step for implementing allergen detection testing. In some embodiments of the present invention, a separate sampler for picking up and collecting test samples (e.g. food samples) is provided. In one aspect, a coring-packer-plunger concept for picking up and collecting a food sample is disclosed herein. Such mechanism may measure and collect one or several sized portions of the test sample and provide pre-processing steps such as cutting, grinding, abrading and/or blending, for facilitating the homogenization and extraction or release of allergen proteins from the test sample. According to the present invention, a separate food corer 200 is designed for picking up different types of food samples and collecting a sized portion of a test sample.

Figure 2A:
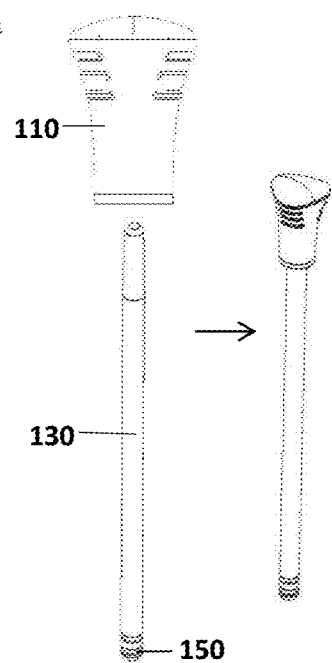
FIG. 2a and FIG. 2b illustrate the parts of the food corer 200.
Figure 2B:
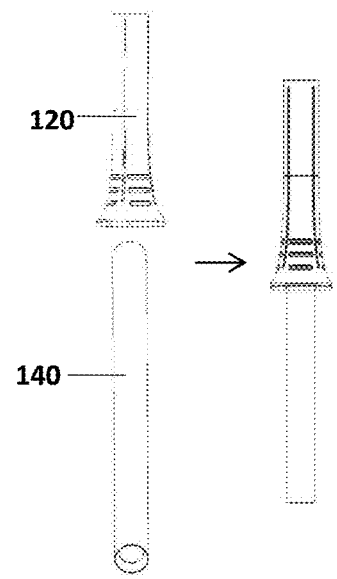
Figure 2C:
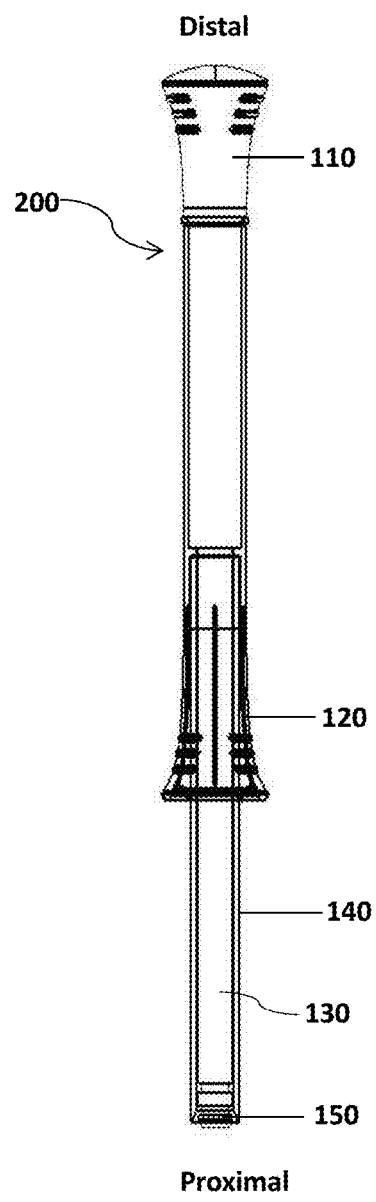
FIG. 2c is an assembled food corer 200 as an example of the sampler.

As shown in FIG. 2*a* to FIG. 2*c*, the food corer 200 has a distal portion provided with a corer top cap 110 (FIG. 2*a*) at the distal end, a proximal portion provided with a sample collecting tube 140 (FIG. 2*b*), a grip 120 (FIG. 2*b*) for handling the food corer 200 which is connected to the collecting tube 140, and a plunger 130 (FIG. 2*a*) inside the sample collecting tube 140 which has a distal end connected to the corer top cap 110 and a proximal plunger tip 150 which may protrude from the sample collecting tube 140 for directly contacting a test sample and picking up a sized portion of the test sample (FIGS. 2*a*-2*c*). The shape of the proximal plunger tip 150 may be configured for pre-processing the collected sample. The proximal end of the food corer 200 may be further featured with a snap or the like, which can reduce the incidence of spillage of the collected test sample when being transferred from the food corer 200 to the test cup 300.

The parts of the food corer 200 may be designed as any shape for easy handling such as triangular, square, octagonal, circular, oval, and the like.

In some embodiments, the size of the food corer 200 is designed to fit in the corer port 213 on the top of the cup lid assembly 210 (FIG. 3*a*). In other embodiments, the food corer 200 may be further provided with a means for weighing a test sample being picked up, such as a spring, a scale or the equivalent thereof. As a non-limiting example, the food corer 200 may be provided with a weigh tension module.

Alternatively, other sample pickups may be designed for picking up and collecting different types of test samples. Other designs for sample pickups may include bisecting corer, syringe corer with a blade (e.g., X-Acto blade) across the diameter of the syringe; or alternatively, a syringe corer which is placed directly on top of X-acto blade. The blade may help to divide the cored sample into two or more small pieces, making them easier to be processed and homogenized.

The food corer 200 and the plunger 130 may be made of plastic materials, including but not limited to, polycarbonate (PC), polystyrene (PS), polymethylmethacrylate (PMMA), polyester (PET), polypropylene (PP), high density polyethylene (HDPE), polyvinylchloride (PVC), thermoplastic elastomer (TPE), thermoplastic urethane (TPU), acetal (POM), polytetrafluoroethylene (PTFE), or any polymer, and combinations thereof. The plunger 130 may be sealed to the corer using any materials that can provide resistance to heat, liquids and UV light, etc., for example, Buna-n, Fluoroelastomer, Silicone, Ethylene propylene diene monomer (EPDM) elastomers, Neoprene, Polyurethane (PU), and PTFE.

Detection System—Disposable Detection Vessel

In accordance with the present invention, at least one separate detection vessel is provided as part of the detection system. The detection vessel is disposable and used for a particular allergen(s). A disposable detection vessel is designed for processing a test sample, extracting allergen proteins from the test sample, storing reaction solutions and detection agents, contacting/mixing the test samples with the detection agents; and/or providing an optical window for fluorescent signal measurement. A disposable detection vessel of the present invention comprises one or more reaction chambers wherein the analytical detection assays occur. That is, a disposable detection vessel is intended to be used only once for an allergen testing in a sample and therefore may be made of low cost plastic materials, for example, transparent high density polyethylene (HDPE), polycarbonate (PC), polymethylmethacrylate (PMMA), polypropylene (PP), polyvinylchloride (PVC), polystyrene (PS), polyester (PET), or other thermoplastics. Accordingly, a disposable detection vessel may be designed for any particular allergen of interest. In some embodiments, these disposable vessels may be designed for one particular allergen only, which may avoid cross contamination with other allergen reactions. In other embodiments, these disposable vessels may be designed for detecting two or more different allergens in a test sample in parallel. In some aspects, the disposable vessels may be designed for detecting two, three, four, five, six, seven, or eight different allergens in parallel.

Figure 6A:
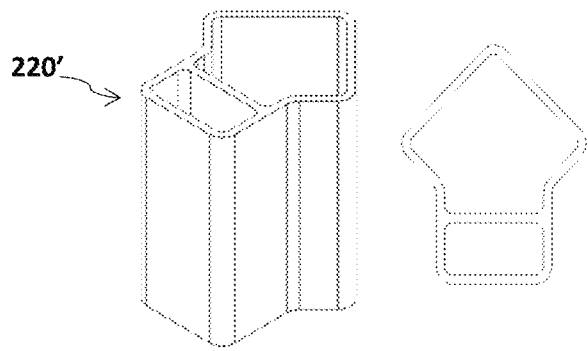
FIG. 6a and FIG. 6b depict two different shapes of the cup body 220' (FIG. 6a, the side view on the left panel and the top view on the right panel) and 220" (FIG. 6b, the side view on the left panel and the top view on the right panel) which is divided into two separate but connected parts.
Figure 6B:
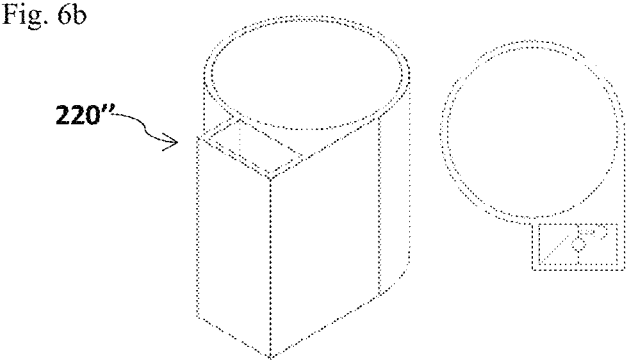
Figure 6C:
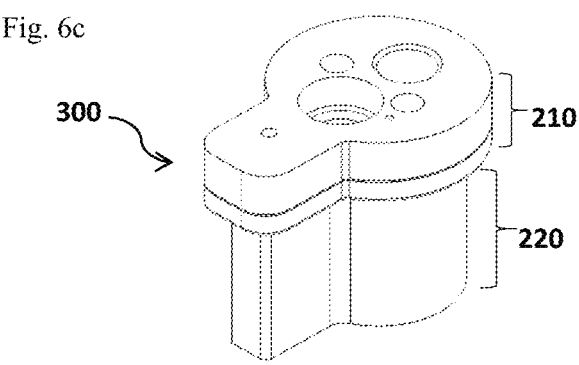
FIG. 6c and FIG. 6d illustrate an assembled test cup 300 with a divided cup body 220 and the exploded view of the cup lid assembly 210 in this alternative design, respectively.
Figure 6D:
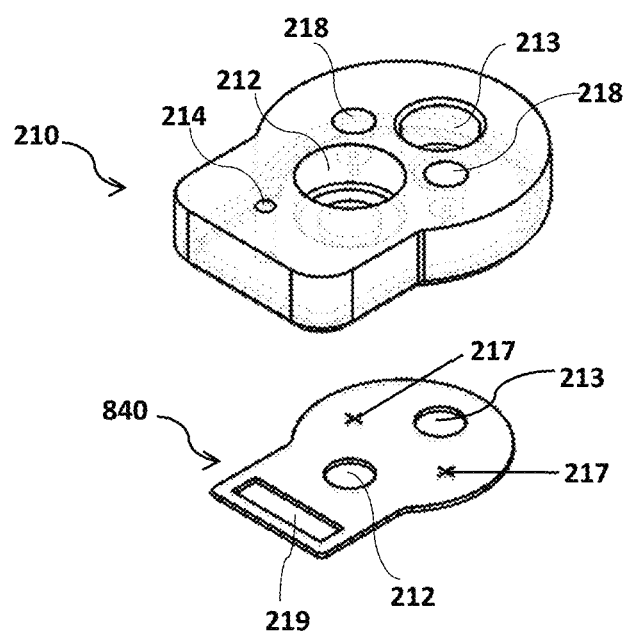

As shown in FIG. 3*a*, the disposable detection vessel may be a disposable test cup 300 or a cup-like container. According to one embodiment of the test cup, as shown in FIG. 3*a*, the assembled disposable test cup 300 includes a cup lid assembly 210 and a cup body 220 for receiving a test sample, processing the test sample and contacting/mixing the processed sample with the detection agents (e.g., signal polynucleotides (SPNs)). FIG. 3*b* through FIG. 3*g* show an exploded view of the disposable test cup 300. FIG. 3*b* illustrates the label/final fluid seal 211, which can inform a user which allergen(s) the test cup is intended to detect. FIG. 3*c* illustrates the optical window/fluid seal 216 with the test cup port 214. The optical window/fluid seal 216 can be aligned with the optical subsystem 520 (FIG. 16 and FIG. 17) of the detection device 100 to allow light through during signal detection. FIG. 3*d* illustrates the homogenizer rotor 240. The homogenizer rotor 240 can be inserted into the test cup 300 through the port 212. FIG. 3e illustrates the cup lid assembly 210. FIG. 3f illustrates the flow tube cap and filter assembly 224. FIG. 3g illustrates the cup body 220. The cup lid assembly 210 has multiple functions in addition to the closure of the disposable test cup 300 (FIG. 3a). As shown in FIG. 3a, FIG. 3e and FIG. 6d, the cup lid assembly 210 has three ports: a rotor port 212 for housing a homogenizer rotor 240 and a homogenizer stator 230; a food corer port 213 for receiving a food corer 200 and receiving a test sample, and a test cup port 214 for connecting the disposable test cup 300 to a flow controlling component (e.g., vacuum or pressure ducts); and a means 218 (as shown in FIG. 6d) for aligning and stabilizing the cup lid assembly 210 when the cup lid assembly 210 is assembled with the cup body 220 to form a test cup 300.

The test cup 300 includes one or more reaction chambers 223. All the analytical reactions occur in the reaction chambers 223. The reaction chambers 223 are places where a processed sample is mixed with the detection agents pre-stored within the test cup 300 and a detectable signal (e.g., a fluorescent signal) is generated. In some aspects, a reaction chamber 223 may be designed as a control chamber for measuring the total protein content in a test sample depending on the detection assay implemented. In other aspects, a reaction chamber 223 may be designed suitable for measuring other background signals depending on the types of assays and detection signals measured. Alternatively, an additional control chamber 225 may be added to any part of the test cup, for example to the cup lid assembly 210 as shown in FIG. 4b. The multiple reaction chambers 223 may be configured at various places inside the test cup 300, including but not limited to the cup lid assembly 210 (FIG. 3a, FIG. 3e and FIGS. 4a-4b), the side or the bottom of the cup body 220 (FIG. 5a and FIG. 5b), a separate part of the divided cup body 220 (FIGS. 7a-7d). The multiple reaction chambers 223 can be in different shapes and are orientated with each other differently (FIGS. 3a, 4b, 5a and 7a-7d).

In one embodiment of the detection system, the reaction chambers 223 are included in the cup lid assembly 210 (FIGS. 3a-3g, and FIGS. 4a-4b). In this embodiment, the cup lid assembly 210 further comprises a fluid channel 215 for bringing the extracted sample solution to the two reaction chambers 223 (FIGS. 3a-3g). Through the food corer port 213, the test sample collected by a food corer 200 can be plunged into the cup body 220 for homogenization and extraction of allergen proteins. Through the test cup port 214, which is used to link the disposable test cup 300 to the flow control component of the detection device 100, the extracted allergen proteins from the test sample may be pumped or pressed out of the cup body 220 and flow through the flow tube 221 into the fluid channel 215 and then to the two reaction chambers 223. An optical window/fluid seal 216 provides liquid sealing and optical access to the two reaction chambers 223. A label/final fluid seal 211 provides final liquid seal and identification for the cup assembly (e.g. a designation of gluten that indicates the disposable test cup 300 is used for detecting the gluten allergen). In one aspect, a flow tube cap and filter assembly 224 is provided to prevent humidification of the solid reagents stored in the two reaction chambers 223 and filtration of the large particles from the homogenized protein and/or buffer solution.

In one preferable embodiment as shown in FIG. 3a and FIG. 4b, two independent reaction chambers 223 are provided in the cup lid assembly 210, including one analytical chamber for the allergen detection reaction in which the detection agents specific to an allergen of interest are provided and wherein the allergen detection reaction occurs, and one control chamber for measurement of background signals in which a chemical solution, if needed, for measuring the background signals in the test sample are provided. The two reaction chambers 223 on the top of the cup lid assembly 210 are connected to the fluid channel 215 through which the flow of the extracted protein solution is pumped or pressed into the two reaction chambers 223. The detection agents specific to an allergen and the chemical solution for measurement of background signals in the reaction chambers 223 may be dry powder and can be mixed with the processed sample solution that flows from the flow tube 221 and the fluid channel 215 to the reaction chambers 223. Alternatively, the detection agents and the chemical solution may be resuspended in an appropriate buffer. The two reaction chambers 223 may be configured to receive the processed sample solution in parallel or sequentially, but preferably in parallel. The fluorescent signals (e.g., fluorescent intensity and fluorescent polarization) from the allergen analytical chamber and the background signals from the control chamber will be detected by an optical subsystem (e.g., the optical subsystem 520 shown in FIG. 16 and FIG. 17) of the detection device 100. In some embodiments, more than one allergen analytical chambers may be configured on the top of the cup lid assembly 210, such as two, or three, or four, or five, or six, or seven, or eight, or more allergen analytical chambers, in each of which the detection agents specific to a different allergen may be provided. Such multiplex design will allow a user to detect several allergens in a test sample at the same time, in condition that the user is allergic to multiple allergens. In some aspects, these reaction chambers are designed for parallel detection reactions. That is to say, all reactions may occur in parallel.

As noted above and shown in FIG. 4b, it is within the scope of the present invention that more than two reaction chambers 223 may be designed on the top of the cup lid assembly 210. In certain embodiments, three or more chambers may be designed on the top of the cup lid assembly 210. In one particular embodiment, three chambers are provided including two reaction chambers 223 and one additional control chamber 225 which may be used to measure non-specific background signals from the allergen detection assay. FIG. 4b illustrates an exemplary configuration of the three chambers, two reaction chambers 223 and one control chamber 225, on the top of the cup lid assembly 210. It is understandable to one of skill in the art that this particular configuration is illustrated to present the concept thus is not limiting. The position of each chamber may vary dependent on the design of the cup lid assembly 210 and the number indications are not limiting either. Each chamber may be designated as an analytic chamber for detecting signals from the interaction between an detection agent and the allergen of interested in the test sample, or a chamber for measuring total proteins isolated from the test sample, or a control chamber for measuring non-specific background signals from the detection assay. The three chambers may be connected to the fluid channel 215, receiving a portion of the processed test sample solution through the flow tube 221. To avoid the interference among different chambers which may cause misleading detection results, one or more air vent 217 (FIG. 4b) may be added within the fluid channel 215 to prevent the liquid flow between reaction chambers 223.

Figure 4B:
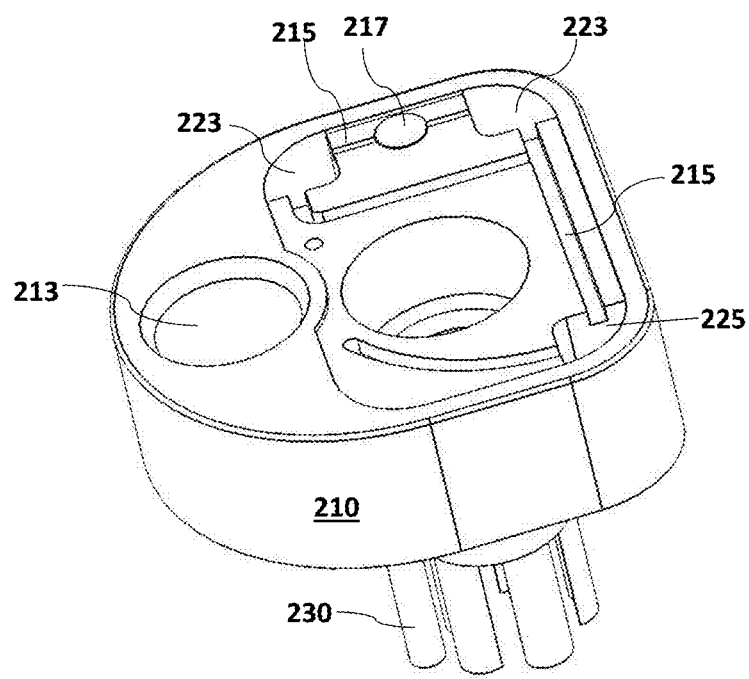
FIG. 4b illustrates an alternative configuration of reaction chambers on the top of the lid assembly 210.
Figure 5A:
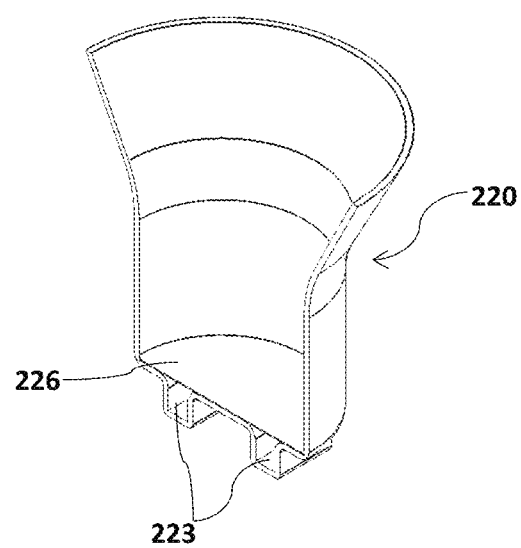
FIG. 5a is a side view of an alternative embodiment of reaction chambers 223 which are located at the bottom of the cup body 220.
Figure 5B:
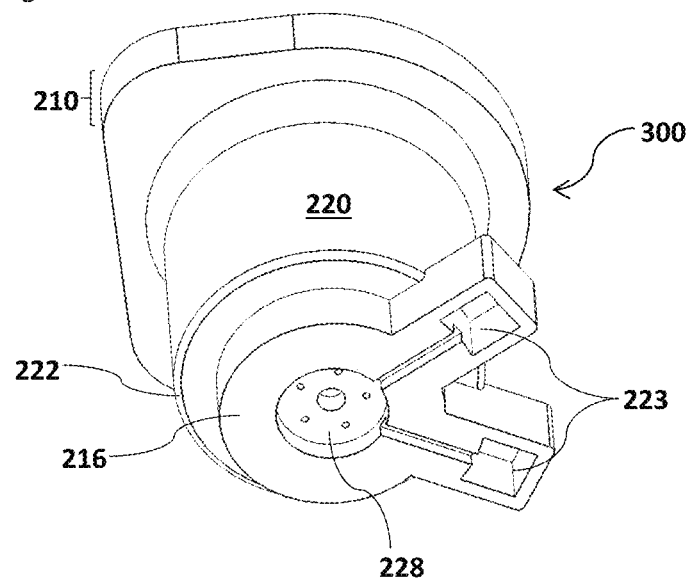
FIG. 5b is a view from the bottom of the test cup 300, demonstrating a valve 228 which is provided to control the fluid flow to the reaction chambers 223 and/or the additional control chamber 225 (not shown).

It is within the scope of the present invention that one or more reaction chambers 223 and the optional control chamber 225 are not necessarily being designed on the top of the cup lid assembly 210. The one or more reaction chambers 223 and the optional control chamber 225 may be located at any parts of the test cup or the cup like container 300. In addition to the configurations illustrated in FIG. 3a and FIG. 4b, alternative embodiments may also be provided. As illustrated in FIGS. 5a and 5b, the one or more reaction chambers 223, and/or the optional control chamber 225 (not shown in FIG. 5a and FIG. 5b) may be located at the bottom of the cup body 220, directly receiving the test sample solution after being filtered by the filter membrane 226 (FIG. 5a). FIG. 5b further illustrates a view from the bottom of the test cup 300. According to this particular embodiment, the optical window/fluid seal 216 is used to seal the reaction chambers 223 and/or the optional control chamber 225 to provide a window to read the detection signals. Additionally a valve 228 may be provided, allowing control of the flow of the processed sample solution. The valve 228 may be an umbrella valve, a duckbill valve, other one way valves, a frangible seal or the like. For example, internal frangible seals may be used to enable the controlled release of the sample solution.

Alternatively, the cup body 220 of a disposable test cup 300 may be divided into two separate parts (FIGS. 6a-6d and FIGS. 7a-7d), one part configured for receiving and processing the test sample collected by the food corer 200 or other types of samplers and extracting allergen proteins from the test sample, and the other configured for including one or more reaction chambers 223 and/or the optional control chamber 225. The shapes of each part of the divided cup body 220 may vary. As non-limiting examples, FIG. 6a illustrates an alternative cup body design 220' with a triangle shaped part for processing the test sample and a rectangle part for holding the reaction chambers. FIG. 6b illustrates another alternative cup body design 220" with a circular part for processing the test sample and a rectangle part for holding the reaction chambers.

Figure 7A:
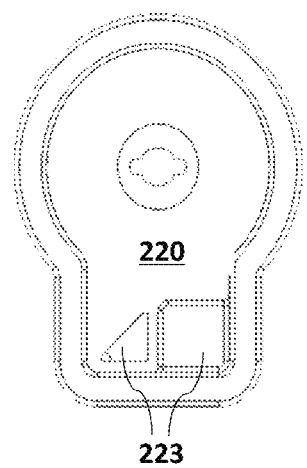
FIG. 7a to FIG. 7d depict other examples of the shapes and layouts of reaction chambers 223.
Figure 7B:
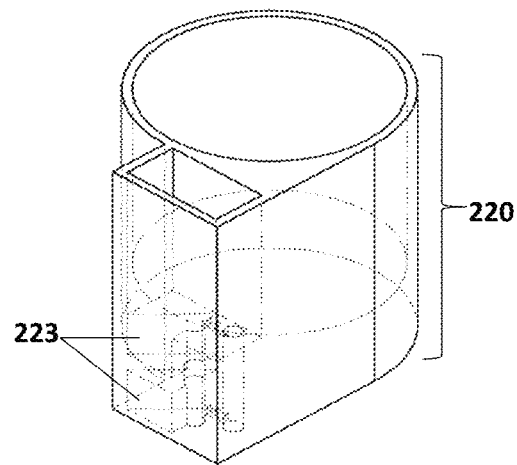
Figure 7C:
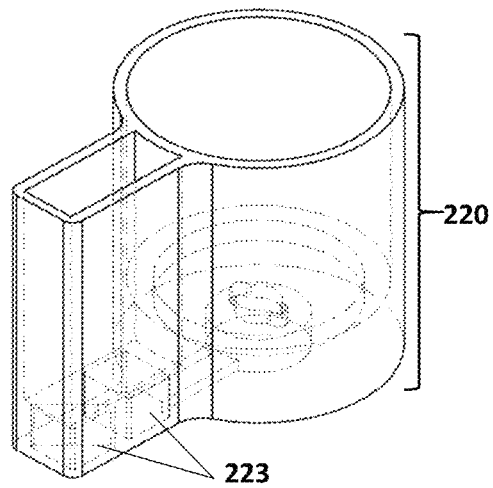
Figure 7D:
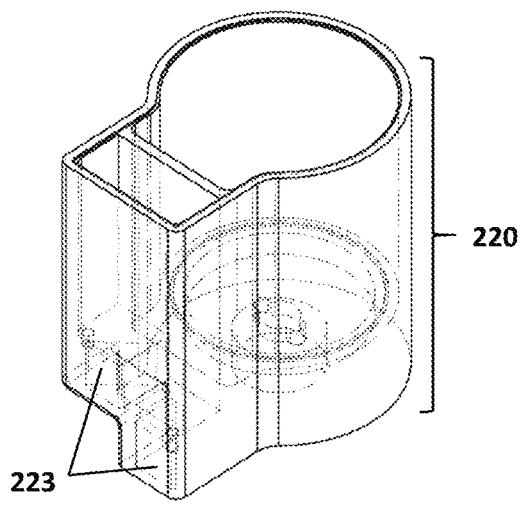

As noted above and shown in FIGS. 7a to 7d, the reaction chambers 223 and the optional control chamber 225 may be configured at one of the two separate parts of the cup body 220. FIGS. 7a to 7d illustrate some examples of arrangements of the reaction chambers 223 and/or the optional control chamber 225 inside the separate part of the cup body 220. The reaction chambers 223 (and the optional control chamber 225) can be configured into any layout arrangement, for example, side-by-side (FIG. 7a, viewed from the top of the cup), stacked orientation as shown in FIG. 7b, front-and-back (FIG. 7c), or in a diagonal orientation (FIG. 7d).

In this aspect, the cup lid assembly 210 of the test cup 300 may be shaped to match the shape of the cup body 220. As shown in FIGS. 6c and 6d, the cup lid assembly 210 of an assembled test cup 300 with two separate parts of the cup body 220 comprises three ports 212, 213 and 214. A means 218 for aligning and stabilizing the assembly may be included too. In the embodiment that the reaction chambers are included in one part of the divided cup body, a vacuum gasket 840 comprising air vent 217 and vacuum port seal 219 may be inserted underneath of the cup lid assembly 210 as shown in an exploded view in FIG. 6d.

In some embodiments, the reaction chambers 223 and the optional control chamber 225 can be in any shapes, including but not limited to circle, triangle, rectangle and wedge.

To form an operable detection vessel, i.e. a test cup 300, the cup lid assembly 210 and the cup body 220 are assembled together. Means for aligning and stabilizing the assembly (e.g., features 218 as illustrated in FIG. 6d) may be included. A label/final fluid seal 211 is attached to the assembled test cup, for example on the top of the cup lid assembly 210. The label indicates the target allergen to be tested using the test cup 300. In one example, when the reaction chambers 223 included in the cup lid assembly 210, the label/final fluid seal 211 is attached to the top of the optical window/fluid seal 216 as shown in FIG. 3c. In another example, when the reaction chambers 223 are positioned at the bottom of the cup body 220 (FIG. 5a) or one of the two separate parts of the cup body 220 (FIGS. 7a-7d), the label/final fluid seal 211 is attached directly to the cup lid assembly 210 and also functions as final seal of the test cup 300.

Figure 4A:
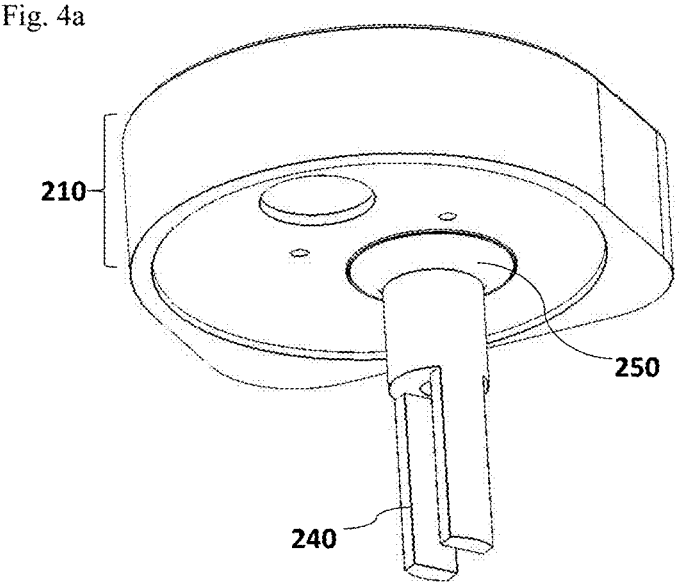
FIG. 4a illustrates an alternative configuration of the homogenizer rotor 240 on the lid assembly 210, which is connected to the rotor port 212 through a membrane seal 250, without the homogenizer stator 230.

In some embodiments, the homogenizer rotor 240 may be connected to the rotor port 212 on the cup lid assembly 210 as shown in FIG. 4a. In this particular embodiment, the homogenizer stator 230 which is as shown in FIG. 3a and FIG. 3e, welded to the rotor port 212 is not necessarily required. The homogenizer rotor 240 may be directly linked to the rotor port 212 at the inner side of the cup lid assembly 210, through a membrane seal 250. The seal materials may include, but are not limited to thermoplastic polyurethane (TPU), thermoplastic elastomer (TPE), thermoset materials such as Silicone, Rubber (e.g., Buna-N, Neoprene, and Santoprene). The connected two parts which may be composed of materials with different thermo-plasticity and hardness may be fabricated using two-shot plastic injection molding. The connection between the homogenizer rotor 240 and the rotor port 212 may also be produced using over-molding injection molding, thermally welding, ultrasonically welding and/or gluing process, or any other appropriate molding technologies.

Figure 8A:
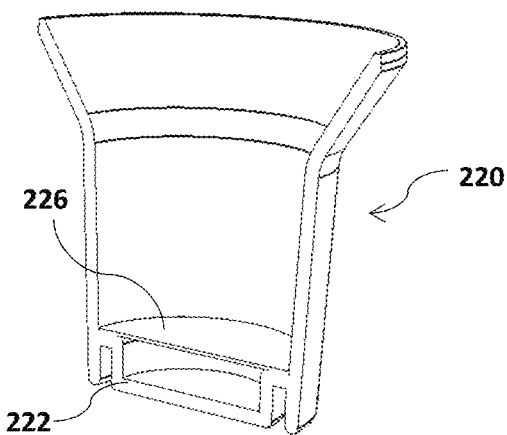
FIG. 8a and FIG. 8b illustrate other embodiments of the filter assembly.
Figure 8B:
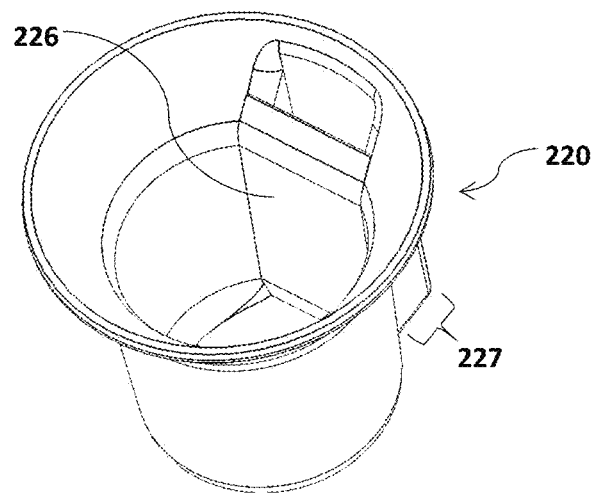

A test cup 300 may further comprise a filter that filters a processed sample solution before it is flowed into the reaction chambers 223 and the optional control chamber 225 for allergen detection testing. In some embodiments, as described in FIG. 3a and FIG. 3f, a flow tube cap and filter assembly 224 may be attached to the flow tube 221 for filtering the processed test sample before being delivered to the reaction chambers 223 and the optional control chamber 225. Alternatively, the flow tube cap and filter assembly 224 may be replaced by a simple filter membrane 226 as shown in FIGS. 5a-5b, 8a-8b and 9a-9b. In some aspects, the filter membrane 226 may be aligned in parallel with the cup base 222 of the cup body 220 with a certain distance to the cup base 222 (FIG. 8a). The room between the filter membrane 226 and the cup base 222 allows holding a filtered sample solution. In other aspects, the filter membrane 226 may be inserted into the cup body 220 in parallel with the wall of the cup body 220 with a certain distance to the wall, allowing enough room for holding the filtered sample solution before being delivered (e.g., by pumping or vacuuming) to the reaction chambers 223 and the optional control chamber 225. Alternatively, a small chamber 227 protruding out from the side wall of the cup body 220 where the filter membrane 226 is attached, may be provided; the small chamber 227 will hold the filtered sample solution before being delivered to the reaction chambers 223 and the optional control chamber 225 (FIG. 8b).

Figure 9A:
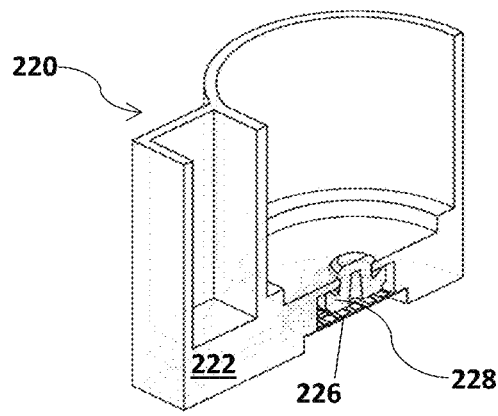
FIG. 9a and FIG. 9b depict alternative designs of the filter membrane 226 inside the cup body 220.
Figure 9B:
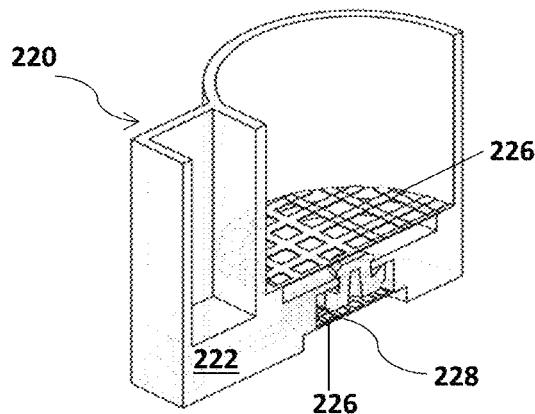

In the embodiments that the reaction chambers 223 and the optional control chamber 225 are included in the separate part of the divided cup body 220, a single filter membrane 226 may be inserted at the bottom of the cup body 220 underneath of the valve 228, as shown in FIG. 9a. The processed sample solution then is filtered before it is flowed into the reaction chambers 223 and the optional control chamber 225 included in the separate part of the cup body 220.

In some aspects, two or more filter membranes 226 may be inserted into the cup body 220. The filter membranes 226 are assembled to form a filter stage. In one example illustrated in FIG. 9b, one filter membrane 226 may be positioned in the middle of the cup body 220 to filter the processed sample solution before it is driven through the valve 228; and another filter membrane 226 is configured at the bottom of the cup body, to re-filter the processed sample solution before it is flowed into the reaction chambers 223 and the optional control chamber 225. In some aspects, the top filter membrane 226 may have a larger pore size than the filter membrane 226 at the bottom.

The filter membrane 226 may be a nylon, PES (polyethersulfone), Porex™, or the membrane polymers such as mixed cellulose esters (MCE), cellulose acetate, PTFE, polycarbonate, or the like. It may be a thin membrane (e.g., 150 μm thick) with high porosity. In some aspects, the pore size of the filter membrane 226 may range from 20 μm to 300 μm, or any size in between. For example, the pore size may be 20 μm, 25 μm, 30 μm, 35 μm, 40 μm, 45 μm, 50 μm, 55 μm, 60 μm, 65 μm, 70 μm, 75 μm, 80 μm, 85 μm, 90 μm 100 μm, 150 μm, 200 μm, 250 μm, or 300 μm.

The cup lid assembly 210 may be composed of a thermoplastic including, but not limited to polymethylmethacrylate (PMMA), polystyrene (PS), polycarbonate (PC), polyester (PET), polypropylene (PP), high density polyethylene (HDPE) and polyvinylchloride (PVC), or combinations thereof.

The cup body 220 is intended to receive a test sample from the food corer 200 to be homogenized for extraction of allergen proteins and may have a wider distal end which is connected to the cup lid assembly 210, and a cup base 222 (FIG. 3g). In certain embodiments, the cup body 220 contains a volume of extraction buffer for extraction and digestion of the test sample. The volume of extraction buffer may range from about 100 μL to about 500 μL, or from about 500 μL to about 2.5 mL. In the cup the digestion volume should be 500 μL-5 mL. In the detection chambers it should range from 10 μl to 300 μl. In some embodiments, the volume of buffer may be 100 μL, or 200 μL, or 300 μL, or 400 μL, or 500 μL, or 1 mL, or 1.2 mL, or 1.4 mL, or 1.6 mL, or 1.8 mL, or 2.0 mL, or 2.5 mL.

In other embodiments of the present invention, the allergen detection reaction may occur in the cup body 220 and the fluorescent signals will be detected by an optical subsystem (e.g., the optical subsystem 520) of the detection device 100. Accordingly, the cup body 220 may include detection molecules (e.g., SPNs) which specifically bind to one or more allergens to be tested. The detection agents may be confined in any local regions of the cup body 220, such as at the bottom of the cup base 222 and released into the cup body and mixed with the extracted protein solution for the detection assay. The allergen and detection agent mixture may be pumped or pressed into the reaction chambers 223 and the optional control chamber 225 for signal analysis.

Typically, a disposable test cup 300 has a capacity suitable for a sample of about 0.25-5 g. The cup body 220, which is intended for dissociating/homogenizing the test sample in an extraction buffer, may have a capacity of about 0.5 mL-10 mL.

In other embodiments, the cup body 220 may be made of soft materials. In such case, after insertion of a test sample, the cup body 220 including the solution inside may be pressed into one of the reaction chambers 223 on the top of the cup lid assembly 210 by an external pressure, such as a pressure from the detection device 100. Such pressure, compression, or agitation may also serve to process the test sample.

As one skilled in the field would expect that the present disposable detection vessel, for example, the test cup 300 as disclosed herein, is not limited to its usage in the present detection system. The detection vessel may be further modified to be operable in other similar analyte detection systems (e.g., protein, nucleic acids and other molecules).

Detection System—the Detection Device

In some embodiments, the detection device 100 may be configured to have two parts: an external housing that provides support surfaces for the components of the detection device 100; and a part that can open the detection device 100 for inserting a disposable test cup 300 and a food corer 200. One embodiment of the allergen detection device 100 according to the present invention is depicted in FIGS. 1a-1b, 10a-10b, 11 and 12a-12b. As illustrated in FIG. 1a and FIG. 1b, the detection device 100 comprising an external housing 10 that provides support for holding the components of the detection device 100 together and integrates them as a functional integrity for implementing an allergen detection testing; and a drawer assembly 20 that may be pulled out from and slide back into the external housing 10. The external housing 10 may be formed of plastic or other suitable support material.

Figure 10A:
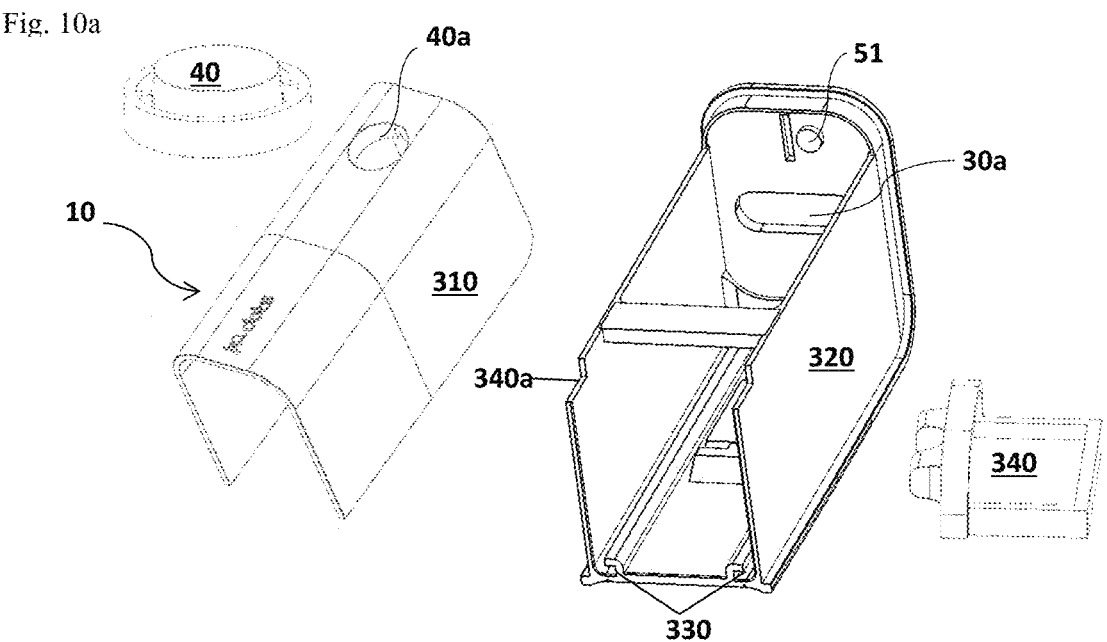
FIG. 10a and FIG. 10b illustrate the external parts of the detection device 100.
Figure 10B:
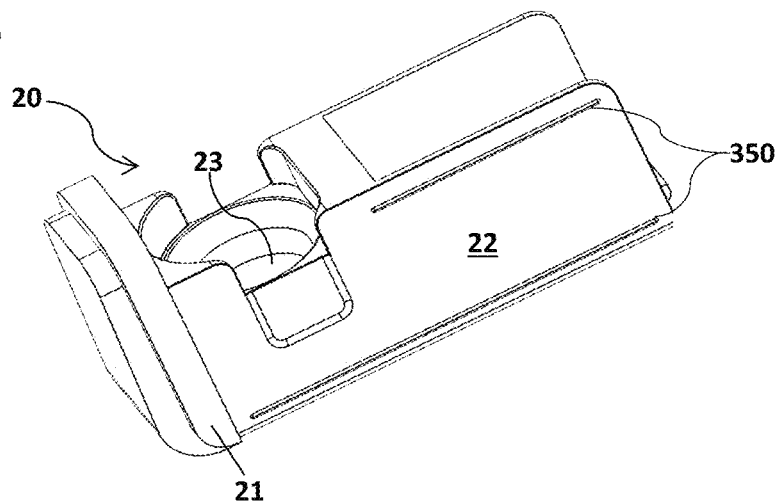

As shown in FIG. 10a, the external housing 10 may include a housing cover 310 and a housing base 320, on which a button port 40a for the execution/action button 40, and an on/off slider port 30a for the on/off slider 30 are provided. Additionally, an alignment 340 may be incorporated into the alignment site 340a on the top front of the external housing 10 for aligning the disposable test cup 300 with the detection device 100 when implementing an allergen detection testing. A groove 330 at each side of the bottom of the housing base 320 is used to sled the drawer assembly 20. The drawer assembly 20 (FIG. 10b) may include a drawer frame 22 on the front of which there is a drawer grip 21 which is configured for a user to handle the drawer assembly 20 during a detection testing, and a drawer well/port 23 for insertion of a disposable test cup 300. A sled (or chimb) 350 at each side of the drawer frame 22 is provided for sliding the drawer assembly 20 along the groove 330 of the housing base 320.

When the detection device 100 is not in use, the drawer assembly 20 is pushed back into the housing 10, so the detection device 100 is closed and may be easily carried with or stored in a bag (e.g., a handbag).

Figure 11:
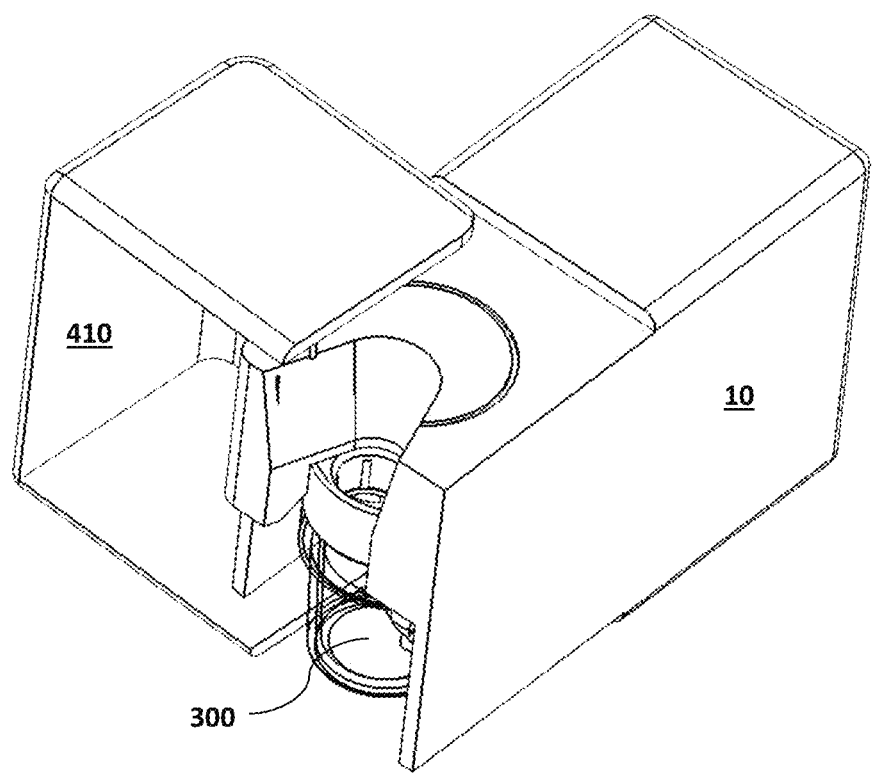
FIG. 11 illustrates an alternative assembly of the detection system of the present invention having a claw-like rotating door 410 or a swinging housing configuration.

Alternatively, other configurations that allow the drawer well/port 23 for holding a disposable test cup 300 being reachable may be designed in accordance with the present invention. As a non-limiting example, a claw-like rotating door 410 may be connected to the external housing 10 (as illustrated in FIG. 11). The detection device 100 may be placed over the disposable test cup 300 with the claw-like rotating door 410 to close over the cup during operation. As another non-limiting example, a hinged door that can be lifted may be designed to open the external housing 10 during an allergen detection testing.

To execute an allergen detection test, the detection device 100 is provided with a homogenizer which is configured for homogenizing a test sample and extracting allergen proteins from the test sample in an extraction buffer; means (e.g., a motor) for operating the homogenizer and necessary connectors that connect the motor to the homogenizer; means for driving and controlling the flow of the processed sample solution during the process of the allergen detection testing; an optical subsystem for providing fluorescence excitation and for filtering of fluorescence emission; means for detecting fluorescence emissions from the detection reaction between the allergen in the test sample and the detection agents, and background signals from the control chamber;

means for visualizing the detection signals including converting and digitizing the detected signals; a user interface that displays the test results; and a power supply. In some embodiments, a molecule probed with a fluorophore dye (e.g., a random aptamer) that cannot bind the target allergen may be stored in the control chamber. The non-binding molecule provides a means to correct for viscosity and temperature effects. By measuring the difference between the read value and the expected value and using that to scale the measurement from the active reaction chambers.

Figure 12A:
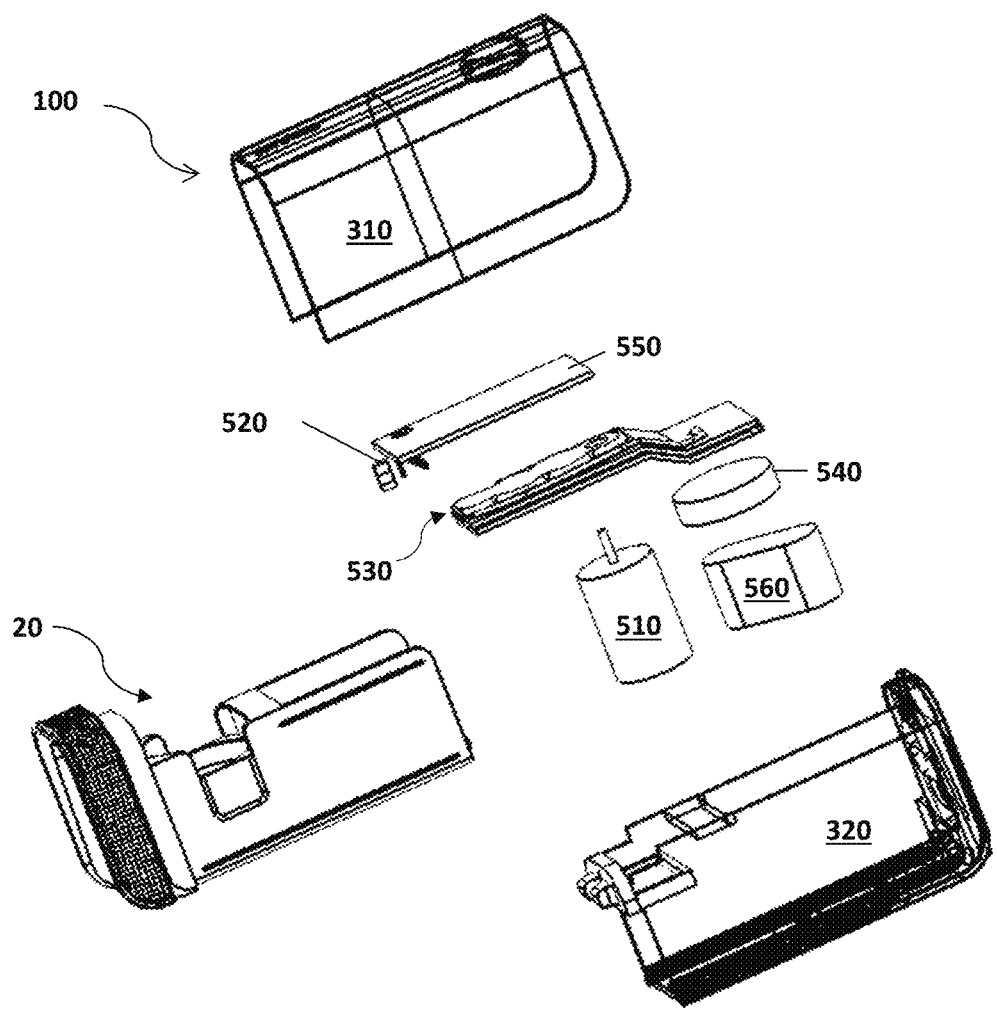
FIG. 12a and FIG. 12b illustrate an assembly of the detection device 100.
Figure 12B:
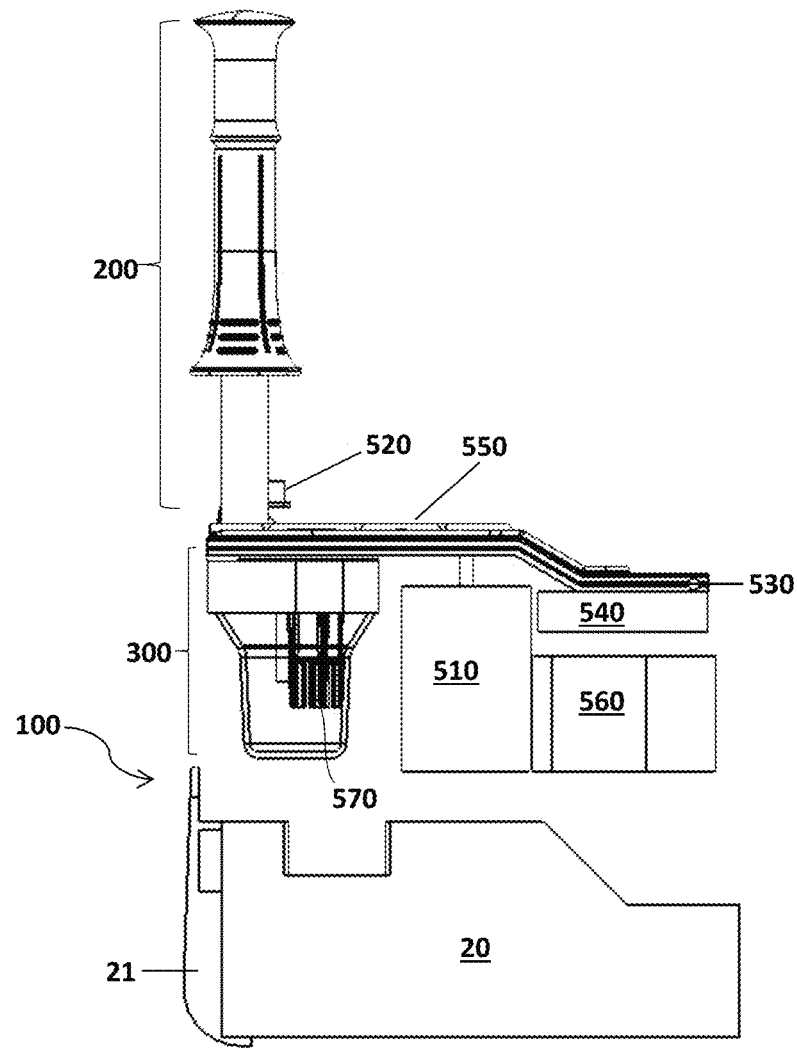

In one embodiment of the present invention, as shown in FIGS. 12a and 12b, the components of the detection device 100 that are integrated to operate a detection testing, include a motor 510 which may be connected to the homogenizer assembly 570 that is assembled inside the cup body 220 (not shown), an optical subsystem 520 that is connected to the reaction chambers 223 (not shown) within the disposable test cup 300, a gear train/drive platen 530 for driving the rotor during homogenization in an allergen detection testing, a pump 540 for controlling and regulating the flow rate, a PCB 550, and a power supply 560. The components are held inside the drawer assembly 20 which may have a drawer grip 21. The detection device is enclosed by a housing cover 310 and a housing base 320. FIG. 12a illustrates different components of the detection device 100 while FIG. 12b illustrates a view of the detection device 100 when different components are assembled and integrated as a functional device with the food corer 200 and the test cup 300.

In accordance with the present invention, a homogenizer is designed small enough to fit into a disposable test cup 300. Additionally, the homogenizer of the detection device 100 may be optimized for increasing the efficacy of sample homogenization and allergen protein extraction.

Figure 13A:
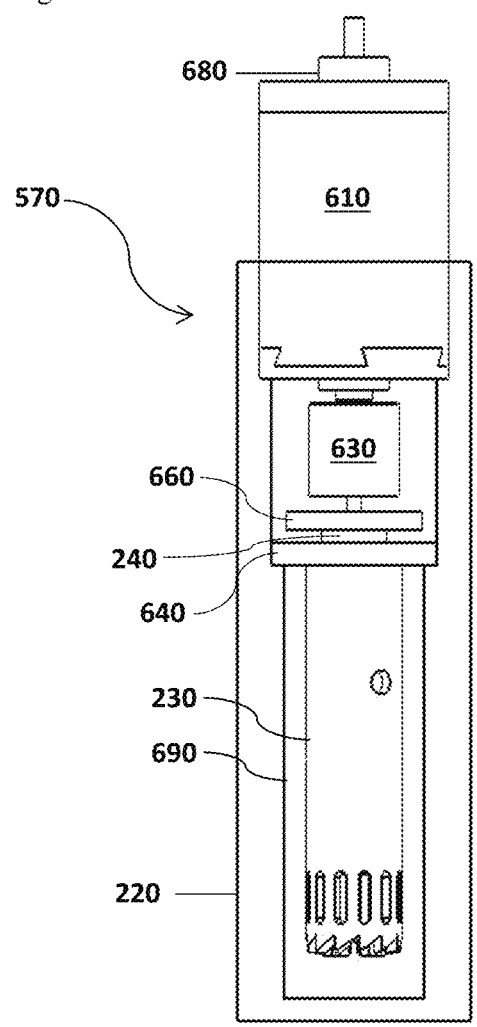
FIG. 13a illustrates an assembled breadboard homogenizer assembly 570 and its components.
Figure 13B:
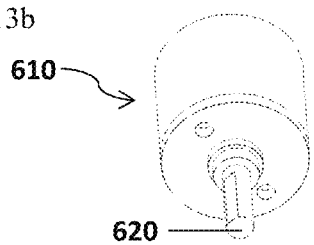
FIGS. 13b-13e illustrate a gearhead 610, a coupling 630, a homogenizer stator 230 and a homogenizer rotor 240.
Figure 13C:
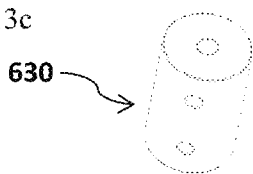
Figure 13D:
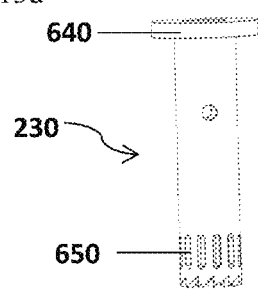
Figure 13E:
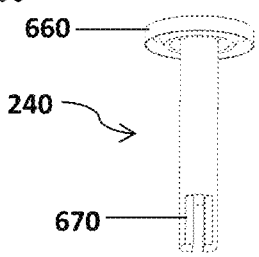

FIG. 13a illustrates an assembled breadboard homogenizer assembly 570 which is held inside a cup body 220 and its components. FIGS. 13b-13e illustrate a gearhead 610, a coupling 630, a homogenizer stator 230 and a homogenizer rotor 240. The homogenizer rotor 240 and the homogenizer stator 230 are assembled through the rotor port 212 on the top of the cup lid assembly 210 (not shown, see FIG. 3a). The homogenizer rotor 240 has a distal end provided with a top rotor cap 660 and a proximal end comprising one or more rotor blades 670 or the equivalent thereof (FIG. 13e). The rotor cap 660 may be connected to the rotor port 212 (not shown) and the homogenizer rotor 240 is inserted into the cup lid assembly 210 (not shown) through the rotor port 212 (not shown). The homogenizer rotor 240 is configured to rotate inside the homogenizer stator 230 and pull the test sample from the food corer 200 (not shown) into the bottom of the processing chamber 690. The homogenizer stator 230 has a distal end provided with a stator cap 640 and a proximal end comprising one or more small stator slots 650 (FIG. 13d), which extend into the cup body 220. Through the stator cap 640, the homogenizer stator 230 is seated within the rotor port 212 of the cup lid assembly 210 (not shown). During processing, the test sample is forced radially out through the stator slots 650 at the proximal end of the homogenizer stator 230. The homogenizer stator 230 acts as a flow breaker to largely prevent rotation of the sample, and to introduce large mechanical energies in very small space. A coupling 630 (FIG. 13c) at the distal portion of the homogenizer links the homogenizer rotor 240 to a gearhead 610 (FIG. 13b), which is a part of a gear train or a drive for connection to a motor 510 (not shown, see FIG. 12b and FIG. 14). The gearhead 610 reduces the speed of the motor 510 and increases torque in the liquid and the coupling 630 connects the actuator shaft 620 to the homogenizer rotor 240. The proximal portion of the homogenizer (i.e., the rotor blades 670 and the stator slots 650) spins within the cup body 220 to create shear in the liquid between the stationary teeth of the homogenizer stator 230 and the rotating tines of the homogenizer rotor 240 (FIG. 13a). The vortex is greatly reduced and more energy is introduced in the shearing gap between the rotor and stator. Particles are reduced in size by hitting sharp edges, shearing between the edges of the rotor blades and stator slots.

In some aspects, a heating system (e.g. resistance heating, or peltier heaters) may be provided to increase the temperature of homogenization, therefore to increase the effectiveness of sample dissociation and shorten the processing time. The temperature may be increased to between 60° C. to 95° C., but below 95° C. Increased temperature may also facilitate the binding between detection molecules and the allergen being detected. Optionally a fan or peltier cooler may be provided to bring the temperature down quickly after implementing the test.

Figure 14:
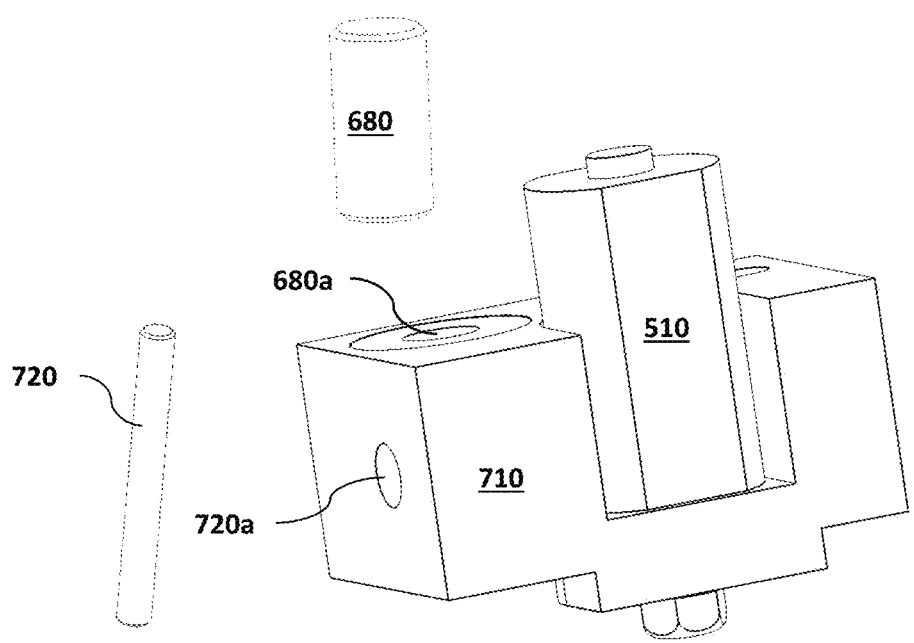
FIG. 14 illustrates a motor shuttle 710 and a motor 510 assembly.

Turning to FIG. 14, in some embodiments of the present invention, a motor 510 may be connected to the homogenizer assembly 570 (not shown) through a motor shuttle 710 for engaging the homogenizer rotor 240 (not shown) and homogenizer stator 230 (not shown). A shuttle vertical guide pin 680 through a pin port 680a on the motor shuttle 710 guides the gearhead 610 and the actuator shaft 620 of the homogenizer assembly 570 to the motor 510. A motor shuttle lift pin 720 can further align and raise/lower the motor shuttle 710 and the motor 510 through a lift pin port 720a.

In the sample processing cup body 220, an extraction buffer preloaded in the cup and a test sample plunged from the food corer 200 are mixed. Driven by the motor 510, the homogenizer assembly 570 will homogenize the test sample in the extraction buffer and dissociate/extract allergen proteins. The processed sample solution may be pumped or pressed through the flow tube 221 to the fluid channel 215 on the cup lid assembly 210, then to the analytical chamber which is one of the reaction chambers 223, in which the processed sample solution is mixed with the pre-loaded detection molecules (e.g., SPNs) for the detection testing. In parallel, a portion of the processed sample solution is pumped or pressed to the other control chamber which is one of the reaction chambers 223 on the top of the cup lid assembly 210, in which the extraction solution is measured for background signals.

In some embodiments, the processed test sample may be further filtered through means that can push the processed sample solution through a filter membrane (e.g., a filtering means connected to the homogenizer assembly 570) prior to the flow of the extraction solution to a reaction chamber 223. One example is a flow tube cap and filter assembly 224 illustrated in FIG. 3f The filter pores can be between 0.2 u to 300 u. The filter can be made from any low binding material including, but not limited to, PES (Polyethersulfone), PCTE (Polycarbonate) or PVDF (polyvinylidene difluoride).

In some embodiments, the coupling 630 may have different sizes at each end of the coupling 630, or the same sizes at each end of the coupling 630.

As compared to other homogenizers with similar structural design (e.g., U.S. Pat. No. 6,398,402), the custom blade core of the present invention spins and draws and forces food into the toothed surfaces of the custom cap. The custom o-ring seals between the custom cap and the custom cup which may be clear for visualization of homogenization progress and results. The homogenizer rotor may be made of any thermoplastics, including, but not limited to, polyamide (PA), Acrylanitrilebutadienestyrene (ABS), Polycarbonate (PC), High Impact Polystyrene (HIPS), and Acetal (POM).

In some embodiments, the homogenizer assembly 570 may be designed and modified for different homogenization mechanisms for different types of test samples, to meet specific requirements such as adding mechanical help to break up food, including grinding, cutting, blending, abrading or mixed movements. In some aspects, the homogenizer may include means (e.g., a stator and a corer) for increasing the agitation of the homogenizer. The homogenizer may have a "star knob" style handle which can be twisted to help for coring. The handle of stator/corer may be designed as herb grinder (textured band around edge); or pill crusher (with 3 flowerette knob); or pill crusher (with two winged knob). In other aspects, the stator/corer may by an object stator (e.g., 1 mm thick), PPE syringe corer, fine microplane, coarse microplane, and pulverizor, bead beating (marble agitator or steel ball agitator). In other embodiments, a homogenizer may be a hybrid with mixed processes to dissociate the test sample, for example by grinding and blending.

In some embodiments, the motor 510 can be a commercially available motor, for example, Maxon motor systems: Maxon RE-max and/or Maxon A-max (Maxon Motor ag, San Mateo, Calif., USA).

In some embodiments, a gear train or a drive may be used to connect the motor 510 to the homogenizer assembly 570. A gear train and/or a drive allows the motor 510 to be packaged so it does not interfere with the ability of the food corer 200 to introduce food sample to the homogenizer assembly 570 while allowing the homogenizer stator 230 to be driven from above, and does not require a liquid tight seal during operation. A label/final fluid seal 211 is provided by the applied label or other removable seal proximal to the area surrounding the stator cap 640. The gear train or the drive may also allow the power from the motor 510 to take two right angle turns and is therefore critical to a particular combination of user experience of the detection device 100 and functional requirement for the disposable test cup 300.

The test sample will be processed in an extraction buffer for protein extraction and allergen retrieval. In some embodiments, the extraction buffer may be optimized for increasing protein extraction. The extraction buffer may contain different agents for different test samples, such as those disclosed in Applicants' PCT Application Serial No. PCT/US2014/062656, the contents of which are incorporated herein by reference in its entirety.

In accordance with the present invention, a means for driving and controlling the flow of the processed sample solution and mixing said extraction solution with one or more detection signal molecules is provided. In some embodiments, the means may be a vacuum system or an external pressure. As a non-limiting example, the means may be a platen (e.g., a welded plastic clamshell) configured to being multifunctional in that it could support the axis of the gear train and it could provide the pumping (sealed air channel) for the vacuum to be applied from the pump to the test cup port 214 on the cup lid assembly 210 of the disposable test cup 300.

Figure 15A:
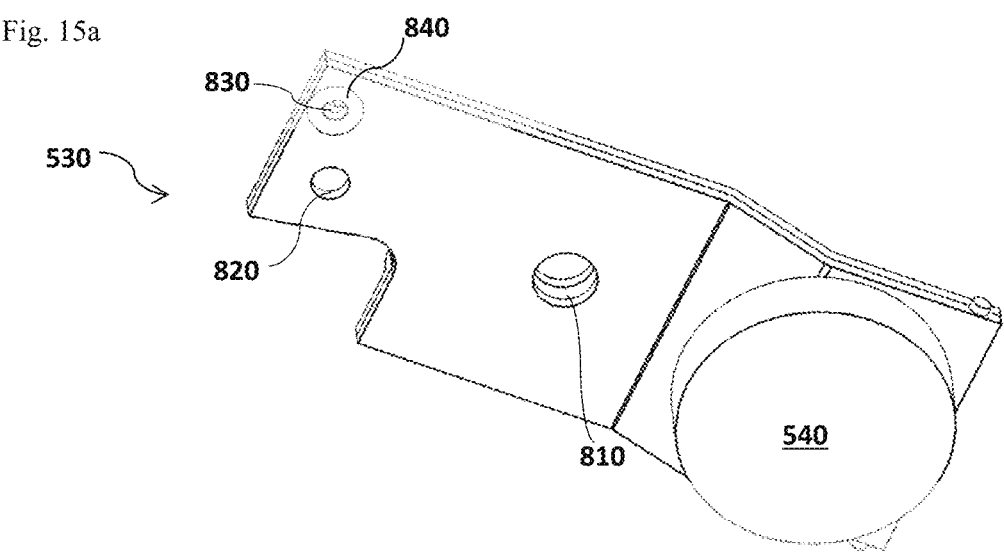
FIG. 15a and FIG. 15b illustrate a gear train/drive platen 530 connected to a pump 540.
Figure 15B:
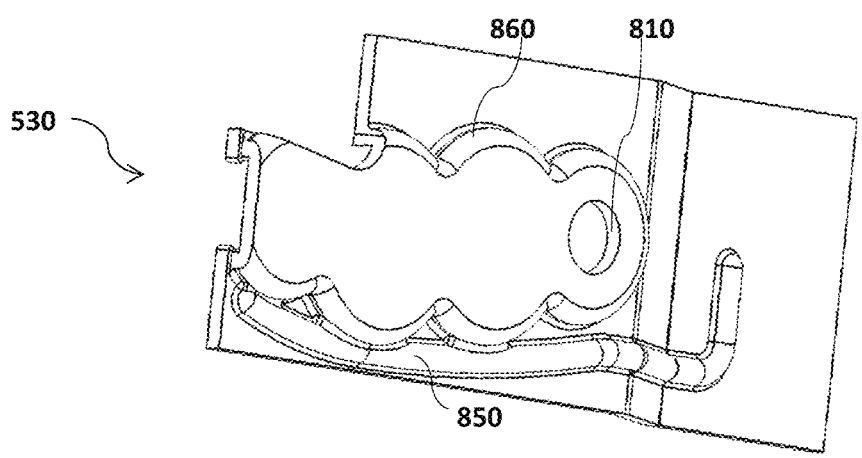

Referring to FIG. 15a and FIG. 15b, a gear train/drive platen 530 may have a underside to which a pump (e.g., Piezo micropump) 540 is connected; and a topside which is provided with a vacuum duct 850 that is connected to the test cup port 214 (as shown in FIG. 3c) on the top of the cup lid assembly 210 (not shown) of the disposable test cup 300; and air channels 860. A gear train/motor port 810 which is configured for connection to the gear train or the drive that is connected to the motor 510 (not shown) and the homogenizer assembly 570 (not shown). A gear train/cup port 830 at the edge of the gear train/drive platen 530 is surrounded by a vacuum gasket 840 which seals the connection between the test cup port 214 (shown in FIG. 3c) on the top of the cup lid assembly 210 and the gear train/cup port 830. The flow control port 820 provides a flow control of the extraction protein solution from the cup body 220 (not shown) to the reaction chambers 223 (not shown) with active feedback from the optical subsystem 520 (not shown, illustrated in FIG. 16 and FIG. 17), or by fluid mechanical means such as a small orifice or hydrophobic membrane.

The pump 540, such as piezoelectric micro pump (Takasago Electric, Inc., Nagoya, Japan) may be used to control and automatically adjust the flow to a target flow rate. The flow rate of a pump is adjustable by changing either the driver voltage or drive frequency. The pump 540 shown in FIG. 15a is a representation of piezo pumps currently on the market that have specifications that indicate they could be suitable for the aliquot function required to bring filtered sample solution into the two reaction chambers 223 and the optional control chamber 225. The pump 540 may be a vacuum pump or other small pumps designed for laboratory use such as KBF pumps (KNF Neuberger, Trenton, N.J., USA).

The vacuum gasket 840 provides a seal between the gear train/drive platen 530 and the test cup port 214 on the top of the cup lid assembly 210. In some embodiments, the vacuum gasket 840 could also be incorporated into the disposable test cup 300 to increase reliability of the detection device 100. The air channel 860 could also be executed with discrete tubing and fittings. The sample flow tube 221 will be isolated from the fluid channel 215 and reaction chambers 223 such that evaporation of the buffer solution will not prematurely dissolve the reactants by means such as a cap, a duckbill valve, an umbrella valve, a cone valve, X-Fragm (Minivalve) or similar arrangement. Opening pressures of any such valve must be controlled to open during operation but not during storage/shipment due to expansion of the air in the cup. In some aspects, the vacuum gasket 840 is positioned directly underneath of the cup lid assembly 210 as shown in FIG. 6d. The vacuum gasket 840 includes a food corer port 213 and a rotor port 212 which are aligned with the corresponding ports of the lid; one or more air vents 217 and a vacuum port seal 219 to seal the test cup port 214 of the lid.

The detection device 100 of the present invention comprises an optical subsystem that detects signals (e.g., a fluorescent signal) generated from the interaction between an allergen(s) in the sample and detection agents (e.g., SPNs). The optical subsystem may comprise different components and variable configurations depending on the types of the fluorescent signal to be detected. The optical subsystem is close and aligned with the detection vessel, for instance, the reaction chambers 223 and the optional control chamber 225 of the test cup 300 as discussed above. As such, the optical subsystem may be close and aligned with the optical window/fluid seal 216 of the reaction chambers 223 (as shown in FIG. 3c).

In accordance with the present invention, a detectable signal generated from the interaction between detection agents and an allergen(s) in a test sample may be a fluorescent signal, including but not limited to absorbance, fluorescence intensity, luminescence, time-resolved fluorescence (TRF), and fluorescence polarization (FP). In one aspect, a detectable signal from the binding interaction between an allergen(s) in the test sample and detection agents may be changes in fluorescence polarization (FP) of a fluorescent probe, e.g., a fluorophore labeled signaling polynucleotide (SPN), upon the binding of an allergen protein to the fluorophore probed SPN. Accordingly, the optical subsystem is assembled to measure fluorescence polarization (FP).

As used herein, the term "fluorescence polarization (FP)" refers to a phenomenon related to an observation that if a fluorescent molecule is excited by polarized light, the subsequently emitted light will also be polarized in a fixed plane if the molecule remains stationary between excitation and emission. The binding of a large compound (e.g., a protein) to a fluorescently labeled agent changes the rotation of the fluorescent molecule, causing a change in the fluorescence polarization during their fluorescent lifetime which is the period of time between absorption of an excitation photon and the emission of a photon through fluorescence. (Checovich et al., Fluorescence polarization—a new tool for cell and molecular biology, Nature, 1995, 375: 254-256; the contents of which are incorporated by reference herein in their entirety.) Measurement of fluorescence polarization of a fluorescent molecule has been intensively employed in biomedical area where a number of various assays for determination of specific biological compounds are developed based on the FP technology. The method is fast, sensitive and accurate.

Figure 16:
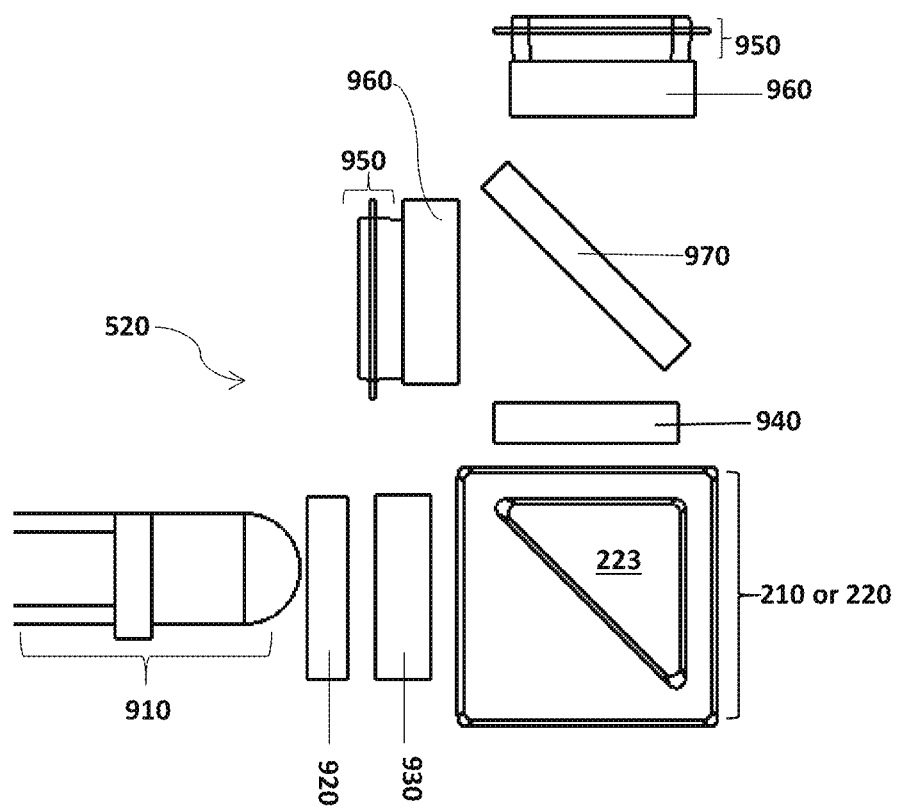
FIG. 16 illustrates an embodiment of the optical subsystem 520.
Figure 17:
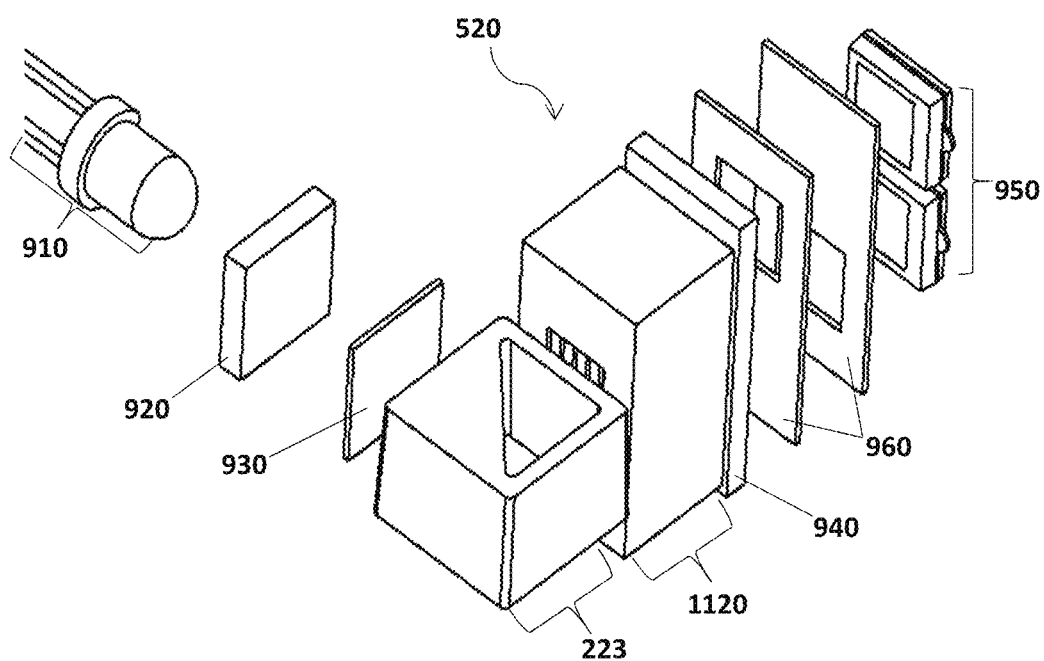
FIG. 17 illustrates an alternative of the optical subsystem 520.

In accordance with the present invention, as shown in FIG. 16 and FIG. 17, an optical subsystem 520 that is configured to measure fluorescence polarization may be included as the detector of the detection device 100. More than one polarizing filters (i.e. polarizers) are included in the optical paths.

FIG. 16 illustrates a configuration of the optical subsystem for measuring FP signal. The optical subsystem 520 of the detection device 100 is connected with the reaction chambers 223 and the optional control chamber 225. The optical subsystem 520 includes an excitation optical path which comprises a light emitting diodes (LEDs) or a diode laser 910 (e.g. Avago LED of Luxeon Rebel LED) held by a LED housing (not shown), an excitation filter 920, a excitation polarization filter 930; and an emission optical path which comprises an emission filter 940, an optional beam splitter 970, a pair of emission polarizing filters or membranes 960 and a pair of photodiodes or a photomultiplier tubes (PMT) (photo detectors) 950. The excitation optical path and emission optical path are aligned with the reaction chamber 223 and the optional control chamber 225 within the cup lid assembly 210 or the cup body 220. Both the excitation and emission optical paths contain beam-shaping and collimation optics.

The LEDs or the diode laser 910 provide light of an excitation wavelength appropriate to excite the fluorophore of signaling polynucleotides, through the excitation filter 920. LEDs may have different shapes, e.g. a bulb or a plate. This light is then plane polarized by passing it through the excitation polarizing filter 930. The resulting plane polarized excitation light is directed into the reaction chambers 223 and the optional control chamber 225. The light LED or diode laser light is polarized in either vertical or horizontal direction. The fluorophore probed detection agent is excited and a fluorescent light is reemitted and passes sequentially through the emission filter 940, an optional beam splitter 970 and the emission polarizing filter or membrane 960, and is detected by a photo detector 950. The emission filter 940 allows only the wavelength of interest to pass through from the fluorescence emitted from the reaction chamber 223 for detection by the photo detector 950, and blocks light scatter and non-specific fluorescence before being detected. The pair of emission polarizing filters or membranes 960 and photodiodes or a photomultiplier tubes (PMT) (photo detectors) 950 are arranged at a 90° angle with each other. The pair of emission polarizing filters or membranes 960 polarizes the light re-emitted from the reaction chamber 223 in opposite orientations for each of the photo detectors 950. Alternatively, a beam splitter 970 may be inserted into the emission optical path before the emission light being detected. Signals from the detector (e.g., a spectrometer and a camera) may be converted to digital signals or processed as analog signals, and the amount of allergen corresponding to the signal is indicated in a corresponding display window 60 (not shown, see FIG. 1b), which functions as a user interface screen.

In an alternative configuration as shown in FIG. 17, the optical subsystem for FP measurement comprises the same optical components: a light emitting diodes (LEDs) or a diode laser 910 (e.g. Avago LED of Luxeon Rebel LED) held by a LED housing (not shown), an excitation filter 920, a excitation polarization filter 930, a baffle 1120, an emission filter 940, a pair of emission polarizing filters or membranes 960 and a pair of photodiodes or a photomultiplier tubes (PMT) (photo detectors) 950. The pair of emission polarizing filters or membranes 960 and the photo detectors 950 is arranged in parallel.

As used herein, the term "polarizer or polarizing filter" refers to an optical filter (e.g., a prism) that passes light of a specific polarization and blocks waves of other polarizations. It can convert a beam of light of undefined or mixed polarization into a beam with well-defined polarization, polarized light. Commonly used polarizers include linear polarizers and circular polarizers. Linear polarizers can be divided into two general categories: absorptive polarizers, where the unwanted polarization states are absorbed by the device, and beam-splitting polarizers, where the un-polarized beam is split into two beams with opposite polarization state.

In some embodiments, the two polarizers in the emission optical path may be crossed polarizers, as shown in FIG. 17. Crossed polarizers are two linear polarizers of which the transmission directions are placed at right angles to eliminate all light.

The LEDs integrated into the optical subsystem 520 may be an Avago LED (Avago Technologies, San Jose, Calif., USA), or a Luxeon Rebel LED (Luxeon LEDs, Ontario Canada).

The above described optical subsystem 520 is illustrative examples of certain embodiments. In some embodiments they might have different configurations and/or different components. In some embodiments, the optical assembly or the alternative optical assembly may be configured together with an absorbance measurement assembly. In such configurations, some of the components, such as reaction chambers, excitation sources (LEDs or a diode laser); detectors (e.g. photodiode or PMT), filters and/or other components might be shared by the assemblies.

Figure 18:
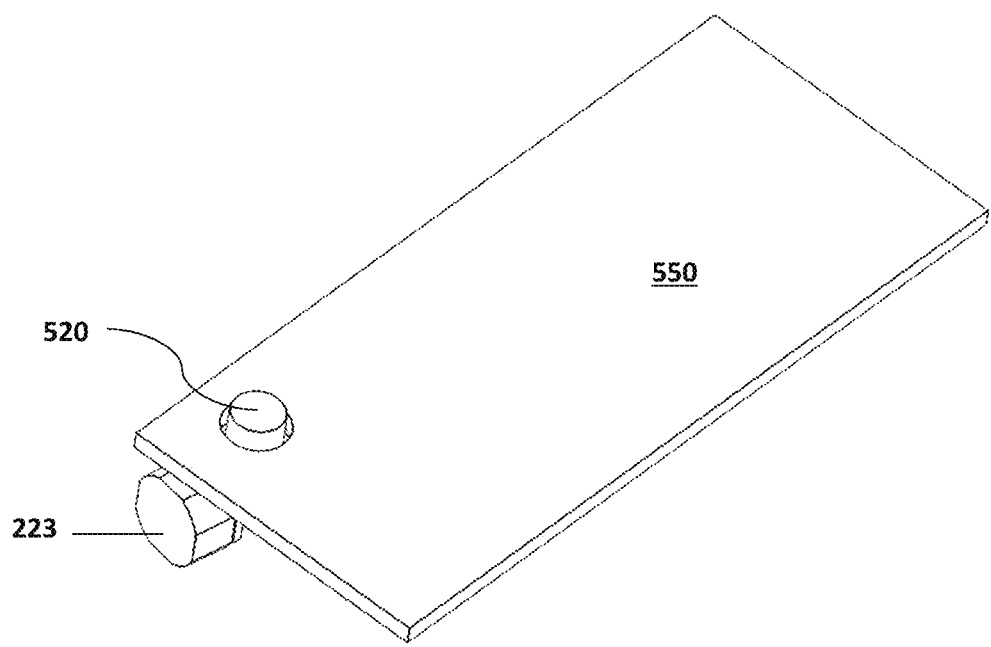
FIG. 18 illustrates a printed circuit board (PCB) 550 which is connected to the optical subsystem 520. The main control PCB contains motor and pump/actuator control electronics.

As shown in FIG. 18, a printed circuit board (PCB) 550 is connected to the optical subsystem 520 and the analytical chamber (i.e. of the reaction chamber 223). The PCB 550 may be configured to be compact with the size of the detection device 100 and at the same time, may provide enough space to display the testing result.

In accordance, the test result may be displayed with back lit icons, LEDs or an LCD screen, OLED, segmented display or on an attached mobile phone application. The user may see an indicator that the sample is being processed, that the sample was processed completely (total protein indictor) and the results of the test. The user may also be able to view the status of the battery and what kind of cartridge he/she placed in the device (bar code on the cartridge or LED assembly). The results of the test will be displayed, for example, as 1) actual number ppm or mg; or 2) binary result yes/no; or 3) risk analysis—high/medium/low or high/low, risk of presence; or 4) range of ppm less than 1/1-10 ppm/more than 10 ppm; or 5) range of mg less than 1 mg/between 1-10 mg/more than 10 mg. The result might also be displayed as number, colors, icons and/or letters. In accordance with the present invention, the detection device 100 may also include other features such as means for providing power supply and means for providing a control of the process. In some embodiments, one or more switches are provided to connect the motor, the micropump and/or the gear train or the drive to the power supply. The switches may be simple microswitches that can turn the detection device on and off by connecting and disconnecting the battery.

The power supply 560 may be a Li-ion AA format battery or any commercially available batteries that are suitable for supporting small medical devices such as Rhino 610 battery, Turntigy Nanotech High dischargeable Li Po battery, or a Pentax D-L163 battery.

Detection Agents of the Invention

A molecule that specifically recognizes an allergen protein may be used in the present invention, such as antibodies, nucleic acid molecules (e.g., aptamers) and SPNs developed by the present inventors. In some embodiments, the present invention further provides signaling polynucleotides (SPNs) that are derived from aptamers specifically bind to an allergen. The SPNs may be labeled with a fluorophore marker at one end of the nucleic acid sequence, i.e. the 5' terminus or 3' terminus.

Aptamers

While a great variety of commercial analytical methods have been developed for allergen detection, most of them rely on antibody based immunoassays. Antibodies as detection agents for allergen detection have generated great specificity. However, immunoassays are time consuming, require trained personnel to read the test results, are difficult to miniaturize, and are not fully standardized. Moreover, immunoassay methods often cause false positive results which are often attributed to matrix and cross-reactivities. One of the more recent reviews of aptamer-based analysis in context of food safety control indicated that the selection of aptamers for this group of ingredients is emerging (Amaya-Gonzalez et al., *Sensors* 2013, 13: 16292-16311, the contents of which are incorporated herein by reference in its entirety).

As used herein, the term "aptamer" refers to a class of small single-stranded nucleic acid species that has been engineered through repeated rounds of in vitro selection or equivalently, SELEX (systematic evolution of ligands by exponential enrichment) that fold into a well-defined three-dimensional structure, to bind to various molecular targets such as small molecules, proteins, nucleic acids, and even cells, tissues and organisms. The binding specify and high affinity to target molecules, the sensitivity and reproductively at ambient temperature, the relatively low production cost, and the possibility to develop an aptamer core sequence that can recognize any protein, ensure an effective but yet simple detection assays for the sensors of the detection device as described herein.

Aptamers are particularly well suited to provide core/binding sequences for detection agents because the iterative approach of the SELEX (systematic evolution of ligands by exponential enrichment) process (described herein below) can be used to produce aptamers against essentially any molecular target (or portion thereof). Such aptamers have high affinity and binding specificity for their targets. The present inventors have recognized that production of signaling polynucleotides (SPNs) (described in detail herein below) using an aptamer as the core/binding sequence allows convenient linkage to various reporter molecules. The relatively low production cost of signaling polynucleotides based on aptamer core/binding sequences is also advantageous with respect to the objective of development of simple, yet effective detection assays for biomolecule sensors. The present inventors have recognized that allergen detection in various matrices of food products can be conveniently performed using aptamer-based detector sequences such as signaling polynucleotides, which are particularly well suited for use in a simple and portable sensor that can be used repetitively with high sensitivity and reproducibility at ambient temperature to ensure food safety.

A recent review describes analytical strategies developed using aptamers for the control of pathogens, allergens, adulterants, toxins and other forbidden contaminants to ensure food safety (Amaya-Gonzalez, et al., Aptamer-Based Analysis: A Promising Alternative for Food Safety Control, *Sensors*, 2013, 13:16292-16311; Amaya-Gonzalez, et al., Aptamer binding to coelic disease-triggering hydrophobic proteins: a sensitive gluten detection system. *Anal. Chem.* 2014, 86(5): 2733-2739; the contents of each of which are incorporated herein by reference in their entirety). A method of detection of gluten is also described in PCT Publication PCT/ES2013/000133, 28 Jun. 2013, to Amaya-Gonzalez, et al; the contents of which are incorporated herein by reference in their entirety.

By way of non-limiting example, a process for in vitro selection of a single stranded DNA aptamer specific for the anaphylactic toxic allergen, β-conglutin, Lup an 1 has been reported (Nadal, et al., DNA Aptamers against the Lup an 1 Food Allergen. *PLoS ONE,* 2012, 7(4): e35253; the contents of which are incorporated herein by reference in its entirety). Briefly, the β-conglutin subunit from lupin was purified and chemically crosslinked to magnetic beads. Peptide mass fingerprinting was used to ensure the presence of the β-conglutin on the surface of the beads. A DNA library pool having a population variability of $10^{14}$ was amplified using a phosphorothioated forward primer and the T7 Gene 6 Exonuclease to generate single stranded 93-mer DNA sequences. The library pool was incubated with the protein-conjugated magnetic beads. Each round of SELEX was monitored using PCR, comparing the amount of DNA liberated from the protein-conjugated beads to that obtained from unconjugated beads. Evolution was monitored using enzyme linked oligonucleotide assay (ELONA) and surface plasmon resonance (SPR). After 15 rounds of SELEX, the enriched DNA was cloned, sequenced and consensus motifs identified, the affinity and specificity of these motifs were evaluated, and their secondary structures predicted. The resulting aptamers were evaluated using competitive ELONA for the detection and quantification of the β-conglutin lupin allergen. Thus, the original 93-mer with $K_D$ $3.6 \times 10^{-7}$ was selected and truncated to an 11-mer with $K_D$ of $1.7 \times 10^{-9}$ (Nadal, et al., Probing high-affinity 11-mer DNA aptamer against Lup an 1 (β-conglutin). *Anal. Bioanal. Chem.* 2013, 405: 9343-9349; the contents of which are incorporated herein by reference in its entirety). This truncated 11-mer is guanine-rich and predicted to fold into G-quadruplex structures, composed of stacked guanine tetrads, which are stabilized by Hoogsteen-type hydrogen bonds between the guanines and by interactions with cations located between the tetrads. A sensitive method exploiting fluorescence resonance energy transfer (FRET) was recently reported for rapid and sensitive detection of Lup an 1, using a high affinity dimeric form of the truncated 11-mer anti-β-conglutin aptamer, with each monomeric aptamer being flanked by donor/acceptor moieties. The dimeric form in the absence of target yields fluorescence emission due to the FRET from the excited fluorophore to the proximal second fluorophore. However, upon addition of β-conglutin, the specific interaction induces a change in the bi-aptameric structure resulting in an increase in fluorescence emission. The method is highly specific and sensitive, with a detection limit of 150 pM, providing an effective tool for the direct detection of the toxic β-conglutin subunit in foodstuffs in just 1 min. at room temperature (Mairal, et al., FRET-based dimeric aptamer probe for selective and sensitive Lup an 1 allergen detection. *Biosensors and Bioelectronics,* 2014, 54: 207-210; the contents of which are incorporated by reference herein in their entirety).

Nucleic acid aptamers (DNA or RNA) are usually engineered through repeated rounds of in vitro selection or equivalently, SELEX (systematic evolution of ligands by exponential enrichment) to bind to various molecular targets such as small molecules, proteins, nucleic acids, and even cells, tissues and organisms. Nucleic acid aptamers have specific binding affinity to molecules through interactions other than classic Watson-Crick base pairing. Nucleic acid aptamers, like peptides generated by phage display or monoclonal antibodies (mAbs), are capable of specifically binding to selected targets and, through binding, block their targets' ability to function.

Aptamers, often called "chemical antibodies," have characteristics which are similar to those of antibodies. A typical nucleic acid aptamer is approximately 10-15 kDa in size (20-45 nucleotides), binds its target with at least nanomolar affinity, and discriminates against closely related targets.

Aptamers may be either monovalent or multivalent. Aptamers may be monomeric, dimeric, trimeric, tetrameric or higher multimeric. Individual aptamer monomers may be linked to form multimeric aptamer fusion molecules. As a non-limiting example, a linking oligonucleotide (i.e., linker) may be designed to contain sequences complementary to both 5'-arm and 3'-arm regions of random aptamers to form dimeric aptamers. For trimeric or tetrameric aptamers, a small trimeric or tetrameric (i.e., a Holiday junction-like) DNA nanostructure will be engineered to include sequences complementary to the 3'-arm region of the random aptamers, therefore creating multimeric aptamer fusion through hybridization. In addition, 3 to 5 or 5 to 10 dT rich nucleotides can be engineered into the linker polynucleotides as a single stranded region between the aptamer-binding motifs, which offers flexibility and freedom of multiple aptamers to coordinate and synergize multivalent interactions with cellular ligands or receptors.

Alternatively, multimeric aptamers can also be formed by mixing biotinylated aptamers with streptavidin.

As used herein, the term "multimeric aptamer" or "multivalent aptamer" refers to an aptamer that comprises multiple monomeric units, wherein each of the monomeric units can be an aptamer on its own. Multivalent aptamers have multivalent binding characteristics. A multimeric aptamer can be a homomultimer or a heteromultimer. The term "homomultimer" refers to a multimeric aptamer that comprises multiple binding units of the same kind, i.e., each unit binds to the same binding site of the same target molecule.

The term "heteromultimer" refers to a multimeric aptamer that comprises multiple binding units of different kinds, i.e., each binding unit binds to a different binding site of the same target molecule, or each binding unit binds to a binding site on different target molecule. Thus, a heteromultimer can refer to a multimeric aptamer that binds to one target molecule at different binding sties or a multimeric aptamer that binds to different target molecules. A heteromultimer that binds to different target molecules can also be referred to as a multi-specific multimer.

Nucleic acid aptamers comprise a series of linked nucleosides or nucleotides. The term "nucleic acid," in its broadest sense, includes any compound and/or substance that comprise a polymer of nucleotides. These polymers are often referred to as polynucleotides. Exemplary nucleic acid molecules or polynucleotides of the invention include, but are not limited to, either D- or L-nucleic acids, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

The skilled artisan will recognize that the term "RNA molecule" or "ribonucleic acid molecule" encompasses not only RNA molecules as expressed or found in nature, but also analogs and derivatives of RNA comprising one or more ribonucleotide/ribonucleoside analogs or derivatives as described herein or as known in the art. Strictly speaking, a "ribonucleoside" includes a nucleoside base and a ribose sugar, and a "ribonucleotide" is a ribonucleoside with one, two or three phosphate moieties. However, the terms "ribonucleoside" and "ribonucleotide" can be considered to be equivalent as used herein. The RNA can be modified in the nucleobase structure, the ribofuranosyl ring or in the ribose-phosphate backbone.

Nucleic acid aptamers may be ribonucleic acid, deoxyribonucleic acid, or mixed ribonucleic acid and deoxyribonucleic acid. Aptamers may be single stranded ribonucleic acid, deoxyribonucleic acid or mixed ribonucleic acid and deoxyribonucleic acid.

In some embodiments, the aptamer comprises at least one chemical modification. In some embodiments, the chemical modification is selected from a chemical substitution of the nucleic acid at a sugar position, a chemical substitution at a phosphate position and a chemical substitution at a base position. In other embodiments, the chemical modification is selected from incorporation of a modified nucleotide; 3' capping; conjugation to a high molecular weight, non-immunogenic compound; conjugation to a lipophilic compound; and incorporation of phosphorothioate into the phosphate backbone. In a preferred embodiment, the high molecular weight, non-immunogenic compound is polyalkylene glycol, and more preferably is polyethylene glycol (PEG). The process of covalent conjugation of PEG to another molecule, normally a drug or therapeutic protein is known as PEGylation. PEGylation is routinely achieved by incubation of a reactive derivative of PEG with the target molecule. The covalent attachment of PEG to a drug or therapeutic protein can mask the agent from the host's immune system, thereby providing reduced immunogenicity and antigenicity, and increase the hydrodynamic size (size in solution) of the agent which prolongs its circulatory time by reducing renal clearance. PEGylation can also provide water solubility to hydrophobic drugs and proteins.

In another preferred embodiment, the 3' cap is an inverted deoxythymidine cap.

In some embodiments, nucleic acid aptamers are provided in which the P(O)O group is replaced by P(O)S ("thioate"), P(S)S ("dithioate"), P(O)NR2 ("amidate"), P(O)R, P(O) OR', CO or CH2 ("formacetal") or 3'-amine (—NH—CH2—CH2-), wherein each R or R' is independently H or substituted or unsubstituted alkyl. Linkage groups can be attached to adjacent nucleotide through a —O—, —N—, or —S— linkage. Not all linkages in the nucleic acid aptamers are required to be identical.

As non-limiting examples, a nucleic acid aptamer can include D-ribose or L-ribose nucleic acid residues and can also include at least one modified ribonucleoside including but not limited to a 2'-O-methyl modified nucleoside, a nucleoside comprising a 5' phosphorothioate group, a terminal nucleoside linked to a cholesteryl derivative or dodecanoic acid bisdecylamide group, a locked nucleoside, an abasic nucleoside, an inverted deoxynucleoside or inverted ribonucleoside, a 2'-deoxy-2'-fluoro-modified nucleoside, a 2'-amino-modified nucleoside, a 2'-alkyl-modified nucleoside, a morpholino nucleoside, a phosphoramidate or a non-natural base comprising nucleoside, or any combination thereof. Alternatively, a nucleic acid aptamer can comprise at least two modified ribonucleosides, at least 3, at least 4, at least 5, at least 6, at least 7, at least 8, at least 9, at least 10, at least 15, at least 20 or more modified ribonucleosides, up to the entire length of the molecule. The modifications need not be the same for each of such a plurality of modified deoxy- or ribonucleosides in a nucleic acid molecule.

Detection agents which are nucleic acid based may include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, those disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993.

A suitable nucleotide length for an aptamer may range from about 15 to about 120 nucleotides (nt), and in various other preferred embodiments, 15-30 nt, 20-25 nt, 50-120 nt, 30-100 nt, 30-60 nt, 25-70 nt, 25-60 nt, 40-60 nt, 25-40 nt, 30-40 nt, any of 15, 16, 17, 18, 19, 20, 21, 22, 23, 24, 25, 26, 27, 28, 29, 30, 31, 32, 33, 34, 35, 36, 37, 38, 39 or 40 nt or 40-70 nt in length. However, the sequence can be designed with sufficient flexibility such that it can accommodate interactions of aptamers with two targets at the distances described herein.

In some embodiments, the nucleic acid aptamer comprises one or more regions of double-stranded character. Such double stranded regions may arise from internal self-complementarity or complementarity with a second or further aptamers or oligonucleotide molecule. In some embodiments the double stranded region may be from 4-12, 4-10, 4-8 base pairs in length. In some embodiments the double stranded region may be 5, 6, 7, 8, 9, 10, 11 or 12 base pairs. In some embodiments the double stranded region may form a stem region. Such extended stem regions having double stranded character can serve to stabilize the nucleic acid aptamer. As used herein, the term "double stranded character" means that over any length of two nucleic acid molecules, their sequences form base pairings (standard or nonstandard) of more than 50 percent of the length.

Aptamers may be further modified to provide protection from nuclease and other enzymatic activities. The aptamer sequence can be modified by any suitable methods known in the art. For example, phosphorothioate can be incorporated into the backbone, and 5'-modified pyrimidine can be included in 5' end of ssDNA for DNA aptamers. For RNA aptamers, modified nucleotides such as substitutions of the 2'-OH groups of the ribose backbone, e.g., with 2'-deoxy-NTP or 2'-fluoro-NTP, can be incorporated into the RNA molecule using T7 RNA polymerase mutants. The resistance of these modified aptamers to nuclease can be tested by incubating them with either purified nucleases or nuclease from mouse serum, and the integrity of aptamers can be analyzed by gel electrophoresis.

In some embodiments, such modified nucleic acid aptamers may be synthesized entirely of modified nucleotides, or with a subset of modified nucleotides. The modifications can be the same or different. All nucleotides may be modified, and all may contain the same modification. All nucleotides may be modified, but contain different modifications, e.g., all nucleotides containing the same base may have one type of modification, while nucleotides containing other bases may have different types of modifications. For example, all purine nucleotides may have one type of modification (or are unmodified), while all pyrimidine nucleotides have another, different type of modification (or are unmodified). In this way, oligonucleotides, or libraries of oligonucleotides are generated using any combination of modifications as disclosed herein.

In accordance with the present invention, a SELEX approach was used to select core binding aptamers that bind 8 major food allergens (i.e. cashew, egg, milk, peanuts, gluten, fish, crustacean and soy). Several aptamers with sequences that can specifically recognize a target allergen were selected and the nucleic acid sequences of selected aptamers were further modified to generate signaling polynucleotides (SPNs). The aptamers with high selectivity, specificity and stability are selected and further labeled as detection agents. The sequences of the selected aptamers for the 8 major allergens are listed in Table 1. For example, 1501 RiboSPN (SEQ ID NO.: 1) is the full sequence of one of the aptamers that bind cashew. The full sequence includes the primers used for the screen and the core binding sequence of the aptamer (SEQ ID NO.: 2). The core binding sequence will be further modified to generate signaling polynucleotides specific to cashew, as discussed herein below.

Signaling Polynucleotides (SPNs)

In accordance with the present invention, a signaling polynucleotide may be developed from the selected aptamers which specifically bind a target allergen molecule. The polynucleotide sequences are detectable when bound at high affinity and specificity to molecular targets.

In some embodiments, SPNs of the present invention comprise the core binding sequences which determine the specificity and affinity of SPNs to a target allergen molecule. The full sequence of a selected aptamer can be shortened by deleting the primers used for aptamer selection without impacting the binding sequence to a target allergen. Additional nucleotides may also be added at the 5' terminus and/or the 3' terminus, without impacting the binding (core) sequence of each aptamer. 3D structures of such SPNs are predicted using standard structure prediction software. The resulting polynucleotide may form an open single structure. In some aspects, the 5' terminus and 3' terminus are not necessary to form a close loop structure to bring both ends together. In other aspects, nucleotides added at the termini may increase the stability of the polynucleotide and facilitate the binding of a fluorescent dye. The length and sequence of additional nucleotides may vary in the context of the core binding sequence of a signaling polynucleotide. SPNs generated from aptamers against common allergens are listed in Table 1. For example, 1501-SPN A (SEQ ID NO.: 3) and 1501 SPN_B (SEQ ID NO.: 4) are two polynucleotides derived from the aptamer 1501 RiboSPN (SEQ ID NO.: 1).

TABLE 1

Aptamers and SPNs that bind common allergens

| Allergen | SPN ID | SEQ ID NO. | Sequence (5'-3') |
|---|---|---|---|
| Cashew | 1501 RiboSPN_full sequence | 1 | TAATACGACTCACTATAGGCGTAGCCTGATGAGGCACAC CACGTCAAAAATCATTGTCACCACGAAGCCGAAACGTGG TGAAAGCCACGT AGCTGCGCC |
| | 1501 SPN_core sequence | 2 | GCACACCACGTCAAAAATCATTGTCACCACGAAGC |
| | 1501 SPN_A | 3 | GCA GCACACCACGTCAAAAATCATTGTCACCACGAAGC TGC |
| | 1501 SPN_B | 4 | ATGCC GCACACCACGUCAAAAAUCAUUGUCACCACGAAGC GGCAT |
| | 1494 RiboSPN_full sequence | 5 | TAATACGACTCACTATAGGCGTAGCCTGATGAGTGCGCA ACATAAGTCTCTTGAAAGACCACGTTCAACGAAACGTGG TGAAAGCCACGTAGCTGCGCC |
| | 1494 SPN_core sequence | 6 | TGCGCAACATAAGTCTCTTGAAAGACCACGTTCAA |
| | 1494 SPN_A | 7 | CCTGATGAG TGCGCAACATAAGTCTCTTGAAAGACCACGTTCAA CGAAA |
| | 1494 SPN_B | 8 | UUCCTGATGAG TGCGCAACATAAGTCTCTTGAAAGACCACGTTCAA CGAAA |
| | 1494 SPN_C | 9 | UAACTGATGAG TGCGCAACATAAGTCTCTTGAAAGACCACGTTCAA CGUA |
| | 1494 SPN_D | 10 | UACGTGATGAG TGCGCAACATAAGTCTCTTGAAAGACCACGTTCAA CGUA |
| | 1494 SPN_E | 11 | ACATGATGAG TGCGCAACATAAGTCTCTTGAAAGACCACGTTCAA AUGU |
| | 1065 RiboSPN_full sequence | 12 | TAATACGACTCACTATAGGCGTAGCCTGATGAGCACCCA CCATACCAGAAATGTTGACACCACGTGGACGAAACGTGG TGAAAGCCACGTAGCTGCGCC |
| | 1065 SPN_core sequence | 13 | CACCCACCATACCAGAAATGTTGACACCACGTGGA |
| | 1065 SPN_A | 14 | CCTGATGAG CACCCACCATACCAGAAATGTTGACACCACGTGGA CGAAACGTGG |
| | 1065 SPN_B | 15 | UGU CACCCACCATACCAGAAATGTTGACACCACGTGGA CGACA |
| | 1065 SPN_C | 16 | UAU CACCCACCATACCAGAAATGTTGACACCACGTGGA GAUA |
| | 1065 SPN_D | 17 | UCG CACCCACCATACCAGAAATGTTGACACCACGTGGA AAACGA |
| | 1065 SPN_E | 18 | UCA CACCCACCATACCAGAAATGTTGACACCACGTGGA AAAUGA |
| | 1065 SPN_F | 19 | UCGUCC CACCCACCATACCAGAAATGTTGACACCACGTGGA AAAACGA |
| | 1065 SPN_G | 20 | CACCCACCATACCAGAAATGTTGACACCACGTGGA CGAAACGTGGTGAAAG |

TABLE 1-continued

Aptamers and SPNs that bind common allergens

| Allergen | SPN ID | SEQ ID NO. | Sequence (5'-3') |
|---|---|---|---|
| | 1065 SPN_H | 21 | CUU CACCCACCATACCAGAAATGTTGACACCACGTGGA CGAAACGTGGTGAAAGAAG |
| | 1065 SPN_I | 22 | UU CACCCACCATACCAGAAATGTTGACACCACGTGGA CGAAACGTGGTGAAAGAA |
| | 1065 SPN_J | 23 | UA CACCCACCATACCAGAAATGTTGACACCACGTGGA CGAAACGTGGTGUGUA |
| | 1065 SPN_K | 24 | UA CACCCACCATACCAGAAATGTTGACACCACGTGGA CGAAACGTGGTGAUGUA |
| | 1065 SPN_L | 25 | UA CACCCACCATACCAGAAATGTTGACACCACGTGGA CGAAACGTGCAGUA |
| | 1904 RiboSPN_full sequence | 26 | TAATACGACTCACTATAGGCGTAGCCTGATGAGTGCACA ATGTAATTATCAAAATACACCACGTTGGCCGAAACGTGG TGAAAGCCACGTAGCTGCGCC |
| | 1904 SPN_core sequence | 27 | TGCACAATGTAATTATCAAAATACACCACGTTGGC |
| | 1904 SPN_A | 28 | CCTGATGAG TGCACAATGTAATTATCAAAATACACCACGTTGGC CGAAACGTGGTGAAAGG |
| | 1904 SPN_B | 29 | CCAAACCTGATGAG TGCACAATGTAATTATCAAAATACACCACGTTGGC CGAAACGTGGTGACCAAGG |
| | 1904 SPN_C | 30 | CCAAAUUTGATGAG TGCACAATGTAATTATCAAAATACACCACGTTGGC CGAAACGTGGTGAAACCAUGG |
| | 1904 SPN_D | 31 | UAUAAUUTGATGAG TGCACAATGTAATTATCAAAATACACCACGTTGGC CGAAACGTGGTGAAAUCUCUA |
| | 1904 SPN_E | 32 | UAUGGUUTGATGAG TGCACAATGTAATTATCAAAATACACCACGTTGGC CGAAACGTGGTGAAAUCAAUA |
| | 1904 SPN_F | 33 | UGUUTGATGAG TGCACAATGTAATTATCAAAATACACCACGTTGGC CGAAACGTGGTGAAAUCAAACA |
| | 1 RiboSPN_full sequence | 34 | TAATACGACTCACTATAGGCGTAGCCTGATGAGCCACAT CGTGCAATGCCCGAAACATACCACGTAGACGAAACGTGG TGAAAGCCACGTAGCTGCGCC |
| | 1 SPN_core sequence | 35 | CCACATCGTGCAATGCCCGAAACATACCACGTAGA |
| | 1 SPN_A | 36 | CTGAG CCACATCGTGCAATGCCCGAAACATACCACGTAGA CUCAG |
| | 1 SPN_B | 37 | G CCACATCGTGCAATGCCCGAAACATACCACGTAGA GGC |
| | 1 SPN_C | 38 | CCACATCGTGCAATGCCCGAAACATACCACGTAGA |
| | 1 SPN_D | 39 | GUCCAAA CCACATCGTGCAATGCCCGAAACATACCACGTAGA UGGAAAC |
| | 1 SPN_E | 40 | CGCAAA CCACATCGTGCAATGCCCGAAACATACCACGTAGA AAGCG |
| | 1 SPN_F | 41 | CCACATCGTGCAATGCCCGAAACATACCACGTAGA UGUGG |
| | 1 SPN_G | 42 | CCACATCGTGCAATGCCCGAAACATACCACGTAGA CAAGG |
| | 28 RiboSPN_full sequence | 43 | TAATACGACTCACTATAGGCGTAGCCTGATGAGCTATGC AGTGATGATTAAAGATACCACCACGTGAGCGAAACGTGG TGAAAGCCACGTAGCTGCGCC |
| | 28 SPN_core sequence | 44 | CTATGCAGTGATGATTAAAGATACCACCACGTGAG |
| | 28 SPN_A | 45 | GATGAG CTATGCAGTGATGATTAAAGATACCACCACGTGAG CGAAACGTGGTGA |
| | 28 SPN_B | 46 | G CTATGCAGTGATGATTAAAGATACCACCACGTGAG CGAAACGTGGTGAAAGC |
| | 28 SPN_C | 47 | A CTATGCAGTGATGATTAAAGATACCACCACGTGAG CGAAACGTGGTGAAAGU |
| | 28 SPN_D | 48 | UA CTATGCAGTGATGATTAAAGATACCACCACGTGAG CGAA ACGTGGTGAGUA |
| | 28 SPN_E | 49 | G CTATGCAGTGATGATTAAAGATACCACCACGTGAG CGAAACGTGGTCCGC |
| | 28 SPN_F | 50 | GGUUGATGAG CTATGCAGTGATGATTAAAGATACCACCACGTGAG CGAAACGTGGTGAAACC |

TABLE 1-continued

Aptamers and SPNs that bind common allergens

| Allergen | SPN ID | SEQ ID NO. | Sequence (5'-3') |
|---|---|---|---|
| | 28 SPN_G | 51 | UUGGATGAG CTATGCAGTGATGATTAAAGATACCACCACGTGAG CGAAACGTGGTGACAA |
| | 28 SPN_H | 52 | UCGGATGAG CTATGCAGTGATGATTAAAGATACCACCACGTGAG CGAAACGTGGTGAAACGA |
| | 28 SPN_I | 53 | AUGATGAG CTATGCAGTGATGATTAAAGATACCACCACGTGAG CGAAACGTGGTGAAACCAU |
| | 28 SPN_J | 54 | AUGGAG CTATGCAGTGATGATTAAAGATACCACCACGTGAG CGAAACGTGGTGAAACAU |
| | 28 SPN_K | 55 | GUAAA CTATGCAGTGATGATTAAAGATACCACCACGTGAG CGAAACGTGGTGAAUGC |
| Peanut | 2047 RiboSPN_full sequence | 56 | TAATACGACTCACTATAGGCGTAGCCTGATGAGCAAATA GTTACAAACACCACGTAGCGAAACGTGGTGAAAGCCACG TAGCTGCGCC |
| | 2047 SPN_core sequence | 57 | CAAATAGTTACAAACACCACGTAG |
| | 2047 SPN_A | 58 | UUCG CAAATAGTTACAAACACCACGTAG CGAA |
| | 2047 SPN_B | 59 | AUCG CAAATAGTTACAAACACCACGTAG CGAU |
| | 1981 RiboSPN_full sequence | 60 | TAATACGACTCACTATAGGCGTAGCCTGATGAGCCCAAC TGTACAGTACACCACGTAGCGAAACGTGGTGAAAGCCAC GTAGCTGCGCC |
| | 1981 SPN_core sequence | 61 | CCCAACTGTACAGTACACCACGTAG |
| | 1981 SPN_A | 62 | GAG CCCAACTGTACAGTACACCACGTAG CGAAACGTGGTGAAACUC |
| | 1981 SPN_B | 63 | UAU CCCAACTGTACAGTACACCACGTAG CGAAACGTGGTGAAAGGAAGAUA |
| | 2108 RiboSPN_full sequence | 64 | TAATACGACTCACTATAGGCGTAGCCTGATGAGCACACA CACATTCCACCACGTCACGCGAAACGTGGTGAAAGCCAC GTAGCTGCGCC |
| | 2108-SPN_core sequence | 65 | CACACACACATTCCACCACGTCACG |
| | 2108-SPN_A | 66 | CTGATGAG CACACACACATTCCACCACGTCACG |
| | 2108 SPN_B | 67 | GAUGATGAG CACACACACATTCCACCACGTCACG |
| | 2108 SPN_C | 68 | UGAUGATGAG CACACACACATTCCACCACGTCACG A |
| | 2108 SPN_D | 69 | UUAUUGATGAG CACACACACATTCCACCACGTCACG UAA |
| | 1785 RiboSPN_full sequence | 70 | TAATACGACTCACTATAGGCGTAGCCTGATGAGCACACG TTACCACACCACGTTGACGCGAAACGTGGTGAAAGCCAC GTAGCTGCGCC |
| | 1785 SPN_core sequence | 71 | CACACGTTACCACACCACGTTGACG |
| | 1785 SPN_A | 72 | AUCTGATGAG CACACGTTACCACACCACGTTGACG CGAAACGAGAU |
| | 1785 SPN_B | 73 | TAUUGAG CACACGTTACCACACCACGTTGACG CGAAUA |
| | 1785 SPN_C | 74 | TGAUUGAG CACACGTTACCACACCACGTTGACG CGAAUCA |
| | 1785 SPN_D | 75 | GUUGAG CACACGTTACCACACCACGTTGACG CGAA |
| | 1785 SPN_E | 76 | AUUGAG CACACGTTACCACACCACGTTGACG CGAU |
| | 1 RiboSPN_full sequence | 77 | TAATACGACTCACTATAGGCGTAGCCTGATGAGCGTGCC CGAAACACACACCACGATGCGAAACGTGGTGAAAGCCAC GTAGCTGCGCC |
| | 1 SPN_core sequence | 78 | CGTGCCCGAAACACACACCACGATG |
| | 1 SPN_A | 79 | UUGAG CGTGCCCGAAACACACACCACGATG CGAAACGUCAA |
| | 1 SPN_B | 80 | UUAG CGTGCCCGAAACACACACCACGATG CGAAACGCUAA |
| | 1 SPN_C | 81 | GAUAGA CGTGCCCGAAACACACACCACGATG CGAAAUGUC |
| | 1 SPN_D | 82 | UGAUAGA CGTGCCCGAAACACACACCACGATG CGAAAUGUCA |
| | 7 RiboSPN_full sequence | 83 | TAATACGACTCACTATAGGCGTAGCCTGATGAGCTCACC ACATACCATGTACCACGTGCGAAACGTGGTGAAAGCCAC GTAGCTGCGCC |
| | 7 SPN_core Sequence | 84 | CTCACCACATACCATGTACCACGTG |
| | 7 SPN_A | 85 | CCTGATGAG CTCACCACATACCATGTACCACGTG CGAAACGTGGTGAAGC |

TABLE 1-continued

Aptamers and SPNs that bind common allergens

| Allergen | SPN ID | SEQ ID NO. | Sequence (5'-3') |
|---|---|---|---|
| | 7 SPN_B | 86 | GAG CTCACCACATACCATGTACCACGTG CGAAUGA |
| | 7 SPN_C | 87 | CTCACCACATACCATGTACCACG TGCGAAUGA |
| | 7 SPN_D | 88 | GCUCCTGATGAG CTCACCACATACCATGTACCACGTG CGAAACGTGGTGAAGC |
| | 7 SPN_E | 89 | CAUGATGAG CTCACCACATACCATGTACCACGTG CGAACAUG |
| | 7 SPN_F | 90 | UCAUACGAG CTCACCACATACCATGTACCACGTG CGAAUGA |
| | 7 SPN_G | 91 | UCAUACGAG CTCACCACATACCATGTACCACGTG CGAAUGA |
| | 7 SPN_H | 92 | GCUCCTGATGAG CTCACCACATACCATGTACCACGTG CGAAACGTGGTGAAGC |
| | 7 SPN_I | 93 | CCTGATGAG CTCACCACATACCATGTACCACGTG CGAAACGTGGTGAAGC |
| | 7 SPN_J | 94 | CAUGATGAG CTCACCACATACCATGTACCACGTG CGAACAUG |
| | 7 SPN_K | 95 | UCAUACGAG CTCACCACATACCATGTACCACGTG CGAAUGA |
| | 7 SPN_L | 96 | UCAUACGAG CTCACCACATACCATGTACCACG TGCGAAUGA |
| Milk | 35 RiboSPN_full sequence | 97 | TAATACGACTCACTATAGGCGTAGCCTGATGAGTTCACTG GCTGCACCCACCACCGCGTTCCACGAAACGTGGTGAAAG CCACGTAGCTGCGCC |
| | 35 SPN_core sequence | 98 | TTCACTGGCTGCACCCACCACCGCGTTCCA |
| | 35 SPN_A | 99 | GATGAG TTCACTGGCTGCACCCACCACCGCGTTCCA CGAAACGTGGTGAAAGCCA |
| | 35 SPN_B | 100 | CGUCCTGATGAG TTCACTGGCTGCACCCACCACCGCGTTCCA CGAAACGTGGTGAAAGCCAACG |
| | 35 SPN_C | 101 | AGCUCCTGATGAG TTCACTGGCTGCACCCACCACCGCGTTCCA CGAAACGTGGTGAAAGCCAAGCU |
| | 35 SPN_D | 102 | AUCUCCTGATGAG TTCACTGGCTGCACCCACCACCGCGTTCCA CGAAACGTGGTGAAAG |
| | 35 SPN_E | 103 | GCUACCTGATGAG TTCACTGGCTGCACCCACCACCGCGTTCCA CGAAACGTGGTGAAAGCCAUAGC |
| | 35 SPN_F | 104 | CCACCTGATGAG TTCACTGGCTGCACCCACCACCGCGTTCCA CGAAACGTGGTGAAAGCCAAAGG |
| | 35 SPN_G | 105 | UACCTGATGAG TTCACTGGCTGCACCCACCACCGCGTTCCA CGAAACGTGGTGAAAGCCAGGUA |
| | 35 SPN_H | 106 | AUACCTGATGAG TTCACTGGCTGCACCCACCACCGCGTTCCA CGAAACGTGGTGAAAGCCAGGUAU |
| | 35 SPN_I | 107 | CUACCTGATGAG TTCACTGGCTGCACCCACCACCGCGTTCCA CGAAACGTGGTGAAAGCCAAAUAG |
| | 35 SPN_J | 108 | UACCTGATGAG TTCACTGGCTGCACCCACCACCGCGTTCCA CGAAACGTGGTGAAAGCCAAAGUA |
| | 45 RiboSPN_full sequence | 109 | TAATACGACTCACTATAGGCGTAGCCTGATGAGCATCCA CGGTGACGCTAATCCCACGTTCGACGAAACGTGGTGAAA GCCACGTAGCTGCGCC |
| | 45 SPN_core sequence | 110 | CATCCACGGTGACGCTAATCCCACGTTCGA |
| | 45 SPN_A | 111 | CCTGATGAG CATCCACGGTGACGCTAATCCCACGTTCGA CGAAAGG |
| | 45 SPN_B | 112 | AGACCTGATGAG CATCCACGGTGACGCTAATCCCACGTTCGA CGAAUCU |
| | 45 SPN_C | 113 | AGCCTGATGAG CATCCACGGTGACGCTAATCCCACGTTCGA CGAAGCU |
| | 45 SPN_D | 114 | UAUCCTGATGAG CATCCACGGTGACGCTAATCCCACGTTCGA CGGAAUA |
| | 45 SPN_E | 115 | GUCGATGAG CATCCACGGTGACGCTAATCCCACGTTCGA GAC |
| | 45 SPN_F | 116 | UCGATGAG CATCCACGGTGACGCTAATCCCACGTTCGA GA |
| | 45 SPN_G | 117 | UCGATGAG CATCCACGGTGACGCTAATCCCACGTTCGA G |

TABLE 1-continued

Aptamers and SPNs that bind common allergens

| Allergen | SPN ID | SEQ ID NO. | Sequence (5'-3') |
|---|---|---|---|
| | 74 RiboSPN_full sequence | 118 | TAATACGACTCACTATAGGCGTAGCCTGATGAGACAATG CAGATGCGCCCACCACGGATCACTCGAAACGTGGTGAAA GCCACGTAGCTGCGCC |
| | 74 SPN_core sequence | 119 | ACAATGCAGATGCGCCCACCACGGATCACT |
| | 74 SPN_A | 120 | CCTGATGAG ACAATGCAGATGCGCCCACCACGGATCACT CGAAACGTGGTGAAAGCCA |
| | 74 SPN_B | 121 | GAG ACAATGCAGATGCGCCCACCACGGATCACT |
| | 74 SPN_C | 122 | GAG ACAATGCAGATGCGCCCACCACGGATCACT C |
| | 74 SPN_D | 123 | GAC ACAATGCAGATGCGCCCACCACGGATCACT CGUC |
| | 74 SPN_E | 124 | CCTGATGAG ACAATGCAGATGCGCCCACCACGGATCACT CGAAACGTGGTGAAAGCCAAGG |
| | 16 RiboSPN_full sequence | 125 | TAATACGACTCACTATAGGCGTAGCCTGATGAGCAACCA AGCACGCTGCATCACGTTTCATCGCGAAACGTGGTGAAA GCCACGTAGCTGCGCC |
| | 16 SPN_core sequence | 126 | CAACCAAGCACGCTGCATCACGTTTCATCG |
| | 16 SPN_A | 127 | GAG CAACCAAGCACGCTGCATCACGTTTCATCG CGAAACGTGGCUC |
| | 16 SPN_B | 128 | GUU CAACCAAGCACGCTGCATCACGTTTCATCG CGAAACGTGGAAC |
| | 16 SPN_C | 129 | UU CAACCAAGCACGCTGCATCACGTTTCATCG CGAAACGTUGAA |
| | 16 SPN_D | 130 | CGATGAG CAACCAAGCACGCTGCATCACGTTTCATCG |
| | 1 RiboSPN_full sequence | 131 | TAATACGACTCACTATAGGCGTAGCCTGATGAGCTCACA GCCCGAAACACATCGCCACGTTCACGAAACGTGGTGAAA GCCACGTAGCTGCGCC |
| | 1 SPN_core sequence | 132 | CTCACAGCCCGAAACACATCGCCACGTTCA |
| | 1 SPN_A | 133 | TGAG CTCACAGCCCGAAACACATCGCCACGTTCA CGAAATGAG |
| | 1 SPN_B | 134 | CTCACAGCCCGAAACACATCGCCACGTTCA AAACG |
| | 1 SPN_C | 135 | UAUCG CTCACAGCCCGAAACACATCGCCACGTTCA CGAAACGTGGTGAAAGAUA |
| Fish | 301 RiboSPN_full sequence | 136 | TAATACGACTCACTATAGGCGTAGCCTGATGAGCTCAAT ACTACGTCAATTCACAGATGATAGACACCACGGACGAAA CGTGGTGAAAGCCACGTAGCTGCGCC |
| | 301 SPN_core sequence | 137 | CTCAATACTACGTCAATTCACAGATGATAGACACCACGG A |
| | 301 SPN_A | 138 | GAG CTCAATACTACGTCAATTCACAGATGATAGACACCAC GGA CGAAACGTGGTGAAAG |
| | 301 SPN_B | 139 | GAG CTCAATACTACGTCAATTCACAGATGATAGACACCAC GGA CGAAACGTGGTGACUC |
| | 301 SPN_C | 140 | GUAAG CTCAATACTACGTCAATTCACAGATGATAGACACCAC GGA CGAAACGTGGTGACUAC |
| | 301 SPN_D | 141 | CUAAG CTCAATACTACGTCAATTCACAGATGATAGACACCAC GGA CGAAACGTGGTGACUAG |
| | 301 SPN_E | 142 | CUGU CTCAATACTACGTCAATTCACAGATGATAGACACCAC GGA CGAAACGTGGTGACAG |
| | 301 SPN_F | 143 | CUGA CTCAATACTACGTCAATTCACAGATGATAGACACCAC GGA CGAAACGTGGTGACAG |
| | 301 SPN_G | 144 | CGA CTCAATACTACGTCAATTCACAGATGATAGACACCAC GGA CGAAACGTGGTGUUUG |
| | 301 SPN_H | 145 | UCUGA CTCAATACTACGTCAATTCACAGATGATAGACACCAC GGA CGAAACGTGGTGAUAGA |
| | 301 SPN_I | 146 | AAAAG CTCAATACTACGTCAATTCACAGATGATAGACACCAC GGA CGAAACGTGGTGACUUAU |
| | 301 SPN_J | 147 | GAAAG CTCAATACTACGTCAATTCACAGATGATAGACACCAC GGA CGAAACGTGGTGACUUAC |
| | 301 SPN_K | 148 | CUCAG CTCAATACTACGTCAATTCACAGATGATAGACACCAC GGA CGAAACGTGGTGACGAG |

TABLE 1-continued

Aptamers and SPNs that bind common allergens

| Allergen | SPN ID | SEQ ID NO. | Sequence (5'-3') |
|---|---|---|---|
| | 333 RiboSPN_full sequence | 149 | TAATACGACTCACTATAGGCGTAGCCTGATGAGTCCAAC ACCACGTAACGTACACTGCATGTGATTGGTGCAACGAAA CGTGGTGAAAGCCACGTAGCTGCGCC |
| | 333 SPN_core sequence | 150 | TCCAACACCACGTAACGTACACTGCATGTGATTGGTGCA A |
| | 333 SPN_A | 151 | CCTGATGAG TCCAACACCACGTAACGTACACTGCATGTGATTGGTG CAA CGAAACGTGG |
| | 333 SPN_B | 152 | TAGCCTGATGAG TCCAACACCACGTAACGTACACTGCATGTGATTGGTG CAA CGAAACGTGGTGA |
| | 333 SPN_C | 153 | GATGAG TCCAACACCACGTAACGTACACTGCATGTGATTGGTG CAA CGAA |
| | 333 SPN_D | 154 | UUAAGATGAG TCCAACACCACGTAACGTACACTGCATGTGATTGGTG CAA CGAAUUAA |
| | 333 SPN_E | 155 | UGAAGATGAG TCCAACACCACGTAACGTACACTGCATGTGATTGGTG CAA CGAAUUCA |
| | 333 SPN_F | 156 | UCACGATGAG TCCAACACCACGTAACGTACACTGCATGTGATTGGTG CAA CGAA GUGA |
| | 365 RiboSPN_full sequence | 157 | TAATACGACTCACTATAGGCGTAGCCTGATGAGTGGCGC CGACTGATCAACTAGACATCACGTTAGCATTCCGCGAAA CGTGGTGAAAGCCACGTAGCTGCGCC |
| | 365 SPN_core sequence | 158 | TGGCGCCGACTGATCAACTAGACATCACGTTAGCATTCCG |
| | 365 SPN_A | 159 | CCTGATGAG TGGCGCCGACTGATCAACTAGACATCACGTTAGCATT CCG CGAAACGTGG |
| | 365 SPN_B | 160 | GATGAG TGGCGCCGACTGATCAACTAGACATCACGTTAGCATT CCG CGAAACG |
| | 365 SPN_C | 161 | UGTGAG TGGCGCCGACTGATCAACTAGACATCACGTTAGCATT CCG CGAAACG |
| | 365 SPN_D | 162 | CCTGATGAG TGGCGCCGACTGATCAACTAGACATCACGTTAGCATT CCG CGAAACGAGG |
| | 365 SPN_E | 163 | GATGAG TGGCGCCGACTGATCAACTAGACATCACGTTAGCATT CCG CGAAACGTGGTGAAAGCCA |
| | 365 SPN_F | 164 | CATGAG TGGCGCCGACTGATCAACTAGACATCACGTTAGCATT CCG CGAAACGTGGTGAAAGCAUG |
| | 365 SPN_G | 165 | TAGAG TGGCGCCGACTGATCAACTAGACATCACGTTAGCATT CCG CGAAACGTGGTGAAAGCUCUA |
| | 365 SPN_H | 166 | AGAG TGGCGCCGACTGATCAACTAGACATCACGTTAGCATT CCG CGAAACGTGGTGAAAGCUUU |
| | 38 RiboSPN_full sequence | 167 | TAATACGACTCACTATAGGCGTAGCCTGATGAGCCAGCA ACCAGGTTACCTCCCATCACGCTTCGTCTCAGGACGAAAC GTGGTGAAAGCCACGTAGCTGCGCC |
| | 38 SPN_core sequence | 168 | CCAGCAACCAGGTTACCTCCCATCACGCTTCGTCTCAGGA |
| | 38 SPN_A | 169 | CCTGATGAG CCAGCAACCAGGTTACCTCCCATCACGCTTCGTCTCA GGA CGAAACG |
| | 38 SPN_B | 170 | GATGAG CCAGCAACCAGGTTACCTCCCATCACGCTTCGTCTCA GGA CGAAACG |
| | 38 SPN_C | 171 | GATGAG CCAGCAACCAGGTTACCTCCCATCACGCTTCGTCTCA GGA CGAA |
| | 38 SPN_D | 172 | CAAGATGAG CCAGCAACCAGGTTACCTCCCATCACGCTTCGTCTCA GGA CGAAUUG |
| | 38 SPN_E | 173 | CAAGATGAG CCAGCAACCAGGTTACCTCCCATCACGCTTCGTCTCA GGA CGAUUUG |
| | 38 SPN_F | 174 | CCAAGATGAG CCAGCAACCAGGTTACCTCCCATCACGCTTCGTCTCA GGA CGACUUUGG |

TABLE 1-continued

Aptamers and SPNs that bind common allergens

| Allergen | SPN ID | SEQ ID NO. | Sequence (5'-3') |
|---|---|---|---|
| | 38 SPN_G | 175 | ACAAGATGAG CCAGCAACCAGGTTACCTCCCATCACGCTTCGTCTCA GGA CGACUUUGU |
| | 38 SPN_H | 176 | ACAGATGAG CCAGCAACCAGGTTACCTCCCATCACGCTTCGTCTCA GGA CGACUUUGU |
| | 1 RiboSPN_full sequence | 177 | TAATACGACTCACTATAGGCGTAGCCTGATGAGCTGACA CCCACAAACGATTATGACCACGTTATCGTACATAGCGAAA CGTGGTGAAAGCCACGTAGCTGCGCC |
| | 1 SPN_core sequence | 178 | CTGACACCACAAACGATTATGACCACGTTATCGTACATA G |
| | 1 SPN_A | 179 | TAGGCGTAGCCTGATGAG CTGACACCACAAACGATTATGACCACGTTATCGTACAT AG CGAA |
| | 1 SPN_B | 180 | GAG CTGACACCACAAACGATTATGACCACGTTATCGTACAT AG CGAAACGTGGTGAAAGCCA |
| | 1 SPN_C | 181 | AGAG CTGACACCACAAACGATTATGACCACGTTATCGTACAT AG CGAAACGTGGTGAAAGCCAU |
| | 1 SPN_D | 182 | UGAG CTGACACCACAAACGATTATGACCACGTTATCGTACAT AG CGAAACGTGGTGAAAGCCUCA |
| | 1 SPN_E | 183 | UGAAG CTGACACCACAAACGATTATGACCACGTTATCGTACAT AG CGAAACGTGGTGAAAGCCGUCA |
| | 1 SPN_F | 184 | UGAAG CTGACACCACAAACGATTATGACCACGTTATCGTACAT AG CGAAACGTGGCGUCA |
| | 1 SPN_G | 185 | AUGAAG CTGACACCACAAACGATTATGACCACGTTATCGTACAT AG CGAAACGTGGCGUCAU |
| | 1 SPN_H | 186 | GUAA CTGACACCACAAACGATTATGACCACGTTATCGTACAT AG CGAAACGTGGTGAAAGCCUAC |
| | 1 SPN_I | 187 | UGUAAG CTGACACCACAAACGATTATGACCACGTTATCGTACAT AG CGAAACGTGGTGAAAGAGGCA |
| | 1 SPN_J | 188 | UGUAAAG CTGACACCACAAACGATTATGACCACGTTATCGTACAT AG CGAAACGTGGTGAAAGAGGCA |
| | 27 RiboSPN_full sequence | 189 | TAATACGACTCACTATAGGCGTAGCCTGATGAGTAGGTC AAGTGCGCTAAAACACACCGCGTTAGTTCACCAACGAAA CGTGGTGAAAGCCACGTAGCTGCGCC |
| | 27 SPN_core sequence | 190 | TAGGTCAAGTGCGCTAAAACACACCGCGTTAGTTCACCA A |
| | 27 SPN_A | 191 | A TAGGTCAAGTGCGCTAAAACACACCGCGTTAGTTCAC CAA CGAAACGTGGTGAAAGAUAAU |
| | 27 SPN_B | 192 | GA TAGGTCAAGTGCGCTAAAACACACCGCGTTAGTTCAC CAA CGAAACGTGGTGAAAGAUAAUC |
| Egg | 1013 RiboSPN_full sequence | 193 | TAATACGACTCACTATAGGCGTAGCCTGATGAGGCCACC TCACTGTGTTTTGTTGCACAACATAATATGATGACGTGCC GAAACGTGGTGAAAGCCACGTAGCTGCGCC |
| | 1013 SPN_core sequence | 194 | GGCCACCTCACTGTGTTTTGTTGCACAACATAATATGATG ACGTGC |
| | 1013 SPN_A | 195 | GCACGA GGCCACCUCACUGUGUUUUGUUGCACAACAUAAUAUG AUGACGUGC |
| | 1013 SPN_B | 196 | GCACGUA GGCCACCUCACUGUGUUUUGUUGCACAACAUAAUAUG AUGACGUGC |
| | 1013 SPN_C | 197 | GCACGUAU GGCCACCUCACUGUGUUUUGUUGCACAACAUAAUAUG AUGACGUGC |
| | 1013 SPN_D | 198 | GCACCUG GGCCACCUCACUGUGUUUUGUUGCACAACAUAAUAUG AUGACGUGC |
| | 1013 SPN_E | 199 | GCAC GGCCACCUCACUGUGUUUUGUUGCACAACAUAAUAUG AUGACGUGC |

TABLE 1-continued

Aptamers and SPNs that bind common allergens

| Allergen | SPN ID | SEQ ID NO. | Sequence (5'-3') |
|---|---|---|---|
| | 1013 SPN_F | 200 | TT GGCCACCUCACUGUGUUUUGUUGCACAACAUAAUAUG AUGACGUGCC GAA |
| | 1013 SPN_G | 201 | GCCACCUCACUGUGUUUUGUUGCACAACAUAAUAUGAU GACGUGCGGUGGC |
| | 1013 SPN_H | 202 | GCACGCCACCUCACUGUGUUUUGUUGCACAACAUAAUA UGAUGACGUGC |
| | 851 RiboSPN_full sequence | 203 | TAATACGACTCACTATAGGCGTAGCCTGATGAGGCGTTCC CCACCGTTGCCCACGCTTAACTGGACAAAGATGGGCCCC GAAACGTGGTGAAAGCCACGTAGCTGCGCC |
| | 851 SPN_core sequence | 204 | GCGTTCCCCACCGTTGCCCACGCTTAACTGGACAAAGATG GGCCC |
| | 851 SPN_A | 205 | GCGTTCCCCACCGTTGCCCACGCTTAACTGGACAAAG ATGGGCCC AACGC |
| | 851 SPN_B | 206 | GGGCCCA GCGTTCCCCACCGTTGCCCACGCTTAACTGGACAAAG ATGGGCCC |
| | 851 SPN_C | 207 | ACC GCGTTCCCCACCGTTGCCCACGCTTAACTGGACAAAG ATGGGCCC AGGA |
| | 851 SPN_D | 208 | TTGG GCGTTCCCCACCGTTGCCCACGCTTAACTGGACAAAG ATGGGCCC GA |
| | 851 SPN_E | 209 | TAGG GCGTTCCCCACCGTTGCCCACGCTTAACTGGACAAAG ATGGGCCC GAA |
| | 851 SPN_F | 210 | TG GCGTTCCCCACCGTTGCCCACGCTTAACTGGACAAAG ATGGGCCC A |
| | 851 SPN_G | 211 | U GCGTTCCCCACCGTTGCCCACGCTTAACTGGACAAAG ATGGGCCC UGUG |
| | 851 SPN_H | 212 | TTGG GCGTTCCCCACCGTTGCCCACGCTTAACTGGACAAAG ATGGGCCC GGAA |
| | 851 SPN_I | 213 | TTC GCGTTCCCCACCGTTGCCCACGCTTAACTGGACAAAG ATGGGCCU GAG |
| | 505 RiboSPN_full sequence | 214 | TAATACGACTCACTATAGGCGTAGCCTGATGAGTCTGTGC ACATCACTCGACCTCTACGGCTGTATTGATCCTGCATACG AAACGTGGTGAAAGCCACGTAGCTGCGCC |
| | 505 SPN_core sequence | 215 | TCTGTGCACATCACTCGACCTCTACGGCTGTATTGATCCT GCATA |
| | 505 SPN_A | 216 | TCTGTGCACATCACTCGACCTCTACGGCTGTATTGATC CTGCATA GUGCACAGA |
| | 505 SPN_B | 217 | CCUAUGC TCTGTGCACATCACTCGACCTCTACGGCTGTATTGATC CTGCATA GG |
| | 505 SPN_C | 218 | GCUAGAGTGCACATCACTCGACCTCTACGGCTGTATT GATCCTGCATA AGAGC |
| | 780 RiboSPN_full sequence | 219 | TAATACGACTCACTATAGGCGTAGCCTGATGAGCGTTCCA ACGTTCGATCAGAACCGCGTTCAGGCTGATGATTGTACGC GAAACGTGGTGAAAGCCACGTAGCTGCGCC |
| | 780 SPN_core sequence | 220 | CGTCCAACGTTCGATCAGAACCGCGTTCAGGCTGATGATT GTACG |
| | 780 SPN_A | 221 | CGTCCAACGTTCGATCAGAACCGCGTTCAGGCTGATG ATTGTACG UUCCACG |
| | 780 SPN_B | 222 | GCUUA CGTCCAACGTTCGATCAGAACCGCGTTCAGGCTGATG ATTGTACG UAAGC |
| | 780 SPN_C | 223 | TGATGAG CGTCCAACGTTCGATCAGAACCGCGTTCAGGCTGATG ATTGTACG CGAAACG |
| | 780 SPN_D | 224 | CGTGATGAG CGTCCAACGTTCGATCAGAACCGCGTTCAGGCTGATG ATTGTACG CGACG |
| | 780 SPN_E | 225 | CAAGTGATGAG CGTCCAACGTTCGATCAGAACCGCGTTCAGGCTGATG ATTGTACG CGACTTG |
| | 780 SPN_F | 226 | AUAGTGATGAG CGTCCAACGTTCGATCAGAACCGCGTTCAGGCTGATG ATTGTACG CGACTAT |
| | 1 RiboSPN_full sequence | 227 | TAATACGACTCACTATAGGCGTAGCCTGATGAGCATCAG TGCGTTCTGCCTTTGCAACCACACAACACACCGTATGAGC GAAACGTGGTGAAAGCCACGTAGCTGCGCC |

TABLE 1-continued

Aptamers and SPNs that bind common allergens

| Allergen | SPN ID | SEQ ID NO. | Sequence (5'-3') |
|---|---|---|---|
| | 1 SPN_core sequence | 228 | CATCAGTGCGTTCTGCCTTTGCAACCACACAACACACCGT ATGAG |
| | 1 SPN_A | 229 | CUCAUA CATCAGTGCGTTCTGCCTTTGCAACCACACAACACAC CGTATGAG |
| | 1 SPN_B | 230 | GCUUA CATCAGTGCGTTCTGCCTTTGCAACCACACAACACAC CGTATGAG UAAGC |
| | 1 SPN_C | 231 | CCTGATGAG CATCAGTGCGTTCTGCCTTTGCAACCACACAACACAC CGTATGAG CGAAACG |
| | 1 SPN_D | 232 | GCAG CATCAGTGCGTTCTGCCTTTGCAACCACACAACACAC CGTATGAG CGC |
| | 1 SPN_E | 233 | TTGAG CATCAGTGCGTTCTGCCTTTGCAACCACACAACACAC CGTATGAG CGAA |
| | 1 SPN_F | 234 | TGCAG CATCAGTGCGTTCTGCCTTTGCAACCACACAACACAC CGTATGAG CGCG |
| | 1 SPN_G | 235 | CGCAG CATCAGTGCGTTCTGCCTTTGCAACCACACAACACAC CGTATGAG CGCG |
| | 17 RiboSPN_full sequence | 236 | TAATACGACTCACTATAGGCGTAGCCTGATGAGCCAACT GTGCACACTGTTCGCTTATCGAGCTGTGTACCTCCATAGC GAAACGTGGTGAAAGCCACGTAGCTGCGCC |
| | 17 SPN_core sequence | 237 | CCAACTGTGCACACTGTTCGCTTATCGAGCTGTGTACCTC CATAG |
| | 17 SPN_A | 238 | CCTGATGAG CCAACTGTGCACACTGTTCGCTTATCGAGCTGTGTAC CTCCATAG CGAAACGTGG |
| | 17 SPN_B | 239 | ACUCCTGATGAG CCAACTGTGCACACTGTTCGCTTATCGAGCTGTGTAC CTCCATAG CGAAACGAGGCAT |
| | 17 SPN_C | 240 | ATGCCTGATGAG CCAACTGTGCACACTGTTCGCTTATCGAGCTGTGTAC CTCCATAG CGAAACGTGGTGAA |
| | 17 SPN_D | 241 | AACCTGATGAG CCAACTGTGCACACTGTTCGCTTATCGAGCTGTGTAC CTCCATAG CGAAACGTGGCA |
| | 17 SPN_E | 242 | AACTGATGAG CCAACTGTGCACACTGTTCGCTTATCGAGCTGTGTAC CTCCATAG CGAAACAGUU |
| | 17 SPN_F | 243 | CATGCCTGATGAG CCAACTGTGCACACTGTTCGCTTATCGAGCTGTGTAC CTCCATAG CGAAACGTGGTGAAGUG |
| | 17 SPN_G | 244 | CCAACTGTGCACACTGTTCGCTTATCGAGCTGTGTAC CTCCATAG GUUGG |
| | 17 SPN_H | 245 | CUAUGG CCAACTGTGCACACTGTTCGCTTATCGAGCTGTGTAC CTCCATAG |
| Gluten | 457 RiboSPN_full sequence | 246 | TAATACGACTCACTATAGGCGTAGCCTGATGAGCTTGGTC ACCTTTCCTGACATTAACACAGGCGAAACGTGGTGAAAG CCACGTAGCTGCGCC |
| | 457 SPN_core sequence | 247 | CTTGGTCACCTTTCCTGACATTAACACAGG |
| | 457 SPN_A | 248 | CTTGGTCACCTTTCCTGACATTAACACAGG CCAAG |
| | 457 SPN_B | 249 | CCUGU CTTGGTCACCTTTCCTGACATTAACACAGG |
| | 491 RiboSPN_full sequence | 250 | TAATACGACTCACTATAGGCGTAGCCTGATGAGTTTTCCC GATACGGCTACGAATTGCGACAACGAAACGTGGTGAAAG CCACGTAGCTGCGCC |
| | 491 SPN_core sequence | 251 | TTTTCCCGATACGGCTACGAATTGCGACAA |
| | 491 SPN_A | 252 | CC TTTTCCCGATACGGCTACGAATTGCGACAA AAGG |
| | 491 SPN_B | 253 | GCUUA TTTTCCCGATACGGCTACGAATTGCGACAA UAAGC |
| | 578 RiboSPN_full sequence | 254 | TAATACGACTCACTATAGGCGTAGCCTGATGAGGCACCA ATTTTACCGATTTTGGTGGACAGCCGAAACGTGGTGAAA GCCACGTAGCTGCGCC |
| | 578 SPN_core sequence | 255 | GCACCAATTTTACCGATTTTGGTGGACAGC |
| | 578 SPN_A | 256 | GCUGUCC GCACCAATTTTACCGATTTTGGTGGACAGC |
| | 578 SPN_B | 257 | GCACCAATTTTACCGATTTTGGTGGACAGC UUGGUGC |
| | 1514 | 258 | TAATACGACTCACTATAGGCGTAGCCTGATGAGCGTACA |

TABLE 1-continued

Aptamers and SPNs that bind common allergens

| Allergen | SPN ID | SEQ ID NO. | Sequence (5'-3') |
|---|---|---|---|
| | RiboSPN_full sequence | | ACCCACCACCGTTGTCCACAAATGCGAAACGTGGTGAAA GCCACGTAGCTGCGCC |
| | 1514 SPN_core sequence | 259 | CGTACAACCCACCACCGTTGTCCACAAATG |
| | 1514 SPN_A | 260 | CAUUUG CGTACAACCCACCACCGTTGTCCACAAATG |
| | 1514 SPN_B | 261 | CGTACAACCCACCACCGTTGTCCACAAATG UUGUACG |
| | 1 RiboSPN_full sequence | 262 | TAATACGACTCACTATAGGCGTAGCCTGATGAGTGCGTC AACGGCCGTCCCGAAACGTGAATACGAAACGTGGTGAAA GCCACGTAGCTGCGCC |
| | 1 SPN_core sequence | 263 | TGCGTCAACGGCCGTCCCGAAACGTGAATA |
| | 1 SPN_A | 264 | UAUUCA TGCGTCAACGGCCGTCCCGAAACGTGAATA |
| | 1 SPN_B | 265 | GCUUA TGCGTCAACGGCCGTCCCGAAACGTGAATA UAAGC |
| | 35 RiboSPN_full sequence | 266 | TAATACGACTCACTATAGGCGTAGCCTGATGAGGTTACCC CGAAACGGCCCTAACTGCATCAGCGAAACGTGGTGAAAG CCACGTAGCTGCGCC |
| | 35 SPN_core sequence | 267 | GTTACCCCGAAACGGCCCTAACTGCATCAG |
| | 35 SPN_A | 268 | CUGAUGC GTTACCCCGAAACGGCCCTAACTGCATCAG |
| | 35 SPN_B | 269 | GTTACCCCGAAACGGCCCTAACTGCATCAG GGGUAAC |
| Soy | 1 RiboSPN_full sequence | 270 | TAATACGACTCACTATAGGCGTAGCCTGATGAGCCGCAT CACCCACCCAAACCACCGTTCGAAACGTGGTGAAAGCCAC GTAGCTGCGCC |
| | 1 SPN_core sequence | 271 | CCGCATCACCACCCAAACCACCGTT |
| | 1 SPN_A | 272 | GCCTGATGAG CCGCATCACCACCCAAACCACCG TTCGAAACGAGGC |
| | 1 SPN_B | 273 | TTCCAATGATGAG CCGCATCACCACCCAAACCACCG TTCGAAACGAGGAA |
| | 1 SPN_C | 274 | TATACAATGATGAG CCGCATCACCACCCAAACCACCG TTCGAAACGAGTAAG |
| | 1 SPN_D | 275 | UUCCTGATGAG CCGCATCACCACCCAAACCACCGTT CGAAAUAGGAA |
| | 1 SPN_E | 276 | TGGACAATGATGAG CCGCATCACCACCCAAACCACCG TTCGAAACGAGTCACA |
| | 1 SPN_F | 277 | TCCACAATGATGAG CCGCATCACCACCCAAACCACCG TTCGAAACGAGTGAGA |
| | 2 RiboSPN_full sequence | 278 | TAATACGACTCACTATAGGCGTAGCCTGATGAGCCTGCTC CATCCGCGCCAGCCTCACCGAAACGTGGTGAAAGCCACG TAGCTGCGCC |
| | 2 SPN_core sequence | 279 | CCTGCTCCATCCGCGCCAGCCTCAC |
| | 2 SPN_A | 280 | CCTGATGAG CCTGCTCCATCCGCGCCAGCCTCAC CGAAACG |
| | 2 SPN_B | 281 | TAGCCTGATGAG CCTGCTCCATCCGCGCCAGCCTCAC CGAAACGTGGCTA |
| | 2 SPN_C | 282 | CTTAGCCTGATGAG CCTGCTCCATCCGCGCCAGCCTCAC CGTAAG |
| | 2 SPN_D | 283 | CTTAGGGTAGAG CCTGCTCCATCCGCGCCAGCCTCAC CUTAAG |
| | 2 SPN_E | 284 | TTAGGGTAGAG CCTGCTCCATCCGCGCCAGCCTCAC CUTAA |
| | 2 SPN_F | 285 | GTTAGGGTAGAG CCTGCTCCATCCGCGCCAGCCTCAC CUAAU |
| | 2 SPN_G | 286 | TTAGGTAGAG CCTGCTCCATCCGCGCCAGCCTCAC CUAA |
| | 2 SPN_H | 287 | GCGTAGCCTGATGAG CCTGCTCCATCCGCGCCAGCCTCAC CGAAACGTGGTGAAAG |
| | 2 SPN_I | 288 | TAATACGAC CCTGCTCCATCCGCGCCAGCCTCAC CGAAACGTGGTGAAAG |
| | 2 SPN_J | 289 | TCACTATAG CCTGCTCCATCCGCGCCAGCCTCAC CGAAACGTGGTGAAAG |
| | 2 SPN_K | 290 | CCACGTAGCTGCGCC CCTGCTCCATCCGCGCCAGCCTCAC CGAAACGTGGTGAAAG |
| | 2 SPN_L | 291 | CUUTCACCTGATGAG CCTGCTCCATCCGCGCCAGCCTCAC CGAAACGTGGTGAAAG |
| | 2 SPN_M | 292 | UAUTCACCTGATGAG CCTGCTCCATCCGCGCCAGCCTCAC CGAAACGTGGTGAAAG |

TABLE 1-continued

Aptamers and SPNs that bind common allergens

| Allergen | SPN ID | SEQ ID NO. | Sequence (5'-3') |
|---|---|---|---|
| | 2 SPN_N | 293 | UTCGATGAG CCTGCTCCATCCGCGCCAGCCTCAC CGAACAG |
| | 2 SPN_O | 294 | CAUTCGATGAG CCTGCTCCATCCGCGCCAGCCTCAC CGAACUG |
| | 3 RiboSPN_full sequence | 295 | TAATACGACTCACTATAGGCGTAGCCTGATGAGCCAATCT CCTGCCCACGCCGTTCCACGAAACGTGGTGAAAGCCACG TAGCTGCGCC |
| | 3 SPN_core sequence | 296 | CCAATCTCCTGCCCACGCCGTTCCA |
| | 3 SPN_A | 297 | TAGGCGTAGCCTGATGAG CCAATCTCCTGCCCACGCCGTTCCA CGAAACGTGGTGAAAG |
| | 3 SPN_B | 298 | TAGGCGTAGCCTGATGAG CCAATCTCCTGCCCACGCCGTTCCA CGAA |
| | 3 SPN_C | 299 | TAGGCGTAGCCTGATGAG CCAATCTCCTGCCCACGCCGTTCCA CCUACGCCUA |
| | 3 SPN_D | 300 | GCGTAGCCTGATGAG CCAATCTCCTGCCCACGCCGTTCCA CCUACGC |
| | 3 SPN_E | 301 | UCGTAGCCTGATGAG CCAATCTCCTGCCCACGCCGTTCCA CCUACCA |
| | 3 SPN_F | 302 | UGCTAGCCTGATGAG CCAATCTCCTGCCCACGCCGTTCCA CCUAGAA |
| | 3 SPN_G | 303 | CGATAGCCTGATGAG CCAATCTCCTGCCCACGCCGTTCCA CCUAUAG |
| | 3 SPN_H | 304 | GUCCTAGCCTGATGAG CCAATCTCCTGCCCACGCCGTTCCA CAUCUUGCUAGAAC |
| | 3 SPN_I | 305 | GATGAG CCAATCTCCTGCCCACGCCGTTCCA CAAGCUCAUC |
| | 3 SPN_J | 306 | CCTGATGAG CCAATCTCCTGCCCACGCCGTTCCA CAUCGAAAGG |
| | 4 RiboSPN_full sequence | 307 | TAATACGACTCACTATAGGCGTAGCCTGATGAGCCAATC AAGGACCGCCTTCACCGCTCGAAACGTGGTGAAAGCCAC GTAGCTGCGCC |
| | 4 SPN_core sequence | 308 | CCAATCAAGGACCGCCTTCACCGCT |
| | 4 SPN_A | 309 | CCTGATGAG CCAATCAAGGACCGCCTTCACCGCT CGAAACG |
| | 4 SPN_B | 310 | GATGAG CCAATCAAGGACCGCCTTCACCGCT CGAU |
| | 4 SPN_C | 311 | TGAG CCAATCAAGGACCGCCTTCACCGCT CG |
| | 4 SPN_D | 312 | GCACAG CCAATCAAGGACCGCCTTCACCGCT UCU |
| | 4 SPN_E | 313 | GCAACAG CCAATCAAGGACCGCCTTCACCGCT UUU |
| | 4 SPN_F | 314 | GACAG CCAATCAAGGACCGCCTTCACCGCT UUU |
| | 5 RiboSPN_full sequence | 315 | TAATACGACTCACTATAGGCGTAGCCTGATGAGACTCTCG CATCACCAGCCAACTCACCGAAACGTGGTGAAAGCCACG TAGCTGCGCC |
| | 5 SPN_core sequence | 316 | ACTCTCGCATCACCAGCCAACTCAC |
| | 5 SPN_A | 317 | TAGCCTGATGAG ACTCTCGCATCACCAGCCAACTCAC CGAAACGTGGTGAAAG |
| | 5 SPN_B | 318 | TAGCCTGATGAG ACTCTCGCATCACCAGCCAACTCAC CGAAACGTGGTGGCUA |
| | 5 SPN_C | 319 | TAGCCAGATGAG ACTCTCGCATCACCAGCCAACTCAC CGAAACGTGGTGGCUA |
| | 5 SPN_D | 320 | TAGCCAGATGAG ACTCTCGCATCACCAGCCAACTCAC CGAACACAUCTGGCUA |
| | 5 SPN_E | 321 | TCGCCAGATGAG ACTCTCGCATCACCAGCCAACTCAC CGAAACGTGGTGGCGA |
| | 5 SPN_F | 322 | TCGCCAGATGAG ACTCTCGCATCACCAGCCAACTCAC CGAAACGTGGAGGCGA |
| | 5 SPN_G | 323 | TUGCCAGATGAG ACTCTCGCATCACCAGCCAACTCAC CGAAACGTGGAGGCGA |
| | 5 SPN_H | 324 | TUGCCAGATGAG ACTCTCGCATCACCAGCCAACTCAC CGAAACGTGGAGUUGCGA |
| | 5 SPN_I | 325 | TUGCCUUGATGAG ACTCTCGCATCACCAGCCAACTCAC CGAAACGTGGAGGCGA |
| | 5 SPN_J | 326 | TUGCCUAUGATGAG ACTCTCGCATCACCAGCCAACTCAC CGAAACGTGGAGGCGA |
| | 5 SPN_K | 327 | TUGCCUGATGAG ACTCTCGCATCACCAGCCAACTCAC CGAAACGAATGGAGGCGA |
| | 5 SPN_L | 328 | TUGCCUGATGAG ACTCTCGCATCACCAGCCAACTCAC CGAAACGGTGGAGGCGA |
| | 5 SPN_M | 329 | TUGCCUGATGAG ACTCTCGCATCACCAGCCAACTCAC CGAAACGTGGAGGCAT |

TABLE 1-continued

Aptamers and SPNs that bind common allergens

| Allergen | SPN ID | SEQ ID NO. | Sequence (5'-3') |
|---|---|---|---|
| | 5 SPN_N | 330 | TUGCCUGAUGAG ACTCTCGCATCACCAGCCAACTCAC CGAAACGTGGAGGCAA |
| Crustacean | 1 RiboSPN_full sequence | 331 | TAATACGACTCACTATAGGCGTAGCCTGATGAGCGGTAC TCAGATTACAGAGTGACATCGAAACGTGGTGAAAGCCAC GTAGCTGCGCC |
| | 1 SPN_core sequence | 332 | CGGTACTCAGATTACAGAGTGACAT |
| | 2 RiboSPN_full sequence | 333 | TAATACGACTCACTATAGGCGTAGCCTGATGAGAGACAC CACGGATCCGAACTGGAGCGAAACGTGGTGAAAGCCACG TAGCTGCGCC |
| | 2 SPN_core sequence | 334 | AGACACCACGGATCCGAACTGGAG |
| | 3 RiboSPN_full sequence | 335 | TAATACGACTCACTATAGGCGTAGCCTGATGAGCCTCGC AAGATTGCATACGTTAGAACGAAACGTGGTGAAAGCCAC GTAGCTGCGCC |
| | 3 SPN_core sequence | 336 | CCTCGCAAGATTGCATACGTTAGAA |
| | 4 RiboSPN_full sequence | 337 | TAATACGACTCACTATAGGCGTAGCCTGATGAGCACGTA GGAAACGACCTCTACGGAGCGAAACGTGGTGAAAGCCAC GTAGCTGCGCC |
| | 4 SPN_core sequence | 338 | CACGTAGGAAACGACCTCTACGGAG |
| | 5 RiboSPN_full sequence | 339 | TAATACGACTCACTATAGGCGTAGCCTGATGAGCCCGAA ACCACCACCGTTGTCCAATACGAAACGTGGTGAAAGCCA CGTAGCTGCGCC |
| | 5 SPN_core sequence | 340 | CCCGAAACCACCACCGTTGTCCAATA |

In some embodiments, SPNs of the present invention may be generated by modifying the original allergen binding aptamers disclosed in the literature. The parent aptamer sequence against a specific allergen is modified to comprise the shortest sequence without changing the binding specificity and affinity of the aptamer. Some exemplary SPNs modified from known parent sequences are listed in Table 2.

TABLE 2

SPNs originated from literature sequences

| Allergen | SPN ID | SEQ ID NO. | Sequence (5'-3') |
|---|---|---|---|
| Gluten | GLI4-parent sequence | 341 | CCAGTCTCCCGTTTAC CGCGCCTACACATGTC TGAATGCC |
| | GLI4 SPN-1 | 342 | TAGTCTCCCGTTTACC GCGCCTACACATGTCT GAATG |
| | GLI4 SPN-2 | 343 | TAGTCTCCCGTTTACC GCGCCTACACATGTCT GAA |
| | GLI1-parent sequence | 344 | CTAGGCGAAATATAGC TACAACTGTCTGAAGG CACCCAAT |
| Egg | 2007-parent sequence | 345 | ATCTACGAATTCATCA GGGCTAAAGAGTGCAG AGTTACTTAG |
| | 2007 SPN-1 | 346 | TACGAATTCATCAGGG CTAAAGAGTGCAGAGT TACT |
| | 2007 SPN-2 | 347 | AAT ATCTACGAATTCATCA GGGCTAAAGAGTGCAG AGTTACTTAG CTC |
| | 2007 SPN-3 | 348 | ATCTACGAATTCATCA GGGCTAAAGAGTGCAG AGTTACTTAG |

TABLE 2-continued

SPNs originated from literature sequences

| Allergen | SPN ID | SEQ ID NO. | Sequence (5'-3') |
|---|---|---|---|
| | 2012- parent sequence | 349 | GCAGCTAAGCAGGCGG CTCACAAAACCATTCG CATGCGGC |
| | 2012 SPN-1 | 350 | GCTAAGCAGGCGGCTC ACAAAACCATTCGCAT GC |
| | 2012 SPN-2 | 351 | GCTAAGCAGGCGGCTC ACAAAACCATTCGCAT GC AA |
| Ellington and Cox | Parent sequence | 352 | GGUUGUGAAGAUUGGG AGCGUCGUGGCUAC |
| Peanut | ARAH1- parent sequence | 353 | TCGCACATTCCGCTTC TACCGGGGGGGTCGAG CTGAGTGGATGCGAAT CTGTGGGTGGGCCGTA AGTCCGTGTGTGCGAA |

In one embodiment, a signaling polynucleotide of the present invention may be probed with a fluorescent marker, for instance, a fluorescent dye. The fluorescent dye may be added at either the 5' terminus or the 3' terminus of the polynucleotide. In some aspects, the fluorescent dyes may include, but are not limited to, Fluorescein, Rhodamine, Oregon green (e.g., Oregon Green 488 dye, Oregon Green 514 dye), Eosin, Texas red, ROX, TAMRA, JOE, HEX, TET, Cyanine, Indocarbocyanine, Oxacarbocyanine, Thiacarbocyanine, Merocyanine, Squaraines and derivatives such as Seta (e.g., Seta-APC-780, Seta-PerCP-680, Seta-555-NHS, Seta-555-Azide, Seta-555-DBCO, Seta-580-NHS and Seta-R-PE-670), SeTau (e.g., SeTau-380-NHS, SeTau-425-NHS, SeTau-647-NHS and SeTau-405-NHS), and Square dyes, Naphthalene derivatives, Coumarin derivatives, Pyridyloxazole, Nitrobenzoxadiazole and Benzoxadiazole, Anthraquinones (e.g., DRAQ5, DRAQ7 and CyTRAK Orange), Pyrene and derivatives (e.g., cascade blue), Oxazine derivatives (e.g., Nile red, Nile blue, cresyl violet, oxazine 170), Proflavin, Acridine orange, Acridine yellow, Auramine, Crystal violet, Malachite green, Porphin, Phthalocyanine, Bilirubin, BODIPY TMR dye, BODIPY FL dye, Tetramethylrhodamine, Hydroxycoumarin, Aminocoumarin, Methoxycoumarin, Cascade Blue, Pacific Blue, Pacific Orange, NBD, R-Phycoerythrin (PE), Red 613, PerCP, TruRed, FluorX, Cy2, Cy3, Cy5, Cy7, TRITC, X-Rhodamine, Lissamine Rhodamine B, Allophycocyanin (APC), and Alexa Fluor dyes (e.g., Alexa Fluor 488 dye, and Alexa Fluor 594 dye).

In another embodiment, more than one fluorophore molecules may be added to the same terminus of the signaling polynucleotide. As a non-limiting example, two FAM (fluorescein) molecules may be added one after another on either the 5' terminus or the 3' terminus of the signaling polynucleotide. In further another embodiment, fluorophore molecules may be added to both the 5' and 3' termini of the signaling polynucleotide.

Detection Agents

Detection agents of the present invention comprise SPNs as discussed herein. According to the present invention, and while not wishing to be bound by theory, the detection agents may completely or partially bind an allergen. In some embodiments, detection agents of the invention comprise one or more aptamers as core sequences which will bind specifically to an allergen molecule.

In some embodiments, detection agents of the present invention may comprise a detectable probe, such as various organic small molecules, inorganic compounds, nanoparticles, quantum dot, enzymes or enzyme substrates, fluorescent materials, luminescent materials (e.g., luminol), bioluminescent materials (e.g., luciferase, luciferin, and aequorin), chemiluminescent materials, radioactive materials (e.g., 18F, 67Ga, 81mKr, 82Rb, 111In, 123I, 133Xe, 201Tl, 125I, 35S, 14C, 3H, or 99mTc (e.g., as pertechnetate (technetate(VII), TcO4)), contrast agents (e.g., gold (e.g., gold nanoparticles) and butyrate quantum dot.

In some embodiments, detection agents of the present invention may further comprise conjugates. In some aspects, detection agents may be conjugated to other polynucleotides, dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases, proteins, e.g., glycoproteins, or peptides, e.g., molecules having a specific affinity for a co-ligand, or antibodies e.g., an antibody, that binds to a specified cell type such as a cancer cell, endothelial cell, or bone cell, hormones and hormone receptors, non-peptidic species, such as lipids, lectins, carbohydrates, vitamins, cofactors, or a drug.

According to certain embodiments of the present invention, variants of detection agents are provided. In some aspects, the variants are polynucleotide variants. As used herein, the term "polynucleotide variants" refers to molecules which differ in their nucleotide sequence from a native or reference sequence. The nucleic acid sequence variants may possess substitutions, deletions, and/or insertions at certain positions within the nucleotide sequence, as compared to a native or reference sequence. Ordinarily, variants will possess at least about 50% identity (homology) to a native or reference sequence, and preferably, they will be at least about 80%, more preferably at least about 90% identical (homologous) to a native or reference sequence. "Native" or "reference" sequence should not be confused with a wild type sequence. As used herein, a native or reference sequence is a relative term referring to an original molecule against which a comparison may be made. "Native" or "reference" sequences or molecules may represent the wild-type (that sequence found in nature) but do not have to be the wild-type sequence. In some examples, the native or reference sequence may be the sequence of a signaling polynucleotide as disclosed herein, such as a SPN specific to peanut listed in Table 1 and Table 2.

In some embodiments, derivatives of detection agents are also provided. As used herein, the term "derivative" is used synonymously with the term "variant" and refers to a molecule that has been modified or changed in any way relative to a reference molecule. The term "derivatives," as referred to herein, includes modifications of a reference polynucleotide with an organic proteinaceous or non-proteinaceous derivatizing agent.

In some embodiments, detection agents of the present invention may be used in combination with other detection molecules such as antibodies against an allergen.

SPNs and detection agents of the present invention may be formulated in a solution which favors the interaction between the detection molecules and the allergen. Such formulations can be packaged for use in a variety of pharmaceutically or diagnostically acceptable containers using any acceptable container closure, Examples of acceptable containers include, but are not limited to, ampules and pre-filled syringes, cartridges and the like. Alternatively, the formulation may contain lyophilized aptamer in one compartment of an admix bag and an acceptable solvent in a separate compartment of the admix bag such that the two compartments may be mixed together prior to its application. The formulations in liquid form may be stored in a refrigerated environment. Alternatively, the lyophilized formulations may be stored at room temperature, or refrigerated or frozen. Preferably, the formulations may be sterile. A "sterile" formulation, as used herein, means a formulation that has been brought to a state of sterility and has not been subsequently exposed to microbiological contamination, i.e., the container holding the sterile composition has not been compromised. Sterile compositions are generally prepared by pharmaceutical manufacturers in accordance with current Good Manufacturing Practice ("cGMP") regulations of the U.S. Food and Drug Administration. In some embodiments, detection agents and compositions of the present invention may be combined with other ingredients or reagents or prepared as components of kits or other retail products for commercial sale or distribution. The kit will contain the compound or composition, along with instructions regarding administration and/or use of the kit. The kit may also contain one or more of the following: a syringe, a bag or bottle.

Target—Allergen Proteins

In some embodiments, detection systems and devices, aptamers, SPNs and detection agents of the present invention may be used to detect the presence and/or absence of an allergen protein or variants thereof. In some embodiments, aptamers, SPNs and detection agents may be designed to bind or associate with proteins or other biomolecules which themselves associated with the allergen. Allergens may include those from foods, the environment or from non-human proteins such as domestic pet dander. In some embodiments, detection systems and devices of the present invention may be used to implement an allergen detection test, for example using SPNs of the invention as detection agents to detect the presence and/or absence of an allergen protein in a test sample.

Food allergens include, but are not limited to proteins in legumes such as peanuts, peas, lentils and beans, as well as the legume-related plant lupin, tree nuts such as almond, cashew, walnut, Brazil nut, filbert/hazelnut, pecan, pistachio, beechnut, butternut, chestnut, chinquapin nut, coconut, ginkgo nut, lychee nut, macadamia nut, nangai nut and pine nut, egg, fish, shellfish such as crab, crawfish, lobster, shrimp and prawns, mollusks such as clams, oysters, mussels and scallops, milk, soy, wheat, gluten, corn, meat such as beef, pork, mutton and chicken, gelatin, sulphite, seeds such as sesame, sunflower and poppy seeds, and spices such as coriander, garlic and mustard, fruits, vegetables such as celery, and rice. For example, the seeds from plants, such as lupin, sunflower or poppy can be used in foods such as seeded bread or can be ground to make flour to be used in making bread or pastries.

Seafood allergens typically belong to a group of muscle proteins, including the parvalbumins in codfish and tropomyosin in crustaceans; other allergens such as arginine kinase and myosin light chain may also play an important part in allergenicity. Tropomyosin is the major allergen responsible for molecular and clinical cross-reactivity between crustaceans and molluscs, and is believed to be the allergen responsible in other inhaled invertebrates such as house dust mites and insects.

In some embodiments, allergens are food allergens. Examples of allergenic proteins associated with food include, but are not limited to, Brine shrimp (Art fr 5), Crab (Cha f 1), North Sea Shrimp (Cra c 1, Cra c 2, Cra c 4, Cra c 5, Cra c 6, Cra c 8), American lobster (Hom a 1, Hom a 3, Hom a 6), white shrimp (Lit v 1, Lit v 2, Lit v 3, Lit v4), giant freshwater prawn (Mac r 1), shrimp (Met e 1, Pen a 1, Pen i 1), northern shrimp (Pan b 1), spiny lobster (Pan s 1), black tiger shrimp (Pen m 1, Pen m 2, Pen m 3, Pen m 4, Pen m 6), narrow-clawed crayfish (Pon i 4, Pon i 7), blue swimmer crab (Por p 1), domestic cattle (Bos d 4, Bos d 5, Bos d 6, Bos d 7, Bos d 8, Bos d 9, Bos d 10, Bos d 11, Bos d 12), Atlantic herring (Clu h 1), common carp (Cyp c 1), Baltic cod (Gad c 1), Atlantic cod (Gad m 1, Gad m 2, Gad m 3), cod (Gad c 1), chicken (Gal d 1, Gal d 2, Gal d 3, Gal d 4, Gal d 5), Barramunda (Lat c 1), Lepidorhombus whiffiagonis (Lep w 1), chum salmon (Onc k 5), Atlantic salmon (Sal s 1, Sal s 2, Sal s 3) rainbow trout (Onc m 1), Mozambique tilapia (Ore m 4), edible frog (Ran e 1, Ran e 2), pacific pilchard (Sar sa 1), ocean perch (Seb m 1), yellowfin tuna (Thu a 1, Thu a 2, Thu a 3), swordfish (Xip g 1), abalone (Hal m 1), brown garden snail (Hel as 1), Squid (Tod p 1), pineapple (Ana c 1, Ana c 2), asparagus (Aspa o 1), barley (Hor v 12, Hor v 15, Hor v 16, Hor v 17, Hor v 20, Hor v 21), banana (Mus a 1, Mus a 2, Mus a 3, Mus a 4, Mus a 5), banana (Musxpl), rice (Ory s 12), rye (Sec c 20), wheat (Tri a 12, Tri a 14, Tri a 18, Tri a 19, Tri a 25, Tri a 26, Tri a 36, Tri a 37), maize (corn) (Zea m 14, Zea m 25), kiwi fruit (Act c1, Act c 2, Act c 5, Act c 8, Act c 10, Act d 1, Act d 2, Act d 3, Act d 4, Act d 5, Act d 6, Act d 7, Act d 8, Act d 9, Act d 10, Act d 11), cashew (Ana o 1, Ana o 2, Ana o 3), celery (Api g 1, Api g 2, Api g 3, Api g 4, Api g 5, Api g 6), peanut (Ara h 1, Ara h 2, Ara h 3, Ara h 4, Ara h 5, Ara h 6, Ara h 7, Ara h 8, Ara h 9, Ara h 10, Ara h 11, Ara h 12, Ara h 13), brazil nut (Ber e 1, Ber e 2), oriental mustard (Bra j 1), rapeseed (Bra n 1), cabbage (Bra o 3), turnip (Bra r 1, Bra r 2), bell pepper (Cap a 1w, Cap a 2), pecan (Car i 1, Car i 4), chestnut (Cas s 1, Cas s 5, Cas s 8, Cas s 9), lemon (Cit l 3), tangerine (Cit r 3), sweet orange (Cit s 1, Cit s 2, Cit s 3), Hazel (Cor a 1, Cor a 2, Cor a 8, Cor a 9, Cor a 11, Cor a 12, Cor a 13, Cor a 14), muskmelon (Cuc m 1, Cuc m 2, Cuc m 3), carrot (Dau c 1, Dau c 4, Dau c 5), common buckwheat (Fag e 2, Fag e 3), tartarian buckwheat (Fag t 2), strawberry (Fra a 1, Fra a 3, Fra a 4), soybean (Gly m 1, Gly m 2, Gly m 3, Gly m 4, Gly m 5, Gly m 6, Gly m 7, Gly m 8), sunflower (Hel a1, Hel a 2, Hel a 3), black walnut (Jug n 1, Jug n 2), English walnut (Jug r 1, Jug r 2, Jug r 3, Jug r 4), Cultivated lettuce (Lac s 1), Lentil (Len c 1, Len c 2, Len c 3), litchi (Lit c 1), narrow-leaved blue lupin (Lup an 1), apple (Mal d 1, Mal d 2, Mal d 3, Mal d 4), Cassava (Man e 5), mulberry (Morn 3), avocado (Pers a 1), green bean (Pha v 3), pistachio (Pis v 1, Pis v 2, Pis v 3, Pis v 4, Pis v 5), pea (Pis s 1, Pis s 2), apricot (Pru ar 1, Pru ar 3), sweet cherry (Pru av 1, Prn av 2, Pru av 3, Pru av 4), European plum (Pru d 3), almond (Pm du 3, Pru du 4, Pru du 5, Pru du 6), peach (Pru p 1, Pru p 2, Pru p 3, Pru p 4, Pru p 7), pomegranate (Pun g 1), pear (Pyr c 1, Pyr c 3, Pyr c 4, Pyr c 5), castor bean (Ric c 1), red raspberry (Rub i 1, Rub i 3), Sesame (Ses i 1, Ses i 2, Ses i 3, Ses i 4, Ses i 5, Ses i 6, Ses i 7), yellow mustard (Sin a 1, Sin a 2, Sin a 3, Sin a 4), tomato (Sola I 1, Sola I 2, Sola I 3, Sola I 4), potato (Sola t 1, Sola t 2, Sola t 3, Sola t 4), Mung bean (Vig r 1, Vig r 2, Vig r 3, Vig r 4, Vig r 5, Vig r 6), grape (Vit v 1), Chinese date (Ziz m 1), *Anacardium occidentale* (Ana o 1.0101, Ana o 1.0102), *Apium graveolens* (Api g 1.0101, Api g 1.0201), *Daucus carota* (Dau c1.0101, Dau c1.0102, Dau c1.0103, Dau c1.0104, Dau c1.0105, Dau c1.0201), *Citrus sinensis* (Cit s3.0101, Cit s3.0102), *Glycine max* (Gly m1.0101, Gly m1.0102, Gly m3.0101, Gly m3.0102), *Lens culinaris* (Len c1.0101, Len c1.0102, Len c1.0103), *Pisum sativum* (Pis s1.0101, Pis s1.0102), *Lycopersicon sativum* (Lyc e2.0101, Lyc e2.0102), *Fragaria ananassa* (Fra a3.0101, Fra a3.0102, Fra a3.0201, Fra a3.0202, Fra a3.0203, Fra a3.0204, Fra a3.0301), *Malus domestica* (Mal d1.0101, Mal d1.0102, Mal d1.0103, Mal d1.0104, Mal d1.0105, Mal d1.0106, Mal d1.0107, Mal d1.0108, Mal d1.0109, Mal d1.0201, Mal d1.0202, Mal d1.0203, Mal d1.0204, Mal d1.0205, Mal d1.0206, Mal d1.0207, Mal d1.0208, Mal d1.0301, Mal d1.0302, Mal d1.0303, Mal d1.0304, Mal d1.0401, Mal d1.0402, Mal d1.0403, Mal d3.0101w, Mal d3.0102w, Mal d3.0201w, Mal d3.0202w, Mal d3.0203w, Mal d4.0101, Mal d4.0102, Mal d4.0201, Mal d4.0202, Mal d4.0301, Mal d4.0302), *Prunus avium* (Pm av1.0101, Pru av1.0201, Pru av1.0202, Pru av1.0203), and *Prunus persica* (Pru p4.0101, Pru p4.0201); and any variants thereof. The names of allergens associated with food are systematically named and listed according to IUIS Allergen Nomenclature Sub-Committee (see, International Union of Immunological Societies Allergen Nomenclature Sub-Committee, List of isoallergens and variants).

In addition to food allergens, aptamers, signaling polynucleotides and detection agents of the present invention may detect airborne particulates/allergens and other environmental allergens. Samples that contain allergens may be obtained from plants (e.g. weeds, grasses, trees, pollens), animals (e.g., allergens found in the dander, urine, saliva, blood or other bodily fluid of mammals such as cat, dog, cow, pig, sheep, horse, rabbit, rat, guinea pig, mouse and gerbil), fungi/mold, insects (e.g., stinging insects such as bee, wasp, and hornet and chirnomidae (non-biting midges), as well as other insects such as the housefly, fruit fly, sheep blow fly, screw worm fly, grain weevil, silkworm, honeybee, non-biting midge larvae, bee moth larvae, mealworm, cockroach and larvae of *Tenibrio molitor* beetle; spiders and mites such as the house dust mite), rubbers (e.g. latex), metals, chemicals (e.g. drugs, protein detergent additives) and autoallergens and human autoallergens (e.g. Hom s 1, Hom s 2, Hom s 3, Hom s 4, Hom s 5) (see, Allergen Nomenclature: International Union of Immunological Societies Allergen Nomenclature Sub-Committee, List of allergens and Allergen Nomenclature: International Union of Immunological Societies Allergen Nomenclature Sub-Committee, List of isoallergens and variants).

Examples of allergenic proteins from plants that can be detected using the aptamers, signaling polynucleotides and detection agents of the present invention include, but are not limited to, ash (Fra e 1), Japanese cypress (Cha o1, Cha o 2), sugi (Cry j 1, Cry j 2), cypress (Cup a 1), common cypress (Cup s 1, Cup s 3), mountain cedar (Jun a 1, Jun a 2, Jun a 3, Jun s 1), prickly juniper (Juno 4), eastern red cedar (Jun v 1, Jun v 3), sweet vernal grass (Ant o 1), saffron *crocus* (Cro s 1, Cro s 2), Bermuda grass (Cyn d 1, Cyn d 7, Cyn d 12, Cyn d 15, Cyn d 22w, Cyn d 23, Cyn d 24), orchard grass (Dac g 1, Dac g 2, Dac g 3, Dac g 4, Dac g 5), meadow fescue (Fes p 4), velvet grass (Hol I 1, Hol I 5), barley (Hor v 1, Hor v 5), rye grass (Lol p 1, Lol p 2, Lol p 3, Lol p 4, Lol p 11), bahia grass (Pas n 1), canary grass (Pha a 1, Pha a 5), timothy (Phl p 1, Phl p 2, Phl p 4, Phl p 5, Phl p 6, Phl p 7, Phl p 11, Phl p 12, Phl p 13), date palm (Pho d 2), Kentucky blue grass (Poa p 1, Poa p 5), rye (Sec c 1, Sec c 5, Sec c 38), Johnson grass (Sor h 1), wheat (Tri a 15, Tri a 21, Tri a 27, Tri a 28, Tri a 29, Tri a 30, Tri a 31, Tri a 32, Tri a 33, Tri a 34, Tri a 35, Tri a 39), maize (Zea m 1, Zea m 12), alder (Aln g 1, Aln g 4), redroot pigweed (Ama r 2), short ragweed (Amb a 1, Amb a 2, Amba 3, Amba 4, Amba 5, Amba 6, Amba 7, Amba 8, Amba 9, Amb a 10, Amba 11), western ragweed (Amb p 5), giant ragweed (Amb t 5), mugwort (Art v 1, Art v 2, Art v 3, Art v 4, Art v 5, Art v 6), sugar beet (Beta v 1, beta v 2), European white birch (Bet v 1, Bet v 2, Bet v 3, Bet v 4, Bet v 6, Bet v 7), turnip (Bra r 5), hornbeam (Car b 1), chestnut (Cas s 1), rosy periwinkle (Cat r 1), lamb's-quarters, pigweed (Che a 1, Che a 2, Che a 3), Arabian coffee (Cof a 1, Cof a 2, Cof a 3), Hazel (Cor a 6, Cor a 10), Hazel nut (Cor a1.04, Cor a2, Cor a8), European beech (Fag s 1), ash (Fra e 1), sunflower (Hel a 1, Hel a 2), para rubber tree (Hey b 1, Hey b 2, Hey b 3, Hey b 4, Hey b 5, Hey b 6, Hey b 7, Hey b 8, Hey b 9, Hey b 10, Hey b 11, Hey b 12, Hey b 13, Hey b 14), Japanese hop (Hum j 1), privet (Lig v 1), *Mercurialis annua* (Mer a 1), olive (Ole e 1, Ole e 2, Ole e 3, Ole e 4, Ole e 5, Ole e 6, Ole e 7, Ole e 8, Ole e 9, Ole e 10, Ole e 11), European hophornbeam (Ost c 1), *Parietaria judaica* (Par j 1, Par j 2, Par j 3, Par j 4), *Parietaria officinalis* (Par o 1), *Plantago lanceolata* (Pal I 1), London plane tree (Pla a 1, Pla a 2, Pla a 3), *Platanus orientalis* (Pla or 1, Pla or 2, Pla or 3), white oak (Que a 1), Russian thistle (Sal k 1, Sal k 2, Sal k 3, Sal k 4, Sal k 5), tomato (Sola I 5), Lilac (Syr v 1, Syr v 5), Russian-thistle (Sal k 1), English plantain (Pla 11), *Ambrosia artemisiifolia* (Amb a8.0101, Amb a8.0102, Amb a9.0101, Amb a9.0102), *Plantago lanceolata* (Pla 11.0101, Pla 11.0102, Pla 11.0103), *Parietaria judaica* (Par j 3.0102), *Cynodon dactylon* (Cyn d1.0101, Cyn d1.0102, Cyn d1.0103, Cyn d1.0104, Cyn d1.0105, Cyn d1.0106, Cyn d1.0107, Cyn d1.0201, Cyn d1.0202, Cyn d1.0203, Cyn d1.0204), *Holcus lanatus* (Hol l1.0101, Hol l1.0102), *Lolium perenne* (Phl p1.0101, Phl p1.0102, Phl p4.0101, Phl p4.0201, Phl p5.0101, Phl p5.0102, Phl p5.0103, Phl p5.0104, Phl p5.0105, Phl p5.0106, Phl p5.0107, Phl p5.0108, Phl p5.0201, Phl p5.0202), *Secale cereale* (Sec c20.0101, Sec c20.0201), *Betula Verrucosa* (Bet v1.0101, Bet v1.0102, Bet v 1.0103, Bet v 1.0201, Bet v 1.0301, Bet v1.0401, Bet v 1.0402, Bet v 1.0501, Bet v 1.0601, Bet v 1.0602, Bet v1.0701, Bet v1.0801, Bet v1.0901, Bet v1.1001, Bet v1.1101, Bet v1.1201, Bet v 1.1301, Bet v1.1401, Bet v1.1402, Bet v1.1501, Bet v1.1502, Bet v1.1601, Bet v1.1701, Bet v 1.1801, Bet v1.1901, Bet v1.2001, Bet v1.2101, Bet v1.2201, Bet v1.2301, Bet v1.2401, Bet v 1.2501, Bet v1.2601, Bet v1.2701, Bet v1.2801, Bet v1.2901, Bet v1.3001, Bet v1.3101, Bet v 6.0101, Bet v6.0102), *Carpinus betulus* (Car b1.0101, Car b1.0102, Car b1.0103, Car b1.0104, Car b1.0105, Car b1.0106, Car b1.0106, Car b1.0106, Car b1.0106, Car b1.0107, Car b1.0107, Car b1.0108, Car b1.0201, Car b1.0301, Car b1.0302), *Corylus avellana* (Cor a1.0101, Cor a1.0102, Cor a1.0103, Cor a1.0104, Cor a1.0201, Cor a1.0301, Cor a1.0401, Cor a1.0402, Cor a1.0403, Cor a1.0404), *Ligustrum vulgare* (Syr v1.0101, Syr v1.0102, Syr v1.0103), *Cryptomeria japonica* (Cry j2.0101, Cry j2.0102), and *Cupressus sempervirens* (Cup s1.0101, Cup s1.0102, Cup s1.0103, Cup s1.0104, Cup s1.0105); and any variants thereof.

Lupin is an herbaceous plant of the leguminous family belonging to the genus *Lupinus*. In Europe, lupin flour and seeds are widely used in bread, cookies, pastry, pasta, sauces, as well as in beverages as a substitute for milk or soy, and in gluten-free foods. The International Union of Immunological Societies (IUIS) allergen nomenclature subcommittee recently designated β-conglutin as the Lup an 1 allergen. (Nadal, et al., DNA Aptamers against the Lup an 1 Food Allergen. *PLoS ONE*, 2012, 7(4): e35253), and more recently, a high-affinity 11-mer DNA aptamer against Lup an 1 (β-conglutin) was reported (Nadal, et al., Probing high-affinity 11-mer DNA aptamer against Lup an 1 (β-conglutin). *Anal. Bioanal. Chem.* 2013, 405: 9343-9349).

Examples of allergenic proteins from mites that can be detected using the aptamers, signaling polynucleotides and detection agents of the present invention include, but are not limited to, mite (Blot 1, Blot 3, Blot 4, Blot 5, Blot 6, Blot 10, Blot 11, Blot 12, Blo t 13, Blot 19, Blot t 21); American house dust mite (Der f 1, Der f 2, Der f 3, Der f 7, Der f 10, Der f 11, Der f 13, Der f 14, Der f 15, Der f 16, Der f 17, Der f 18, Der f 22, Der f 24); *Dermatophagoides microceras* (house dust mite) (Der m 1); European house dust mite (Der p 1, Der p 2, Der p 3, Der p 4, Der p 5, Der p 6, Der p 7, Der p 8, Der p 9, Der p 10, Der p 11, Der p 14, Der p 15, Der p 20, Der p 21, Der p 23); *Euroglyphus maynei* (House dust mite) (Eur m 2, Eur m 2, Eur m 3, Eur m 4, Eur m 14); storage mite (Aca s 13, Gly d 2, Lep d 2, Lep d 5, Lep d 7, Lep d 10, Lep d 13, Tyr p 2, Tyr p 3, Tyr p 10, Tyr p 13, Tyr p 24), *Dermatophagoides farinae* (Der f1.0101, Der f1.0102, Der f1.0103, Der f1.0104, Der f1.0105, Der f2.0101, Der f2.0102, Der f2.0103, Der f2.0104, Der f2.0105, Der f2.0106, Der f2.0107, Der f2.0108, Der f2.0109, Der f2.0110, Der f2.0111, Der f2.0112, Der f2.0113, Der 12.0114, Der f2.0115, Der f2.0116, Der f2.0117), *Dermatophagoides pteronyssinus* (Der p1.0101, Der p1.0102, Der p1.0103, Der p1.0104, Der p1.0105, Der p1.0106, Der p1.0107, Der p1.0108, Der p1.0109, Der p1.0110, Der p1.0111, Der p1.0112, Der p1.0113, Der p1.0114, Der p1.0115, Der p1.0116, Der p1.0117, Der p1.0118, Der p1.0119, Der p1.0120, Der p1.0121, Der p1.0122, Der p1.0123, Der p2.0101, Der p2.0102, Der p2.0103, Der p2.0104, Der p2.0105, Der p2.0106, Der p2.0107, Der p2.0108, Der p2.0109, Der p2.0110, Der p2.0111, Der p2.0112, Der p2.0113), *Euroglyphus maynei* (Eur m2.0101, Eur m2.0102), *Lepidoglyphus destructor*

(Lep d2.0101, Lep d2.0101, Lep d2.0101, Lep d2.0102, Lep d2.0201, Lep d2.020) and *Glycyphagus domesticus* (Gly d2.0101, Gly d2.0201); and any variants thereof.

Examples of allergenic proteins from animals that can be detected using the aptamers, signaling polynucleotides and detection agents of the present invention include, but are not limited to, domestic cattle (Bos d 2, Bos d 3, Bos d 4, Bos d 5, Bos d 6, Bos d 7, Bos d 8), dog (Can f 1, Can f 2, Can f 3, Can f 4, Can f 5, Can f 6), domestic horse (Equ c 1, Equ c 2, Equ c 3, Equ c 4, Equ c 5), cat (Fel d 1, Fel d 2, Fel d 3, Fel d 4, Fel d 5w, Fel d 6w, Fel d 7, Fel d 8), mouse (Mus m 1), guinea pig (Cav p 1, Cav p 2, Cav p 3, Cav p 4, Cav p 6), rabbit (Ory c 1, Ory c 3, Ory c 4) rat (Rat n 1), *Bos domesticus* (Bos d 2.0101, Bos d 2.0102, Bos d 2.0103) and *Equus caballus* (Equ c2.0101, Equ c 2.0102).; and any variants thereof.

Examples of allergenic proteins from insects that can be detected using the aptamers, signaling polynucleotides and detection agents of the present invention include, but are not limited to, yellow fever mosquito (Aed a 1, Aed a 2, Aed a 3), Eastern hive bee (Api c 1), giant honeybee (Api d 1), honey bee (Api m 1, Api m 2, Api m 3, Api m 4, Api m 5, Api m 6, Api m 7, Api m 8, Api m 9, Api m 10, Api m 11, Api m 12), pigeon tick (Arg r 1), German cockroach (Bla g 1, Bla g 2, Bla g 3, Bla g 4, Bla g 5, Bla g 6, Bla g 7, Bla g 8, Bla g 11), bumble bee (Bom p 1, Bom p 4, Bom t 1, Bom t 4), silk moth (Bomb m 1), midge (Chi k 10, Chit 1, Chit 1.01, Chit 2, Chit 2. 0101, Chit 2. 0102, Chit 3, Chit 4, Chit 5, Chit 6, Chit 6. 01, Chit 7, Chit 8, Chit 9), cat flea (Cte f 1, Cte f 2, Cte f 3), yellow hornet (Dol a 5), white face hornet (Dol m 1, Dol m 2, Dol m 5), biting midge (Fort 1, Fort 2), Savannah Tsetse fly (Glo m 5), Asian ladybeetle (Har a 1, Har a 2), silverfish (Lep s 1), booklouse (Lip b 1), Australian jumper ant (Myr p 1, Myr p 2, Myr p 3), American cockroach (Per a 1, Per a 3, Per a 6, Per a 7, Per a 9, Per a 10), Indian meal moth (Plo i 1, Plo i 2), wasp (Pol a 1, Pol a 2, Pol a 5, Pole 1, Pole 4, Pole 5, Pol f 5, Pol g 1, Pol g 5, Pol m 5, Polyp 1, Polys 5, Ves vi 5), Mediterranean paper wasp (Pol d 1, Pol d 4, Pol d 5), tropical fire ant (Sol g 2, Sol g 3, Sol g 4), *Solenopsis invicta* (red imported fire ant) (Sol I 1, Sol I 2, Sol I 3, Sol I 4), black fire ant (Sol r 2, Sol r 3), Brazilian fire ant (Sol s 2, Sol s 3), horsefly (Tab y 1, Tab y 2, Tab y 5), pine processionary moth (Tha p 1, Tha p 2), California kissing bug (Tria p 1), European hornet (Vesp c 1, Vesp c 5), *Vespa magnifica* (hornet) (Vesp ma 2, Vesp ma 5), *Vespa* mandarinia (Giant asian hornet) (Vesp m1, Vesp m 5), yellow jacket (Ves f 5, Ves g 5, Ves m 1, Ves m 2, Ves m 5), *Vespula germanica* (yellow jacket) (Ves p 5), *Vespula squamosa* (Yellow jacket) (Ves s 1, Ve s s5), *Vespula vulgaris* (Yellow jacket) (Ves v 1, Ves v 2, Ves v 3, Ves v 4, Ves v 5, Ves v 6), *Blattella germanica* (Bla g 1.0101, Bla g 1.0102, Bla g 1.0103, Bla g 1.02, Bla g 6.0101, Bla g 6.0201, Bla g 6.0301), *Periplaneta Americana* (Per a1.0101, Per a1.0102, Per a1.0103, Per a1.0104, Per a1.02, Per a3.01, Per a3.0201, Per a3.0202, Per a3.0203, Per a7.0101, Per a7.0102), *Vespa crabo* (Ves pc 5.0101, Ves pc 5.0101), *Vespa mandarina* (Vesp m 1.01, Vesp m 1.02); and any variants thereof.

Examples of allergenic proteins from fungi/mold that can be detected using the aptamers, signaling polynucleotides and detection agents of the present invention include, but are not limited to, *Alternaria alternata* (*Alternaria* rot fungus) (Alt a 1, Alt a 3, Alt a 4, Alt a 5, Alt a 6, Alt a 7, Alt a 8, Alt a 10, Alt a 12, Alt a 13), *Aspergillus flavus* (fungus) (Asp fl 13), *Aspergillus fumigatus* (fungus) (Asp f 1, Asp f 2, Asp f 3, Asp f 4, Asp f 5, Asp f 6, Asp f 7, Asp f 8, Asp f 9, Asp f 10, Asp f 11, Asp f 12, Asp f 13, Asp f 15, Asp f 16, Asp f 17, Asp f 18, Asp f 22, Asp f 23, Asp f 27, Asp f 28, Asp f 29, Asp f 34), *Aspergillus niger* (Asp n 14, Asp n 18, Asp n 25), *Aspergillus oryzae* (Asp o 13, Asp o 21), *Aspergillus versicolor* (Asp v 13), *Candida albicans* (Yeast) (Cand a 1, Cand a 3), *Candida boidinii* (Yeast) (Cand b 2), *Cladosporium* cladosporioides (Cla c 9, Cla c 14), *Cladosporium herbarum* (Cla h 2, Cla h 5, Cla h 6, Cla h 7, Cla h 8, Cla h 9, Cla h 10, Cla h 12), *Curvularia lunata* (Synonym: *Cochliobolus lunatus*) (Curl 1, Cur I 2, Cur I 3, Cur I 4), *Epicoccum purpurascens* (Soil fungus) (Epi p 1), *Fusarium culmorum* (N.A.) (Fus c 1, Fus c 2), *Fusarium proliferatum* (Fus p 4), *Penicillium brevicompactum* (Pen b 13, Pen b 26), *Penicillium chrysogenum* (Pen ch 13, Pen ch 18, Pen ch 20, Pen ch 31, Pen ch 33, Pen ch 35), *Penicillium citrinum* (Pen c 3, Pen c 13, Pen c 19, Pen c 22, Pen c 24, Pen c 30, Pen c 32), *Penicillium crustosum* (Pen cr 26), *Penicillium oxalicum* (Pen o 18), *Stachybotrys chartarum* (Sta c 3), *Trichophyton rubrum* (Tri r 2, Tri r 4), *Trichophyton tonsurans* (Tri t 1, Tri t 4), *Psilocybe cubensis* (Psi c 1, Psi c 2), Shaggy cap (Cop c 1, Cop c 2, Cop c 3, Cop c 5, Cop c 7), *Rhodotorula mucilaginosa* (Rho m 1, Rho m 2), *Malassezia furfur* (Malaf2, Malaf3, Malaf4), *Malassezia sympodialis* (Malas1, Malas5, Malas6, Malas7, Malas8, Malas9, Malas10, Malas11, Malas12, Malas13) and *Alternaria* alternate (Alt a1.0101, Alt a1.0102); and any variants thereof.

Examples of additional allergens include, but are not limited to, Nematode (Ani s 1, Ani s 2, Ani s 3, Ani s 4), worm (Asc s 1), soft coral (Den n 1), rubber (Latex) (Hey b 1, Hey b 2, Hey b 3, Hey b 5, Hey b 6, Hey b 7, Hey b 8, Hey b 9, Hey b 10, Hey b 11, Hey b 12, Hey b 13), obeche (Trip s 1) and Heveabrasiliensis (Hey b6.01, Hey b6.0201, Hey b6.0202, Hey b6.03, Hey b8.0101, Hey b8.0102, Hey b8.0201, Hey b8.0202, Hey b8.0203, Hey b8.0204, Hey b10.0101, Hey b10.0102, Hey b10.0103, Hey b11.0101, Hey b11.0102); and any variants thereof.

Some new allergens may include allergen secretoglobin from horse dander (U.S. Pat. No. 9,164,101) and prostate kallikrein allergen from dog (U.S. Pat. No. 9,182,400).

Other Target Molecules

In addition to allergens, detection systems, devices, aptamers, SPNs and detection agents of the present invention may be used to detect any target content in a sample.

In some embodiments, detection systems, devices, aptamers, SPNs and detection agents of the present invention may detect one or more target proteins specific to a pathogenic microorganism. The target protein may be a molecule secreted by a pathogen, a surface protein, a protein induced in a host which a pathogen attacks, or a portion of a target protein. The present invention allows for the detection and identification of many different types of pathogenic microorganisms, such as bacteria, yeasts, fungi, spores, viruses or prions. As used herein, the term "pathogen" means any disease-producing agent (especially a virus or bacterium or other microorganism).

In some embodiments, detection systems, devices, aptamers, SPNs and detection agents of the present invention may detect other target molecules such as diseases associated proteins to diagnose, stage diseases, disorders and other clinical conditions. Disease associated proteins may be secreted polypeptides and peptides (e.g. circulating molecules); cell surface proteins (e.g. receptors); biomarkers that are expressed or overexpressed in a particular disease condition; isoforms, derivatives and/or variants of a particular protein that are only present in a disease condition; mutated proteins that cause a disorder; and proteins derived from another organism which causes a clinical condition in the host such as viral infection.

In other embodiments, detection systems, devices, aptamers, SPNs and detection agents of the present invention may detect non-protein target molecules, for example, a ganglioside, a lipid, a phospholipid, a carbohydrate, a small molecule (e.g. a mycotoxin and an antibiotic), a hapten, and a nucleic acid (DNA or RNA), a pesticide, a fertilizer and other chloroaromatic pollutants.

Assays and Methods

The present invention further provides methods for detecting the presence and/or absence of an allergen of interest in a food sample. Various methods and assays may be used in combination with detection systems, devices, aptamers, SPNs, detection agents and compositions of the present invention; the choice may depend on the application field. In some embodiments, an allergen detection testing assay is provided using aptamer-based signal polynucleotides as detection agents. In some embodiments, the signal polynucleotide is labeled with a fluorophore at one terminus of the polynucleotide. In other embodiments, changes in fluorescence polarization upon allergen protein binding may be detected to measure the presence of an allergen. In some embodiments, the SPNs and detection agents may comprise nucleic acid sequences included in Table 1 and Table 2.

In general, assays and methods for detecting a target allergen protein in a sample using systems, device, aptamers, SPNs and detection agents of the present invention comprise steps of (a) obtaining a test sample suspected of containing an allergen of interest; (b) processing the sample of (a) with an extraction buffer; (c) contacting the processed sample with a detection agent specific to the allergen on interest; (d) treating the mixed processed sample and detection agent with an excitation means; and (e) visualizing the interaction between the allergen of interest contained in the processed sample and the detection agent. Assays and methods provided can detect the presence and/or absence of an allergen of interest in a sample, and/or determine the amount of the allergen in a sample.

Assays and methods for detecting the allergen content in a sample are applicable to foods containing the allergens without any restriction. Examples of foods include eggs, milk, meat, fishes, crustacea and mollusks, cereals, legumes and nuts, fruits, vegetables, beer yeast, and gelatin; more particularly, egg white and egg yolk of the eggs, milk and cheese of the milk, pork, beef, chicken and mutton of the meat, mackerel, horse mackerel, sardine, tuna, salmon, codfish, flatfish and salmon caviar of the fishes, crab, shrimp, blue mussel, squid, octopus, lobster and abalone of the crustacea and mollusks, wheat, rice, buckwheat, rye, barley, oat, corn, millet, foxtail millet and barnyardgrass of the cereals, soybean, peanut, cacao, pea, kidney bean, hazelnut, Brazil nut, almond, coconut and walnut of the legumes and nuts, apple, banana, orange, peach, kiwi, strawberry, melon, avocado, grapefruit, mango, pear, sesame and mustard of the fruits, tomato, carrot, potato, spinach, onion, garlic, bamboo shoot, pumpkin, sweet potato, celery, parsley, yam and Matsutake mushroom of the vegetables, the foods containing them, and the ingredients thereof (e.g., ovoalbumin, ovomucoid, lysozyme, casein, beta-lactoglobulin, alpha-lactoalbumin, gluten, and alpha-amylase inhibitor).

The foods could be fresh foods, frozen foods, cooled foods or processed foods containing animal derived meat and/or vegetables. These foods may be processed by heating, freezing, drying, salting, fermentation, enzymatic processing, etc.

In some embodiments, food sample processing may involve use of a universal formulation. This universal formulation will be clinically relevant as to try to minimally affect the food tested and only sample approximately 0.5 g of food, allowing detection of traces of allergens when their concentration will be minimal in the sample. This optimized protein extraction process will provide a fast, accurate and universal protocol that allows detection of an allergen in any food matrix. In some aspects, the universal buffer may be a Tris based buffer (T buffer), a HEPES based buffer, TGK based buffer, or PBS based buffer. A detailed discussion is provided below.

In some embodiments, one or more detection agents (e.g. SPNs) may be used, depending on the nature of the food matrixes. Some food contains several allergenic proteins, e.g., at least eight peanut proteins, such as Ara h1 and Ara h2, can potentially cause an immunological response. In such case, more than one SPN against more than one allergenic protein may be used in a mixed cocktail for detecting the absence or presence of peanut. In other aspects, some food matrixes such as fish, shellfish and mollusks, contain only one major allergenic protein. One or more SPNs that specifically bind to this major allergen protein may be used for allergen detection. In some aspects, detection agents may be pre-stored in the detection system, and be released during the process of a detection assay, for example, in the disposable test cup of the present invention.

In some embodiments, allergen detection assays and methods of the present invention can detect a lower concentration of allergen in a food sample. The sensitivity of nucleic acid aptamers and SPNs and optical design makes it possible to detect the presence of an allergen as low as 0.0001 ppm. In some aspects, the concentration or mass of allergen that can be detected may range from 0.001 ppm to 5 ppm, or from 0.001 ppm to 0.1 ppm, or from 0.1 ppm to 3 ppm, or from 1 ppm to 5 ppm, or from 5 ppm to 10 ppm, or from 10 ppm to 30 ppm. In some aspects, the concentration or mass of allergen in a food sample that can be detected may be 0.001 ppm, 0.002 ppm, 0.003 ppm, 0.004 ppm, 0.005 ppm, 0.006 ppm, 0.007 ppm, 0.008 ppm, 0.009 ppm, 0.01 ppm, 0.02 ppm, 0.03 ppm, 0.04 ppm, 0.05 ppm, 0.06 ppm, 0.07 ppm, 0.08 ppm, 0.09 ppm, 0.1 ppm, 0.2 ppm, 0.3 ppm, 0.4 ppm, 0.5 ppm, 0.6 ppm, 0.7 ppm, 0.8 ppm, 0.9 ppm, 1.0 ppm, 1.5 ppm, 2 ppm, 2.5 ppm, 3 ppm, 3.5 ppm, 4 ppm, 4.5 ppm, 5 ppm, 10 ppm, 15 ppm, 20 ppm, or 30 ppm.

In some embodiments, allergen detection assays and methods of the present invention may complete the implementation in less than 5 minutes. In some aspects, the assay time may be from about 1 minute to about 5 minutes, about 1 minute to about 3 minute, about 2 minutes to about 10 minutes, about 5 minutes to about 10 minutes. In other aspects, the assay time may last less than 1 min, 2 min 3 min, 4 min, 5 min, 6 min, 7 min, 8 min, 9 min, or 10 min. In further other aspects, the assay time may last less than about 10 seconds, about 15 seconds, about 20 seconds, about 25 seconds, about 30 seconds, about 35 seconds, about 40 seconds, about 45 seconds, about 50 seconds, about 55 seconds or about 60 seconds.

Any methods and systems used to detect and display nucleic acid molecule (e.g., SPN) and protein interaction may be used to display the detection results. In some embodiments, fluorescence polarization (FP) changes from a fluorophore probed detection molecule (e.g. SPN) upon the binding of a target allergen are measured to indicate the presence and absence of the target allergen in a sample. To measure fluorescence polarization, the sample is excited with linearly polarized light. When the emission polarizer is oriented parallel to the direction of the polarized excitation, the fluorescence intensity in parallel is measured and when the emission polarizer is oriented perpendicularly to the polarization plane of the excitation light, the perpendicular fluorescence intensity is measured. Fluorescence emission may be depolarized by a number of phenomena, including rotational diffusion of the fluorophore during the lifetime of the excited state, energy transfer, reabsorption, etc. Following the principle of FP technology, the binding of a target allergen to the relatively small signaling polynucleotide can significantly change the rotational diffusion; such change cause FP and can be used to quantify the bound target.

In some embodiments, the FP change may be measured using an optical system and the detected signal may be visualized to report to the consumer. In one aspect, the device of the present invention may be used. Accordingly, the polarized light emitter in the system emits lights having an excitation wavelength appropriate to excite the fluorophore of the SPNs and the light detector in the system can filter fluorescence emitted from the fluorophores of the SPNs and transmit the wavelength(s) of interest. A means then may be used to process and convert the fluorescence signals to useful readouts (i.e. digital signals). In another aspect, changes in FP may be measured in any commercial FP equipment.

In some embodiments, the wavelength of the polarized light is in a range of 200 nm and 800 nm.

In some embodiments, signals from the interaction between a SPN and a target allergen may be detected and visualized by a detection system. Some non-limiting examples include lateral flow devices (LFD), microfluidic chips (U.S. Pat. No. 8,617,903), portable detection devices/systems described in the commonly owned U.S. patent application No. 62/133,632 filed on Mar. 16, 2015 and 62/182,900 filed Jun. 22, 2015, and the cartridge as described in the commonly owned PCT patent application NO.: PCT/US14/62656 filed on Oct. 28, 2014, the contents of each of which are incorporated herein by reference in their entirety.

The detection result from the present assay may be displayed in a platform that a user can easily read such as a display window. In one embodiment, it may be a platform application in a computer, a pad and/or a smartphone (Coskun et al., *A personalized food allergen testing platform on a cellphone*, Lab Chip., 2013, 13(4), 636-640; the contents of which are incorporated herein by reference in its entirety).

In one embodiment, a method for detecting the presence and/or absence of an allergen protein of interest may be implemented with the present detection systems and compositions. A detailed description of the method is set forth in the following sections.

Sampling

To provide a reliable and sensitive result from an allergen detection testing, a right size of a testing sample is important. The inventors of the present invention developed a sampling mechanism that can collect a test sample effectively and non-destructively for fast and efficient extraction of allergen proteins for detection.

A sized portion of the test sample can be collected using, for example, a food corer 200 illustrated in FIG. 2c. The sample pickup (e.g., food corer 200) can measure the size and collect a rightly sized sample which can provide enough protein extraction for the detection testing. The sized portion may be ranged from 0.1 g to 1 g food sample. Furthermore, the food corer 200 may pre-process the collected test sample by cutting, grinding, blending, abrading and/or filtering. Pre-processed test sample will be introduced into the sample processing cup body 220 for homogenization and allergen protein extraction. As illustrated in FIG. 1a and FIG. 3a, the food corer 200 may be inserted into the food corer port 213 on the top of the cup lid assembly 210 and releases the test sample into the disposable test cup 300.

The collected test sample is processed in an extraction buffer. In some aspects, an extraction buffer is present in the cup body 220 and may be mixed with the test sample by the homogenizer assembly 570. In other aspects, the extraction buffer may be released into the cup body 220 from a local region (e.g., at the bottom of the cup body 220) by manual plunging or automatically release from the storage place to the cup chamber. The test sample and the extraction buffer will be mixed together by the homogenizer assembly 570 and the sample being homogenized.

The extraction buffer may be universal target extraction buffer that can retrieve enough target protein (e.g., minimum 1 mg/ml total protein) from any test sample and be optimized for maximizing protein extraction and allergen retrieval. In some embodiments, the formulation of the universal protein extraction buffer can extract protein at room temperature and in minimal time, e.g., less than about 2 minutes, or less than about 1 minute, or less than about 30 seconds. The same buffer may be used during food sampling, homogenization and filtering. The universal extraction buffer will be applicable to any allergen and to all foods (e.g. pre-processed or post-processed). Additionally, the universal extraction buffer can improve signaling polynucleotides (SPNs) binding affinity, minimize non-specific binding and increase signal to noise ratio. In certain aspects, the extraction buffer may be PBS based buffer containing 10%, 20% or 40% ethanol, or Tris based buffer containing Tris base Ph8.0, 5 mM MEDTA and 20% Ethanol, or a modified PBS or Tris buffer. In some examples, the buffer may be a HEPES based buffer. Some examples of modified PBS buffers may include: P+ buffer and K buffer. Some examples of Tris based buffers may include Buffer A+, Buffer A, B, C, D, E, and Buffer T. A detailed description of each modified buffer is disclosed in the PCT patent application No.: PCT/US2014/062656; the content of which is incorporated herein by reference in its entirety.

The volume of the extraction buffer may be from 0.5 mL to 3 mL, which has been determined to be efficient and repeatable over time and in different food matrices.

In accordance with the present invention, the test sample is homogenized and processed using a homogenizer (e.g. the homogenizer assembly 570) that has been optimized with high speed homogenization for maximally processing the test sample. In some aspects, a filtering mechanism may be linked to the homogenizer. The homogenized sample solution is then driven to flow through a filter processing to further extract allergen proteins, lowering the amount of other molecules extracted from the test sample. A filter membrane such as cell strainer from CORNING (CORNING, N.Y., USA) or similar custom embodiment may be connected to the homogenizer. The filter pores can be between 0.2 μm to 600 μm. The filter can be made from any low binding material, including, but not limited to, PES (Polyethersulfone), PCTE (Polycarbonate) or PVDF (polyvinylidene difluoride). The filtering process may be a multi-stage arrangement with changing pore sizes from first filter to second. Filters may be in any configuration relative to the FLOW VALVE (get the right name of this from above), above, below or in between any of the stages of the filtration.

In some aspects, the sampling procedure may reach effective protein extraction in less than 1 minute. In one aspect, speed of digestion may be less than 2 minutes including food pickup, digestion and readout. Approximately, the procedure may be 15 seconds, 30 seconds, 45 seconds, 50 seconds, 55 seconds or 1 minute.

Sensors and Detection Agents

Extracted allergen proteins may be mixed with one or more detection agents that are specific to one or more allergens of interest. The interaction between allergen protein extraction and detection agents will generate a detectable signal which indicates the presence, or absence or the amount of one or more allergens in the test sample. As used herein, the term "detection agent" or "allergen detection agent" refers to any molecule which is capable of, or does, interact with and/or bind to one or more allergens in a way that allows detection of such allergen in a sample.

In one aspect of the present invention, the detection agents are nucleic acid molecules based SPNs.

In other embodiments, aptamer molecules that can be used as detection agents in reaction chambers 223 may be aptamers described in applicants' relevant patent applications including U.S. Provisional Application Ser. No. 62/026,361, filed on Jul. 18, 2014; U.S. Provisional Application Ser. No. 62/009,958, filed on Jun. 10, 2014; U.S. Provisional Application Ser. No. 61/991,068, filed on May 9, 2014; U.S. Provisional Application Ser. No. 61/938,528, filed on Feb. 11, 2014; U.S. Provisional Application Ser. No. 61/896,399, filed on Oct. 28, 2013; and PCT Application Serial No.: PCT/US2014/062656, filed on Oct. 28, 2014; and U.S. Provisional Application Ser. No. 62/154,200 filed on Apr. 29, 2015; the contents of each of which are herein incorporated by reference in their entirety.

In addition to aptamers based SPNs, detection agents used in the detection device 100 may be any molecules or agents which are capable of association or binding to one or more allergens such as small molecules, antibodies and variants thereof. The antibodies detectors may be polyclonal antibodies, monoclonal antibodies, single chain antibodies, antibody fragments and other functional variants.

In some embodiments, aptamers and SPNs of the present invention which are labeled with a fluorescent marker may be used as the detection agents. The SPNs may comprise nucleic acid sequences as included in Table 1 and Table 2. In some aspects, the SPNs may be labeled at one end of the polynucleotide with a fluorescent marker. In this aspect, a change in fluorescence polarization of the fluorescent probed detection agent upon the binding of an allergen presented in a test sample is measured and used to calculate the allergen content in the test sample. Fluorescence polarization changes may be measured by the optical subsystems 520 as shown in FIG. 16 and FIG. 17 of the present detection system.

The fluorescent marker, fluorophore may suitably have an excitation maximum in the range of 200 to 800 nm, while the emission maximum may be in the range of 300 to 700 nm. The fluorophore may further have a fluorescence relaxation time in the range of 1-7 nanoseconds, preferably 3-5 nanoseconds. As non-limiting examples, a fluorophore that can be probed at one terminus of a SPN may include derivatives of BODIPY (e.g., BODIPY TMR dye; BODIPY FL dye), Fluorescein including derivatives thereof, Rhodamine including derivatives thereof, Dansyls including derivatives thereof (e.g. dansyl cadaverine), Texas red, Eosin, Cyanine dyes, Indocarbocyanine, Oxacarbocyanine, Thiacarbocyanine, Merocyanine, Squaraines and derivatives Seta, SeTau, and Square dyes, Naphthalene and derivatives thereof, Coumarin and derivatives thereof, Pyridyloxazole, Nitrobenzoxadiazole, Benzoxadiazole, Anthraquinones, Pyrene and derivatives thereof, Oxazine and derivatives, Nile red, Nile blue, Cresyl violet, Oxazine 170, Proflavin, Acridine orange, Acridine yellow, Auramine, Crystal violet, Malachite green, Porphin, Phthalocyanine, Bilirubin, Tetramethylrhodamine, Hydroxycoumarin, Aminocoumarin; Methoxycoumarin, Cascade Blue, Pacific Blue, Pacific Orange, NBD, R-Phycoerythrin (PE), Red 613; PerCP, TruRed; FluorX, Cy2, Cy3, Cy5 and Cy7, TRITC, X-Rhodamine, Lissamine Rhodamine B, Allophycocyanin (APC) and Alexa Fluor dyes.

In addition to fluorescence polarization changes, the specific interaction between the detection agent labeled with a fluorophore and an allergen may also be detected by measuring other optical properties including but not limited to absorbance, fluorescence intensity, fluorescent spectrum and fluorescence lifetime. The measurement of fluorescence signals provides a sensitive method of monitoring the biochemical changes in an environment such as the sample mixture of the present detection assay.

In some embodiments, detection agents for 8 major food allergens (i.e. wheat, egg, milk, peanuts, tree-nuts, fish, shell-fish and soy) may be provided as disposables. In one aspect, constructs of the detection agents may be stored with MgCl, or buffer doped with KCl. MgCl keeps constructs closed tightly, while KCl opens them slightly for bonding.

Detection System

The mixture of allergen protein extraction and detection agents is analyzed in the reaction chamber 223. As described above, a detection agent (e.g., SPN) probed with a fluorophore (e.g., Texas red) is a small molecule and rotates fast. In general, the plane polarized excitation light absorbed by a fluorophore is rotated to the same degree of molecular rotation the fluorophore undergoes before emission of fluorescence. Fluorescence emission may be depolarized by a number of phenomena, including rotational diffusion of the fluorophore during the lifetime of the excited state, energy transfer, reabsorption, etc. The binding of a target allergen to the relatively smaller signaling polynucleotide can significantly slow down the rotation and change the rotational diffusion; such changes can be used to quantify the bound allergen protein. According to the present invention, an optical subsystem 520 as shown in FIG. 16 and FIG. 17 measures such signals and converts the detected signals to digital signals, or compare analog signals to thresholds which are used to indicate the user the presence, or absence, or the amount of allergen in the test sample.

Fluorophores being excited by lights at this range would allow for inexpensive laser or LED illumination. A printed circuit board (PCB) 550 may be used to convert the fluorescent signals into digital signals or comparing analog signals to thresholds for displaying the readouts of the detection testing to the user. In some embodiments, a polystyrene window can be designed for reading, as fluorescent readings are very precise and repeatable in polystyrene well plate.

In addition to above described detection methods comprising fluorescence polarization measurement, the detection mechanism may be based on a chemiluminescence measurement, a colorimetric measurement, a pH measurement, a measurement of dissolved oxygen, a redox measurement and/or other suitable measurement.

Applications

In accordance with the present invention, detection systems, devices and methods described herein contemplate the use of nucleic acid-based detector molecules such as aptamers, or aptamer derived SPNs for detection of allergens in samples such as food samples. The portable devices allow a user to test the presence or absence of one or more allergens in food samples that the user is allergic to. Allergen families that can be detected using the systems and compositions described herein include allergens from foods, the environment or from non-human proteins such as domestic pet dander. Food allergen, may include, but are not limited to, legumes such as peanuts, peas, lentils and beans, as well as the legume-related plant lupin, tree nuts such as almond, cashew, walnut, Brazil nut, filbert/hazelnut, pecan, pistachio, beechnut, butternut, chestnut, chinquapin nut, coconut, ginkgo nut, lychee nut, macadamia nut, nangai nut and pine nut, egg, fish, shellfish such as crab, crawfish, lobster, shrimp and prawns, mollusks such as clams, oysters, mussels and scallops, milk, soy, wheat, gluten, corn, meat such as beef, pork, mutton and chicken, gelatin, sulphite, seeds such as sesame, sunflower and poppy seeds, and spices such as coriander, garlic and mustard, fruits, vegetables such as celery, and rice. The allergen may be present in a flour or meal, or in any format of products. For example, the seeds from plants, such as lupin, sunflower or poppy can be used in foods such as seeded bread or can be ground to make flour to be used in making bread or pastries. The device is capable of confirming the presence or absence of these allergens as well as quantifying the amounts of these allergens.

In some embodiments, detection systems, devices, aptamers, SPNs, detection agents and assays of the present invention may be used in a hospital for clinical food allergy or allergy test and to identify food/allergen(s) to which a patient is allergic. Such assays and methods may also be used to monitor allergen contamination in food industry. Additionally, they may also be used at home or in a restaurant by a person who has allergy to test the allergen content before he/she consumes the food.

In a broad concept, the detection systems, devices, aptamers, SPNs, detection agents and methods described herein may be used for detection of any protein content in a sample in a large variety of applications in addition to food safety, such as, for example, medical diagnosis and prognosis of diseases in civilian and battlefield settings, environmental monitoring/control and military use for the detection of biological weapons. In even broad applications, the detection systems, devices, SPNs, compositions and methods of the present invention may be used to detect any biomolecules which nucleic acid-based detector molecules bind. As some non-limiting examples, the detection systems, devices, SPNs, agents and methods may be used on the spot detection of cancer markers, in-field diagnostics (exposure the chemical agents, traumatic head injuries etc.), third-world applications (TB, HIV tests etc.), emergency care (stroke markers, head injury etc.) and many others.

As a non-limiting example of applications, the detection systems, devices, aptamers, SPNs, detection agents and methods of the present invention can detect and identify pathogenic microorganisms in a sample. Pathogens that can be detected include bacteria, yeasts, fungi, viruses and virus-like organisms. Pathogens could cause diseases in animals and plants; contaminate food, water, soil or other sources; or is used as biological agents in military fields. The device is capable of detecting and identifying these pathogens.

Another important application includes the use of the detection systems, devices, SPNs, detection agents and methods of the present invention for medical care, for example, to diagnose a disease, to stage a disease progression and to monitor a response to a certain treatment. As a non-limiting example, detection devices and SPNs of the present invention may be used to test the presence or absence, or the amount of a biomarker associated with a disease (e.g. cancer) to predict a disease or disease progression. The detection systems, devices and methods of the present invention are designed to analyze a small amount of test sample and can be implemented by a user without extensive laboratory training.

Other expanded applications outside of the field of food safety include in-field use by military organizations, testing of antibiotics and biological drugs, environmental testing of products such as pesticides and fertilizers, testing of dietary supplements and various food components and additives prepared in bulk such as caffeine and nicotine, as well as testing of clinical samples such as saliva, skin and blood to determine if an individual has been exposed to significant levels of an individual allergen.

Definitions

At various places in the present specification, substituents of compounds of the present disclosure are disclosed in groups or in ranges. It is specifically intended that the present disclosure include each and every individual subcombination of the members of such groups and ranges. The following is a non-limiting list of term definitions.

About: As used herein, the term "about" when referring to a measurable value such as an amount of weight, time, dose, etc. is meant to encompass variations of ±20% or ±10%, more preferably ±5%, even more preferably ±1%, and still more preferably ±0.1% from the specified amount, as such variations are appropriate to perform the disclosed method.

Activity: As used herein, the term "activity" refers to the condition in which things are happening or being done. Compositions of the invention may have activity and this activity may involve the binding to a target molecule.

Allergen: as used herein, the term "allergen" means a compound, substance or composition that causes, elicits or triggers and immune reaction in a subject. As such, allergens are typically referred to as antigens. An allergen is typically a protein or a polypeptide.

Allergen detection agent: As used herein, the term "an allergen detection agent" refers to Any agent which is capable of, or does, interact with and/or bind to one or more allergens in a way that allows detection of such allergen in a sample is referred to herein as an "allergen detection agent" or "detection agent".

Binding affinity: As used herein, the term "binding affinity" refers to the tendency of a detection molecule (e.g., aptamer) to bind or not bind a target (e.g., allergen) and describes the measure of the strength of the binding or affinity of the detection molecule to bind the target.

Local conformational shape: As used herein the term "local conformational shape" means a structural manifestation which is located within a definable space of the polynucleotide.

Detection: As used herein, the term "detection" means an extraction of a particular target protein from a mixture of many non-target proteins, indicating the absence, presence, and/or amount of a target protein from a mixture of many non-target proteins.

Detectable label: As used herein, "detectable label" refers to one or more markers, signals, or moieties which are attached, incorporated or associated with another entity, which markers, signals or moieties are readily detected by methods known in the art including radiography, fluorescence, chemiluminescence, enzymatic activity, absorbance, immunological detection and the like. Detectable labels may include radioisotopes, fluorophores, chromophores, enzymes, dyes, metal ions, ligands, biotin, avidin, streptavidin and haptens, quantum dots, polyhistidine tags, myc tags, flag tags, human influenza hemagglutinin (HA) tags and the like. Detectable labels may be located at any position in the entity with which they are attached, incorporated or associated. For example, when attached, incorporated in or associated with a peptide or protein, they may be within the amino acids, the peptides, or proteins, or located at the N- or C-termini.

Domain: as used herein the term "domain" refers to a motif of a polynucleotide having one or more identifiable structural or functional characteristics or properties (e.g., binding capacity, serving as a site for molecular interactions.

Fluorescence polarization (FP): as used herein, the term "fluorescence polarization (FP)" refers to changes in the orientation of plane polarized light brought by fluorophores that undergo significant molecular motion during their fluorescent lifetime. This lifetime is defined as the period of time between absorption of an excitation photon and the emission of a photon through fluorescence. In general, the plane polarized excitation light absorbed by a fluorophore is rotated to the same degree of molecular rotation the fluorophore undergoes before emission of fluorescence. Most fluorophore are small molecules and rotate fast. Measurable changes in polarization or depolarization of plane polarized light, can occur during its fluorescence lifetime. Significant depolarization can still occur if the fluorophore is attached to a small ligand. The extent of depolarization provides a basis for quantifying specific binding of fluorescent ligands (detection agents) to targets (such as allergen proteins). If the small detection agent binds a target of significantly greater size (e.g. an allergen protein), the ability of the detection agent to depolarize plane polarized light is severely reduced, the added molecular volume of the target protein will greatly reduce molecular rotation over the fluorescence lifetime. In fact, the extent of specific binding can be quantified by measuring the extent of depolarization. The greater the specific binding, the less depolarization of the original plane polarized light. The FP signal is expressed as a ratio of fluorescence intensities. Thus, the signal is not influenced by changes in intensity brought about by detection agent concentration changes. This is because the ability of a fluorophore to depolarize light is not a function of its concentration; rather, it is a function of its ability to rotate freely during the fluorescence lifetime.

Including: As used herein, the term "including" refers to "including but not limited to". "Including" and "including but not limited to" are used interchangeably.

Interaction: As used herein, the term "interaction" refers to a kind of action that occurs as two or more molecules have effect upon one another. In the context of the present invention, an interaction between a detection molecule and a target affects the structure of the detection molecule and such effect will generate energetic changes that can be visualized.

Loop: as used herein the term "loop" refers to a structural feature of a polynucleotide which reverses the direction of the backbone of the sequence and comprises four or more nucleoside (or nucleotide) residues.

Polynucleotide: As used herein, the term "polynucleotide" refers to nucleobase polymers or oligomers in which the nucleobases are connected by sugar phosphate linkages (sugar-phosphate backbone). Exemplary poly- and oligonucleotides include polymers of 2' deoxyribonucleotides (DNA) and polymers of ribonucleotides (RNA). A polynucleotide may be composed entirely of ribonucleotides, entirely of 2' deoxyribonucleotides or combinations thereof.

Polynucleotide variants: As used herein, the term "polynucleotide variants" refers to molecules with some differences in their nucleic acid sequences as compared to a native or starting sequence.

Sample: As used herein, the term "sample" refers to any composition that might contain a target of interest to be analyzed including, but not limited to, biological samples obtained from subjects (including humans and animals as detailed below), samples obtained from the environment for example soil samples, water samples, agriculture samples (including plant and crop samples), or food samples. Food samples may be obtained from fresh food, processed/cooked food or frozen food.

Sensitivity: As used herein, the term "sensitivity" means the ability of a detection molecule to bind to a target molecule.

Specifically bind(s): As used herein, the term "specifically bind(s)" means that a detection molecule (e.g., aptamer) reacts or associates more frequently, more rapidly, with greater duration and/or with greater affinity with a particular target such as an allergen protein than it does with alternative targets. For example, an aptamer that specifically binds to an allergen protein binds that protein or a fragment thereof with greater affinity, avidity, more readily, and/or with greater duration than it binds to unrelated protein and/or the fragments thereof. It is also understood by an artisan by this definition, for example, a detection molecule (e.g., aptamer) that specifically binds to a first target may or may not specifically bind to a second target. As such, "specific binding" does not necessarily require exclusive binding or non-detectable binding of another molecule, this is encompassed by the term "selective binding". Generally, but not necessarily, reference to binding means specific binding. The specificity of binding is defined in terms of the comparative dissociation constants (Kd) of the aptamer for target as compared to the dissociation constant with respect to the aptamer and other materials in the environment or unrelated molecules in general. Typically, the Kd for the aptamer with respect to the target will be 2-fold, 5-fold, or 10-fold less than the Kd with respect to the target and the unrelated material or accompanying material in the environment. Even more preferably, the Kd will be 25-fold, 50-fold, 75-fold, 100-fold, 150 fold or 200-fold less.

Target: as used herein, the term "target" and "target molecule" refers to a molecule which may be found in a tested sample and which is capable of binding to a detection molecule such as an aptamer or an antibody.

Termini or terminus: as used herein the terms "termini" or "terminus" refers to an extremity of a polynucleotide. Such extremity is not limited only to the first or final site of the polynucleotide but may include additional nucleosides (or nucleotides) in the terminal regions. The polynucleotides of the present invention may be characterized as having both a 5' terminus and a 3' terminus.

Universal buffer: As used herein, the term "universal buffer" refers to a buffer that may be used for a variety of samples.

Other Embodiments

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

EXAMPLES

Example 1: Selection of Aptamers that Bind an Allergen Protein

An in vitro screening experiment based on SELEX method was carried out and aptamers were selected against the allergen targets including egg, gluten, milk, soy, fish, peanut, cashew and crustacean, over the counter-target (combinations of the non-target proteins) and were further engineered for their capability in detecting targeted food allergens.

Experimental Plan

Various RNA libraries were used to select for binding ability in selection buffer consisting of 100 mM Tris (pH 8), 5 mM EDTA, 150 mM NaCl, 10 mM MgCl2, 0.1% SDS, 0.1% Gelatin, 1% NP-40 (Tergitol), 0.5% Deoxycholate Sodium at 23° C. A given round of selection began with incubating RNA library members in either the buffer alone (negative selection), then collecting the portion of the library that did not respond (i.e. cleave). The second part of each round (when called for) consisted of incubating the non-responsive molecules from the prior negative selection step with the full combination of non-positive targets (as the counter), or with just the selection buffer again for a second negative selection. Once again, the non-responsive (non-cleaving) molecules would be collected. The final step of each round consists of incubating the material from the previous step with the positive target (each of the allergens as appropriate) in buffer, then collecting the responsive material (i.e. cleaved RNA). Each selection round was followed by reverse transcription to generate cDNA, library amplification through PCR, and regeneration of the RNA library by transcription. After subjecting the initial library of diverse random sequences to varying consecutive rounds of selection (i.e. negative, counter and positive selections), again project-dependent, and the enriched libraries were divided into three fractions to perform the parallel assessments.

The parallel assessment of libraries enriched after rounds of negative, counter and positive selections, involves simultaneously exposing one third of the enriched library to selection buffer alone, another one-third to the counter-target complex in selection buffer, and the final one-third of the enriched library to the target allergen in buffer. Any residual RNA molecules that react indiscriminately to both target allergen and counter-targets, or that still generate a response in the absence of the target allergen were identified and discarded during further bioinformatics analysis.

The enriched RNA libraries after the parallel assessment were subjected to PAGE gel assessment. 40 pmoles of enriched library was exposed separately to either the negative (buffer only), counter target, or target allergen (e.g., milk, wheat, egg white and peanut) in selection buffer. After 5 minutes incubation at 23° C., libraries exhibiting a positive response (i.e. cleavage) material were collected, ethanol precipitated, reverse transcribed, and PCR-amplified for sequencing and bioinformatics analysis.

Materials and Methods

Targets (complexes of proteins from cashew, peanut, fish, milk, soy, gluten, egg and crustacean) were dried down, if necessary, before being combined with RNase-free water for preliminary analysis and aptamer screening. When needed, targets were pooled to produce counter-target mixture by combining appropriate amounts of the targets which were not designated as positive target for the selection. The initial aptamer library template and primers were synthesized by IDT (Coralville, Iowa) as single-stranded DNA. The library was then primer extended to provide double-stranded DNA (dsDNA) using Titanium Taq DNA polymerase from Clontech (Mountain View, Calif.).

Following the experimental plan, for a given generation of the library, RNA was transcribed from the previous dsDNA with AmpliScribe T7 Transcription kits from Epicentre (Madison, Wis.) and purified using a 10% denaturing polyacrylamide gel electrophoresis (PAGE). The purified RNA was combined with Selection Buffer, which was then diluted to 1× concentration (100 mM Tris (pH 8), 5 mM EDTA, 150 mM NaCl, 10 mM MgCl2, 0.1% SDS, 0.1% Gelatin, 1% NP-40 (Tergitol), 0.5% Deoxycholate Sodium) for negative selection. Negative selection began with a refolding cycle, which involved heating the sample to 65° C. to denature the RNA before bringing the sample to 23° C. for the remainder of the incubation. After incubation, non-cleaved RNA was separated from cleaved RNA using 10% denaturing PAGE. Recovered non-cleaved material was combined with counter-target and buffer, target and buffer, or buffer alone depending on the selection step, incubated at 23° C., and partitioned on 10% denaturing PAGE. Recovery and another selection step was implemented if called for. cDNA was then generated from eluted post-selection library using SuperScript II Reverse Transcriptase (Life Technologies; Carlsbad, Calif.), then PCR-amplified with Titanium Taq DNA polymerase (Clontech; Mountain View, Calif.) to complete the round of selection. After several rounds of selection steps, libraries were enriched and showed that the negative cleavage amount was less than 30%, and that there was at least 5% more cleavage in the positive treatment when compared to the counter.

The initial libraries consisting of approximately $10^{14}$ random sequences was subjected to varying rounds of ribozyme-based SELEX to enrich for sequences that bind to the target allergens and to eliminated sequences that bind to the counter-targets over multiple rounds of selection. As a result, the population to be sequenced is expected to contain multiple copies of potential aptamer candidates (Van Simaeys et al., *Study of the Molecular Recognition of Aptamers Selected through Ovarian Cancer Cell-SELEX*, 2010, PLOS One, 5(11): e13770).

Sequencing and Bioinformatics

The Illumina (San Diego, Calif.) MiSeq system was implemented to sequence the aptamers after the selections using a paired-end read technique. Bioinformatics analysis of the sequencing data identified candidate aptamer molecules. The deep sequencing and subsequent data analysis reduced the traditional approach of performing a large number of selections, which may introduce error and bias due to the screening process (Schütze et al., *Probing the SELEX Process with Next-Generation Sequencing*, PLos One, 2011, 6(12): e29604).

Selection of Aptamer Candicates

Sequence family construction focused on motif presence which means that a sequence's frequency in the positive target population was factored in, but places greater emphasis on the prevalence of sub-sequences in the overall population (100% match over the entire sequence not necessary to join a family). Two other factors were used to adjust the importance of motif-family size to determine candidate sequences. One factor is the presence of the sequence in the negative and counter-target population. Three libraries were collected from the parallel assessment: the positive target-exposed library, the buffer-only negative library, and the counter-target-exposed library. All libraries were analyzed to discover any sequences that have yet to be removed during a negative- or counter-selection step, but still have affinity for both the target and counter-target. A given sequence appears more frequently in the positive population than in the counter-target-exposed population, making it an attractive candidate for further testing.

The secondary structure of a given candidate sequence was also predicted using the Mfold secondary structure modeling software (Zucker, *Mfold web server for nucleic acid folding and hybridization prediction*, Nucleic Acids Res., 2003, 31 (13): 3406-3415).

A set of aptamer sequences were selected and further designed as signaling polynucleotides for detecting different food allergens, including cashew, peanut, egg white, wheat, fish, soy, milk and crustacean. The full sequences and core sequences which define the binding specificity to each allergen of selected aptamers are listed in Table 1. The selected aptamers for each food allergen are then further modified at either one or both of the 5' terminus and the 3' terminus to optimize the binding affinity to its targeted allergen. Modified sequences that are intended to have a fluorophore probe (e.g., Texas Red) at the 5' terminus are the signaling polynucleotides that will be tested for allergen detection as described herein.

Example 2: Generation of Signaling Polynucleotides

As a proof-of-concept example, two aptamers selected from the screen as indicated in Example 1 were used to design different signaling polynucleotides. The strategy was to delete as much of the primers used for the screen as possible but maintain the core binding sequence to ensure the specificity to a target allergen.

Signaling Polynucleotides Specific to Peanut

An aptamer selected from the screen (Example 1) that is specific to peanut was used. The full Sequence of the aptamer is shown below.

```
(7 RiboSPN_full sequence; SEQ ID NO.: 83)
5'TAATACGACTCACTATAGGCGTAGCCTGATGAGCTCACCACATA
CCATGTACCACGTGCGAAACGTGGTGAAAGCCACGTAGCTGCGCC3'
```

The core sequence to bind to peanut is shown below.

```
(7 SPN-core sequence; SEQ ID NO.: 84)
5'CTCACCACATACCATGTACCACGTG3'
```

The original full sequence of SEQ ID NO.:83 was modified to delete as much of the primers as possible at both 5' terminus and 3' terminus without changing the binding sequence of SEQ ID NO.: 84. Additional nucleotides were also added at either 5' terminus or 3' terminus or both termini. The shortest sequences without impacting the binding sequence and forming an open single structure were tested for allergen detection. The resulted signaling polynucleotides include 7 SPN-A (SEQ ID NO.: 85), 7 SPN-B (SEQ ID NO.: 86), 7 SPN-C (SEQ ID NO.: 87), 7 SPN-D (SEQ ID NO.: 88), 7 SPN-E (SEQ ID NO.: 89), 7 SPN-F (SEQ ID NO.: 90), 7 SPN-G (SEQ ID NO.: 91), 7 SPN-H (SEQ ID NO.: 92), 7 SPN-I (SEQ ID NO.: 93), 7 SPN-J (SEQ ID NO.: 94), 7 SPN-K (SEQ ID NO.: 95), and 7 SPN-L (SEQ ID NO.: 96).

Signaling Polynucleotides Specific to Egg

An aptamer selected from the screen (Example 1) that is specific to egg was used. The full Sequence of the aptamer is shown below.

```
(17 RiboSPN_full sequence; SEQ ID NO.: 228)
5'TAATACGACTCACTATAGGCGTAGCCTGATGAGCCAACTGTGCAC
ACTGTTCGCTTATCGAGCTGTGTACCTCCATAGCGAAACGTGGTGAA
AGCCACGTAGCTGCGCC3'.
```

The core sequence to bind to peanut is shown below.

```
(17 SPN-core sequence; SEQ ID NO.: 229)
5'CCAACTGTGCACACTGTTCGCTTATCGAGCTGTGTACCTCCAT
AG3'
```

The original full sequence of SEQ ID NO.:228 was modified to delete as much of the primers as possible at both 5' terminus and 3' terminus without changing the binding sequence of SEQ ID NO.: 229. Additional nucleotides were also added at either 5' terminus or 3' terminus or both termini. The shortest sequences without impacting the binding sequence and forming an open single structure were tested for allergen detection. The resulted signaling polynucleotides include 17 SPN-A (SEQ ID NO.: 230), 17 SPN-B (SEQ ID NO.: 231), 17 SPN-C (SEQ ID NO.: 232), 17 SPN-D (SEQ ID NO.: 233), 17 SPN-E (SEQ ID NO.: 234), 17 SPN-F (SEQ ID NO.: 235), 17 SPN-G (SEQ ID NO.: 236), and 17 SPN-H (SEQ ID NO.: 237).

In a similar manner, signaling polynucleotides were designed based upon the sequences of aptamers selected from the screen (Table 1) and disclosed literature sequences (Table 2). The signaling polynucleotides are used for allergen detection by measuring fluorescence polarization changes.

Example 3: Fluorescence Polarization Measurement

The signaling polynucleotides 7 SPN-A (SEQ ID NO.: 85), 7 SPN-B (SEQ ID NO.: 86), 7 SPN-C (SEQ ID NO.: 87) which bind peanut allergens are labeled with a fluorophore Texas Red at the 5' terminus (marked as SPN-P). Several different food samples containing peanut are processed using T buffer. 20 μl sample for each test is used. The fluorescence polarization with SPN-P (20 μl SPN-P at the concentration of 100 μM) or without SPN-P are measured. Table 3 lists the study design. Changes in FP are measured in a commercial FP equipment.

TABLE 3

| | 1 | 2 | 3 | 4 | 5 | 6 | 7 | 8 |
|---|---|---|---|---|---|---|---|---|
| | | | + SPN-P | | | | −SPN-P | |
| A | PB Pretzel | PB ice cream | PB cookie | Granola Bar | PB Pretzel | PB ice cream | PB cookie | Granola Bar |
| B | PB Pretzel | PB ice cream | PB cookie | Granola Bar | PB Pretzel | PB ice cream | PB cookie | Granola Bar |
| C | PB Pretzel | PB ice cream | PB cookie | Granola Bar | PB Pretzel | PB ice cream | PB cookie | Granola Bar |
| D | PB Pretzel 1:10 | PB ice cream 1:10 | PB cookie 1:10 | Granola Bar 1:10 | PB Pretzel 1:10 | PB ice cream 1:10 | PB cookie 1:10 | Granola Bar 1:10 |
| E | PB Pretzel 1:10 | PB ice cream 1:10 | PB cookie 1:10 | Granola Bar 1:10 | PB Pretzel 1:10 | PB ice cream 1:10 | PB cookie 1:10 | Granola Bar 1:10 |
| F | PB Pretzel 1:10 | PB ice cream 1:10 | PB cookie 1:10 | Granola Bar 1:10 | PB Pretzel 1:10 | PB ice cream 1:10 | PB cookie 1:10 | Granola Bar 1:10 |
| G | SPN-P + T buffer | SPN-P + T buffer | SPN-P + T buffer | | T buffer | T buffer | T buffer | |

SPN binding test on samples containing peanut butter (PB)

Similarly the signaling polynucleotides 17 SPN-A (SEQ ID NO.: 230), 17 SPN-B (SEQ ID NO.: 231), 17 SPN-C (SEQ ID NO.: 232), 17 SPN-D (SEQ ID NO.: 233) which bind egg allergens, are labeled with a fluorophore Texas Red at the 5' terminus. The Texas Red labeled signaling polynucleotides are used to test fluorescent polarization changes upon allergen binding.

What is claimed is:

1. An allergen detection system comprising:
   (a) at least one sampler for collecting a test sample suspected of containing one or more allergens;
   (b) at least one detection vessel for receiving and processing the test sample, and contacting detection agents with said one or more allergens in the test sample; and
   (c) a detection device for detecting allergen content in the test sample by measuring and visualizing a signal from binding interaction between the detection agents and the one or more allergens in the test sample;
   wherein the detection device comprises an optical assembly for detecting a fluorescence polarization signal, and wherein the optical assembly comprises an excitation optical path including a light source, an excitation filter, and an excitation polarizing filter; and an emission optical path including an emission filter, a pair of emission polarizing filters, and a pair of photo detectors;
   wherein the detection vessel is a disposable test cup or cup-like container comprising a cup lid assembly and a cup body; wherein the cup lid assembly further comprises a top cap and at least one port on the top cap; and wherein the cup body has a proximal base and wider distal end connected to the cup lid assembly, and wherein the at least one port further includes three ports:
   a first port for holding a food pickup corer,
   a second port through which a homogenizer is assembled, and
   a third port for connection to a flow controlling means for driving and controlling a flow rate of a processed sample solution during allergen detection testing; and
   a means for aligning and stabilizing the cup lid assembly and the cup body when both are assembled together to form a test cup or cup-like container.

2. The detection system of claim 1, wherein the at least one sampler is a food pickup corer comprising a distal portion with a top cap at a distal end, a proximal portion with a sample collecting tube, a grip for handling the corer which is connected to the sample collecting tube, and a plunger inside the sample collecting tube, the plunger having a distal end connected to the top cap and a plunger tip at the proximal end, wherein the plunger tip can protrude out from the sample collecting tube for picking up the test sample.

3. The detection system of claim 2, wherein the food pickup corer further comprises a means for weighing the test sample and a snap at the proximal end.

4. The detection system of claim 1, wherein the cup lid assembly further comprises:
  (a) two or more reaction chambers on the top cap of the cup lid assembly for detection of the one or more allergens in the test sample; and a fluid channel for conveying the processed sample solution from the cup body to said two or more reaction chambers, wherein the two or more reaction chambers comprise one or more allergen analytical chambers with detection agents to the one or more allergens;
  (b) a flow tube through which the processed sample solution can pass from the cup body to the two or more reaction chambers; and
  (c) a flow tube cap and filter assembly in the cup lid assembly capable of filtering large particles in the processed sample solution and preventing humidification of molecules in said two or more reaction chambers.

5. The detection system of claim 1, wherein the cup body further comprises two or more reaction chambers and a filter membrane, wherein the two or more reaction chambers are positioned at a bottom of the cup body and the filter membrane is located above the one or more reaction chambers; the filter membrane may be used to filter the processed test sample before it flows to the one or more reaction chambers at the bottom of the cup body.

6. The detection system of claim 1, wherein the cup body is divided into a first part and a second part, the first part is configured for receiving and processing the test sample, and the second part includes two or more reaction chambers,
  wherein the first part and the second part are connected by a fluid tube and a valve through which the processed sample solution can flow from the first part to the two or more reaction chambers within the second part of the cup body, wherein the two or more reaction chambers within the second part are configured in a side-to-side orientation, or a stack orientation, or a front-to-back orientation, or in a diagonal orientation.

7. The allergen detection system of claim 1, wherein the cup body is configured for receiving the test sample collected by the corer and for processing the test sample using the homogenizer assembled through the second port,
  wherein a homogenizer rotor having a distal cap and a stator having a distal cap may be inserted into the cup body through the second port, wherein the distal caps of the homogenizer rotor and stator are connected to the second port and the proximal portions of the homogenizer rotor and stator extend to the cup body.

8. The allergen detection system of claim 7, wherein the cup body contains a volume of an extraction buffer for dissociating the test sample and extracting allergen proteins.

9. The allergen detection system of claim 1, wherein the detection vessel is a disposable test cup or cup-like assembly; and
  wherein the detection device further comprises:
  (a) an external housing comprising a housing cover, a housing base, and an alignment on a top front of the housing for aligning the disposable test cup or cup-like container during allergen detection testing;
  (b) a first part openable for insertion of the disposable test cup or cup-like container and the food pickup corer;
  (c) components integrated for operating an allergen detection testing; and
  (d) a power supply;
  wherein the components integrated for operating the detection testing (c) comprise,
    (i) means for driving and controlling a homogenizer that is configured for homogenizing the test sample and extracting allergen proteins from the test sample;
    (ii) means for driving and controlling the flow of processed sample solution during the process of the allergen detection testing;
    (iii) means for converting and digitizing the fluorescent signals; and
    (iv) a display window for receiving the detected signals and indicating the presence and/or absence of the allergen in the test sample.

10. The detection system of claim 9, wherein the first part is a drawer assembly which comprises an open well for inserting the disposable test cup or cup-like container and a drawer frame comprising one chimb on each side of the drawer frame, respectively.

11. The detection system of claim 9, wherein the homogenizer comprises a homogenizer stator, a homogenizer rotor inside the stator which are inserted to the cup body through the second port, and a coupling that couples the homogenizer stator and the rotor to a gearhead, wherein the gearhead is configured to connect the homogenizer to a gear train, by which the homogenizer is connected to the means for driving and controlling the homogenization.

12. The detection system of claim 11, wherein the homogenizer stator has a distal portion provided with a cap connected to the second port and a proximal end with one or more slots on an axis of the stator which extend to the cup body.

13. The detection system of claim 9, wherein the homogenizer comprises a homogenizer rotor connected to the second port on the top cap of the cup lid assembly, by a membrane seal.

14. The detection system of claim 11, wherein the means for driving and controlling the homogenization is a motor.

15. The detection system of claim 9, wherein a vacuum micro pump is used for driving and controlling flow of solution, which is connected to an underside of a platen connected to the disposable test cup or cup-like container through the third port,
  wherein the platen includes: a vacuum duct connected to the third port, an air channel, a gear train port configured for connection to means for driving and controlling the flow, and a cup port for connection to the third port.

16. The detection system of claim 15, wherein the cup port is sealed to the gear train port by a vacuum gasket.

17. The detection system of claim 9, wherein the optical assembly is connected to reaction chambers within the test cup or cup-like container for providing plane polarization excitation light, detecting light remitted from the detection agents, and measuring a detectable signal upon the binding of said one or more allergens in the test sample to the detection agents.

18. The detection system of claim 17, wherein the detection agents are aptamer based signaling polynucleotides probed with a fluorophore and the detectable signals are changes in fluorescence polarization.

19. The detection system of claim 18, wherein the pair of emission polarizing filters and the pair of photo detectors are arranged perpendicular to each other.

20. The detection system of claim 18, wherein the pair of emission polarizing filters and the pair of photo detectors are arranged parallel to each other.

21. The detection system of claim 9, wherein the power supply is a rechargeable or replaceable battery.

22. The detection system of claim 9, wherein the display is a printed circuit board.

* * * * *

SEQUENCE LISTING

<160> NUMBER OF SEQ ID NOS: 353

<210> SEQ ID NO 1
<211> LENGTH: 99
<212> TYPE: DNA
<213> ORGANISM: Artificial Sequence
<220> FEATURE:
<223> OTHER INFORMATION: Aptamer

<400> SEQUENCE: 1
taatacgact cactataggc gtagcctgat gaggcacacc acgtcaaaaa tcattgtcac    60
cacgaagccg aaacgtggtg aaagccacgt agctgcgcc    99

<210> SEQ ID NO 2
<211> LENGTH: 35
<212> TYPE: DNA
<213> ORGANISM: Artificial Sequence
<220> FEATURE:
<223> OTHER INFORMATION: signaling polynucleotide

<400> SEQUENCE: 2
gcacaccacg tcaaaaatca ttgtcaccac gaagc    35

<210> SEQ ID NO 3
<211> LENGTH: 41
<212> TYPE: DNA
<213> ORGANISM: Artificial Sequence
<220> FEATURE:
<223> OTHER INFORMATION: Signaling polynucleotide

<400> SEQUENCE: 3
gcagcacacc acgtcaaaaa tcattgtcac cacgaagctg c    41

<210> SEQ ID NO 4
<211> LENGTH: 45
<212> TYPE: DNA
<213> ORGANISM: Artificial Sequence
<220> FEATURE:
<223> OTHER INFORMATION: Signaling Polynucleotide

<400> SEQUENCE: 4
atgccgcaca ccacgucaaa aaucauuguc accacgaagc ggcat        45

<210> SEQ ID NO 5
<211> LENGTH: 99
<212> TYPE: DNA
<213> ORGANISM: Artificial Sequence
<220> FEATURE:
<223> OTHER INFORMATION: Aptamer

<400> SEQUENCE: 5
taatacgact cactataggc gtagcctgat gagtgcgcaa cataagtctc ttgaaagacc        60
acgttcaacg aaacgtggtg aaagccacgt agctgcgcc        99

<210> SEQ ID NO 6
<211> LENGTH: 35
<212> TYPE: DNA
<213> ORGANISM: Artificial Sequence
<220> FEATURE:
<223> OTHER INFORMATION: Signaling Polynucleotide

<400> SEQUENCE: 6
tgcgcaacat aagtctcttg aaagaccacg ttcaa        35

<210> SEQ ID NO 7
<211> LENGTH: 49
<212> TYPE: DNA
<213> ORGANISM: Artificial Sequence
<220> FEATURE:
<223> OTHER INFORMATION: Signaling Polynucleotide

<400> SEQUENCE: 7
cctgatgagt gcgcaacata agtctcttga aagaccacgt tcaacgaaa        49

<210> SEQ ID NO 8
<211> LENGTH: 51
<212> TYPE: DNA
<213> ORGANISM: Artificial Sequence
<220> FEATURE:
<223> OTHER INFORMATION: Signaling Polynucleotide

<400> SEQUENCE: 8
uucctgatga gtgcgcaaca taagtctctt gaaagaccac gttcaacgaa a        51

<210> SEQ ID NO 9
<211> LENGTH: 50
<212> TYPE: DNA
<213> ORGANISM: Artificial Sequence
<220> FEATURE:
<223> OTHER INFORMATION: Signaling Polynucleotide

<400> SEQUENCE: 9
uaactgatga gtgcgcaaca taagtctctt gaaagaccac gttcaacgua        50

<210> SEQ ID NO 10
<211> LENGTH: 50
<212> TYPE: DNA

<213> ORGANISM: Artificial Sequence
<220> FEATURE:
<223> OTHER INFORMATION: Signaling Polynucleotide

<400> SEQUENCE: 10
uacgugauga gugcgcaaca uaagucucuu gaaagaccac guucaacgua        50

<210> SEQ ID NO 11
<211> LENGTH: 49
<212> TYPE: DNA
<213> ORGANISM: Artificial Sequence
<220> FEATURE:
<223> OTHER INFORMATION: Signaling Polynucleotide

<400> SEQUENCE: 11
acatgatgag tgcgcaacat aagtctcttg aaagaccacg ttcaaaugu         49

<210> SEQ ID NO 12
<211> LENGTH: 99
<212> TYPE: DNA
<213> ORGANISM: Artificial Sequence
<220> FEATURE:
<223> OTHER INFORMATION: Aptamer

<400> SEQUENCE: 12
taatacgact cactataggc gtagcctgat gagcacccac cataccagaa atgttgacac        60
cacgtggacg aaacgtggtg aaagccacgt agctgcgcc                              99

<210> SEQ ID NO 13
<211> LENGTH: 35
<212> TYPE: DNA
<213> ORGANISM: Artificial Sequence
<220> FEATURE:
<223> OTHER INFORMATION: Signaling Polynucleotide

<400> SEQUENCE: 13
cacccaccat accagaaatg ttgacaccac gtgga        35

<210> SEQ ID NO 14
<211> LENGTH: 54
<212> TYPE: DNA
<213> ORGANISM: Artificial Sequence
<220> FEATURE:
<223> OTHER INFORMATION: Signaling Polynucleotide

<400> SEQUENCE: 14
cctgatgagc acccaccata ccagaaatgt tgacaccacg tggacgaaac gtgg        54

<210> SEQ ID NO 15
<211> LENGTH: 43
<212> TYPE: DNA
<213> ORGANISM: Artificial Sequence
<220> FEATURE:
<223> OTHER INFORMATION: Signaling Polynucleotide

<400> SEQUENCE: 15
ugucacccac cataccagaa atgttgacac cacgtggacg aca        43

<210> SEQ ID NO 16
<211> LENGTH: 42
<212> TYPE: DNA
<213> ORGANISM: Artificial Sequence
<220> FEATURE:
<223> OTHER INFORMATION: Signaling Polynucleotide

<400> SEQUENCE: 16
uaucacccac cataccagaa atgttgacac cacgtggaga ua                42

<210> SEQ ID NO 17
<211> LENGTH: 44
<212> TYPE: DNA
<213> ORGANISM: Artificial Sequence
<220> FEATURE:
<223> OTHER INFORMATION: Signaling Polynucleotide

<400> SEQUENCE: 17
ucgcacccac cataccagaa atgttgacac cacgtggaaa acga              44

<210> SEQ ID NO 18
<211> LENGTH: 44
<212> TYPE: DNA
<213> ORGANISM: Artificial Sequence
<220> FEATURE:
<223> OTHER INFORMATION: Signaling Polynucleotide

<400> SEQUENCE: 18
ucacacccac cataccagaa atgttgacac cacgtggaaa auga              44

<210> SEQ ID NO 19
<211> LENGTH: 48
<212> TYPE: DNA
<213> ORGANISM: Artificial Sequence
<220> FEATURE:
<223> OTHER INFORMATION: Signaling Polynucleotide

<400> SEQUENCE: 19
ucgucccacc caccatacca gaaatgttga caccacgtgg aaaaacga          48

<210> SEQ ID NO 20
<211> LENGTH: 51
<212> TYPE: DNA
<213> ORGANISM: Artificial Sequence
<220> FEATURE:
<223> OTHER INFORMATION: Signaling Polynucleotide

<400> SEQUENCE: 20
cacccaccat accagaaatg ttgacaccac gtggacgaaa cgtggtgaaa g       51

<210> SEQ ID NO 21
<211> LENGTH: 57
<212> TYPE: DNA
<213> ORGANISM: Artificial Sequence
<220> FEATURE:
<223> OTHER INFORMATION: Signaling Polynucleotide

<400> SEQUENCE: 21
cuucacccac cataccagaa atgttgacac cacgtggacg aaacgtggtg aaagaag  57

<210> SEQ ID NO 22
<211> LENGTH: 55
<212> TYPE: DNA
<213> ORGANISM: Artificial Sequence
<220> FEATURE:
<223> OTHER INFORMATION: Signaling Polynucleotide

<400> SEQUENCE: 22
uucacccacc ataccagaaa tgttgacacc acgtggacga aacgtggtga aagaa    55

<210> SEQ ID NO 23
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 23
uacacccacc ataccagaaa tgttgacacc acgtggacga aacgtggtgu gua        53

<210> SEQ ID NO 24
<211> LENGTH: 54
<212> TYPE: DNA
<213> ORGANISM: Artificial Sequence
<220> FEATURE:
<223> OTHER INFORMATION: Signaling Polynucleotide

<400> SEQUENCE: 24
uacacccacc ataccagaaa tgttgacacc acgtggacga aacgtggtga ugua       54

<210> SEQ ID NO 25
<211> LENGTH: 51
<212> TYPE: DNA
<213> ORGANISM: Artificial Sequence
<220> FEATURE:
<223> OTHER INFORMATION: Signaling Polynucleotide

<400> SEQUENCE: 25
uacacccacc ataccagaaa tgttgacacc acgtggacga aacgtgcagu a          51

<210> SEQ ID NO 26
<211> LENGTH: 99
<212> TYPE: DNA
<213> ORGANISM: Artificial Sequence
<220> FEATURE:
<223> OTHER INFORMATION: Aptamer

<400> SEQUENCE: 26
taatacgact cactataggc gtagcctgat gagtgcacaa tgtaattatc aaaatacacc    60
acgttggccg aaacgtggtg aaagccacgt agctgcgcc                          99

<210> SEQ ID NO 27
<211> LENGTH: 35
<212> TYPE: DNA
<213> ORGANISM: Artificial Sequence
<220> FEATURE:
<223> OTHER INFORMATION: Signaling Polynucleotide

<400> SEQUENCE: 27
tgcacaatgt aattatcaaa ataccacg ttggc                               35

<210> SEQ ID NO 28
<211> LENGTH: 61
<212> TYPE: DNA
<213> ORGANISM: Artificial Sequence
<220> FEATURE:
<223> OTHER INFORMATION: Signaling Polynucleotide

<400> SEQUENCE: 28
cctgatgagt gcacaatgta attatcaaaa tacaccacgt tggccgaaac gtggtgaaag    60
g                                                                   61

<210> SEQ ID NO 29

```
<211> LENGTH: 68
<212> TYPE: DNA
<213> ORGANISM: Artificial Sequence
<220> FEATURE:
<223> OTHER INFORMATION: Signaling Polynucleotide

<400> SEQUENCE: 29
ccaaacctga tgagtgcaca atgtaattat caaaatacac cacgttggcc gaaacgtggt      60
gaccaagg                                                              68

<210> SEQ ID NO 30
<211> LENGTH: 70
<212> TYPE: DNA
<213> ORGANISM: Artificial Sequence
<220> FEATURE:
<223> OTHER INFORMATION: Signaling Polynucleotide

<400> SEQUENCE: 30
ccaaauutga tgagtgcaca atgtaattat caaaatacac cacgttggcc gaaacgtggt      60
gaaaccaugg                                                            70

<210> SEQ ID NO 31
<211> LENGTH: 70
<212> TYPE: DNA
<213> ORGANISM: Artificial Sequence
<220> FEATURE:
<223> OTHER INFORMATION: Signaling Polynucleotide

<400> SEQUENCE: 31
uauaauutga tgagtgcaca atgtaattat caaaatacac cacgttggcc gaaacgtggt      60
gaaaucucua                                                            70

<210> SEQ ID NO 32
<211> LENGTH: 70
<212> TYPE: DNA
<213> ORGANISM: Artificial Sequence
<220> FEATURE:
<223> OTHER INFORMATION: Signaling Polynucleotide

<400> SEQUENCE: 32
uaugguutga tgagtgcaca atgtaattat caaaatacac cacgttggcc gaaacgtggt      60
gaaaucaaua                                                            70

<210> SEQ ID NO 33
<211> LENGTH: 68
<212> TYPE: DNA
<213> ORGANISM: Artificial Sequence
<220> FEATURE:
<223> OTHER INFORMATION: Signaling Polynucleotide

<400> SEQUENCE: 33
uguutgatga gtgcacaatg taattatcaa aatacaccac gttggccgaa acgtggtgaa      60
aucaaaca                                                              68

<210> SEQ ID NO 34
<211> LENGTH: 99
<212> TYPE: DNA
<213> ORGANISM: Artificial Sequence
<220> FEATURE:
<223> OTHER INFORMATION: Aptamer

<400> SEQUENCE: 34
taatacgact cactataggc gtagcctgat gagccacatc gtgcaatgcc cgaaacatac      60
```

```
cacgtagacg aaacgtggtg aaagccacgt agctgcgcc                              99

<210> SEQ ID NO 35
<211> LENGTH: 35
<212> TYPE: DNA
<213> ORGANISM: Artificial Sequence
<220> FEATURE:
<223> OTHER INFORMATION: Signaling Polynucleotide

<400> SEQUENCE: 35
ccacatcgtg caatgcccga aacataccac gtaga                                  35

<210> SEQ ID NO 36
<211> LENGTH: 45
<212> TYPE: DNA
<213> ORGANISM: Artificial Sequence
<220> FEATURE:
<223> OTHER INFORMATION: Signaling Polynucleotide

<400> SEQUENCE: 36
ctgagccaca tcgtgcaatg cccgaaacat accacgtaga cucag                       45

<210> SEQ ID NO 37
<211> LENGTH: 39
<212> TYPE: DNA
<213> ORGANISM: Artificial Sequence
<220> FEATURE:
<223> OTHER INFORMATION: Signaling Polynucleotide

<400> SEQUENCE: 37
gccacatcgt gcaatgcccg aaacatacca cgtagaggc                              39

<210> SEQ ID NO 38
<211> LENGTH: 35
<212> TYPE: DNA
<213> ORGANISM: Artificial Sequence
<220> FEATURE:
<223> OTHER INFORMATION: Signaling Polynucleotide

<400> SEQUENCE: 38
ccacatcgtg caatgcccga aacataccac gtaga                                  35

<210> SEQ ID NO 39
<211> LENGTH: 49
<212> TYPE: DNA
<213> ORGANISM: Artificial Sequence
<220> FEATURE:
<223> OTHER INFORMATION: Signaling Polynucleotide

<400> SEQUENCE: 39
guccaaacca catcgtgcaa tgcccgaaac ataccacgta gauggaaac                   49

<210> SEQ ID NO 40
<211> LENGTH: 46
<212> TYPE: DNA
<213> ORGANISM: Artificial Sequence
<220> FEATURE:
<223> OTHER INFORMATION: Signaling Polynucleotide

<400> SEQUENCE: 40
cgcaaaccac atcgtgcaat gcccgaaaca taccgtag aaagcg                        46

<210> SEQ ID NO 41
<211> LENGTH: 40
<212> TYPE: DNA
```

```
<213> ORGANISM: Artificial Sequence
<220> FEATURE:
<223> OTHER INFORMATION: Signaling Polynucleotide

<400> SEQUENCE: 41
ccacatcgtg caatgcccga aacataccac gtagaugugg                          40

<210> SEQ ID NO 42
<211> LENGTH: 40
<212> TYPE: DNA
<213> ORGANISM: Artificial Sequence
<220> FEATURE:
<223> OTHER INFORMATION: Signaling Polynucleotide

<400> SEQUENCE: 42
ccacatcgtg caatgcccga aacataccac gtagacaagg                          40

<210> SEQ ID NO 43
<211> LENGTH: 99
<212> TYPE: DNA
<213> ORGANISM: Artificial Sequence
<220> FEATURE:
<223> OTHER INFORMATION: Aptamer

<400> SEQUENCE: 43
taatacgact cactataggc gtagcctgat gagctatgca gtgatgatta aagataccac    60
cacgtgagcg aaacgtggtg aaagccacgt agctgcgcc                          99

<210> SEQ ID NO 44
<211> LENGTH: 35
<212> TYPE: DNA
<213> ORGANISM: Artificial Sequence
<220> FEATURE:
<223> OTHER INFORMATION: Signaling Polynucleotide

<400> SEQUENCE: 44
ctatgcagtg atgattaaag ataccaccac gtgag                              35

<210> SEQ ID NO 45
<211> LENGTH: 54
<212> TYPE: DNA
<213> ORGANISM: Artificial Sequence
<220> FEATURE:
<223> OTHER INFORMATION: Signaling Polynucleotide

<400> SEQUENCE: 45
gatgagctat gcagtgatga ttaaagatac caccacgtga gcgaaacgtg gtga         54

<210> SEQ ID NO 46
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 46
gctatgcagt gatgattaaa gataccacca cgtgagcgaa acgtggtgaa agc          53

<210> SEQ ID NO 47
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 47
```
actatgcagt gatgattaaa gataccacca cgtgagcgaa acgtggtgaa agu    53

<210> SEQ ID NO 48
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 48
uactatgcag tgatgattaa agataccacc acgtgagcga aacgtggtga gua    53

<210> SEQ ID NO 49
<211> LENGTH: 51
<212> TYPE: DNA
<213> ORGANISM: Artificial Sequence
<220> FEATURE:
<223> OTHER INFORMATION: Signaling Polynucleotide

<400> SEQUENCE: 49
gctatgcagt gatgattaaa gataccacca cgtgagcgaa acgtggtccg c    51

<210> SEQ ID NO 50
<211> LENGTH: 62
<212> TYPE: DNA
<213> ORGANISM: Artificial Sequence
<220> FEATURE:
<223> OTHER INFORMATION: Signaling Polynucleotide

<400> SEQUENCE: 50
gguugatgag ctatgcagtg atgattaaag ataccaccac gtgagcgaaa cgtggtgaaa    60
cc    62

<210> SEQ ID NO 51
<211> LENGTH: 60
<212> TYPE: DNA
<213> ORGANISM: Artificial Sequence
<220> FEATURE:
<223> OTHER INFORMATION: Signaling Polynucleotide

<400> SEQUENCE: 51
uuggatgagc tatgcagtga tgattaaaga taccaccacg tgagcgaaac gtggtgacaa    60

<210> SEQ ID NO 52
<211> LENGTH: 62
<212> TYPE: DNA
<213> ORGANISM: Artificial Sequence
<220> FEATURE:
<223> OTHER INFORMATION: Signaling Polynucleotide

<400> SEQUENCE: 52
ucggatgagc tatgcagtga tgattaaaga taccaccacg tgagcgaaac gtggtgaaac    60
ga    62

<210> SEQ ID NO 53
<211> LENGTH: 62
<212> TYPE: DNA
<213> ORGANISM: Artificial Sequence
<220> FEATURE:
<223> OTHER INFORMATION: Signaling Polynucleotide

<400> SEQUENCE: 53
augatgagct atgcagtgat gattaaagat accaccacgt gagcgaaacg tggtgaaacc    60
au                                                              62

<210> SEQ ID NO 54
<211> LENGTH: 59
<212> TYPE: DNA
<213> ORGANISM: Artificial Sequence
<220> FEATURE:
<223> OTHER INFORMATION: Signaling Polynucleotide

<400> SEQUENCE: 54
auggagctat gcagtgatga ttaaagatac caccacgtga gcgaaacgtg gtgaaacau    59

<210> SEQ ID NO 55
<211> LENGTH: 57
<212> TYPE: DNA
<213> ORGANISM: Artificial Sequence
<220> FEATURE:
<223> OTHER INFORMATION: Signaling Polynucleotide

<400> SEQUENCE: 55
guaaactatg cagtgatgat taaagatacc accacgtgag cgaaacgtgg tgaaugc      57

<210> SEQ ID NO 56
<211> LENGTH: 88
<212> TYPE: DNA
<213> ORGANISM: Artificial Sequence
<220> FEATURE:
<223> OTHER INFORMATION: Aptamer

<400> SEQUENCE: 56
taatacgact cactataggc gtagcctgat gagcaaatag ttacaaacac cacgtagcga    60
aacgtggtga agccacgta gctgcgcc                                       88

<210> SEQ ID NO 57
<211> LENGTH: 24
<212> TYPE: DNA
<213> ORGANISM: Artificial Sequence
<220> FEATURE:
<223> OTHER INFORMATION: Signaling Polynucleotide

<400> SEQUENCE: 57
caaatagtta caaacaccac gtag                                          24

<210> SEQ ID NO 58
<211> LENGTH: 32
<212> TYPE: DNA
<213> ORGANISM: Artificial Sequence
<220> FEATURE:
<223> OTHER INFORMATION: Signaling Polynucleotide

<400> SEQUENCE: 58
uucgcaaata gttacaaaca ccacgtagcg aa                                 32

<210> SEQ ID NO 59
<211> LENGTH: 32
<212> TYPE: DNA
<213> ORGANISM: Artificial Sequence
<220> FEATURE:
<223> OTHER INFORMATION: Signaling Polynucleotide

<400> SEQUENCE: 59
aucgcaaata gttacaaaca ccacgtagcg au                                 32

<210> SEQ ID NO 60
<211> LENGTH: 89

<212> TYPE: DNA
<213> ORGANISM: Artificial Sequence
<220> FEATURE:
<223> OTHER INFORMATION: Aptamer

<400> SEQUENCE: 60
taatacgact cactataggc gtagcctgat gagcccaact gtacagtaca ccacgtagcg    60
aaacgtggtg aaagccacgt agctgcgcc                                     89

<210> SEQ ID NO 61
<211> LENGTH: 25
<212> TYPE: DNA
<213> ORGANISM: Artificial Sequence
<220> FEATURE:
<223> OTHER INFORMATION: Signaling Polynucleotide

<400> SEQUENCE: 61
cccaactgta cagtacacca cgtag                                         25

<210> SEQ ID NO 62
<211> LENGTH: 46
<212> TYPE: DNA
<213> ORGANISM: Artificial Sequence
<220> FEATURE:
<223> OTHER INFORMATION: Signaling Polynucleotide

<400> SEQUENCE: 62
gagcccaact gtacagtaca ccacgtagcg aaacgtggtg aaacuc                  46

<210> SEQ ID NO 63
<211> LENGTH: 51
<212> TYPE: DNA
<213> ORGANISM: Artificial Sequence
<220> FEATURE:
<223> OTHER INFORMATION: Signaling Polynucleotide

<400> SEQUENCE: 63
uaucccaact gtacagtaca ccacgtagcg aaacgtggtg aaaggaagau a            51

<210> SEQ ID NO 64
<211> LENGTH: 89
<212> TYPE: DNA
<213> ORGANISM: Artificial Sequence
<220> FEATURE:
<223> OTHER INFORMATION: Aptamer

<400> SEQUENCE: 64
taatacgact cactataggc gtagcctgat gagcacacac acattccacc acgtcacgcg    60
aaacgtggtg aaagccacgt agctgcgcc                                     89

<210> SEQ ID NO 65
<211> LENGTH: 25
<212> TYPE: DNA
<213> ORGANISM: Artificial Sequence
<220> FEATURE:
<223> OTHER INFORMATION: Signaling Polynucleotide

<400> SEQUENCE: 65
cacacacaca ttccaccacg tcacg                                         25

<210> SEQ ID NO 66
<211> LENGTH: 33
<212> TYPE: DNA
<213> ORGANISM: Artificial Sequence
<220> FEATURE:

```
<223> OTHER INFORMATION: Signaling Polynucleotide

<400> SEQUENCE: 66
ctgatgagca cacacacatt ccaccacgtc acg                                    33

<210> SEQ ID NO 67
<211> LENGTH: 34
<212> TYPE: DNA
<213> ORGANISM: Artificial Sequence
<220> FEATURE:
<223> OTHER INFORMATION: Signaling Polynucleotide

<400> SEQUENCE: 67
gaugatgagc acacacacat tccaccacgt cacg                                   34

<210> SEQ ID NO 68
<211> LENGTH: 36
<212> TYPE: DNA
<213> ORGANISM: Artificial Sequence
<220> FEATURE:
<223> OTHER INFORMATION: Signaling Polynucleotide

<400> SEQUENCE: 68
ugaugatgag cacacacaca ttccaccacg tcacga                                 36

<210> SEQ ID NO 69
<211> LENGTH: 39
<212> TYPE: DNA
<213> ORGANISM: Artificial Sequence
<220> FEATURE:
<223> OTHER INFORMATION: Signaling Polynucleotide

<400> SEQUENCE: 69
uuauugatga gcacacacac attccaccac gtcacguaa                              39

<210> SEQ ID NO 70
<211> LENGTH: 89
<212> TYPE: DNA
<213> ORGANISM: Artificial Sequence
<220> FEATURE:
<223> OTHER INFORMATION: Aptamer

<400> SEQUENCE: 70
taatacgact cactataggc gtagcctgat gagcacacgt taccacacca cgttgacgcg       60
aaacgtggtg aaagccacgt agctgcgcc                                         89

<210> SEQ ID NO 71
<211> LENGTH: 25
<212> TYPE: DNA
<213> ORGANISM: Artificial Sequence
<220> FEATURE:
<223> OTHER INFORMATION: Signaling Polynucleotide

<400> SEQUENCE: 71
cacacgttac cacaccacgt tgacg                                             25

<210> SEQ ID NO 72
<211> LENGTH: 46
<212> TYPE: DNA
<213> ORGANISM: Artificial Sequence
<220> FEATURE:
<223> OTHER INFORMATION: Signaling Polynucleotide

<400> SEQUENCE: 72
auctgatgag cacacgttac cacaccacgt tgacgcgaaa cgagau                      46
```

<210> SEQ ID NO 73
<211> LENGTH: 38
<212> TYPE: DNA
<213> ORGANISM: Artificial Sequence
<220> FEATURE:
<223> OTHER INFORMATION: Signaling Polynucleotide

<400> SEQUENCE: 73
tauugagcac acgttaccac accacgttga cgcgaaua                            38

<210> SEQ ID NO 74
<211> LENGTH: 40
<212> TYPE: DNA
<213> ORGANISM: Artificial Sequence
<220> FEATURE:
<223> OTHER INFORMATION: Signaling Polynucleotide

<400> SEQUENCE: 74
tgauugagca cacgttacca caccacgttg acgcgaauca                          40

<210> SEQ ID NO 75
<211> LENGTH: 35
<212> TYPE: DNA
<213> ORGANISM: Artificial Sequence
<220> FEATURE:
<223> OTHER INFORMATION: Signaling Polynucleotide

<400> SEQUENCE: 75
guugagcaca cgttaccaca ccacgttgac gcgaa                               35

<210> SEQ ID NO 76
<211> LENGTH: 35
<212> TYPE: DNA
<213> ORGANISM: Artificial Sequence
<220> FEATURE:
<223> OTHER INFORMATION: Signaling Polynucleotide

<400> SEQUENCE: 76
auugagcaca cgttaccaca ccacgttgac gcgau                               35

<210> SEQ ID NO 77
<211> LENGTH: 89
<212> TYPE: DNA
<213> ORGANISM: Artificial Sequence
<220> FEATURE:
<223> OTHER INFORMATION: Aptamer

<400> SEQUENCE: 77
taatacgact cactataggc gtagcctgat gagcgtgccc gaaacacaca ccacgatgcg    60
aaacgtggtg aaagccacgt agctgcgcc                                      89

<210> SEQ ID NO 78
<211> LENGTH: 25
<212> TYPE: DNA
<213> ORGANISM: Artificial Sequence
<220> FEATURE:
<223> OTHER INFORMATION: Signaling Polynucleotide

<400> SEQUENCE: 78
cgtgcccgaa acacacacca cgatg                                          25

<210> SEQ ID NO 79
<211> LENGTH: 41
<212> TYPE: DNA

<213> ORGANISM: Artificial Sequence
<220> FEATURE:
<223> OTHER INFORMATION: Signaling Polynucleotide

<400> SEQUENCE: 79
uugagcgtgc ccgaaacaca caccacgatg cgaaacguca a    41

<210> SEQ ID NO 80
<211> LENGTH: 40
<212> TYPE: DNA
<213> ORGANISM: Artificial Sequence
<220> FEATURE:
<223> OTHER INFORMATION: Signaling Polynucleotide

<400> SEQUENCE: 80
uuagcgtgcc cgaaacacac accacgatgc gaaacgcuaa    40

<210> SEQ ID NO 81
<211> LENGTH: 40
<212> TYPE: DNA
<213> ORGANISM: Artificial Sequence
<220> FEATURE:
<223> OTHER INFORMATION: Signaling Polynucleotide

<400> SEQUENCE: 81
gauagacgtg cccgaaacac acaccacgat gcgaaauguc    40

<210> SEQ ID NO 82
<211> LENGTH: 42
<212> TYPE: DNA
<213> ORGANISM: Artificial Sequence
<220> FEATURE:
<223> OTHER INFORMATION: Signaling Polynucleotide

<400> SEQUENCE: 82
ugauagacgt gcccgaaaca cacaccacga tgcgaaaugu ca    42

<210> SEQ ID NO 83
<211> LENGTH: 89
<212> TYPE: DNA
<213> ORGANISM: Artificial Sequence
<220> FEATURE:
<223> OTHER INFORMATION: Aptamer

<400> SEQUENCE: 83
taatacgact cactataggc gtagcctgat gagctcacca cataccatgt accacgtgcg    60
aaacgtggtg aaagccacgt agctgcgcc    89

<210> SEQ ID NO 84
<211> LENGTH: 25
<212> TYPE: DNA
<213> ORGANISM: Artificial Sequence
<220> FEATURE:
<223> OTHER INFORMATION: Signaling Polynucleotide

<400> SEQUENCE: 84
ctcaccacat accatgtacc acgtg    25

<210> SEQ ID NO 85
<211> LENGTH: 50
<212> TYPE: DNA
<213> ORGANISM: Artificial Sequence
<220> FEATURE:
<223> OTHER INFORMATION: Signaling Polynucleotide

<400> SEQUENCE: 85
cctgatgagc tcaccacata ccatgtacca cgtgcgaaac gtggtgaagc          50

<210> SEQ ID NO 86
<211> LENGTH: 35
<212> TYPE: DNA
<213> ORGANISM: Artificial Sequence
<220> FEATURE:
<223> OTHER INFORMATION: Signaling Polynucleotide

<400> SEQUENCE: 86
gagctcacca cataccatgt accacgtgcg aauga                          35

<210> SEQ ID NO 87
<211> LENGTH: 32
<212> TYPE: DNA
<213> ORGANISM: Artificial Sequence
<220> FEATURE:
<223> OTHER INFORMATION: Signaling Polynucleotide

<400> SEQUENCE: 87
ctcaccacat accatgtacc acgtgcgaau ga                             32

<210> SEQ ID NO 88
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 88
gcucctgatg agctcaccac ataccatgta ccacgtgcga acgtggtga agc        53

<210> SEQ ID NO 89
<211> LENGTH: 42
<212> TYPE: DNA
<213> ORGANISM: Artificial Sequence
<220> FEATURE:
<223> OTHER INFORMATION: Signaling Polynucleotide

<400> SEQUENCE: 89
caugatgagc tcaccacata ccatgtacca cgtgcgaaca ug                  42

<210> SEQ ID NO 90
<211> LENGTH: 41
<212> TYPE: DNA
<213> ORGANISM: Artificial Sequence
<220> FEATURE:
<223> OTHER INFORMATION: Signaling Polynucleotide

<400> SEQUENCE: 90
ucauacgagc tcaccacata ccatgtacca cgtgcgaaug a                   41

<210> SEQ ID NO 91
<211> LENGTH: 41
<212> TYPE: DNA
<213> ORGANISM: Artificial Sequence
<220> FEATURE:
<223> OTHER INFORMATION: Signaling Polynucleotide

<400> SEQUENCE: 91
ucauacgagc tcaccacata ccatgtacca cgtgcgaaug a                   41

<210> SEQ ID NO 92
<211> LENGTH: 53
<212> TYPE: DNA

<210> SEQ ID NO 92
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 92
gcucctgatg agctcaccac ataccatgta ccacgtgcga aacgtggtga agc    53

<210> SEQ ID NO 93
<211> LENGTH: 50
<212> TYPE: DNA
<213> ORGANISM: Artificial Sequence
<220> FEATURE:
<223> OTHER INFORMATION: Signaling Polynucleotide

<400> SEQUENCE: 93
cctgatgagc tcaccacata ccatgtacca cgtgcgaaac gtggtgaagc    50

<210> SEQ ID NO 94
<211> LENGTH: 42
<212> TYPE: DNA
<213> ORGANISM: Artificial Sequence
<220> FEATURE:
<223> OTHER INFORMATION: Signaling Polynucleotide

<400> SEQUENCE: 94
caugatgagc tcaccacata ccatgtacca cgtgcgaaca ug    42

<210> SEQ ID NO 95
<211> LENGTH: 41
<212> TYPE: DNA
<213> ORGANISM: Artificial Sequence
<220> FEATURE:
<223> OTHER INFORMATION: Signaling Polynucleotide

<400> SEQUENCE: 95
ucauacgagc tcaccacata ccatgtacca cgtgcgaaug a    41

<210> SEQ ID NO 96
<211> LENGTH: 41
<212> TYPE: DNA
<213> ORGANISM: Artificial Sequence
<220> FEATURE:
<223> OTHER INFORMATION: Signaling Polynucleotide

<400> SEQUENCE: 96
ucauacgagc tcaccacata ccatgtacca cgtgcgaaug a    41

<210> SEQ ID NO 97
<211> LENGTH: 94
<212> TYPE: DNA
<213> ORGANISM: Artificial Sequence
<220> FEATURE:
<223> OTHER INFORMATION: Aptamer

<400> SEQUENCE: 97
taatacgact cactataggc gtagcctgat gagttcactg gctgcaccca ccaccgcgtt    60
ccacgaaacg tggtgaaagc cacgtagctg cgcc    94

<210> SEQ ID NO 98
<211> LENGTH: 30
<212> TYPE: DNA
<213> ORGANISM: Artificial Sequence
<220> FEATURE:
<223> OTHER INFORMATION: Signaling Polynucleotide

<400> SEQUENCE: 98

```
ttcactggct gcacccacca ccgcgttcca                              30

<210> SEQ ID NO 99
<211> LENGTH: 55
<212> TYPE: DNA
<213> ORGANISM: Artificial Sequence
<220> FEATURE:
<223> OTHER INFORMATION: Signaling Polynucleotide

<400> SEQUENCE: 99
gatgagttca ctggctgcac ccaccaccgc gttccacgaa acgtggtgaa agcca    55

<210> SEQ ID NO 100
<211> LENGTH: 64
<212> TYPE: DNA
<213> ORGANISM: Artificial Sequence
<220> FEATURE:
<223> OTHER INFORMATION: Signaling Polynucleotide

<400> SEQUENCE: 100
cgucctgatg agttcactgg ctgcacccac caccgcgttc acgaaacgt ggtgaaagcc    60 aacg                                                              64

<210> SEQ ID NO 101
<211> LENGTH: 66
<212> TYPE: DNA
<213> ORGANISM: Artificial Sequence
<220> FEATURE:
<223> OTHER INFORMATION: Signaling Polynucleotide

<400> SEQUENCE: 101
agcucctgat gagttcactg gctgcaccca ccaccgcgtt ccacgaaacg tggtgaaagc    60
caagcu                                                              66

<210> SEQ ID NO 102
<211> LENGTH: 59
<212> TYPE: DNA
<213> ORGANISM: Artificial Sequence
<220> FEATURE:
<223> OTHER INFORMATION: Signaling Polynucleotide

<400> SEQUENCE: 102
aucucctgat gagttcactg gctgcaccca ccaccgcgtt ccacgaaacg tggtgaaag    59

<210> SEQ ID NO 103
<211> LENGTH: 66
<212> TYPE: DNA
<213> ORGANISM: Artificial Sequence
<220> FEATURE:
<223> OTHER INFORMATION: Signaling Polynucleotide

<400> SEQUENCE: 103
gcuacctgat gagttcactg gctgcaccca ccaccgcgtt ccacgaaacg tggtgaaagc    60
cauagc                                                              66

<210> SEQ ID NO 104
<211> LENGTH: 65
<212> TYPE: DNA
<213> ORGANISM: Artificial Sequence
<220> FEATURE:
<223> OTHER INFORMATION: Signaling Polynucleotide

<400> SEQUENCE: 104
```

```
ccacctgatg agttcactgg ctgcacccac caccgcgttc cacgaaacgt ggtgaaagcc    60
aaagg                                                                65

<210> SEQ ID NO 105
<211> LENGTH: 64
<212> TYPE: DNA
<213> ORGANISM: Artificial Sequence
<220> FEATURE:
<223> OTHER INFORMATION: Signaling Polynucleotide

<400> SEQUENCE: 105
uacctgatga gttcactggc tgcacccacc accgcgttcc acgaaacgtg gtgaaagcca    60
ggua                                                                 64

<210> SEQ ID NO 106
<211> LENGTH: 66
<212> TYPE: DNA
<213> ORGANISM: Artificial Sequence
<220> FEATURE:
<223> OTHER INFORMATION: Signaling Polynucleotide

<400> SEQUENCE: 106
auacctgatg agttcactgg ctgcacccac caccgcgttc cacgaaacgt ggtgaaagcc    60
agguau                                                               66

<210> SEQ ID NO 107
<211> LENGTH: 66
<212> TYPE: DNA
<213> ORGANISM: Artificial Sequence
<220> FEATURE:
<223> OTHER INFORMATION: Signaling Polynucleotide

<400> SEQUENCE: 107
cuacctgatg agttcactgg ctgcacccac caccgcgttc cacgaaacgt ggtgaaagcc    60
aaauag                                                               66

<210> SEQ ID NO 108
<211> LENGTH: 65
<212> TYPE: DNA
<213> ORGANISM: Artificial Sequence
<220> FEATURE:
<223> OTHER INFORMATION: Signaling Polynucleotide

<400> SEQUENCE: 108
uacctgatga gttcactggc tgcacccacc accgcgttcc acgaaacgtg gtgaaagcca    60
aagua                                                                65

<210> SEQ ID NO 109
<211> LENGTH: 94
<212> TYPE: DNA
<213> ORGANISM: Artificial Sequence
<220> FEATURE:
<223> OTHER INFORMATION: Aptamer

<400> SEQUENCE: 109
taatacgact cactataggc gtagcctgat gagcatccac ggtgacgcta atcccacgtt    60
cgacgaaacg tggtgaaagc cacgtagctg cgcc                                94

<210> SEQ ID NO 110
<211> LENGTH: 30
<212> TYPE: DNA
<213> ORGANISM: Artificial Sequence
```

-continued

```
<220> FEATURE:
<223> OTHER INFORMATION: Signaling Polynucleotide

<400> SEQUENCE: 110
catccacggt gacgctaatc ccacgttcga                                          30

<210> SEQ ID NO 111
<211> LENGTH: 46
<212> TYPE: DNA
<213> ORGANISM: Artificial Sequence
<220> FEATURE:
<223> OTHER INFORMATION: Signaling Polynucleotide

<400> SEQUENCE: 111
cctgatgagc atccacggtg acgctaatcc cacgttcgac gaaagg                        46

<210> SEQ ID NO 112
<211> LENGTH: 49
<212> TYPE: DNA
<213> ORGANISM: Artificial Sequence
<220> FEATURE:
<223> OTHER INFORMATION: Signaling Polynucleotide

<400> SEQUENCE: 112
agacctgatg agcatccacg gtgacgctaa tcccacgttc gacgaaucu                     49

<210> SEQ ID NO 113
<211> LENGTH: 48
<212> TYPE: DNA
<213> ORGANISM: Artificial Sequence
<220> FEATURE:
<223> OTHER INFORMATION: Signaling Polynucleotide

<400> SEQUENCE: 113
agcctgatga gcatccacgg tgacgctaat cccacgttcg acgaagcu                      48

<210> SEQ ID NO 114
<211> LENGTH: 49
<212> TYPE: DNA
<213> ORGANISM: Artificial Sequence
<220> FEATURE:
<223> OTHER INFORMATION: Signaling Polynucleotide

<400> SEQUENCE: 114
uaucctgatg agcatccacg gtgacgctaa tcccacgttc gacggaaua                     49

<210> SEQ ID NO 115
<211> LENGTH: 42
<212> TYPE: DNA
<213> ORGANISM: Artificial Sequence
<220> FEATURE:
<223> OTHER INFORMATION: Signaling Polynucleotide

<400> SEQUENCE: 115
gucgatgagc atccacggtg acgctaatcc cacgttcgag ac                            42

<210> SEQ ID NO 116
<211> LENGTH: 40
<212> TYPE: DNA
<213> ORGANISM: Artificial Sequence
<220> FEATURE:
<223> OTHER INFORMATION: Signaling Polynucleotide

<400> SEQUENCE: 116
ucgatgagca tccacggtga cgctaatccc acgttcgaga                               40
```

<210> SEQ ID NO 117
<211> LENGTH: 39
<212> TYPE: DNA
<213> ORGANISM: Artificial Sequence
<220> FEATURE:
<223> OTHER INFORMATION: Signaling Polynucleotide

<400> SEQUENCE: 117
ucgatgagca tccacggtga cgctaatccc acgttcgag                    39

<210> SEQ ID NO 118
<211> LENGTH: 94
<212> TYPE: DNA
<213> ORGANISM: Artificial Sequence
<220> FEATURE:
<223> OTHER INFORMATION: Aptamer

<400> SEQUENCE: 118
taatacgact cactataggc gtagcctgat gagacaatgc agatgcgccc accacggatc    60
actcgaaacg tggtgaaagc cacgtagctg cgcc                              94

<210> SEQ ID NO 119
<211> LENGTH: 30
<212> TYPE: DNA
<213> ORGANISM: Artificial Sequence
<220> FEATURE:
<223> OTHER INFORMATION: Signaling Polynucleotide

<400> SEQUENCE: 119
acaatgcaga tgcgcccacc acggatcact                              30

<210> SEQ ID NO 120
<211> LENGTH: 58
<212> TYPE: DNA
<213> ORGANISM: Artificial Sequence
<220> FEATURE:
<223> OTHER INFORMATION: Signaling Polynucleotide

<400> SEQUENCE: 120
cctgatgaga caatgcagat gcgcccacca cggatcactc gaaacgtggt gaaagcca    58

<210> SEQ ID NO 121
<211> LENGTH: 33
<212> TYPE: DNA
<213> ORGANISM: Artificial Sequence
<220> FEATURE:
<223> OTHER INFORMATION: Signaling Polynucleotide

<400> SEQUENCE: 121
gagacaatgc agatgcgccc accacggatc act                          33

<210> SEQ ID NO 122
<211> LENGTH: 34
<212> TYPE: DNA
<213> ORGANISM: Artificial Sequence
<220> FEATURE:
<223> OTHER INFORMATION: Signaling Polynucleotide

<400> SEQUENCE: 122
gagacaatgc agatgcgccc accacggatc actc                         34

<210> SEQ ID NO 123
<211> LENGTH: 37
<212> TYPE: DNA
<213> ORGANISM: Artificial Sequence
<220> FEATURE:
<223> OTHER INFORMATION: Signaling Polynucleotide

<400> SEQUENCE: 123
gacacaatgc agatgcgccc accacggatc actcguc                                    37

<210> SEQ ID NO 124
<211> LENGTH: 61
<212> TYPE: DNA
<213> ORGANISM: Artificial Sequence
<220> FEATURE:
<223> OTHER INFORMATION: Signaling Polynucleotide

<400> SEQUENCE: 124
cctgatgaga caatgcagat gcgcccacca cggatcactc gaaacgtggt gaaagccaag          60
g                                                                           61

<210> SEQ ID NO 125
<211> LENGTH: 94
<212> TYPE: DNA
<213> ORGANISM: Artificial Sequence
<220> FEATURE:
<223> OTHER INFORMATION: Aptamer

<400> SEQUENCE: 125
taatacgact cactataggc gtagcctgat gagcaaccaa gcacgctgca tcacgtttca          60
tcgcgaaacg tggtgaaagc cacgtagctg cgcc                                       94

<210> SEQ ID NO 126
<211> LENGTH: 30
<212> TYPE: DNA
<213> ORGANISM: Artificial Sequence
<220> FEATURE:
<223> OTHER INFORMATION: Signaling Polynucleotide

<400> SEQUENCE: 126
caaccaagca cgctgcatca cgtttcatcg                                            30

<210> SEQ ID NO 127
<211> LENGTH: 46
<212> TYPE: DNA
<213> ORGANISM: Artificial Sequence
<220> FEATURE:
<223> OTHER INFORMATION: Signaling Polynucleotide

<400> SEQUENCE: 127
gagcaaccaa gcacgctgca tcacgtttca tcgcgaaacg tggcuc                          46

<210> SEQ ID NO 128
<211> LENGTH: 46
<212> TYPE: DNA
<213> ORGANISM: Artificial Sequence
<220> FEATURE:
<223> OTHER INFORMATION: Signaling Polynucleotide

<400> SEQUENCE: 128
guucaaccaa gcacgctgca tcacgtttca tcgcgaaacg tggaac                          46

<210> SEQ ID NO 129
<211> LENGTH: 44
<212> TYPE: DNA
<213> ORGANISM: Artificial Sequence
<220> FEATURE:
<223> OTHER INFORMATION: Signaling Polynucleotide

<400> SEQUENCE: 129
uucaaccaag cacgcugcau cacguuucau cgcgaaacgu ugaa        44

<210> SEQ ID NO 130
<211> LENGTH: 37
<212> TYPE: DNA
<213> ORGANISM: Artificial Sequence
<220> FEATURE:
<223> OTHER INFORMATION: Signaling Polynucleotide

<400> SEQUENCE: 130
cgatgagcaa ccaagcacgc tgcatcacgt ttcatcg        37

<210> SEQ ID NO 131
<211> LENGTH: 94
<212> TYPE: DNA
<213> ORGANISM: Artificial Sequence
<220> FEATURE:
<223> OTHER INFORMATION: Aptamer

<400> SEQUENCE: 131
taatacgact cactataggc gtagcctgat gagctcacag cccgaaacac atcgccacgt        60
tcacgaaacg tggtgaaagc cacgtagctg cgcc        94

<210> SEQ ID NO 132
<211> LENGTH: 30
<212> TYPE: DNA
<213> ORGANISM: Artificial Sequence
<220> FEATURE:
<223> OTHER INFORMATION: Signaling Polynucleotide

<400> SEQUENCE: 132
ctcacagccc gaaacacatc gccacgttca        30

<210> SEQ ID NO 133
<211> LENGTH: 34
<212> TYPE: DNA
<213> ORGANISM: Artificial Sequence
<220> FEATURE:
<223> OTHER INFORMATION: Signaling Polynucleotide

<400> SEQUENCE: 133
tgagctcaca gcccgaaaca catcgccacg ttca        34

<210> SEQ ID NO 134
<211> LENGTH: 44
<212> TYPE: DNA
<213> ORGANISM: Artificial Sequence
<220> FEATURE:
<223> OTHER INFORMATION: Signaling Polynucleotide

<400> SEQUENCE: 134
cgaaatgagc tcacagcccg aaacacatcg ccacgttcaa aacg        44

<210> SEQ ID NO 135
<211> LENGTH: 54
<212> TYPE: DNA
<213> ORGANISM: Artificial Sequence
<220> FEATURE:
<223> OTHER INFORMATION: Signaling Polynucleotide

<400> SEQUENCE: 135
uaucgcucac agcccgaaac acaucgccac guucacgaaa cguggugaaa gaua        54

```
<210> SEQ ID NO 136
<211> LENGTH: 104
<212> TYPE: DNA
<213> ORGANISM: Artificial Sequence
<220> FEATURE:
<223> OTHER INFORMATION: Aptamer

<400> SEQUENCE: 136
taatacgact cactataggc gtagcctgat gagctcaata ctacgtcaat tcacagatga    60
tagacaccac ggacgaaacg tggtgaaagc cacgtagctg cgcc                   104

<210> SEQ ID NO 137
<211> LENGTH: 40
<212> TYPE: DNA
<213> ORGANISM: Artificial Sequence
<220> FEATURE:
<223> OTHER INFORMATION: Signaling Polynucleotide

<400> SEQUENCE: 137
ctcaatacta cgtcaattca cagatgatag acaccacgga                         40

<210> SEQ ID NO 138
<211> LENGTH: 59
<212> TYPE: DNA
<213> ORGANISM: Artificial Sequence
<220> FEATURE:
<223> OTHER INFORMATION: Signaling Polynucleotide

<400> SEQUENCE: 138
gagctcaata ctacgtcaat tcacagatga tagacaccac ggacgaaacg tggtgaaag    59

<210> SEQ ID NO 139
<211> LENGTH: 59
<212> TYPE: DNA
<213> ORGANISM: Artificial Sequence
<220> FEATURE:
<223> OTHER INFORMATION: Signaling Polynucleotide

<400> SEQUENCE: 139
gagctcaata ctacgtcaat tcacagatga tagacaccac ggacgaaacg tggtgacuc    59

<210> SEQ ID NO 140
<211> LENGTH: 62
<212> TYPE: DNA
<213> ORGANISM: Artificial Sequence
<220> FEATURE:
<223> OTHER INFORMATION: Signaling Polynucleotide

<400> SEQUENCE: 140
guaagctcaa tactacgtca attcacagat gatagacacc acggacgaaa cgtggtgacu    60
ac                                                                   62

<210> SEQ ID NO 141
<211> LENGTH: 62
<212> TYPE: DNA
<213> ORGANISM: Artificial Sequence
<220> FEATURE:
<223> OTHER INFORMATION: Signaling Polynucleotide

<400> SEQUENCE: 141
cuaagctcaa tactacgtca attcacagat gatagacacc acggacgaaa cgtggtgacu    60
ag                                                                   62

<210> SEQ ID NO 142
```

-continued

```
<211> LENGTH: 60
<212> TYPE: DNA
<213> ORGANISM: Artificial Sequence
<220> FEATURE:
<223> OTHER INFORMATION: Signaling Polynucleotide

<400> SEQUENCE: 142
cuguctcaat actacgtcaa ttcacagatg atagacacca cggacgaaac gtggtgacag        60

<210> SEQ ID NO 143
<211> LENGTH: 60
<212> TYPE: DNA
<213> ORGANISM: Artificial Sequence
<220> FEATURE:
<223> OTHER INFORMATION: Signaling Polynucleotide

<400> SEQUENCE: 143
cugactcaat actacgtcaa ttcacagatg atagacacca cggacgaaac gtggtgacag        60

<210> SEQ ID NO 144
<211> LENGTH: 59
<212> TYPE: DNA
<213> ORGANISM: Artificial Sequence
<220> FEATURE:
<223> OTHER INFORMATION: Signaling Polynucleotide

<400> SEQUENCE: 144
cgactcaata ctacgtcaat tcacagatga tagacaccac ggacgaaacg tggtguuug         59

<210> SEQ ID NO 145
<211> LENGTH: 62
<212> TYPE: DNA
<213> ORGANISM: Artificial Sequence
<220> FEATURE:
<223> OTHER INFORMATION: Signaling Polynucleotide

<400> SEQUENCE: 145
ucugactcaa tactacgtca attcacagat gatagacacc acggacgaaa cgtggtgaua        60
ga                                                                       62

<210> SEQ ID NO 146
<211> LENGTH: 63
<212> TYPE: DNA
<213> ORGANISM: Artificial Sequence
<220> FEATURE:
<223> OTHER INFORMATION: Signaling Polynucleotide

<400> SEQUENCE: 146
aaaagctcaa tactacgtca attcacagat gatagacacc acggacgaaa cgtggtgacu        60
uau                                                                      63

<210> SEQ ID NO 147
<211> LENGTH: 63
<212> TYPE: DNA
<213> ORGANISM: Artificial Sequence
<220> FEATURE:
<223> OTHER INFORMATION: Signaling Polynucleotide

<400> SEQUENCE: 147
gaaagctcaa tactacgtca attcacagat gatagacacc acggacgaaa cgtggtgacu        60
uac                                                                      63

<210> SEQ ID NO 148
<211> LENGTH: 62
```

<212> TYPE: DNA
<213> ORGANISM: Artificial Sequence
<220> FEATURE:
<223> OTHER INFORMATION: Signaling Polynucleotide

<400> SEQUENCE: 148
cucagcucaa tactacgtca attcacagat gatagacacc acggacgaaa cgtggtgacg    60
ag    62

<210> SEQ ID NO 149
<211> LENGTH: 104
<212> TYPE: DNA
<213> ORGANISM: Artificial Sequence
<220> FEATURE:
<223> OTHER INFORMATION: Aptamer

<400> SEQUENCE: 149
taatacgact cactataggc gtagcctgat gagtccaaca ccacgtaacg tacactgcat    60
gtgattggtg caacgaaacg tggtgaaagc cacgtagctg cgcc    104

<210> SEQ ID NO 150
<211> LENGTH: 40
<212> TYPE: DNA
<213> ORGANISM: Artificial Sequence
<220> FEATURE:
<223> OTHER INFORMATION: Signaling Polynucleotide

<400> SEQUENCE: 150
tccaacacca cgtaacgtac actgcatgtg attggtgcaa    40

<210> SEQ ID NO 151
<211> LENGTH: 59
<212> TYPE: DNA
<213> ORGANISM: Artificial Sequence
<220> FEATURE:
<223> OTHER INFORMATION: Signaling Polynucleotide

<400> SEQUENCE: 151
cctgatgagt ccaacaccac gtaacgtaca ctgcatgtga ttggtgcaac gaaacgtgg    59

<210> SEQ ID NO 152
<211> LENGTH: 65
<212> TYPE: DNA
<213> ORGANISM: Artificial Sequence
<220> FEATURE:
<223> OTHER INFORMATION: Signaling Polynucleotide

<400> SEQUENCE: 152
tagcctgatg agtccaacac cacgtaacgt acactgcatg tgattggtgc aacgaaacgt    60
ggtga    65

<210> SEQ ID NO 153
<211> LENGTH: 50
<212> TYPE: DNA
<213> ORGANISM: Artificial Sequence
<220> FEATURE:
<223> OTHER INFORMATION: Signaling Polynucleotide

<400> SEQUENCE: 153
gatgagtcca acaccacgta acgtacactg catgtgattg gtgcaacgaa    50

<210> SEQ ID NO 154
<211> LENGTH: 58
<212> TYPE: DNA

<213> ORGANISM: Artificial Sequence
<220> FEATURE:
<223> OTHER INFORMATION: Signaling Polynucleotide

<400> SEQUENCE: 154
uuaagatgag tccaacacca cgtaacgtac actgcatgtg attggtgcaa cgaauuaa        58

<210> SEQ ID NO 155
<211> LENGTH: 58
<212> TYPE: DNA
<213> ORGANISM: Artificial Sequence
<220> FEATURE:
<223> OTHER INFORMATION: Signaling Polynucleotide

<400> SEQUENCE: 155
ugaagatgag tccaacacca cgtaacgtac actgcatgtg attggtgcaa cgaauuca        58

<210> SEQ ID NO 156
<211> LENGTH: 58
<212> TYPE: DNA
<213> ORGANISM: Artificial Sequence
<220> FEATURE:
<223> OTHER INFORMATION: Signaling Polynucleotide

<400> SEQUENCE: 156
ucacgatgag tccaacacca cgtaacgtac actgcatgtg attggtgcaa cgaaguga        58

<210> SEQ ID NO 157
<211> LENGTH: 104
<212> TYPE: DNA
<213> ORGANISM: Artificial Sequence
<220> FEATURE:
<223> OTHER INFORMATION: Aptamer

<400> SEQUENCE: 157
taatacgact cactataggc gtagcctgat gagtggcgcc gactgatcaa ctagacatca        60
cgttagcatt ccgcgaaacg tggtgaaagc cacgtagctg cgcc                       104

<210> SEQ ID NO 158
<211> LENGTH: 40
<212> TYPE: DNA
<213> ORGANISM: Artificial Sequence
<220> FEATURE:
<223> OTHER INFORMATION: Signaling Polynucleotide

<400> SEQUENCE: 158
tggcgccgac tgatcaacta gacatcacgt tagcattccg                            40

<210> SEQ ID NO 159
<211> LENGTH: 59
<212> TYPE: DNA
<213> ORGANISM: Artificial Sequence
<220> FEATURE:
<223> OTHER INFORMATION: Signaling Polynucleotide

<400> SEQUENCE: 159
cctgatgagt ggcgccgact gatcaactag acatcacgtt agcattccgc gaaacgtgg       59

<210> SEQ ID NO 160
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 160

```
gatgagtggc gccgactgat caactagaca tcacgttagc attccgcgaa acg            53
```

<210> SEQ ID NO 161
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 161

```
ugtgagtggc gccgactgat caactagaca tcacgttagc attccgcgaa acg            53
```

<210> SEQ ID NO 162
<211> LENGTH: 59
<212> TYPE: DNA
<213> ORGANISM: Artificial Sequence
<220> FEATURE:
<223> OTHER INFORMATION: Signaling Polynucleotide

<400> SEQUENCE: 162

```
cctgatgagt ggcgccgact gatcaactag acatcacgtt agcattccgc gaaacgagg     59
```

<210> SEQ ID NO 163
<211> LENGTH: 65
<212> TYPE: DNA
<213> ORGANISM: Artificial Sequence
<220> FEATURE:
<223> OTHER INFORMATION: Signaling Polynucleotide

<400> SEQUENCE: 163

```
gatgagtggc gccgactgat caactagaca tcacgttagc attccgcgaa acgtggtgaa    60
agcca                                                                65
```

<210> SEQ ID NO 164
<211> LENGTH: 66
<212> TYPE: DNA
<213> ORGANISM: Artificial Sequence
<220> FEATURE:
<223> OTHER INFORMATION: Signaling Polynucleotide

<400> SEQUENCE: 164

```
catgagtggc gccgactgat caactagaca tcacgttagc attccgcgaa acgtggtgaa    60
agcaug                                                               66
```

<210> SEQ ID NO 165
<211> LENGTH: 66
<212> TYPE: DNA
<213> ORGANISM: Artificial Sequence
<220> FEATURE:
<223> OTHER INFORMATION: Signaling Polynucleotide

<400> SEQUENCE: 165

```
tagagtggcg ccgactgatc aactagacat cacgttagca ttccgcgaaa cgtggtgaaa    60
gcucua                                                               66
```

<210> SEQ ID NO 166
<211> LENGTH: 64
<212> TYPE: DNA
<213> ORGANISM: Artificial Sequence
<220> FEATURE:
<223> OTHER INFORMATION: Signaling Polynucleotide

<400> SEQUENCE: 166

```
agagtggcgc cgactgatca actagacatc acgttagcat tccgcgaaac gtggtgaaag    60
cuuu                                                                  64
```

<210> SEQ ID NO 167
<211> LENGTH: 104
<212> TYPE: DNA
<213> ORGANISM: Artificial Sequence
<220> FEATURE:
<223> OTHER INFORMATION: Aptamer

<400> SEQUENCE: 167

```
taatacgact cactataggc gtagcctgat gagccagcaa ccaggttacc tcccatcacg    60
cttcgtctca ggacgaaacg tggtgaaagc cacgtagctg cgcc                    104
```

<210> SEQ ID NO 168
<211> LENGTH: 40
<212> TYPE: DNA
<213> ORGANISM: Artificial Sequence
<220> FEATURE:
<223> OTHER INFORMATION: Signaling Polynucleotide

<400> SEQUENCE: 168

```
ccagcaacca ggttacctcc catcacgctt cgtctcagga                          40
```

<210> SEQ ID NO 169
<211> LENGTH: 56
<212> TYPE: DNA
<213> ORGANISM: Artificial Sequence
<220> FEATURE:
<223> OTHER INFORMATION: Signaling Polynucleotide

<400> SEQUENCE: 169

```
cctgatgagc cagcaaccag gttacctccc atcacgcttc gtctcaggac gaaacg        56
```

<210> SEQ ID NO 170
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 170

```
gatgagccag caaccaggtt acctcccatc acgcttcgtc tcaggacgaa acg           53
```

<210> SEQ ID NO 171
<211> LENGTH: 50
<212> TYPE: DNA
<213> ORGANISM: Artificial Sequence
<220> FEATURE:
<223> OTHER INFORMATION: Signaling Polynucleotide

<400> SEQUENCE: 171

```
gatgagccag caaccaggtt acctcccatc acgcttcgtc tcaggacgaa               50
```

<210> SEQ ID NO 172
<211> LENGTH: 56
<212> TYPE: DNA
<213> ORGANISM: Artificial Sequence
<220> FEATURE:
<223> OTHER INFORMATION: Signaling Polynucleotide

<400> SEQUENCE: 172

```
caagatgagc cagcaaccag gttacctccc atcacgcttc gtctcaggac gaauug        56
```

<210> SEQ ID NO 173
<211> LENGTH: 56
<212> TYPE: DNA
<213> ORGANISM: Artificial Sequence
<220> FEATURE:
<223> OTHER INFORMATION: Signaling Polynucleotide

<400> SEQUENCE: 173
caagatgagc cagcaaccag gttacctccc atcacgcttc gtctcaggac gauuug      56

<210> SEQ ID NO 174
<211> LENGTH: 59
<212> TYPE: DNA
<213> ORGANISM: Artificial Sequence
<220> FEATURE:
<223> OTHER INFORMATION: Signaling Polynucleotide

<400> SEQUENCE: 174
ccaagatgag ccagcaacca ggttacctcc catcacgctt cgtctcagga cgacuuugg   59

<210> SEQ ID NO 175
<211> LENGTH: 59
<212> TYPE: DNA
<213> ORGANISM: Artificial Sequence
<220> FEATURE:
<223> OTHER INFORMATION: Signaling Polynucleotide

<400> SEQUENCE: 175
acaagatgag ccagcaacca ggttacctcc catcacgctt cgtctcagga cgacuuugu   59

<210> SEQ ID NO 176
<211> LENGTH: 58
<212> TYPE: DNA
<213> ORGANISM: Artificial Sequence
<220> FEATURE:
<223> OTHER INFORMATION: Signaling Polynucleotide

<400> SEQUENCE: 176
acagatgagc cagcaaccag gttacctccc atcacgcttc gtctcaggac gacuuugu    58

<210> SEQ ID NO 177
<211> LENGTH: 104
<212> TYPE: DNA
<213> ORGANISM: Artificial Sequence
<220> FEATURE:
<223> OTHER INFORMATION: Aptamer

<400> SEQUENCE: 177
taatacgact cactataggc gtagcctgat gagctgacac cacaaacgat tatgaccacg   60
ttatcgtaca tagcgaaacg tggtgaaagc cacgtagctg cgcc                  104

<210> SEQ ID NO 178
<211> LENGTH: 40
<212> TYPE: DNA
<213> ORGANISM: Artificial Sequence
<220> FEATURE:
<223> OTHER INFORMATION: Signaling Polynucleotide

<400> SEQUENCE: 178
ctgacaccac aaacgattat gaccacgtta tcgtacatag                         40

<210> SEQ ID NO 179
<211> LENGTH: 62
<212> TYPE: DNA
<213> ORGANISM: Artificial Sequence
<220> FEATURE:

<223> OTHER INFORMATION: Signaling Polynucleotide

<400> SEQUENCE: 179
taggcgtagc ctgatgagct gacaccacaa acgattatga ccacgttatc gtacatagcg    60
aa    62

<210> SEQ ID NO 180
<211> LENGTH: 62
<212> TYPE: DNA
<213> ORGANISM: Artificial Sequence
<220> FEATURE:
<223> OTHER INFORMATION: Signaling Polynucleotide

<400> SEQUENCE: 180
gagctgacac cacaaacgat tatgaccacg ttatcgtaca tagcgaaacg tggtgaaagc    60
ca    62

<210> SEQ ID NO 181
<211> LENGTH: 64
<212> TYPE: DNA
<213> ORGANISM: Artificial Sequence
<220> FEATURE:
<223> OTHER INFORMATION: Signaling Polynucleotide

<400> SEQUENCE: 181
agagctgaca ccacaaacga ttatgaccac gttatcgtac atagcgaaac gtggtgaaag    60
ccau    64

<210> SEQ ID NO 182
<211> LENGTH: 65
<212> TYPE: DNA
<213> ORGANISM: Artificial Sequence
<220> FEATURE:
<223> OTHER INFORMATION: Signaling Polynucleotide

<400> SEQUENCE: 182
ugagctgaca ccacaaacga ttatgaccac gttatcgtac atagcgaaac gtggtgaaag    60
ccuca    65

<210> SEQ ID NO 183
<211> LENGTH: 67
<212> TYPE: DNA
<213> ORGANISM: Artificial Sequence
<220> FEATURE:
<223> OTHER INFORMATION: Signaling Polynucleotide

<400> SEQUENCE: 183
ugaagctgac accacaaacg attatgacca cgttatcgta catagcgaaa cgtggtgaaa    60
gccguca    67

<210> SEQ ID NO 184
<211> LENGTH: 60
<212> TYPE: DNA
<213> ORGANISM: Artificial Sequence
<220> FEATURE:
<223> OTHER INFORMATION: Signaling Polynucleotide

<400> SEQUENCE: 184
ugaagctgac accacaaacg attatgacca cgttatcgta catagcgaaa cgtggcguca    60

<210> SEQ ID NO 185
<211> LENGTH: 62

```
<212> TYPE: DNA
<213> ORGANISM: Artificial Sequence
<220> FEATURE:
<223> OTHER INFORMATION: Signaling Polynucleotide

<400> SEQUENCE: 185
augaagcuga caccacaaac gauuaugacc acguuaucgu acauagcgaa acguggcguc      60
au                                                                    62

<210> SEQ ID NO 186
<211> LENGTH: 65
<212> TYPE: DNA
<213> ORGANISM: Artificial Sequence
<220> FEATURE:
<223> OTHER INFORMATION: Signaling Polynucleotide

<400> SEQUENCE: 186
guaacugaca ccacaaacga uuaugaccac guuaucguac auagcgaaac guggugaaag      60
ccuac                                                                 65

<210> SEQ ID NO 187
<211> LENGTH: 67
<212> TYPE: DNA
<213> ORGANISM: Artificial Sequence
<220> FEATURE:
<223> OTHER INFORMATION: Signaling Polynucleotide

<400> SEQUENCE: 187
uguaagcuga caccacaaac gauuaugacc acguuaucgu acauagcgaa acguggugaa      60
agaggca                                                               67

<210> SEQ ID NO 188
<211> LENGTH: 68
<212> TYPE: DNA
<213> ORGANISM: Artificial Sequence
<220> FEATURE:
<223> OTHER INFORMATION: Signaling Polynucleotide

<400> SEQUENCE: 188
uguaaagcug acaccacaaa cgauuaugac cacguuaucg uacauagcga aacgugguga      60
aagaggca                                                              68

<210> SEQ ID NO 189
<211> LENGTH: 104
<212> TYPE: DNA
<213> ORGANISM: Artificial Sequence
<220> FEATURE:
<223> OTHER INFORMATION: Aptamer

<400> SEQUENCE: 189
taatacgact cactataggc gtagcctgat gagtaggtca agtgcgctaa aacacaccgc      60
gttagttcac caacgaaacg tggtgaaagc cacgtagctg cgcc                     104

<210> SEQ ID NO 190
<211> LENGTH: 40
<212> TYPE: DNA
<213> ORGANISM: Artificial Sequence
<220> FEATURE:
<223> OTHER INFORMATION: Signaling Polynucleotide

<400> SEQUENCE: 190
taggtcaagt gcgctaaaac acaccgcgtt agttcaccaa                           40
```

<210> SEQ ID NO 191
<211> LENGTH: 62
<212> TYPE: DNA
<213> ORGANISM: Artificial Sequence
<220> FEATURE:
<223> OTHER INFORMATION: Signaling Polynucleotide

<400> SEQUENCE: 191
ataggtcaag tgcgctaaaa cacaccgcgt tagttcacca acgaaacgtg gtgaaagaua    60
au                                                                  62

<210> SEQ ID NO 192
<211> LENGTH: 64
<212> TYPE: DNA
<213> ORGANISM: Artificial Sequence
<220> FEATURE:
<223> OTHER INFORMATION: Signaling Polynucleotide

<400> SEQUENCE: 192
gataggtcaa gtgcgctaaa acacaccgcg ttagttcacc aacgaaacgt ggtgaaagau    60
aauc                                                                64

<210> SEQ ID NO 193
<211> LENGTH: 109
<212> TYPE: DNA
<213> ORGANISM: Artificial Sequence
<220> FEATURE:
<223> OTHER INFORMATION: Aptamer

<400> SEQUENCE: 193
taatacgact cactataggc gtagcctgat gaggccacct cactgtgttt tgttgcacaa    60
cataatatga tgacgtgccg aaacgtggtg aaagccacgt agctgcgcc              109

<210> SEQ ID NO 194
<211> LENGTH: 46
<212> TYPE: DNA
<213> ORGANISM: Artificial Sequence
<220> FEATURE:
<223> OTHER INFORMATION: Signaling Polynucleotide

<400> SEQUENCE: 194
ggccacctca ctgtgttttg ttgcacaaca taatatgatg acgtgc                  46

<210> SEQ ID NO 195
<211> LENGTH: 52
<212> TYPE: RNA
<213> ORGANISM: Artificial Sequence
<220> FEATURE:
<223> OTHER INFORMATION: Signaling Polynucleotide

<400> SEQUENCE: 195
gcacgaggcc accucacugu guuuguugc acaacauaau augaugacgu gc             52

<210> SEQ ID NO 196
<211> LENGTH: 53
<212> TYPE: RNA
<213> ORGANISM: Artificial Sequence
<220> FEATURE:
<223> OTHER INFORMATION: Signaling Polynucleotide

<400> SEQUENCE: 196
gcacguaggc caccucacug uguuuguug cacaacauaa uaugaugacg ugc            53

<210> SEQ ID NO 197
<211> LENGTH: 54
<212> TYPE: RNA
<213> ORGANISM: Artificial Sequence
<220> FEATURE:
<223> OTHER INFORMATION: Signaling Polynucleotide

<400> SEQUENCE: 197
gcacguaugg ccaccucacu guguuuuguu gcacaacaua auaugaugac gugc         54

<210> SEQ ID NO 198
<211> LENGTH: 53
<212> TYPE: RNA
<213> ORGANISM: Artificial Sequence
<220> FEATURE:
<223> OTHER INFORMATION: Signaling Polynucleotide

<400> SEQUENCE: 198
gcaccugggc caccucacug uguuuguug cacaacauaa uaugaugacg ugc            53

<210> SEQ ID NO 199
<211> LENGTH: 50
<212> TYPE: RNA
<213> ORGANISM: Artificial Sequence
<220> FEATURE:
<223> OTHER INFORMATION: Signaling Polynucleotide

<400> SEQUENCE: 199
gcacggccac cucacugugu uuguugcac aacauaauau gaugacgugc               50

<210> SEQ ID NO 200
<211> LENGTH: 52
<212> TYPE: DNA
<213> ORGANISM: Artificial Sequence
<220> FEATURE:
<223> OTHER INFORMATION: Signaling Polynucleotide

<400> SEQUENCE: 200
ttggccaccu cacuguguuu uguugcacaa cauaauauga ugacgugccg aa           52

<210> SEQ ID NO 201
<211> LENGTH: 51
<212> TYPE: RNA
<213> ORGANISM: Artificial Sequence
<220> FEATURE:
<223> OTHER INFORMATION: Signaling Polynucleotide

<400> SEQUENCE: 201
gccaccucac uguguuuugu ugcacaacau aauaugauga cgugcggugg c             51

<210> SEQ ID NO 202
<211> LENGTH: 49
<212> TYPE: RNA
<213> ORGANISM: Artificial Sequence
<220> FEATURE:
<223> OTHER INFORMATION: Signaling Polynucleotide

<400> SEQUENCE: 202
gcacgccacc ucacuguguu uuguugcaca acauaauaug augacgugc               49

<210> SEQ ID NO 203
<211> LENGTH: 109
<212> TYPE: DNA
<213> ORGANISM: Artificial Sequence
<220> FEATURE:
<223> OTHER INFORMATION: Aptamer

```
<400> SEQUENCE: 203
taatacgact cactataggc gtagcctgat gaggcgttcc ccaccgttgc ccacgcttaa      60
ctggacaaag atgggcccccg aaacgtggtg aaagccacgt agctgcgcc                109

<210> SEQ ID NO 204
<211> LENGTH: 45
<212> TYPE: DNA
<213> ORGANISM: Artificial Sequence
<220> FEATURE:
<223> OTHER INFORMATION: Signaling Polynucleotide

<400> SEQUENCE: 204
gcgttcccca ccgttgccca cgcttaactg dacaaagatg ggccc                      45

<210> SEQ ID NO 205
<211> LENGTH: 50
<212> TYPE: DNA
<213> ORGANISM: Artificial Sequence
<220> FEATURE:
<223> OTHER INFORMATION: Signaling Polynucleotide

<400> SEQUENCE: 205
gcgttcccca ccgttgccca cgcttaactg gacaaagatg ggcccaacgc                 50

<210> SEQ ID NO 206
<211> LENGTH: 52
<212> TYPE: DNA
<213> ORGANISM: Artificial Sequence
<220> FEATURE:
<223> OTHER INFORMATION: Signaling Polynucleotide

<400> SEQUENCE: 206
gggcccagcg ttccccaccg ttgcccacgc ttaactggac aaagatgggc cc              52

<210> SEQ ID NO 207
<211> LENGTH: 52
<212> TYPE: DNA
<213> ORGANISM: Artificial Sequence
<220> FEATURE:
<223> OTHER INFORMATION: Signaling Polynucleotide

<400> SEQUENCE: 207
accgcgttcc ccaccgttgc ccacgcttaa ctggacaaag atgggcccag ga              52

<210> SEQ ID NO 208
<211> LENGTH: 51
<212> TYPE: DNA
<213> ORGANISM: Artificial Sequence
<220> FEATURE:
<223> OTHER INFORMATION: Signaling Polynucleotide

<400> SEQUENCE: 208
ttgggcgttc ccaccgttg cccacgctta actggacaaa gatgggcccg a                51

<210> SEQ ID NO 209
<211> LENGTH: 52
<212> TYPE: DNA
<213> ORGANISM: Artificial Sequence
<220> FEATURE:
<223> OTHER INFORMATION: Signaling Polynucleotide

<400> SEQUENCE: 209
tagggcgttc cccaccgttg cccacgctta actggacaaa gatgggcccg aa              52
```

```
<210> SEQ ID NO 210
<211> LENGTH: 48
<212> TYPE: DNA
<213> ORGANISM: Artificial Sequence
<220> FEATURE:
<223> OTHER INFORMATION: Signaling Polynucleotide

<400> SEQUENCE: 210
tggcgttccc caccgttgcc cacgcttaac tggacaaaga tgggccca            48

<210> SEQ ID NO 211
<211> LENGTH: 50
<212> TYPE: DNA
<213> ORGANISM: Artificial Sequence
<220> FEATURE:
<223> OTHER INFORMATION: Signaling Polynucleotide

<400> SEQUENCE: 211
ugcgttcccc accgttgccc acgcttaact ggacaaagat gggcccgug           50

<210> SEQ ID NO 212
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 212
ttgggcgttc ccaccgttg cccacgctta actggacaaa gatgggcccg gaa       53

<210> SEQ ID NO 213
<211> LENGTH: 51
<212> TYPE: DNA
<213> ORGANISM: Artificial Sequence
<220> FEATURE:
<223> OTHER INFORMATION: Signaling Polynucleotide

<400> SEQUENCE: 213
ttcgcgttcc ccaccgttgc ccacgcttaa ctggacaaag atgggccuga g        51

<210> SEQ ID NO 214
<211> LENGTH: 109
<212> TYPE: DNA
<213> ORGANISM: Artificial Sequence
<220> FEATURE:
<223> OTHER INFORMATION: Aptamer

<400> SEQUENCE: 214
taatacgact cactataggc gtagcctgat gagtctgtgc acatcactcg acctctacgg   60
ctgtattgat cctgcatacg aaacgtggtg aaagccacgt agctgcgcc              109

<210> SEQ ID NO 215
<211> LENGTH: 45
<212> TYPE: DNA
<213> ORGANISM: Artificial Sequence
<220> FEATURE:
<223> OTHER INFORMATION: Signaling Polynucleotide

<400> SEQUENCE: 215
tctgtgcaca tcactcgacc tctacggctg tattgatcct gcata               45

<210> SEQ ID NO 216
<211> LENGTH: 54
<212> TYPE: DNA
<213> ORGANISM: Artificial Sequence
<220> FEATURE:
```

<223> OTHER INFORMATION: Signaling Polynucleotide

<400> SEQUENCE: 216
tctgtgcaca tcactcgacc tctacggctg tattgatcct gcatagugca caga        54

<210> SEQ ID NO 217
<211> LENGTH: 54
<212> TYPE: DNA
<213> ORGANISM: Artificial Sequence
<220> FEATURE:
<223> OTHER INFORMATION: Signaling Polynucleotide

<400> SEQUENCE: 217
ccuaugctct gtgcacatca ctcgacctct acggctgtat tgatcctgca tagg        54

<210> SEQ ID NO 218
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 218
gcuagagtgc acatcactcg acctctacgg ctgtattgat cctgcataag agc         53

<210> SEQ ID NO 219
<211> LENGTH: 109
<212> TYPE: DNA
<213> ORGANISM: Artificial Sequence
<220> FEATURE:
<223> OTHER INFORMATION: Aptamer

<400> SEQUENCE: 219
taatacgact cactataggc gtagcctgat gagcgtccaa cgttcgatca gaaccgcgtt   60
caggctgatg attgtacgcg aaacgtggtg aaagccacgt agctgcgcc              109

<210> SEQ ID NO 220
<211> LENGTH: 45
<212> TYPE: DNA
<213> ORGANISM: Artificial Sequence
<220> FEATURE:
<223> OTHER INFORMATION: Signaling Polynucleotide

<400> SEQUENCE: 220
cgtccaacgt tcgatcagaa ccgcgttcag gctgatgatt gtacg                  45

<210> SEQ ID NO 221
<211> LENGTH: 52
<212> TYPE: DNA
<213> ORGANISM: Artificial Sequence
<220> FEATURE:
<223> OTHER INFORMATION: Signaling Polynucleotide

<400> SEQUENCE: 221
cgtccaacgt tcgatcagaa ccgcgttcag gctgatgatt gtacguucca cg          52

<210> SEQ ID NO 222
<211> LENGTH: 55
<212> TYPE: DNA
<213> ORGANISM: Artificial Sequence
<220> FEATURE:
<223> OTHER INFORMATION: Signaling Polynucleotide

<400> SEQUENCE: 222
gcuuacgtcc aacgttcgat cagaaccgcg ttcaggctga tgattgtacg uaagc       55

<210> SEQ ID NO 223
<211> LENGTH: 59
<212> TYPE: DNA
<213> ORGANISM: Artificial Sequence
<220> FEATURE:
<223> OTHER INFORMATION: Signaling Polynucleotide

<400> SEQUENCE: 223
tgatgagcgt ccaacgttcg atcagaaccg cgttcaggct gatgattgta cgcgaaacg    59

<210> SEQ ID NO 224
<211> LENGTH: 59
<212> TYPE: DNA
<213> ORGANISM: Artificial Sequence
<220> FEATURE:
<223> OTHER INFORMATION: Signaling Polynucleotide

<400> SEQUENCE: 224
cgtgatgagc gtccaacgtt cgatcagaac cgcgttcagg ctgatgattg tacgcgacg    59

<210> SEQ ID NO 225
<211> LENGTH: 63
<212> TYPE: DNA
<213> ORGANISM: Artificial Sequence
<220> FEATURE:
<223> OTHER INFORMATION: Signaling Polynucleotide

<400> SEQUENCE: 225
caagtgatga gcgtccaacg ttcgatcaga accgcgttca ggctgatgat tgtacgcgac    60
ttg                                                                 63

<210> SEQ ID NO 226
<211> LENGTH: 63
<212> TYPE: DNA
<213> ORGANISM: Artificial Sequence
<220> FEATURE:
<223> OTHER INFORMATION: Signaling Polynucleotide

<400> SEQUENCE: 226
auagtgatga gcgtccaacg ttcgatcaga accgcgttca ggctgatgat tgtacgcgac    60
tat                                                                 63

<210> SEQ ID NO 227
<211> LENGTH: 109
<212> TYPE: DNA
<213> ORGANISM: Artificial Sequence
<220> FEATURE:
<223> OTHER INFORMATION: Aptamer

<400> SEQUENCE: 227
taatacgact cactataggc gtagcctgat gagcatcagt gcgttctgcc tttgcaacca    60
cacaacacac cgtatgagcg aaacgtggtg aaagccacgt agctgcgcc              109

<210> SEQ ID NO 228
<211> LENGTH: 45
<212> TYPE: DNA
<213> ORGANISM: Artificial Sequence
<220> FEATURE:
<223> OTHER INFORMATION: Signaling Polynucleotide

<400> SEQUENCE: 228
catcagtgcg ttctgccttt gcaaccacac aacacaccgt atgag                  45

<210> SEQ ID NO 229
<211> LENGTH: 51
<212> TYPE: DNA
<213> ORGANISM: Artificial Sequence
<220> FEATURE:
<223> OTHER INFORMATION: Signaling Polynucleotide

<400> SEQUENCE: 229
cucauacauc agtgcgttct gcctttgcaa ccacacaaca caccgtatga g    51

<210> SEQ ID NO 230
<211> LENGTH: 55
<212> TYPE: DNA
<213> ORGANISM: Artificial Sequence
<220> FEATURE:
<223> OTHER INFORMATION: Signaling Polynucleotide

<400> SEQUENCE: 230
gcuuacauca gtgcgttctg cctttgcaac cacacaacac accgtatgag uaagc    55

<210> SEQ ID NO 231
<211> LENGTH: 61
<212> TYPE: DNA
<213> ORGANISM: Artificial Sequence
<220> FEATURE:
<223> OTHER INFORMATION: Signaling Polynucleotide

<400> SEQUENCE: 231
cctgatgagc atcagtgcgt tctgcctttg caaccacaca acaccgta tgagcgaaac    60 g    61

<210> SEQ ID NO 232
<211> LENGTH: 52
<212> TYPE: DNA
<213> ORGANISM: Artificial Sequence
<220> FEATURE:
<223> OTHER INFORMATION: Signaling Polynucleotide

<400> SEQUENCE: 232
gcagcatcag tgcgttctgc ctttgcaacc acacaacaca ccgtatgagc gc    52

<210> SEQ ID NO 233
<211> LENGTH: 54
<212> TYPE: DNA
<213> ORGANISM: Artificial Sequence
<220> FEATURE:
<223> OTHER INFORMATION: Signaling Polynucleotide

<400> SEQUENCE: 233
ttgagcatca gtgcgttctg cctttgcaac cacacaacac accgtatgag cgaa    54

<210> SEQ ID NO 234
<211> LENGTH: 54
<212> TYPE: DNA
<213> ORGANISM: Artificial Sequence
<220> FEATURE:
<223> OTHER INFORMATION: Signaling Polynucleotide

<400> SEQUENCE: 234
tgcagcatca gtgcgttctg cctttgcaac cacacaacac accgtatgag cgcg    54

<210> SEQ ID NO 235
<211> LENGTH: 54
<212> TYPE: DNA
<213> ORGANISM: Artificial Sequence

```
<220> FEATURE:
<223> OTHER INFORMATION: Signaling Polynucleotide

<400> SEQUENCE: 235
cgcagcatca gtgcgttctg cctttgcaac cacacaacac accgtatgag cgcg        54

<210> SEQ ID NO 236
<211> LENGTH: 109
<212> TYPE: DNA
<213> ORGANISM: Artificial Sequence
<220> FEATURE:
<223> OTHER INFORMATION: Aptamer

<400> SEQUENCE: 236
taatacgact cactataggc gtagcctgat gagccaactg tgcacactgt tcgcttatcg   60
agctgtgtac ctccatagcg aaacgtggtg aaagccacgt agctgcgcc              109

<210> SEQ ID NO 237
<211> LENGTH: 45
<212> TYPE: DNA
<213> ORGANISM: Artificial Sequence
<220> FEATURE:
<223> OTHER INFORMATION: Signaling Polynucleotide

<400> SEQUENCE: 237
ccaactgtgc acactgttcg cttatcgagc tgtgtacctc catag                  45

<210> SEQ ID NO 238
<211> LENGTH: 64
<212> TYPE: DNA
<213> ORGANISM: Artificial Sequence
<220> FEATURE:
<223> OTHER INFORMATION: Signaling Polynucleotide

<400> SEQUENCE: 238
cctgatgagc caactgtgca cactgttcgc ttatcgagct gtgtacctcc atagcgaaac   60
gtgg                                                                64

<210> SEQ ID NO 239
<211> LENGTH: 70
<212> TYPE: DNA
<213> ORGANISM: Artificial Sequence
<220> FEATURE:
<223> OTHER INFORMATION: Signaling Polynucleotide

<400> SEQUENCE: 239
acucctgatg agccaactgt gcacactgtt cgcttatcga gctgtgtacc tccatagcga   60
aacgaggcat                                                         70

<210> SEQ ID NO 240
<211> LENGTH: 71
<212> TYPE: DNA
<213> ORGANISM: Artificial Sequence
<220> FEATURE:
<223> OTHER INFORMATION: Signaling Polynucleotide

<400> SEQUENCE: 240
atgcctgatg agccaactgt gcacactgtt cgcttatcga gctgtgtacc tccatagcga   60
aacgtggtga a                                                       71

<210> SEQ ID NO 241
<211> LENGTH: 68
<212> TYPE: DNA
```

```
<213> ORGANISM: Artificial Sequence
<220> FEATURE:
<223> OTHER INFORMATION: Signaling Polynucleotide

<400> SEQUENCE: 241
aacctgatga gccaactgtg cacactgttc gcttatcgag ctgtgtacct ccatagcgaa    60
acgtggca                                                             68

<210> SEQ ID NO 242
<211> LENGTH: 65
<212> TYPE: DNA
<213> ORGANISM: Artificial Sequence
<220> FEATURE:
<223> OTHER INFORMATION: Signaling Polynucleotide

<400> SEQUENCE: 242
aactgatgag ccaactgtgc acactgttcg cttatcgagc tgtgtacctc catagcgaaa    60
caguu                                                                65

<210> SEQ ID NO 243
<211> LENGTH: 75
<212> TYPE: DNA
<213> ORGANISM: Artificial Sequence
<220> FEATURE:
<223> OTHER INFORMATION: Signaling Polynucleotide

<400> SEQUENCE: 243
catgcctgat gagccaactg tgcacactgt tcgcttatcg agctgtgtac ctccatagcg    60
aaacgtggtg aagug                                                     75

<210> SEQ ID NO 244
<211> LENGTH: 50
<212> TYPE: DNA
<213> ORGANISM: Artificial Sequence
<220> FEATURE:
<223> OTHER INFORMATION: Signaling Polynucleotide

<400> SEQUENCE: 244
ccaactgtgc acactgttcg cttatcgagc tgtgtacctc cataggtugg              50

<210> SEQ ID NO 245
<211> LENGTH: 51
<212> TYPE: DNA
<213> ORGANISM: Artificial Sequence
<220> FEATURE:
<223> OTHER INFORMATION: Signaling Polynucleotide

<400> SEQUENCE: 245
cuauggccaa ctgtgcacac tgttcgctta tcgagctgtg tacctccata g             51

<210> SEQ ID NO 246
<211> LENGTH: 94
<212> TYPE: DNA
<213> ORGANISM: Artificial Sequence
<220> FEATURE:
<223> OTHER INFORMATION: Aptamer

<400> SEQUENCE: 246
taatacgact cactataggc gtagcctgat gagcttggtc acctttcctg acattaacac    60
aggcgaaacg tggtgaaagc cacgtagctg cgcc                                94

<210> SEQ ID NO 247
<211> LENGTH: 30
```

```
<212> TYPE: DNA
<213> ORGANISM: Artificial Sequence
<220> FEATURE:
<223> OTHER INFORMATION: Signaling Polynucleotide

<400> SEQUENCE: 247
cttggtcacc tttcctgaca ttaacacagg                                30

<210> SEQ ID NO 248
<211> LENGTH: 35
<212> TYPE: DNA
<213> ORGANISM: Artificial Sequence
<220> FEATURE:
<223> OTHER INFORMATION: Signaling Polynucleotide

<400> SEQUENCE: 248
cttggtcacc tttcctgaca ttaacacagg ccaag                          35

<210> SEQ ID NO 249
<211> LENGTH: 35
<212> TYPE: DNA
<213> ORGANISM: Artificial Sequence
<220> FEATURE:
<223> OTHER INFORMATION: Signaling Polynucleotide

<400> SEQUENCE: 249
ccugucttgg tcacctttcc tgacattaac acagg                          35

<210> SEQ ID NO 250
<211> LENGTH: 94
<212> TYPE: DNA
<213> ORGANISM: Artificial Sequence
<220> FEATURE:
<223> OTHER INFORMATION: Aptamer

<400> SEQUENCE: 250
taatacgact cactataggc gtagcctgat gagttttccc gatacggcta cgaattgcga    60
caacgaaacg tggtgaaagc cacgtagctg cgcc                           94

<210> SEQ ID NO 251
<211> LENGTH: 30
<212> TYPE: DNA
<213> ORGANISM: Artificial Sequence
<220> FEATURE:
<223> OTHER INFORMATION: Signaling Polynucleotide

<400> SEQUENCE: 251
ttttcccgat acggctacga attgcgacaa                                30

<210> SEQ ID NO 252
<211> LENGTH: 36
<212> TYPE: DNA
<213> ORGANISM: Artificial Sequence
<220> FEATURE:
<223> OTHER INFORMATION: Signaling Polynucleotide

<400> SEQUENCE: 252 cctttttcccg atacggctac gaattgcgac aaaagg                        36

<210> SEQ ID NO 253
<211> LENGTH: 40
<212> TYPE: DNA
<213> ORGANISM: Artificial Sequence
<220> FEATURE:
<223> OTHER INFORMATION: Signaling Polynucleotide
```

<400> SEQUENCE: 253
gcuuattttc ccgatacggc tacgaattgc gacaauaagc    40

<210> SEQ ID NO 254
<211> LENGTH: 94
<212> TYPE: DNA
<213> ORGANISM: Artificial Sequence
<220> FEATURE:
<223> OTHER INFORMATION: Aptamer

<400> SEQUENCE: 254
taatacgact cactataggc gtagcctgat gaggcaccaa ttttaccgat tttggtggac    60
agccgaaacg tggtgaaagc cacgtagctg cgcc    94

<210> SEQ ID NO 255
<211> LENGTH: 30
<212> TYPE: DNA
<213> ORGANISM: Artificial Sequence
<220> FEATURE:
<223> OTHER INFORMATION: Signaling Polynucleotide

<400> SEQUENCE: 255
gcaccaattt taccgatttt ggtggacagc    30

<210> SEQ ID NO 256
<211> LENGTH: 37
<212> TYPE: DNA
<213> ORGANISM: Artificial Sequence
<220> FEATURE:
<223> OTHER INFORMATION: Signaling Polynucleotide

<400> SEQUENCE: 256
gcuguccgca ccaattttac cgattttggt ggacagc    37

<210> SEQ ID NO 257
<211> LENGTH: 37
<212> TYPE: DNA
<213> ORGANISM: Artificial Sequence
<220> FEATURE:
<223> OTHER INFORMATION: Signaling Polynucleotide

<400> SEQUENCE: 257
gcaccaattt taccgatttt ggtggacagc uuggugc    37

<210> SEQ ID NO 258
<211> LENGTH: 94
<212> TYPE: DNA
<213> ORGANISM: Artificial Sequence
<220> FEATURE:
<223> OTHER INFORMATION: Aptamer

<400> SEQUENCE: 258
taatacgact cactataggc gtagcctgat gagcgtacaa cccaccaccg ttgtccacaa    60
atgcgaaacg tggtgaaagc cacgtagctg cgcc    94

<210> SEQ ID NO 259
<211> LENGTH: 30
<212> TYPE: DNA
<213> ORGANISM: Artificial Sequence
<220> FEATURE:
<223> OTHER INFORMATION: Signaling Polynucleotide

<400> SEQUENCE: 259
cgtacaaccc accaccgttg tccacaaatg    30

<210> SEQ ID NO 260
<211> LENGTH: 36
<212> TYPE: DNA
<213> ORGANISM: Artificial Sequence
<220> FEATURE:
<223> OTHER INFORMATION: Signaling Polynucleotide

<400> SEQUENCE: 260
cauuugcgta caacccacca ccgttgtcca caaatg                      36

<210> SEQ ID NO 261
<211> LENGTH: 37
<212> TYPE: DNA
<213> ORGANISM: Artificial Sequence
<220> FEATURE:
<223> OTHER INFORMATION: Signaling Polynucleotide

<400> SEQUENCE: 261
cgtacaaccc accaccgttg tccacaaatg uuguacg                     37

<210> SEQ ID NO 262
<211> LENGTH: 94
<212> TYPE: DNA
<213> ORGANISM: Artificial Sequence
<220> FEATURE:
<223> OTHER INFORMATION: Aptamer

<400> SEQUENCE: 262
taatacgact cactataggc gtagcctgat gagtgcgtca acggccgtcc cgaaacgtga    60
atacgaaacg tggtgaaagc cacgtagctg cgcc                        94

<210> SEQ ID NO 263
<211> LENGTH: 30
<212> TYPE: DNA
<213> ORGANISM: Artificial Sequence
<220> FEATURE:
<223> OTHER INFORMATION: Signaling Polynucleotide

<400> SEQUENCE: 263
tgcgtcaacg gccgtcccga aacgtgaata                             30

<210> SEQ ID NO 264
<211> LENGTH: 36
<212> TYPE: DNA
<213> ORGANISM: Artificial Sequence
<220> FEATURE:
<223> OTHER INFORMATION: Signaling Polynucleotide

<400> SEQUENCE: 264
uauucatgcg tcaacggccg tcccgaaacg tgaata                      36

<210> SEQ ID NO 265
<211> LENGTH: 40
<212> TYPE: DNA
<213> ORGANISM: Artificial Sequence
<220> FEATURE:
<223> OTHER INFORMATION: Signaling Polynucleotide

<400> SEQUENCE: 265
gcuuatgcgt caacggccgt cccgaaacgt gaatauaagc                  40

<210> SEQ ID NO 266
<211> LENGTH: 94
<212> TYPE: DNA

```
<213> ORGANISM: Artificial Sequence
<220> FEATURE:
<223> OTHER INFORMATION: Aptamer

<400> SEQUENCE: 266
taatacgact cactataggc gtagcctgat gaggttaccc cgaaacggcc ctaactgcat    60
cagcgaaacg tggtgaaagc cacgtagctg cgcc                              94

<210> SEQ ID NO 267
<211> LENGTH: 30
<212> TYPE: DNA
<213> ORGANISM: Artificial Sequence
<220> FEATURE:
<223> OTHER INFORMATION: Signaling Polynucleotide

<400> SEQUENCE: 267
gttaccccga aacggcccta actgcatcag                                   30

<210> SEQ ID NO 268
<211> LENGTH: 37
<212> TYPE: DNA
<213> ORGANISM: Artificial Sequence
<220> FEATURE:
<223> OTHER INFORMATION: Signaling Polynucleotide

<400> SEQUENCE: 268
cugaugcgtt accccgaaac ggccctaact gcatcag                           37

<210> SEQ ID NO 269
<211> LENGTH: 37
<212> TYPE: DNA
<213> ORGANISM: Artificial Sequence
<220> FEATURE:
<223> OTHER INFORMATION: Signaling Polynucleotide

<400> SEQUENCE: 269
gttaccccga aacggcccta actgcatcag ggguaac                           37

<210> SEQ ID NO 270
<211> LENGTH: 89
<212> TYPE: DNA
<213> ORGANISM: Artificial Sequence
<220> FEATURE:
<223> OTHER INFORMATION: Aptamer

<400> SEQUENCE: 270
taatacgact cactataggc gtagcctgat gagccgcatc accacccaaa ccaccgttcg    60
aaacgtggtg aaagccacgt agctgcgcc                                    89

<210> SEQ ID NO 271
<211> LENGTH: 25
<212> TYPE: DNA
<213> ORGANISM: Artificial Sequence
<220> FEATURE:
<223> OTHER INFORMATION: Signaling Polynucleotide

<400> SEQUENCE: 271
ccgcatcacc acccaaacca ccgtt                                        25

<210> SEQ ID NO 272
<211> LENGTH: 46
<212> TYPE: DNA
<213> ORGANISM: Artificial Sequence
<220> FEATURE:
<223> OTHER INFORMATION: Signaling Polynucleotide
```

<400> SEQUENCE: 272
gcctgatgag ccgcatcacc acccaaacca ccgttcgaaa cgaggc                    46

<210> SEQ ID NO 273
<211> LENGTH: 50
<212> TYPE: DNA
<213> ORGANISM: Artificial Sequence
<220> FEATURE:
<223> OTHER INFORMATION: Signaling Polynucleotide

<400> SEQUENCE: 273
ttccaatgat gagccgcatc accacccaaa ccaccgttcg aaacgaggaa                50

<210> SEQ ID NO 274
<211> LENGTH: 52
<212> TYPE: DNA
<213> ORGANISM: Artificial Sequence
<220> FEATURE:
<223> OTHER INFORMATION: Signaling Polynucleotide

<400> SEQUENCE: 274
tatacaatga tgagccgcat caccacccaa accaccgttc gaaacgagta ag             52

<210> SEQ ID NO 275
<211> LENGTH: 47
<212> TYPE: DNA
<213> ORGANISM: Artificial Sequence
<220> FEATURE:
<223> OTHER INFORMATION: Signaling Polynucleotide

<400> SEQUENCE: 275
uucctgatga gccgcatcac cacccaaacc accgttcgaa auaggaa                   47

<210> SEQ ID NO 276
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 276
tggacaatga tgagccgcat caccacccaa accaccgttc gaaacgagtc aca            53

<210> SEQ ID NO 277
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 277
tccacaatga tgagccgcat caccacccaa accaccgttc gaaacgagtg aga            53

<210> SEQ ID NO 278
<211> LENGTH: 89
<212> TYPE: DNA
<213> ORGANISM: Artificial Sequence
<220> FEATURE:
<223> OTHER INFORMATION: Aptamer

<400> SEQUENCE: 278
taatacgact cactataggc gtagcctgat gagcctgctc catccgcgcc agcctcaccg     60
aaacgtggtg aaagccacgt agctgcgcc                                       89

```
<210> SEQ ID NO 279
<211> LENGTH: 25
<212> TYPE: DNA
<213> ORGANISM: Artificial Sequence
<220> FEATURE:
<223> OTHER INFORMATION: Signaling Polynucleotide

<400> SEQUENCE: 279
cctgctccat ccgcgccagc ctcac                                           25

<210> SEQ ID NO 280
<211> LENGTH: 41
<212> TYPE: DNA
<213> ORGANISM: Artificial Sequence
<220> FEATURE:
<223> OTHER INFORMATION: Signaling Polynucleotide

<400> SEQUENCE: 280
cctgatgagc ctgctccatc cgcgccagcc tcaccgaaac g                         41

<210> SEQ ID NO 281
<211> LENGTH: 50
<212> TYPE: DNA
<213> ORGANISM: Artificial Sequence
<220> FEATURE:
<223> OTHER INFORMATION: Signaling Polynucleotide

<400> SEQUENCE: 281
tagcctgatg agcctgctcc atccgcgcca gcctcaccga aacgtggcta               50

<210> SEQ ID NO 282
<211> LENGTH: 45
<212> TYPE: DNA
<213> ORGANISM: Artificial Sequence
<220> FEATURE:
<223> OTHER INFORMATION: Signaling Polynucleotide

<400> SEQUENCE: 282
cttagcctga tgagcctgct ccatccgcgc cagcctcacc gtaag                    45

<210> SEQ ID NO 283
<211> LENGTH: 43
<212> TYPE: DNA
<213> ORGANISM: Artificial Sequence
<220> FEATURE:
<223> OTHER INFORMATION: Signaling Polynucleotide

<400> SEQUENCE: 283
cttagggtag agcctgctcc atccgcgcca gcctcaccut aag                      43

<210> SEQ ID NO 284
<211> LENGTH: 41
<212> TYPE: DNA
<213> ORGANISM: Artificial Sequence
<220> FEATURE:
<223> OTHER INFORMATION: Signaling Polynucleotide

<400> SEQUENCE: 284
ttagggtaga gcctgctcca tccgcgccag cctcaccuta a                        41

<210> SEQ ID NO 285
<211> LENGTH: 42
<212> TYPE: DNA
<213> ORGANISM: Artificial Sequence
<220> FEATURE:
<223> OTHER INFORMATION: Signaling Polynucleotide
```

```
<400> SEQUENCE: 285
gttagggtag agcctgctcc atccgcgcca gcctcaccua au                42

<210> SEQ ID NO 286
<211> LENGTH: 39
<212> TYPE: DNA
<213> ORGANISM: Artificial Sequence
<220> FEATURE:
<223> OTHER INFORMATION: Signaling Polynucleotide

<400> SEQUENCE: 286
ttaggtagag cctgctccat ccgcgccagc ctcaccuaa                    39

<210> SEQ ID NO 287
<211> LENGTH: 56
<212> TYPE: DNA
<213> ORGANISM: Artificial Sequence
<220> FEATURE:
<223> OTHER INFORMATION: Signaling Polynucleotide

<400> SEQUENCE: 287
gcgtagcctg atgagcctgc tccatccgcg ccagcctcac cgaaacgtgg tgaaag    56

<210> SEQ ID NO 288
<211> LENGTH: 50
<212> TYPE: DNA
<213> ORGANISM: Artificial Sequence
<220> FEATURE:
<223> OTHER INFORMATION: Signaling Polynucleotide

<400> SEQUENCE: 288
taatacgacc ctgctccatc cgcgccagcc tcaccgaaac gtggtgaaag          50

<210> SEQ ID NO 289
<211> LENGTH: 50
<212> TYPE: DNA
<213> ORGANISM: Artificial Sequence
<220> FEATURE:
<223> OTHER INFORMATION: Signaling Polynucleotide

<400> SEQUENCE: 289
tcactatagc ctgctccatc cgcgccagcc tcaccgaaac gtggtgaaag          50

<210> SEQ ID NO 290
<211> LENGTH: 56
<212> TYPE: DNA
<213> ORGANISM: Artificial Sequence
<220> FEATURE:
<223> OTHER INFORMATION: Signaling Polynucleotide

<400> SEQUENCE: 290
ccacgtagct gcgcccctgc tccatccgcg ccagcctcac cgaaacgtgg tgaaag    56

<210> SEQ ID NO 291
<211> LENGTH: 56
<212> TYPE: DNA
<213> ORGANISM: Artificial Sequence
<220> FEATURE:
<223> OTHER INFORMATION: Signaling Polynucleotide

<400> SEQUENCE: 291
cuutcacctg atgagcctgc tccatccgcg ccagcctcac cgaaacgtgg tgaaag    56

<210> SEQ ID NO 292
```

```
<211> LENGTH: 56
<212> TYPE: DNA
<213> ORGANISM: Artificial Sequence
<220> FEATURE:
<223> OTHER INFORMATION: Signaling Polynucleotide

<400> SEQUENCE: 292
uautcacctg atgagcctgc tccatccgcg ccagcctcac cgaaacgtgg tgaaag        56

<210> SEQ ID NO 293
<211> LENGTH: 41
<212> TYPE: DNA
<213> ORGANISM: Artificial Sequence
<220> FEATURE:
<223> OTHER INFORMATION: Signaling Polynucleotide

<400> SEQUENCE: 293
utcgatgagc ctgctccatc cgcgccagcc tcaccgaaca g                        41

<210> SEQ ID NO 294
<211> LENGTH: 43
<212> TYPE: DNA
<213> ORGANISM: Artificial Sequence
<220> FEATURE:
<223> OTHER INFORMATION: Signaling Polynucleotide

<400> SEQUENCE: 294
cautcgatga gcctgctcca tccgcgccag cctcaccgaa cug                      43

<210> SEQ ID NO 295
<211> LENGTH: 89
<212> TYPE: DNA
<213> ORGANISM: Artificial Sequence
<220> FEATURE:
<223> OTHER INFORMATION: Aptamer

<400> SEQUENCE: 295
taatacgact cactataggc gtagcctgat gagccaatct cctgcccacg ccgttccacg    60
aaacgtggtg aaagccacgt agctgcgcc                                      89

<210> SEQ ID NO 296
<211> LENGTH: 25
<212> TYPE: DNA
<213> ORGANISM: Artificial Sequence
<220> FEATURE:
<223> OTHER INFORMATION: Signaling Polynucleotide

<400> SEQUENCE: 296
ccaatctcct gcccacgccg ttcca                                          25

<210> SEQ ID NO 297
<211> LENGTH: 59
<212> TYPE: DNA
<213> ORGANISM: Artificial Sequence
<220> FEATURE:
<223> OTHER INFORMATION: Signaling Polynucleotide

<400> SEQUENCE: 297
taggcgtagc ctgatgagcc aatctcctgc ccacgccgtt ccacgaaacg tggtgaaag     59

<210> SEQ ID NO 298
<211> LENGTH: 47
<212> TYPE: DNA
<213> ORGANISM: Artificial Sequence
<220> FEATURE:
<223> OTHER INFORMATION: Signaling Polynucleotide
```

-continued

<400> SEQUENCE: 298
taggcgtagc ctgatgagcc aatctcctgc ccacgccgtt ccacgaa					47

<210> SEQ ID NO 299
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 299
taggcgtagc ctgatgagcc aatctcctgc ccacgccgtt ccaccuacgc cua					53

<210> SEQ ID NO 300
<211> LENGTH: 47
<212> TYPE: DNA
<213> ORGANISM: Artificial Sequence
<220> FEATURE:
<223> OTHER INFORMATION: Signaling Polynucleotide

<400> SEQUENCE: 300
gcgtagcctg atgagccaat ctcctgccca cgccgttcca ccuacgc					47

<210> SEQ ID NO 301
<211> LENGTH: 47
<212> TYPE: DNA
<213> ORGANISM: Artificial Sequence
<220> FEATURE:
<223> OTHER INFORMATION: Signaling Polynucleotide

<400> SEQUENCE: 301
ucgtagcctg atgagccaat ctcctgccca cgccgttcca ccuacca					47

<210> SEQ ID NO 302
<211> LENGTH: 47
<212> TYPE: DNA
<213> ORGANISM: Artificial Sequence
<220> FEATURE:
<223> OTHER INFORMATION: Signaling Polynucleotide

<400> SEQUENCE: 302
ugctagcctg atgagccaat ctcctgccca cgccgttcca ccuagaa					47

<210> SEQ ID NO 303
<211> LENGTH: 47
<212> TYPE: DNA
<213> ORGANISM: Artificial Sequence
<220> FEATURE:
<223> OTHER INFORMATION: Signaling Polynucleotide

<400> SEQUENCE: 303
cgatagcctg atgagccaat ctcctgccca cgccgttcca ccuatag					47

<210> SEQ ID NO 304
<211> LENGTH: 55
<212> TYPE: DNA
<213> ORGANISM: Artificial Sequence
<220> FEATURE:
<223> OTHER INFORMATION: Signaling Polynucleotide

<400> SEQUENCE: 304
gucctagcct gatgagccaa tctcctgccc acgccgttcc acaucuugcu agaac					55

<210> SEQ ID NO 305

<211> LENGTH: 41
<212> TYPE: DNA
<213> ORGANISM: Artificial Sequence
<220> FEATURE:
<223> OTHER INFORMATION: Signaling Polynucleotide

<400> SEQUENCE: 305
gatgagccaa tctcctgccc acgccgttcc acaagcucau c        41

<210> SEQ ID NO 306
<211> LENGTH: 44
<212> TYPE: DNA
<213> ORGANISM: Artificial Sequence
<220> FEATURE:
<223> OTHER INFORMATION: Signaling Polynucleotide

<400> SEQUENCE: 306
cctgatgagc aatctcctg cccacgccgt tccacaucga aagg        44

<210> SEQ ID NO 307
<211> LENGTH: 89
<212> TYPE: DNA
<213> ORGANISM: Artificial Sequence
<220> FEATURE:
<223> OTHER INFORMATION: Aptamer

<400> SEQUENCE: 307
taatacgact cactataggc gtagcctgat gagccaatca aggaccgcct tcaccgctcg        60
aaacgtggtg aaagccacgt agctgcgcc        89

<210> SEQ ID NO 308
<211> LENGTH: 25
<212> TYPE: DNA
<213> ORGANISM: Artificial Sequence
<220> FEATURE:
<223> OTHER INFORMATION: Signaling Polynucleotide

<400> SEQUENCE: 308
ccaatcaagg accgccttca ccgct        25

<210> SEQ ID NO 309
<211> LENGTH: 41
<212> TYPE: DNA
<213> ORGANISM: Artificial Sequence
<220> FEATURE:
<223> OTHER INFORMATION: Signaling Polynucleotide

<400> SEQUENCE: 309
cctgatgagc caatcaagga ccgccttcac cgctcgaaac g        41

<210> SEQ ID NO 310
<211> LENGTH: 35
<212> TYPE: DNA
<213> ORGANISM: Artificial Sequence
<220> FEATURE:
<223> OTHER INFORMATION: Signaling Polynucleotide

<400> SEQUENCE: 310
gatgagccaa tcaaggaccg ccttcaccgc tcgau        35

<210> SEQ ID NO 311
<211> LENGTH: 31
<212> TYPE: DNA
<213> ORGANISM: Artificial Sequence
<220> FEATURE:
<223> OTHER INFORMATION: Signaling Polynucleotide -continued

<400> SEQUENCE: 311
tgagccaatc aaggaccgcc ttcaccgctc g                                      31

<210> SEQ ID NO 312
<211> LENGTH: 34
<212> TYPE: DNA
<213> ORGANISM: Artificial Sequence
<220> FEATURE:
<223> OTHER INFORMATION: Signaling Polynucleotide

<400> SEQUENCE: 312
gcacagccaa tcaaggaccg ccttcaccgc tucu                                   34

<210> SEQ ID NO 313
<211> LENGTH: 35
<212> TYPE: DNA
<213> ORGANISM: Artificial Sequence
<220> FEATURE:
<223> OTHER INFORMATION: Signaling Polynucleotide

<400> SEQUENCE: 313
gcaacagcca atcaaggacc gccttcaccg ctuuu                                  35

<210> SEQ ID NO 314
<211> LENGTH: 33
<212> TYPE: DNA
<213> ORGANISM: Artificial Sequence
<220> FEATURE:
<223> OTHER INFORMATION: Signaling Polynucleotide

<400> SEQUENCE: 314
gacagccaat caaggaccgc cttcaccgct uuu                                    33

<210> SEQ ID NO 315
<211> LENGTH: 89
<212> TYPE: DNA
<213> ORGANISM: Artificial Sequence
<220> FEATURE:
<223> OTHER INFORMATION: Aptamer

<400> SEQUENCE: 315
taatacgact cactataggc gtagcctgat gagactctcg catcaccagc caactcaccg       60
aaacgtggtg aaagccacgt agctgcgcc                                         89

<210> SEQ ID NO 316
<211> LENGTH: 25
<212> TYPE: DNA
<213> ORGANISM: Artificial Sequence
<220> FEATURE:
<223> OTHER INFORMATION: Signaling Polynucleotide

<400> SEQUENCE: 316
actctcgcat caccagccaa ctcac                                             25

<210> SEQ ID NO 317
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 317
tagcctgatg agactctcgc atcaccagcc aactcaccga aacgtggtga aag              53

<210> SEQ ID NO 318
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 318
tagcctgatg agactctcgc atcaccagcc aactcaccga aacgtggtgg cua            53

<210> SEQ ID NO 319
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 319
tagccagatg agactctcgc atcaccagcc aactcaccga aacgtggtgg cua            53

<210> SEQ ID NO 320
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 320
tagccagatg agactctcgc atcaccagcc aactcaccga acacauctgg cua            53

<210> SEQ ID NO 321
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 321
tcgccagatg agactctcgc atcaccagcc aactcaccga aacgtggtgg cga            53

<210> SEQ ID NO 322
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 322
tcgccagatg agactctcgc atcaccagcc aactcaccga aacgtggagg cga            53

<210> SEQ ID NO 323
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 323
tugccagatg agactctcgc atcaccagcc aactcaccga aacgtggagg cga            53

<210> SEQ ID NO 324
<211> LENGTH: 55
<212> TYPE: DNA
<213> ORGANISM: Artificial Sequence
<220> FEATURE:
<223> OTHER INFORMATION: Signaling Polynucleotide

```
<400> SEQUENCE: 324
tugccagatg agactctcgc atcaccagcc aactcaccga aacgtggagu ugcga        55

<210> SEQ ID NO 325
<211> LENGTH: 54
<212> TYPE: DNA
<213> ORGANISM: Artificial Sequence
<220> FEATURE:
<223> OTHER INFORMATION: Signaling Polynucleotide

<400> SEQUENCE: 325
tugccuugat gagactctcg catcaccagc caactcaccg aaacgtggag gcga         54

<210> SEQ ID NO 326
<211> LENGTH: 55
<212> TYPE: DNA
<213> ORGANISM: Artificial Sequence
<220> FEATURE:
<223> OTHER INFORMATION: Signaling Polynucleotide

<400> SEQUENCE: 326
tugccuauga tgagactctc gcatcaccag ccaactcacc gaaacgtgga ggcga        55

<210> SEQ ID NO 327
<211> LENGTH: 55
<212> TYPE: DNA
<213> ORGANISM: Artificial Sequence
<220> FEATURE:
<223> OTHER INFORMATION: Signaling Polynucleotide

<400> SEQUENCE: 327
tugccugatg agactctcgc atcaccagcc aactcaccga aacgaatgga ggcga        55

<210> SEQ ID NO 328
<211> LENGTH: 54
<212> TYPE: DNA
<213> ORGANISM: Artificial Sequence
<220> FEATURE:
<223> OTHER INFORMATION: Signaling Polynucleotide

<400> SEQUENCE: 328
tugccugatg agactctcgc atcaccagcc aactcaccga aacggtggag gcga         54

<210> SEQ ID NO 329
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 329
tugccugatg agactctcgc atcaccagcc aactcaccga aacgtggagg cat          53

<210> SEQ ID NO 330
<211> LENGTH: 53
<212> TYPE: DNA
<213> ORGANISM: Artificial Sequence
<220> FEATURE:
<223> OTHER INFORMATION: Signaling Polynucleotide

<400> SEQUENCE: 330
tugccugatg agactctcgc atcaccagcc aactcaccga aacgtggagg caa          53

<210> SEQ ID NO 331
```

```
<211> LENGTH: 89
<212> TYPE: DNA
<213> ORGANISM: Artificial Sequence
<220> FEATURE:
<223> OTHER INFORMATION: Aptamer

<400> SEQUENCE: 331
taatacgact cactataggc gtagcctgat gagcggtact cagattacag agtgacatcg    60
aaacgtggtg aaagccacgt agctgcgcc                                     89

<210> SEQ ID NO 332
<211> LENGTH: 25
<212> TYPE: DNA
<213> ORGANISM: Artificial Sequence
<220> FEATURE:
<223> OTHER INFORMATION: Signaling Polynucleotide

<400> SEQUENCE: 332
cggtactcag attacagagt gacat                                         25

<210> SEQ ID NO 333
<211> LENGTH: 88
<212> TYPE: DNA
<213> ORGANISM: Artificial Sequence
<220> FEATURE:
<223> OTHER INFORMATION: Aptamer

<400> SEQUENCE: 333
taatacgact cactataggc gtagcctgat gagagacacc acggatccga actggagcga    60
aacgtggtga agccacgta gctgcgcc                                       88

<210> SEQ ID NO 334
<211> LENGTH: 24
<212> TYPE: DNA
<213> ORGANISM: Artificial Sequence
<220> FEATURE:
<223> OTHER INFORMATION: Signaling Polynucleotide

<400> SEQUENCE: 334
agacaccacg gatccgaact ggag                                          24

<210> SEQ ID NO 335
<211> LENGTH: 89
<212> TYPE: DNA
<213> ORGANISM: Artificial Sequence
<220> FEATURE:
<223> OTHER INFORMATION: Aptamer

<400> SEQUENCE: 335
taatacgact cactataggc gtagcctgat gagcctcgca agattgcata cgttagaacg    60
aaacgtggtg aaagccacgt agctgcgcc                                     89

<210> SEQ ID NO 336
<211> LENGTH: 25
<212> TYPE: DNA
<213> ORGANISM: Artificial Sequence
<220> FEATURE:
<223> OTHER INFORMATION: Signaling Polynucleotide

<400> SEQUENCE: 336
cctcgcaaga ttgcatacgt tagaa                                         25

<210> SEQ ID NO 337
<211> LENGTH: 89
```

```
<212> TYPE: DNA
<213> ORGANISM: Artificial Sequence
<220> FEATURE:
<223> OTHER INFORMATION: Aptamer

<400> SEQUENCE: 337
taatacgact cactataggc gtagcctgat gagcacgtag gaaacgacct ctacggagcg    60
aaacgtggtg aaagccacgt agctgcgcc                                     89

<210> SEQ ID NO 338
<211> LENGTH: 25
<212> TYPE: DNA
<213> ORGANISM: Artificial Sequence
<220> FEATURE:
<223> OTHER INFORMATION: Signaling Polynucleotide

<400> SEQUENCE: 338
cacgtaggaa acgacctcta cggag                                         25

<210> SEQ ID NO 339
<211> LENGTH: 90
<212> TYPE: DNA
<213> ORGANISM: Artificial Sequence
<220> FEATURE:
<223> OTHER INFORMATION: Aptamer

<400> SEQUENCE: 339
taatacgact cactataggc gtagcctgat gagcccgaaa ccaccaccgt tgtccaatac    60
gaaacgtggt gaaagccacg tagctgcgcc                                    90

<210> SEQ ID NO 340
<211> LENGTH: 26
<212> TYPE: DNA
<213> ORGANISM: Artificial Sequence
<220> FEATURE:
<223> OTHER INFORMATION: Signaling Polynucleotide

<400> SEQUENCE: 340
cccgaaacca ccaccgttgt ccaata                                        26

<210> SEQ ID NO 341
<211> LENGTH: 40
<212> TYPE: DNA
<213> ORGANISM: Artificial Sequence
<220> FEATURE:
<223> OTHER INFORMATION: Signaling Polynucleotide

<400> SEQUENCE: 341
ccagtctccc gtttaccgcg cctacacatg tctgaatgcc                         40

<210> SEQ ID NO 342
<211> LENGTH: 37
<212> TYPE: DNA
<213> ORGANISM: Artificial Sequence
<220> FEATURE:
<223> OTHER INFORMATION: Signaling Polynucleotide

<400> SEQUENCE: 342
tagtctcccg tttaccgcgc ctacacatgt ctgaatg                            37

<210> SEQ ID NO 343
<211> LENGTH: 35
<212> TYPE: DNA
<213> ORGANISM: Artificial Sequence
<220> FEATURE:
```

<223> OTHER INFORMATION: Signaling Polynucleotide

<400> SEQUENCE: 343
tagtctcccg tttaccgcgc ctacacatgt ctgaa                                    35

<210> SEQ ID NO 344
<211> LENGTH: 40
<212> TYPE: DNA
<213> ORGANISM: Artificial Sequence
<220> FEATURE:
<223> OTHER INFORMATION: Signaling Polynucleotide

<400> SEQUENCE: 344
ctaggcgaaa tatagctaca actgtctgaa ggcacccaat                               40

<210> SEQ ID NO 345
<211> LENGTH: 42
<212> TYPE: DNA
<213> ORGANISM: Artificial Sequence
<220> FEATURE:
<223> OTHER INFORMATION: Signaling Polynucleotide

<400> SEQUENCE: 345
atctacgaat tcatcagggc taaagagtgc agagttactt ag                            42

<210> SEQ ID NO 346
<211> LENGTH: 36
<212> TYPE: DNA
<213> ORGANISM: Artificial Sequence
<220> FEATURE:
<223> OTHER INFORMATION: Signaling Polynucleotide

<400> SEQUENCE: 346
tacgaattca tcagggctaa agagtgcaga gttact                                   36

<210> SEQ ID NO 347
<211> LENGTH: 48
<212> TYPE: DNA
<213> ORGANISM: Artificial Sequence
<220> FEATURE:
<223> OTHER INFORMATION: Signaling Polynucleotide

<400> SEQUENCE: 347
aatatctacg aattcatcag ggctaaagag tgcagagtta cttagctc                      48

<210> SEQ ID NO 348
<211> LENGTH: 42
<212> TYPE: DNA
<213> ORGANISM: Artificial Sequence
<220> FEATURE:
<223> OTHER INFORMATION: Signaling Polynucleotide

<400> SEQUENCE: 348
atctacgaat tcatcagggc taaagagtgc agagttactt ag                            42

<210> SEQ ID NO 349
<211> LENGTH: 40
<212> TYPE: DNA
<213> ORGANISM: Artificial Sequence
<220> FEATURE:
<223> OTHER INFORMATION: Signaling Polynucleotide

<400> SEQUENCE: 349
gcagctaagc aggcggctca caaaaccatt cgcatgcggc                               40

-continued

```
<210> SEQ ID NO 350
<211> LENGTH: 34
<212> TYPE: DNA
<213> ORGANISM: Artificial Sequence
<220> FEATURE:
<223> OTHER INFORMATION: Signaling Polynucleotide

<400> SEQUENCE: 350
gctaagcagg cggctcacaa aaccattcgc atgc                              34

<210> SEQ ID NO 351
<211> LENGTH: 36
<212> TYPE: DNA
<213> ORGANISM: Artificial Sequence
<220> FEATURE:
<223> OTHER INFORMATION: Signaling Polynucleotide

<400> SEQUENCE: 351
gctaagcagg cggctcacaa aaccattcgc atgcaa                            36

<210> SEQ ID NO 352
<211> LENGTH: 30
<212> TYPE: RNA
<213> ORGANISM: Artificial Sequence
<220> FEATURE:
<223> OTHER INFORMATION: Signaling Polynucleotide

<400> SEQUENCE: 352
gguugugaag auugggagcg ucguggcuac                                   30

<210> SEQ ID NO 353
<211> LENGTH: 80
<212> TYPE: DNA
<213> ORGANISM: Artificial Sequence
<220> FEATURE:
<223> OTHER INFORMATION: Signaling Polynucleotide

<400> SEQUENCE: 353
tcgcacattc cgcttctacc ggggggtcg agctgagtgg atgcgaatct gtgggtgggc   60
cgtaagtccg tgtgtgcgaa                                              80
```